US008143212B2

(12) United States Patent
Stogniew et al.

(10) Patent No.: US 8,143,212 B2
(45) Date of Patent: *Mar. 27, 2012

(54) DALBAVANCIN COMPOSITIONS FOR TREATMENT OF BACTERIAL INFECTIONS

(75) Inventors: Martin Stogniew, Blue Bell, PA (US); Luigi Colombo, Malnate (IT); Romeo Ciabatti, Novate Milanese (IT)

(73) Assignee: Vicuron Pharmaceuticals Inc., Morristown, NJ (US)

( * ) Notice: Subject to any disclaimer, the term of this patent is extended or adjusted under 35 U.S.C. 154(b) by 59 days.

This patent is subject to a terminal disclaimer.

(21) Appl. No.: 12/476,785

(22) Filed: Jun. 2, 2009

(65) Prior Publication Data

US 2009/0298749 A1    Dec. 3, 2009

Related U.S. Application Data

(63) Continuation of application No. 11/116,064, filed on Apr. 26, 2005, now abandoned, which is a continuation-in-part of application No. 10/834,395, filed on Apr. 27, 2004, now Pat. No. 7,119,061, which is a continuation-in-part of application No. 10/714,261, filed on Nov. 14, 2003, now Pat. No. 6,900,175.

(60) Provisional application No. 60/496,483, filed on Aug. 19, 2003, provisional application No. 60/495,048, filed on Aug. 13, 2003, provisional application No. 60/485,694, filed on Jul. 8, 2003, provisional application No. 60/427,654, filed on Nov. 18, 2002.

(51) Int. Cl.
*A61K 38/04* (2006.01)

(52) U.S. Cl. ........................................................ 514/3.1

(58) Field of Classification Search .................. None
See application file for complete search history.

(56) References Cited

U.S. PATENT DOCUMENTS

| 4,102,999 | A | 7/1978 | Umezawa et al. ............. 424/123 |
| 4,195,079 | A | 3/1980 | Celmer et al. .................. 424/122 |
| 4,239,751 | A | 12/1980 | Coronelli et al. .............. 424/118 |
| 4,510,126 | A | 4/1985 | Fuhge et al. ..................... 424/3 |
| 4,542,018 | A | 9/1985 | Borghi et al. .................. 424/119 |
| 4,661,470 | A | 4/1987 | Malabarba et al. ................ 519/9 |
| 4,782,042 | A | 11/1988 | Selva et al. ........................ 514/9 |
| 4,868,171 | A | 9/1989 | Selva et al. .................... 514/183 |
| 4,882,313 | A | 11/1989 | Sitrin ................................... 514/8 |
| 4,914,187 | A | 4/1990 | Malabarba et al. ............. 530/317 |
| 4,935,238 | A | 6/1990 | Selva et al. .................... 424/118 |
| 4,954,483 | A | 9/1990 | Malabarba et al. ................ 514/9 |
| 5,004,605 | A | 4/1991 | Hershenson et al. |
| 5,030,619 | A | 7/1991 | Hector ................................. 514/8 |
| 5,064,811 | A | 11/1991 | Borghi et al. ....................... 514/8 |
| 5,606,036 | A | 2/1997 | Hermann et al. .............. 536/4.1 |
| 5,631,238 | A | 5/1997 | Otake et al. ...................... 514/45 |
| 5,750,509 | A | 5/1998 | Malabarba et al. .............. 514/11 |
| 5,843,679 | A | 12/1998 | Selva et al. ................... 435/71.3 |
| 5,882,900 | A | 3/1999 | Rizzo et al. ................... 435/71.3 |
| 5,888,531 | A | 3/1999 | Ohshika et al. ................ 424/423 |
| 5,891,869 | A | 4/1999 | Lociuro et al. ................. 514/183 |
| 5,925,550 | A | 7/1999 | Lancini et al. ................ 435/71.3 |
| 5,935,238 | A | 8/1999 | Talcott et al. .................. 712/206 |
| 6,008,225 | A | 12/1999 | Lociuro et al. ................ 514/279 |
| 6,143,739 | A | 11/2000 | Lociuro et al. ................ 514/183 |
| 6,218,505 | B1 | 4/2001 | Panzone et al. ............... 530/322 |
| 6,384,013 | B1 | 5/2002 | Burkhardt et al. ............... 514/11 |
| 6,417,180 | B1 | 7/2002 | Brown et al. .................. 514/183 |
| 6,455,669 | B1 | 9/2002 | Judice et al. |
| 6,468,967 | B1 | 10/2002 | Oleson et al. ....................... 514/9 |
| 6,541,616 | B1 | 4/2003 | Tucker et al. |
| 6,774,104 | B1 | 8/2004 | Sawai et al. |
| 6,900,175 | B2 | 5/2005 | Cavaleri et al. .................... 514/8 |
| 7,112,565 | B2 | 9/2006 | Sawai et al. ........................ 514/9 |
| 7,115,564 | B2 | 10/2006 | Cavaleri et al. |
| 7,119,061 | B2 | 10/2006 | Stogniew |
| 2004/0197415 | A1 | 10/2004 | Cavaleri et al. ............... 424/489 |
| 2004/0198715 | A1 | 10/2004 | Cavaleri et al. ............... 514/200 |
| 2004/0220122 | A1 | 11/2004 | Cavaleri et al. ................. 514/37 |
| 2004/0224908 | A1 | 11/2004 | Cavaleri et al. ................. 514/37 |
| 2005/0004011 | A1 | 1/2005 | Cavaleri et al. ................... 514/8 |
| 2005/0004050 | A1 | 1/2005 | Stogniew ......................... 514/37 |
| 2005/0004051 | A1 | 1/2005 | Stogniew ......................... 514/37 |
| 2005/0032721 | A1 | 2/2005 | Cavaleri et al. ................. 517/37 |
| 2005/0090433 | A1 | 4/2005 | Colombo et al. ............... 514/11 |
| 2005/0130909 | A1 | 6/2005 | Colombo et al. ............... 514/23 |
| 2005/0130914 | A1 | 6/2005 | Cavaleri et al. ................. 514/35 |

(Continued)

FOREIGN PATENT DOCUMENTS

EP        0071970        2/1983

(Continued)

OTHER PUBLICATIONS

Eliopoulos, GM, Newer glycopeptides, 42nd ICAAC abstracts, Sep. 2002.
Abramson and Sexton, *Infect. Control Hosp. Epidemiol.*, vol. 20(6), pp. 408-411 (1999).
Adamczyk, et al., *Bioorganic & Medicinal Chemistry Letters*, vol. 9, pp. 2437-2440 (1999).
Ahrendt, *Biorganic & Medicinal Chemistry Letters*, vol. 13, pp. 1683-1686 (2003).
Allen and Nicas, *FEMS Microbiology Reviews*, vol. 26, pp. 511-532 (2003).
Anderegg, et al., *J. Clin. Microbiol.*, vol. 41(6), pp. 2795-2796 (2003).

(Continued)

*Primary Examiner* — Elli Peselev
(74) *Attorney, Agent, or Firm* — O'Melveny & Myers LLP

(57) ABSTRACT

The invention provides methods and compositions for treatment of bacterial infections. The composition may be a combination of factors, which include $A_0$, $A_1$, $B_1$, $B_2$, $C_0$, $C_1$, $isoB_0$, and MAG, in the presence of low level solvent. Methods of the invention include administration of dalbavancin formulations for treatment of a bacterial infection, in particular a Gram-positive bacterial infection of skin and soft tissue. Dosing regimens include multiple dose administration of dalbavancin, which often remains at therapeutic levels in the bloodstream for at least one week, providing prolonged therapeutic action against a bacterial infection. Dosing regimens for renal patients are also included.

16 Claims, 41 Drawing Sheets

U.S. PATENT DOCUMENTS

| | | | |
|---|---|---|---|
| 2005/0277581 A1 | 12/2005 | Stogniew et al. | 514/338 |
| 2006/0074014 A1 | 4/2006 | Stogniew et al. | 514/8 |
| 2009/0298748 A1 | 12/2009 | Cavaleri | |
| 2009/0298749 A1 | 12/2009 | Stogniew et al. | |

FOREIGN PATENT DOCUMENTS

| | | |
|---|---|---|
| EP | 0095154 | 11/1983 |
| EP | 0078451 | 4/1985 |
| EP | 0177882 | 4/1986 |
| EP | 0204179 | 12/1986 |
| EP | 0228015 | 7/1987 |
| EP | 0240609 | 10/1987 |
| EP | 0259781 | 3/1988 |
| EP | 0301785 | 2/1989 |
| EP | 0316712 | 5/1989 |
| EP | 0376041 | 7/1990 |
| EP | 0438747 | 7/1991 |
| EP | 0318146 | 3/1992 |
| EP | 0306312 | 4/1992 |
| EP | 0525499 | 2/1993 |
| EP | 0801075 | 10/1997 |
| EP | 0931834 | 7/1999 |
| FR | 2101041 | 3/1972 |
| FR | 2396019 | 1/1979 |
| GB | 2121401 | 12/1983 |
| GB | 2142234 | 2/1984 |
| JP | 1050900 | 2/1989 |
| WO | WO8802755 | 4/1988 |
| WO | WO9011300 | 10/1990 |
| WO | WO 93/03060 A1 | 2/1993 |
| WO | WO0020556 | 4/2000 |
| WO | WO 2004/045636 A1 | 3/2004 |
| WO | WO2004045636 | 6/2004 |
| WO | WO 2006/078277 A2 | 7/2006 |

OTHER PUBLICATIONS

Anderegg, et al., *ASM*, May 2003, Poster No. A-090, one page (2003).
Arimoto, et al., *Chem. Commun.*, Issue 15, pp. 1361-1362 (1999).
Arimoto, et al., *Tetrahedron Letters*, vol. 42, pp. 3347-3350 (2001).
Arioli, et al., *Journal of Antibiotics*, vol. 29(5), pp. 511-515 (1976).
Arthur and Courvalin, *Antimicrobial Agents and Chemotherapy*, vol. 37(8), pp. 1563-1571 (1993).
Author Unknown, "Dalbavancin tested for soft tissue infections", located at <http://www.qxhealth.com/news_archive/cfml/search_details.cfm?sum_ID=8777>, last visited on Sep. 8, 2003 (one page).
Author Unknown, "Molecule of the Month V-Glycopeptide", located at <http://www.prous.com/mom/nov_00/mom.html >, last visited on Aug. 27, 2002 (2 pages).
Author Unknown, "Dalbavancin: The Staph Drug", located at < http://www.versicor.com/products/dalbava.html>, last visited on Aug. 27, 2002 (one page).
Author Unknown, "Treatment Hope for Bloodstream Infections Introduced in Five Per5cent of Intravenous Catheter Cases", http://www.biosearch.it, (2002) (one page).
Barna and Williams, *Ann. Rev. Microbiol.*, vol. 38, pp. 339-357 (1984).
Biavasco, et al., *Antimicrobial Agents and Chemotherapy*, vol. 44(11), pp. 3122-3126 (2000).
Campbell, et al., *J. Amer. Acad. Audiology*, vol. 14(3), pp. 157-168 (2003).
Candiani, et al., *J. Antimicrob. Chemother.*, vol. 44, pp. 179-192 (1999).
Cavaleri, et al., "Protein Binding of Dalbavancin Using Isotherman Titration Microcalorimetry", *42$^{nd}$ ICAAC Abstracts*, San Diego, CA, Sep. 27-30, 2002, Abstract No. A-1385, p. 18 (2002).
Cavaleri, et al., "Protein Binding of Dalbavancin Using Isotherman Titration Microcalorimetry", *42$^{nd}$ ICAAC Abstracts*, San Diego, CA, Sep. 27-30, 2002, Poster No. A-1385, (one page).
Chaix, et al., *JAMA*, vol. 282(18), pp. 1745-1751 (1999).
Crowe, et al., *Eur. J. Microbiol. Infect. Dis.*, vol. 17, pp. 377-384 (1998).
Darouiche and Mansouri, "Dalbavancin Versus Vancomycin for Prevention of *Staphylococcus aureus* Colonization of Devices in an Animal Model", Poster #174 (one page) (Date unknown).

Dorr, et al., "Rationale for Once Weekly Dosing of Dalbavancin, a New Semisynthetic Glycopeptide", *Abstracts of the IDSA 40$^{th}$ Annual Meeting*, Oct. 24-27, 2002, Abstract No. 52, p. 53 (one page).
Dorr, et al., "Rationale for Once Weekly Dosing of Dalbavancin, a New Semisynthetic Glycopeptide", *Abstracts of the IDSA 40$^{th}$ Annual Meeting*, Oct. 24-27, 2002, Poster No. 52 (one page).
Dowell, et al., "Dalbavancin Dosage Adjustments Not Required for Patients with Mild Renal Impairment", *ECCMID: Clinical Microbiology and Infection*, Abstract No. P1224, vol. 9, Suppl. 1, pp. 291 (2003).
Dowell, et al., "Dalbavancin Dosage Adjustments Not Required for Patients with Mild Renal Impairment", *ECCMID: Clinical Microbiology and Infection*, Poster No. P1224 (one page).
Dowell, et al., "The Pharmacokinetics and Renal Excretion of Dalbavancin in Healthy Subjects", *42nd ICAAC Abstracts*, San Diego, CA, Sep. 27-30, 2002, Abstract No. A-1386, p. 18.
Dowell, et al., "The Pharmacokinetics and Renal Excretion of Dalbavancin in Healthy Subjects", *42nd ICAAC Abstracts*, San Diego, CA, Sep. 27-30, 2002, Poster No. A-1386 (one page).
Dowell, et al., "Dalbavancin (DAL) Pharmacokinetics (PK) in Subjects with Mild or Moderate Hepatic Impairment (HI)", *43$^{rd}$ Annual ICAAC*, Chicago, IL, Sep. 14, 17, 2003, Poster #A-19 (one page).
Ednie, et al., "Antistaphylococcal Activity of Dalbavancin Compared to Those of Six Other Agents", *43$^{rd}$ Annual ICACC*, Chicago, IL, Sep. 14-17, 2003, Poster #C1-1631 (one page).
Fieser and Fieser, *Reagents for Organic Synthesis*, John Wiley & Sons, Inc., pp. 128-130 (1967).
Fridkin, et al., *Clinical Infectious Diseases*, vol. 36, pp. 429-439 (2003).
Ge, et al., *Science*, vol. 284, pp. 507-511 (1999).
Goldstein, et al., "Comparative Antibacterial Activity of Semi-Synthetic Derivatives of the Glycopeptide Antibiotic A40926 (MDL 62,476)", *Abstracts of the 34$^{th}$ ICAAC*, Orlando, FL, Oct. 4-7, 1994, Abstract No. F142, p. 225.
Goldstein (May 10, 2001) "Versicor, Inc. Will Host Conference Call to Discuss Advanced Clinical Development Programs for Lead Antifungal and Antibiotic Products", Press Release (2 pages).
Goldstein and Halsey (Nov. 28, 2001) "Versicor Announces Plans to Develop Dalbavancin As the First Once-Weekly Injectable Antibiotic." Press Release (3 pages).
Goldstein and Halsey (Dec. 17, 2001) "Versicor Announces Data Demonstrating Tolerability of Anidulafungin at Higher Doses." Press Release (3 pages).
Goldstein and Halsey (Mar. 12, 2002) "Versicor Announces Start of Phase II Study of Once-Weekly Dalbavancin for Bloodstream Infections." Press Release (3 pages).
Goldstein and Halsey (May 21, 2002) "Versicor Announces Completion of Phase II Study of Once-Weekly Dalbavancin for Skin and Soft Tissue Infections." Press Release (3 pages).
Goldstein, et al. (May 22, 2001) "Versicor Begins Phase II Trial of Dalbavancin, Its Novel Glycopeptide Antibiotic." Press Release (3 pages).
Goldstein, et al. (Dec. 17, 2001) "Versicor Announces Positive Phase I Data for Dalbavancin, Demonstrating Feasability of Once-Weekly Dosing." Press Release (4 pages).
Goldstein, et al. (Sep. 5, 2002) "Versicor Announces Positive Phase 2 Study Results With Dalbavancin for Skin and Soft Tissue Infections." Press Release (3 pages).
Goldstein, et al. (Sep. 19, 2002) "Versicor Announces 24 Abstracts to be Presented at Annual ICAAC Meeting Next Week." Press Release (3 pages).
Goldstein, et al. (Oct. 23, 2002) "Versicor Announces Data Presentations Highlighting Advanced Product Candidates at IDSA Annual Meeting." Press Release (3 pages).
Goldstein, et al. (Dec. 17, 2002) "Versicor Begins Phase III Trials of Dalbavancin for Skin and Soft Tissue Infections." Press Release (3 pages).
Goldstein and Citron, "In Vitro Activities of Dalbavancin and Nine Comparator Agents against Fastidious and Anaerobic Gram-Positive Species", *42$^{nd}$ ICAAC Abstracts*, San Diego, CA, Sep. 27-30, 2002, Abstract No. E1454, p. 163 (2002).
Goldstein, et al., *Antimicrob. Agents and Chemother.*, vol. 47(6), pp. 1968-1971 (2003).

Greene, *Protective Groups in Organic Synthesis,* John Wiley and Sons, Inc., pp. ix-x (Table of Contents only) (1981).

Griffith, *JACS,* vol. 125, pp. 6517-6531 (2003).

Hackbarth, et al., "In Vitro Activity of the Glycopeptide BI 397 Agent *Staphylococcus aureus* and *Staphylococcus epidermidis*", *39th Annual ICAAC,* San Francisco, CA, Sep. 1999, Abstract No. 1283, p. 332 (1999).

Hackbarth, et al., "In Vitro Activity of the Glycopeptide BI 397 Agent *Staphylococcus aureus* and *Staphylococcus epidermidis*", *39th Annual ICAAC,* San Francisco, CA, Sep. 1999, Poster No. 1283 (one page) (1999).

Hackbarth, et al, "Antibacterial Activity of V-Glycopeptide (VER001), A Semi-Synthetic Glycopeptide, Against *Staphylococcus aureus*," *ASM,* May 2001, Abstract No. A-4.

Hackbarth, et al., "Antibacterial Activity of V-Glycopeptide (VER001), A Semi-Synthetic Glycopeptide, Against *Staphylococcus aureus*," *ASM,* May 2001, Poster No. A-4 (one page).

Harding, et al., *JACS,* vol. 45, pp. 835-841 (2000).

Heiselman, *JAMA,* vol. 272(23), pp. 1819-1820 (1994).

Hiramatsu, et al., *Lancet.* vol. 350, pp. 1670-1673 (1997).

Jabes, et al., "Efficacy of a Single Dalbavancin (DA) Dose Compared with Multiple Linezolid (LN) Doses against Penicillin-Resistant Pneumococci (PRSP) in a Lobar Pneumonia (LP) Model in the Immunocompetent Rat (IR)", *41st ICAAC Abstracts,* Chicago, IL, Sep. 22-25, 2001, Abstract No. B-989, p. 54.

Jabes, et al. (Dec. 2000) "In vitro and in vivo Bacterial Activity of the New Glycopeptide BI 397 and Correlations with Drug Concentrations," BioSearch Italia, S.P.A., San Antonio, Dec. 2000, Poster No. F5 (one page).

Jabes, et al. (2001) "Efficacy of a Single Dalbabancin (DA) Dose Compared with Multiple Vancomcin (VA) Doses against MRSA in the Rat Pouch Model of Infection," *41st ICAAC Abstracts,* Chicago, IL, Sep. 22-25, 2001, Abstract No. B-1654, p. 68.

Jabes, et al. (2001) "Efficacy of a Single Dalbabancin (DA) Dose Compared with Multiple Vancomcin (VA) Doses against MRSA in the Rat Pouch Model of Infection," *41st ICAAC Abstracts,* Chicago, IL, Sep. 22-25, 2001, Poster. No. B-1654 (one page).

Jabes, et al., "Efficacy of Dalbavancin Compared with Vancomycin and Linezolid in the Rat Granuloma Pouch Model of Staphylococcal Infection," *Symposium on Surgical Infections,* Como, Italy, Poster No. P1 (one page).

Jabes, et al., "Efficacy of dalbavancin against methicillin-resistent *Staphylococcus aureus* in the rat granuloma pouch infection model", *Antimicrobial Agents and Chemotherapy,* vol. 48(4), pp. 1118-1123 (2004).

Jain, *JACS,* vol. 125, pp. 8740-8741 (2003).

Jones, et al., (2001) "Activity and Spectrum Evaluation of Dalbavancin (V-Glycopeptide and BI397), A Novel "Glycopeptide" Class Antimicrobial," *41st ICAAC Abstracts,* Chicago, IL, Sep. 22-25, 2001, Abstract No. 2276, p. 200.

Jones, et al., (2001) "Activity and Spectrum Evaluation of Dalbavancin (V-Glycopeptide and BI397), A Novel "Glycopeptide" Class Antimicrobial," *41st ICAAC Abstracts,* Chicago, IL, Sep. 22-25, 2001, Poster No. 2276 (one page).

Jones, et al., *Journal of Chemotherapy,* vol. 13(3), pp. 244-254 (2001).

Jordan, et al. "A Novel Use of Optimal Sampling Theory (OST) During Drug Development" *American Society of Clinical Pharmacology & Therapeutics,* Atlanta, GA, Mar. 2002, Poster (one page).

Kenny, et al., *Antimicrobial Agents and Chemotherapy,* vol. 39(7), pp. 1589-1590 (1995).

Lefort, et al., "Activity of Dalbavancin (BI-397) in Vitro and in Experimental Endocarditis due to Methicillin-Resistant *Staphylococcus aureus* (MRSA) Susceptible or Intermediate to Glycopeptides (GISA)," *42nd ICAAC Abstracts,* San Diego, CA. Sep. 27-30, 2002, Abstract No. B-278, p. 33.

Leighton, et al., "Dalbavancin: Phase I Single and Multiple-Dose Placebo Controlled Intravenous Safety, Pharmacokinetic Study in Healthy Volunteers," *41st ICAAC Abstracts,* Chicago, IL, Sep. 22-25, 2001, Abstract No. 951, p. 25.

Leighton, et al., "Dalbavancin: Phase I Single and Multiple-Dose Placebo Controlled Intravenous Safety, Pharmacokinetic Study in Healthy Volunteers," *41st ICAAC Abstracts,* Chicago, IL, Sep. 22-25, 2001, Poster No. 951 (one page).

Leighton, et al., "Stringent Audiology Assessments in a Healthy Volunteer Study with the Glycopeptide Dalbavancin," *41st ICAAC Abstracts,* Chicago, IL, Sep. 22-25, 2001, Abstract No. A-2192, p. 37.

Leighton, et al., "Stringent Audiology Assessments in a Healthy Volunteer Study with the Glycopeptide Dalbavancin," *41st ICAAC Abstracts,* Chicago, IL, Sep. 22-25, 2001, Poster No. A-2192 (one page).

Lopez, et al., *Clinical Microbiology and Infection,* vol. 9, Suppl. 1, p. 375, Abstract No. P1539 (2003).

Lopez, et al., *ECCMID,* May 2003, Poster No. P1539 (one page).

Lyght, et al., *The Merck Manual of Diagnosis & Therapy,* 11th Edition, Merck Sharp & Dohme Research Laboratories, pp. 799-862 (1966).

Malabarba and Ciabatti, *Current Medicinal Chemistry,* vol. 8(14), pp. 1759-1773 (2001).

Malabarba and Donadio, *Drugs of the Future,* vol. 24(8), pp. 839-846 (1999).

Malabarba, et al., *Journal of Antibiotics,* vol. 40(11), pp. 1572-1587 (1987).

Malabarba, et al., *Journal of Antibiotics,* vol. 48(8), pp. 869-883 (1995).

Malabarba, et al., *Medicinal Research Reviews,* vol. 17(1), pp. 69-137 (1997).

Malabarba, et al., "BI 397: A New Developmental Semisynthetic Glycopeptide Antibiotic," *Abstracts of the 38th ICAAC,* Sep. 24-27, 1998, San Diego, CA, Abstract No. F107, p. 259.

Mammen, et al., *Angew. Chem. Int Ed.,* vol. 37, pp. 2754-2794 (1998).

McGovern, et al., *J. Med. Chem.,* vol. 45, pp. 1712-1722 (2002).

McOmie, J.F.W. ed., *Protective Groups in Organic Chemistry,* Plenum Press, New York, NY, p. xi (Table of Contents Only) (1973).

Neu, *Science,* vol. 257, pp. 1064-1073 (1992).

Newell, et al., *Transplantation,* vol. 65(3), pp. 439-442 (1998).

Nicolaou, et al., *Angew. Chem. Int. Ed.,* vol. 38, pp. 2096-2152 (1999).

Nicolaou, et al., *Angew. Chem. Int. Ed.,* vol. 39(21), pp. 3823-3828 (2000).

Nicolaou, et al., *Chem. Eur. J.,* vol. 7(17), pp. 3824-3843 (2001).

Nisbet, et al., "Discovery, Comparative Antibacterial Activity and Structure Elucidation of AAJ-271, a Novel Group of Glycopeptides," *26th Annual ICAAC,* New Orleans, LA, Oct. 1986, Abstract No. 226, p. 137.

Ochalski and Zuk, *Acta Phys. Pol.,* vol. 94(3), pp. 463-467 (1998).

Omura, et al., *The Journal of Antibiotics,* vol. 37(5), pp. 494-502 (1984).

Omura, et al., *Chemical Abstracts,* Abstract No. 51459t; 101; 318 (1984).

Pavlov and Preobrazhenskaya, *Journal of Antibiotics,* vol. 51(5), pp. 525-527 (1998).

Popieniek and Pratt, *Analytical Biochemistry,* vol. 165, pp. 108-113 (1987).

Printsevskaya, et al., *J. Med. Chem.,* vol. 45, pp. 1340-1347 (2002).

Printsevskaya, et al., *J. Med. Chem.,* vol. 46, pp. 1204-1209 (2003).

Rao and Whitesides, *J. Am. Chem. Soc.,* vol. 119, pp. 10286-10290 (1997).

Rao, et al., *Chemistry & Biology,* vol. 6, p. 353-359 (1999).

Rao, et al., *J. Am. Chem. Soc.,* vol. 121, pp. 2629-2630 (1999).

Richards, et al., *Crit. Care. Med.,* vol. 27(5), pp. 887-892 (1999).

Riva, et al., *Chromatographia,* vol. 24, pp. 295-301 (1987).

Romano, et al., "In Vitro Antibacterial Properties of dalbavancin and Reference Compounds Against Recent Clinical Isolates," *Symposium on Surgical Infections,* Como, Italy, Poster P3 (one page) (2003).

Roy, et al., *Chemistry & Biology,* vol. 8(11), pp. 1095-1106 (2001).

Schäfer, et al., *Helvetica Chimic Acta,* vol. 79, pp. 1916-1924 (1996).

Schwyzer, et al., *Helvetica Chimic Acta,* vol. 38(7/8), pp. 69-79 (1955) (English Abstract, p. 79).

Seltzer, et al., "Dalbavancin: Phase 2 Demonstration of Efficacy of a Novel, Weekly Dosing Regimen in Skin and Soft Tissue Infections," ECCMID, May 2003, Abstract No. O143, p. 22.
Selva, et al., The Journal of Antibiotics, vol. 41(9), pp. 1243-1252 (1988).
Shopsin, et al., The Journal of Infectious Diseases, vol. 182, pp. 359-362 (2000).
Sieradzki, et al., Antimicrobial Agents and Chemotherapy, vol. 42(1); pp. 100-107 (1998).
Sieradzki, et al., NEJM, vol. 340(7), pp. 517-523 (1999).
Staroske and Williams, Tetrahedron Letters, vol. 39, pp. 4917-4920 (1998).
Stephan, et al., "Worldwide Assessment of Dalbavancin Activity and Spectrum (2002)", $43^{rd}$ Annual ICAAC, Chicago, IL, Sep. 14-17, 2003, Poster #F-2107 (one page).
Stogniew, et al., "Pharmacokinetic Attributes of Dalbavancin: Well Distributed and Completely Eliminated with Dual Routes of Elimination", ECCMID, May 2003, poster (one page).
Stogniew, at al., "Pharmacokinetic Attributes of Dalbavancin: Well Distributed, Weekly Dosing, and Completely Eliminated," ECCMID Clinical Microbiology and Infection, Abstract No. P1225, vol. 9(1), pp. 291 (2003).
Sundram and Griffin, J. Am. Chem. Soc., vol. 118, pp. 13107-13108 (1996).
Süssmuth, Chem. Bio. Chem., vol. 3, pp. 295-298 (2002).
Tenover, et al., Emerging Infectious Diseases, vol. 7(2), pp. 327-332 (2001).
Tsuji, et al., "New Glycopeptide Antibiotics: II. The Isolation and Structures of Chloroorienticins", The Journal of Antibiotics, vol. 41(10), pp. 1506-1510 (1988).
Verhoef, Clinical Infectious Diseases, vol. 17(S2), pp. S359-S367 (1993).
Walsh, Nature, vol. 406, pp. 775-781 (2000).
Walsh, et al., Chemistry & Biology, vol. 3, pp. 21-28 (1996).
White, et al., "V-Glycopeptide: Phase 2 Single and Multiple-Dose Placebo Controlled Intravenous Safety, Pharmacokinetic, and Pharmacodynamic Study in Healthy Subjects", $40^{th}$ ICAAC Abstracts, Toronto, Canada, Sep. 17-20, 2000, Poster No. 2196 (one page).
White, et al., "V-Glycopeptide: Phase 2 Single and Multiple-Dose Placebo Controlled Intravenous Safety, Pharmacokinetic, and Pharmacodynamic Study in Healthy Subjects", $40^{th}$ ICAAC Abstracts, Toronto, Canada, Sep. 17-20, 2000, Abstract No. 2196 (one page).
Williams, et al., Science, vol. 280, pp. 711-714 (1998).
Xu, et al., J. Am. Chem.. Soc., vol. 121, pp. 4898-4899 (1999).
Zerilli, et al., Rapid Communications in Mass Spectrometry, vol. 6, pp. 109-114 (1992).
Andes, et al., "In-vivo Pharmacodynamic Characterization of Dalbavancin (DAL) in the Murine Thigh Infection Model" (PosterA-1872), presented at the 2004 ICAAC, Washington, DC, Oct. 30-Nov. 2, 2004.
Feroggio thesis "Caratterizzazione Di Metaboliti Secondari Bioattivi Di Origine fermentative Mediate Tecnologie Analitiche Avanzate", University of Milan, Jan. 16, 2004.
Seltzer, et al., CID, vol. 37, pp. 1298-1303 (2003).
Rodvold, et al., Antimicrobial Agents and Chemotherapy, vol. 32(6), pp. 848-852 (1988).
Beckers et al., "Efficacy and Pharmacokinetics of Teicoplanin in Hemodialysis Patients," Infection 21(1):71-74 (1993).
Burgess et al., "Pharmacokinetics and Pharmacodynamics of Piperacillin/Tazobactam When Administered by Continuous Infusion and Intermittent Dosing," Clin. Ther. 24(7):1090-104 (Jul. 2002).
Claudius, J.S. And Neau, S.H., "The solution stability of vancomycin in the presence and absence of sodium carboxymethyl starch," International Journal of Pharmaceutics, 168:41-48 (1998).
Cooper, A. (1998). "Microcalorimetry of Protein-Protein Interactions" Chapter 7 in Biocalorimetry: The Applications of Calorimetry in the Biological Sciences, Ladbury, J.E. et al. eds. John Wiley & Sons, Ltd., pp. 103-111.
Cooper, A. (1999). "Thermodynamic Analysis of Biomolecular Interactions," Curr. Opin. Chem, Biol. 3:557-563.
Cooper, A. et al. (1993). "Microcalorimetry and the Molecular Recognition of Peptides and Proteins," Philos. Trans. R. Soc. Lond. Ser. A-Math. Phys. Eng. Sci. 345:23-35.
Cooper, A. et al. (1994). "Isothermal Titration Microcalorimetry" Chapter 11 in Methods in Molecular Biology:Microscopy, Optical Spectroscopy, and Macroscopic Techniques Jones, C. et al. eds. Humana Press: Totowa, NJ. 22:137-150.
Goldstein, B.P. et al. (Dec., 1987). "A40926, A New Glycopeptide Antibiotic with Anti-Neisseria Activity," Antimicrobial Agents and Chemotherapy 31(12):1961-1966.
"Guidance for Industry (FDA). Estimating the Maximum Safe Starting Dose in Initial Clinical Trials for Therapeutics in Adult Healthy Volunteers." Jul. 2005, available at http://www.fda.gov/downloads/Drugs/GuidanceComplianceRepulatoryInformation/Guidances/ucm078932.pdf.
International Search Report mailed on Apr. 14, 2004, for PCT patent application PCT/US03/36127 filed on Nov. 14, 2003, 10 pages.
Kemp, et al. Organic Chemistry, Chapter 11, Acyl Derivatives, pp. 351, 985-986; Chapter 34, Simple Functional-Group Chemistry of Nitrogen, Sulfur and Phosphorus; Heterocyclic Chemistry, pp. 1220-221, Worth Publishers (Mar. 1980).
Knudsen et al., Antimicrobial Agents and Chemotherapy, V. 44, No. 5, pp. 1247-1254 (2000).
MacGowan, A.P., "Pharmacodynamics, Pharmacokinetics, and Therapeutics Drug Monitoring of Glycopeptides," Ther. Drug Monit., 20(5):473-477 (Oct. 1998).
Mahmood I and Balian JD, "The pharmacokinetic principles behind scaling from preclinical results to phase I protocols," Clin Pharmacokinet 1999; 36:1-11.
Mahmood I, "Application of allometric principles for the prediction of pharmacokinetics in human and veterinary drug development," Adv Drug Deliv Rev. 2007; 59:1177-1192.
Martin, A., Physical Pharmacy (4th ed.), Chapter 18, "Coarse Dispersions", pp. 477-494, Lea & Febiger, Philadelphia (1993).
McPhail, D. et al. (1997). "Thermodynamics and Kinetics of Dissociation of Ligand-Induced Dimers of Vancomycin Antibodies," J. Chem. Soc.-Faraday Trans. 93(13):2283-2289.
Pitkin, D. et al., "Charge and Lipophilicity Govern the Pharmacokinetics of Glycopeptide Antibiotics," Antimicrob. Agents Chemother., 29(3):440-444 (Mar. 1986).
Ross, G. et al., Chapter 8, "Glycopeptide Pharmacodynamics," in Antimicrobial Pharmacodynamics in Theory and Clinical Practice, Nightingale, C.H., et al. ed., pp. 177-204, Marcel Dekker, Inc., New York, NY (2002).
Swarbrick, J., Chapter 21, "Coarse Dispersions," in Remington: The Science and Practice of Pharmacy, Gennero, A.R., ed., pp. 278-291, and 1395, Mack Publishing Co, Easton, Pennsylvania (1995).
Wirth et al., "Maillard Reaction of Lactose and Fluoxetine Hydrochloride, a Secondary Amine," Journal of Pharmaceutical Sciences, 87(1):31-39 (Jan. 1998).
Wiseman, T. et al. (1989). "Rapid Measurement of Binding Constants and Heats of Binding Using a New Titration Calorimeter," Anal. Biochem. 179:131-137.

| Time (Months) | Compound A | Compound B | Compound C | Compound D | Compound E | Compound F | Compound G |
|---|---|---|---|---|---|---|---|
| 0 | 86.20 | 84.20 | 85.80 | 83.60 | 85.50 | 85.40 | 86.10 |
| 3 | 84.70 | 79.80 | 83.80 | 77.10 | 83.00 | 81.50 | 83.60 |
| 6 | 84.70 | 79.00 | 83.80 | 77.10 | 83.00 | 81.00 | 84.10 |
| 9 | 84.50 | 78.40 | 83.40 | 76.20 | 82.60 | 80.70 | 84.20 |
| 12 | 84.70 | 78.10 | 83.50 | 75.70 | 82.40 | 80.30 | 84.20 |
| ΔBo | 1.50 | 6.10 | 2.30 | 7.90 | 3.10 | 5.10 | 1.90 |

| Time (Months) | Compound A | Compound B | Compound C | Compound D | Compound E | Compound F | Compound G |
|---|---|---|---|---|---|---|---|
| 0 | 86.20 | 84.20 | 85.80 | 83.60 | 85.50 | 85.40 | 86.10 |
| 2 | 83.50 | 76.30 | 82.20 | 72.70 | 80.30 | 79.00 | 83.10 |
| 3 | 81.90 | 72.40 | 80.00 | 68.60 | 78.10 | 75.50 | 81.60 |
| 6 | 80.90 | 70.10 | 79.10 | 66.20 | 77.10 | 74.50 | 81.50 |
| ΔBo | 5.30 | 14.10 | 6.70 | 17.40 | 8.40 | 10.90 | 4.60 |

| Time (Months) | Compound A | Compound B | Compound C | Compound D | Compound E | Compound F | Compound G |
|---|---|---|---|---|---|---|---|
| 0 | 1.50 | 3.50 | 1.80 | 4.50 | 2.10 | 2.30 | 1.60 |
| 2 | 4.10 | 12.50 | 5.50 | 16.60 | 7.30 | 9.50 | 4.40 |
| 3 | 5.40 | 18.60 | 7.50 | 21.00 | 9.80 | 13.10 | 5.80 |
| 6 | 6.60 | 18.80 | 9.10 | 23.70 | 10.80 | 14.40 | 6.40 |
| ΔMAG | 5.10 | 15.30 | 7.30 | 19.20 | 8.70 | 12.10 | 4.80 |

| Time (Months) | Compound H | Compound I | Compound J | Compound K | Compound L | Compound M | Compound N | Compound O |
|---|---|---|---|---|---|---|---|---|
| 0 | 85.3 | 85.5 | 85.7 | 85.3 | 85.1 | 85.6 | 85.0 | 88.3 |
| 3 | 84.8 | 85.1 | 84.6 | 85.0 | 84.5 | 85.0 | 84.4 | 87.8 |
| 6 | 85.2 | 85.5 | 85.1 | 85.3 | 84.8 | 85.4 | 84.9 | 88.2 |
| 9 | 84.9 | 85.5 | 84.8 | 85.3 | 84.3 | 84.9 | 84.5 | 87.9 |
| 12 | 84.6 | 85.2 | 84.5 | 85.2 | 84.1 | 85.0 | 84.4 | 87.8 |
| ΔBo | 0.70 | 0.30 | 1.20 | 0.10 | 1.00 | 0.60 | 0.60 | 0.50 |

| Time (Months) | Compound H | Compound I | Compound J | Compound K | Compound L | Compound M | Compound N | Compound O |
|---|---|---|---|---|---|---|---|---|
| 0 | 1.5 | 1.5 | 1.6 | 1.5 | 1.6 | 1.6 | 1.7 | 1.8 |
| 3 | 2.4 | 2.0 | 2.6 | 2.2 | 2.6 | 2.3 | 2.8 | 2.7 |
| 6 | 2.4 | 2.0 | 2.6 | 2.2 | 2.9 | 2.2 | 2.8 | 2.6 |
| 9 | 2.4 | 1.8 | 2.6 | 2.1 | 2.9 | 2.1 | 2.7 | 2.6 |
| 12 | 2.6 | 2.0 | 2.8 | 2.0 | 3.1 | 2.2 | 2.9 | 2.8 |
| ΔMAG | 1.10 | 0.50 | 1.20 | 0.50 | 1.50 | 0.60 | 1.20 | 1.00 |

| Time (Months) | Compound H | Compound I | Compound J | Compound K | Compound L | Compound M | Compound N | Compound O |
|---|---|---|---|---|---|---|---|---|
| 0 | 85.3 | 85.5 | 85.7 | 85.3 | 85.1 | 85.6 | 85.0 | 85.30 |
| 2 | 84.2 | 84.9 | 83.8 | 84.3 | 83.0 | 84.6 | 83.6 | 88.40 |
| 3 | 82.8 | 83.6 | 82.3 | 83.1 | 81.8 | 83.6 | 82.8 | 84.60 |
| 6 | 83.0 | 83.4 | 82.5 | 83.0 | 81.6 | 84.4 | 83.2 | 84.30 |
| ΔBo | 2.3 | 2.1 | 3.2 | 2.3 | 3.6 | 1.2 | 1.8 | 4 |

| Time (Months) | Compound H | Compound I | Compound J | Compound K | Compound L | Compound M | Compound N | Compound O |
|---|---|---|---|---|---|---|---|---|
| 0 | 1.5 | 1.5 | 1.6 | 1.5 | 1.6 | 1.6 | 1.7 | 1.50 |
| 2 | 3.5 | 2.7 | 3.8 | 3.1 | 4.4 | 2.7 | 3.5 | 4.60 |
| 3 | 4.6 | 3.7 | 5.2 | 4.4 | 6.0 | 3.7 | 4.6 | 6.20 |
| 6 | 4.9 | 4.4 | 5.5 | 4.6 | 6.6 | 3.8 | 4.7 | 7.00 |
| ΔMAG | 3.4 | 2.9 | 3.9 | 3.3 | 5.0 | 2.2 | 3.0 | 5.2 |

DALBAVANCIN COMPOSITIONS FOR TREATMENT OF BACTERIAL INFECTIONS

CROSS-REFERENCE TO RELATED APPLICATIONS

This application is a continuation of U.S. application Ser. No. 11/116,064, now abandoned, filed Apr. 26, 2005, which is a continuation-in-part of U.S. application Ser. No. 10/834,395, now U.S. Pat. No. 7,119,061, filed Apr. 27, 2004, which is a continuation-in-part of U.S. application Ser. No. 10/714,261, now U.S. Pat. No. 6,900,175, filed Nov. 14, 2003, which claims the benefit of U.S. Provisional Patent Application Ser. Nos. 60/427,654, filed Nov. 18, 2002, 60/485,694, filed Jul. 8, 2003, 60/495,048, filed Aug. 13, 2003, and 60/496,483, filed Aug. 19, 2003, the disclosures of all of which are incorporated herein by reference in their entireties.

FIELD OF THE INVENTION

This application relates to dalbavancin compositions and methods of use of such compositions in methods of treatment of bacterial infections.

BACKGROUND OF THE INVENTION

According to the U.S. Center for Disease Control and Prevention, nosocomial bloodstream infections are a leading cause of death in the United States. Approximately five percent of the seven million central venous catheters (CVCs) inserted annually in the United States are associated with at least one episode of bloodstream infection (approximately 350,000 a year). Catheter-related bloodstream infections occur when bacteria enter the bloodstream through an intravenous catheter and can be life threatening.

Skin and soft tissue infections (SSTIs) (also known as complicated and/or uncomplicated skin and skin structure infections (SSSIs)) are a common medical condition and often the consequence of trauma or surgical procedures. *Staphylococcus aureus* and *Streptococcus pyogenes* are the pathogens most frequently isolated from patients with deep tissue infections, although any pathogenic organism, including those found on healthy skin, may cause infection. Many SSTIs are mild to moderate in severity, permitting successful treatment with oral antimicrobial agents and local cleansing. In contrast, more severe or complicated infections, which frequently occur in patients with underlying risk factors (e.g., vascular compromise, diabetes) and/or infections caused by difficult-to-treat or multiply-resistant bacteria, may require potent intravenous antimicrobial therapy and aggressive surgical debridement.

Staphylococci are a clinical and therapeutic problem and have been increasingly associated with nosocomial infections since the early 1960s. The coagulase-positive species methicillin-resistant *Staphylococcus aureus* (MRSA) has long been problematic in both community-acquired and nosocomial infections, and several coagulase-negative staphylococci have been recognized as opportunistic human pathogens, especially in the treatment of critically ill patients in intensive care units. Another major cause for clinical concern is the increasing isolation of penicillin-resistant *Streptococcus pneumoniae* strains in many parts of the world.

The glycopeptide antibiotics vancomycin and teicoplanin have been used against serious nosocomial infections caused by multi-drug-resistant Gram-positive pathogens, particularly MRSA, coagulase-negative staphylococci (CoNS), and enterococci. Vancomycin and teicoplanin are used for infections caused by MRSA, and until recently, all isolates were uniformly susceptible. However, the isolation of *Staphylococcus aureus* strains with intermediate susceptibility or resistance to teicoplanin as well as vancomycin has now been reported with increasing frequency. A number of vancomycin-resistant strains, classified "VanA," "VanB," or "VanC," based on the mechanism of resistance, have been reported. Thus, alternative treatment options are needed.

Teicoplanin is at least as active as vancomycin against most Gram-positive bacteria and appears to cause fewer adverse events. Both forms of treatment require at least once daily dosing to effect complete recovery. Currently, the therapeutic options for severe infections caused by some of these pathogens are quite limited. The emerging resistance of Gram-positive pathogens to vancomycin makes the availability of new antibiotics with potential for increased effectiveness highly desirable.

In addition, less frequent dosing regimens than currently-available therapies would be desirable to enhance patient comfort, especially for parenteral, e.g., intravenous or intramuscular, antibiotic administration. Hospital stays are sometimes necessitated by the need for multi-daily antibiotic administration by parenteral means, and less frequent dosing would be advantageous to permit such treatment to be done on an outpatient basis.

Although less frequent dosing is a desirable feature of an antibiotic administration regimen, the "pharmaceutical window," i.e., the toxicity profile, of the administered antibiotic must be sufficiently acceptable to permit a large single dose to be administered without jeopardizing treatment by causing severe adverse reactions in the treated patient. Further, even when an antibiotic exhibits a suitable pharmaceutical window, less frequent dosing is possible only if the antibiotic exhibits a suitable serum half-life to maintain therapeutic effectiveness over the dosing interval desired. The serum half-life of an antibiotic dictates both the longevity of a drug in vivo and the length of time after administration when the serum level will reach a minimum trough level which is still bactericidally effective. The serum trough level over time after administration of a first dose of antibiotic dictates when a further dose must be administered to retain a minimum bactericidal level of the antibiotic in vivo.

Recently, successful glycopeptide antibiotics have been rationally synthesized from natural glycopeptides. For example, the semisynthetic glycopeptide dalbavancin was synthesized from the natural antibiotic A 40926, originally isolated from an *Actinomadura* culture (Malabarba et al., 1998, U.S. Pat. No. 5,750,509). Dalbavancin has shown greater efficacy against various bacterial strains than vancomycin or the antibiotic linezolid and represents a promising new treatment for skin and soft tissue infections (see, e.g., Jabés et al., 2004, *Antimicrob. Agents Chemother.* 48:1118-1123). According to U.S. Pat. No. 5,750,509, dalbavancin is a glycopeptide antibiotic with a monomethyl moiety at its $N^{15}$ amino (see FIG. 1 for numbering), and this $N^{15}$-monomethyl amino could be free (i.e. —NHCH$_3$) or protected with an amino protecting group such as t-butoxycarbonyl, carbobenzyloxy, arylalkyl or benzyl. The method for making certain of the dalbavancin components reported in the '509 patent also produced $N^{15}, N^{15}$-dialkyl analogs of dalbavancin in minor quantities, but these molecules were not characterized.

In view of the above pathogens, further antibiotics possessing activity against one or more microbes, including antibiotic resistant bacteria, would be of commercial value and would satisfy a long-felt need in the art.

SUMMARY OF THE INVENTION

The invention provides compositions, methods and kits for treatment or prevention of a bacterial infection with dalbavancin. Surprisingly, stabilized formulations of dalbavancin have been found to exhibit both a pharmaceutical window as well as a prolonged serum half-life to permit treatment regimens of about once every 5-7 days or longer, while retaining antibacterial properties in vivo.

Accordingly, in one aspect, a pharmaceutical composition is provided that includes a unit dose of dalbavancin in an amount sufficient to provide a therapeutically or prophylactically effective plasma level of dalbavancin in an individual for at least five days, a stabilizer, and a pharmaceutically acceptable carrier.

Pharmaceutical compositions of the invention are generally formulated in a pharmaceutically acceptable form for administration to an individual, such as a pharmaceutically acceptable aqueous formulation. Such pharmaceutical compositions are preferably administered by parenteral, e.g., intravenous or intramuscular, routes. Accordingly, in this preferred embodiment, these pharmaceutical compositions are typically sterile.

In some embodiments, a unit dose of dalbavancin is provided in dry powder (e.g., lyophilized) form and reconstituted in a pharmaceutically acceptable carrier, such as a sterile aqueous formulation, prior to administration to an individual. In one embodiment, the pharmaceutically acceptable carrier includes 5% dextrose in water. A pharmaceutical composition of the invention may be administered to a mammal in need of treatment or prevention of a bacterial infection, such as a human. In some embodiments, a pharmaceutical composition may include at least one antibiotic that is not dalbavancin, such as an antibiotic that is effective (e.g., bactericidal) against a Gram-negative bacterium and/or an antibiotic that is effective against Gram-positive species against which dalbavancin is not effective, such as VanA vancomycin-resistant bacterial strains.

The invention provides compositions, methods of making, and methods for treatment or prevention of a bacterial infection with a room-temperature stable dalbavancin pharmaceutical composition.

In some embodiments, one or more stabilizing substances are employed to inhibit degradation of one or more dalbavancin components during storage as a dry powder (e.g., lyophilized) formulation and/or as an aqueous formulation prior to administration to an individual. Over time, degradation can result in the undesirable formation of less active and/or inactive components which could potentially cause adverse effects in vivo. Preferred stabilizers include nonionic components such as sugars or sugar alcohols, e.g., a mono-, di-, or polysaccharide, or derivative thereof, such as, for example, mannitol, lactose, sucrose, sorbitol, glycerol, cellulose, trehalose, maltose, or dextrose, or mixtures thereof.

In one embodiment, the invention encompasses a pharmaceutical composition comprising stable dalbavancin.

In another embodiment, the invention encompasses a pharmaceutical composition comprising dalbavancin and a stabilizer.

In yet another embodiment, the invention encompasses a pharmaceutical composition comprising dalbavancin and a stabilizer at a pH of about 1-7, more preferably 2-6. In another embodiment, the composition is at a pH of about 3-5. The stabilizer may comprise a carbohydrate or an amino acid. The carbohydrate may be mannitol, lactose, or a combination of mannitol and lactose. The mannitol and lactose may be added in equal or unequal amounts. In one embodiment, equal amounts of mannitol and lactose are added and the pH is adjusted to about pH 4.5.

In another embodiment, the invention also encompasses a pharmaceutical composition comprising dalbavancin and mannitol at a pH of about 3. In one embodiment, the pH of the composition is about 3.3. In another embodiment, this composition may further comprise lactose. The lactose and mannitol may be added in equal or unequal amounts.

In another embodiment, the invention also encompasses a pharmaceutical composition comprising dalbavancin and a stabilizer, wherein the stabilizer comprises mannitol and lactose. The mannitol and lactose may be added in equal amounts. The pH of this composition may optionally range from 1-7, more preferably 2-6, more preferably 3-5, more preferably 4-5, more preferably approximately 4.5.

Glycopeptides, and dalbavancin in particular, are very unstable due to the glycosidic linkage. There may be some degradation at room temperature and more degradation at 40° C. Some of the formulations described above may need special storage conditions. In particular, refrigeration may be desirable (e.g., −40 to 10° C., alternatively −20 to 9° C., more preferably 2 to 8° C.). The formulations may additionally be sterilized. They will form a stable, clear, particle free solution when administered. The solution should be stable and not contain a precipitate.

The pharmaceutical compositions described above preferably degrade by no more than about 4% at about 25° C. after about 2 years, more preferably by no more than about 3%, more preferably by no more than about 2%, more preferably by no more than about 1%, more preferably by no more than about 0.5%. Alternatively, the pharmaceutical compositions described above have no more than about 4% MAG at about 25° C. after about 2 years, more preferably have no more than about 3% MAG, more preferably have no more than about 2% MAG, more preferably have no more than about 1% MAG, more preferably have no more than about 0.5% MAG.

In another embodiment, the pharmaceutical compositions described above preferably degrade by no more than about 6% at about 40° C. after about 3-6 months, more preferably by no more than about 5%, preferably by no more than about 4%, preferably by no more than about 3%, preferably by no more than about 2%, preferably by no more than about 1%. Alternatively, the pharmaceutical compositions described above preferably have no more than about 6% MAG at about 40° C. after about 3-6 months, more preferably have no more than about 5% MAG, preferably have no more than about 4% MAG, preferably have no more than about 3% MAG, preferably have no more than about 2% MAG, and even more preferably have no more than about 1% MAG. A stable compound at 40° C. would be desirable, especially in places that are not able to store the compounds in a refrigerator or at room temperature (e.g., third world countries and Indian reservations).

In yet another embodiment, the pharmaceutical compositions degrade by no more than 3% at about 2-8° C. after about 2 years, more preferably by no more than about 2%; more preferably by no more than about 1%; more preferably by no more than about 0.5%. Alternatively, the pharmaceutical compositions have no more than 3% MAG at about 2-8° C. after about 2 years, more preferably have no more than about 2% MAG; more preferably have no more than about 1% MAG; more preferably have no more than about 0.5% MAG.

The invention includes dalbavancin compositions that may comprise a combination of any of the dalbavancin factors. These factors include dalbavancin factor $A_0$, $A_1$, $B_1$, $B_2$, $C_0$, $C_1$, $isoB_0$, and MAG.

The invention also include a drying process for reducing the level of solvent in the dalbavancin composition. The method includes the steps of providing wet dalbavancin comprising dalbavancin, water, and a solvent, drying the wet dalbavancin at a temperature of about 30° C. or less and at a vacuum pressure of about 50 mbar or less, until the water level of the wet dalbavancin is less than about 20% (w/w). Water is then added to the wet dalbavancin and the drying step is repeated. These steps of adding water and drying the wet dalbavancin are repeated until the solvent level is less than about 3.0% (w/w). These steps can be repeated once, twice, three times, four times, five times, six times, or as many as necessary to reach the desired solvent content. Similarly, the invention also includes a dalbavancin composition that has a low level of solvent. In one embodiment, the level of solvent may be below 3.0% (w/w), alternatively below 2.5% (w/w), alternatively below 2.0% (w/w), alternatively below 1.5% (w/w), alternatively below 1.0% (w/w), alternatively below 0.5% (w/w), alternatively below 0.1% (w/w). The solvent may be acetone. Alternatively, the solvent may be any of ethanol, methanol, propanol, butanol, ether, methylene chloride, tetrahydrofuran, chloroform, 1,4-dioxane, trichloroethylene, benzene, carbon tetrachloride, 1,2-dichloroethane, 1,1-dichloroethane, 1,1,1-trichloroethane, acetonitrile, chlorobenzene, cyclohexane, dichloromethane, 1,2-dimethoxyethane, N,N-dimethylacetamide, N,N-dimethylformamide, 1,4-dioxane, 2-ethoxyethanol, ethyleneglycol, formamide, hexane, 2-methoxyethanol, methylbutyl ketone, methylcyclohexane, N-methylpyrrolidone, nitromethane, pyridine, sulfolane, tetralin, toluene, 1,1,2-trichloroethane, xylene, acetic acid, anisole, 1-butanol, 2-butanol, butyl acetate, tert-butylmethyl ether, cumene, dimethyl sulfoxide, ethyl acetate, ethyl ether, ethyl formate, formic acid, heptane, isobutyl acetate, isopropyl acetate, 3-methyl-1-butanol, methylethyl ketone, methylisobutyl ketone, 2-methyl-1-propanol, pentane, 1-pentanol, 1-propanol, 2-propanol, propyl acetate, 1-1, diethoxypropane, 1,1-dimethoxymethane, 2,2-dimethoxypropane, isooctane, isopropyl ether, methylisopropyl ketone, methyltetrahydrofuran, petroleum ether, trichloroacetic acid, and trifluoroacetic acid. Additionally, the drying process may be conducted at a temperature of about 28° C. or less, alternatively at a temperature of about 26° C. or less, alternatively at a temperature of about 24° C. or less, alternatively at a temperature of about 22° C. or less, alternatively at a temperature of about 20° C. or less, alternatively at a temperature of about 15° C. or less, alternatively at a temperature of about 10° C. or less. The vacuum pressure of the drying procedure may be about 50 mbar or less, alternatively about 45 mbar or less, alternatively about 40 mbar or less, alternatively about 35 mbar or less, alternatively about 30 mbar or less, alternatively about 25 mbar or less, alternatively about 20 mbar or less, alternatively about 15 mbar or less, alternatively about 10 mbar or less, alternatively about 5 mbar or less. Additionally, the water level may be less than about 25% (w/w), alternatively less than about 20% (w/w), alternatively less than about 15% (w/w).

In addition to the low solvent content, the drying process may also reduce the amount of MAG present in the dalbavancin composition. The amount of MAG present may be below about 5% HPLC distribution, alternatively below about 4.5% HPLC distribution, alternatively below about 4.0% HPLC distribution, alternatively below about 3.5% HPLC distribution, alternatively below about 3.0% HPLC distribution, alternatively below about 2.5% HPLC distribution, alternatively below about 2.0% HPLC distribution, alternatively below about 1.5% HPLC distribution, alternatively below about 1.0% HPLC distribution, alternatively below about 0.8% HPLC distribution, alternatively below about 0.6% HPLC distribution, alternatively below about 0.5% HPLC distribution, alternatively below about 0.4% HPLC distribution, alternatively below about 0.3% HPLC distribution, alternatively below about 0.2% HPLC distribution, alternatively below about 0.1% HPLC distribution.

The invention also includes a pharmaceutical composition comprising dalbavancin factors $B_2$ and iso$B_0$. The content of each of $B_2$ and iso$B_0$ can independently not exceed about 3.0 percent HPLC distribution, alternatively can independently not exceed about 2.5 percent HPLC distribution, alternatively can independently not exceed about 2.0 percent HPLC distribution, alternatively can independently not exceed about 1.5 percent HPLC distribution, alternatively can independently not exceed about 1.0 percent HPLC distribution, alternatively can independently not exceed about 0.5 percent HPLC distribution, or alternatively can independently not exceed about 0.1 percent HPLC distribution.

Additionally, the invention also includes a pharmaceutical composition comprising dalbavancin factors $B_2$, iso$B_0$, and MAG. The content of each of $B_2$, iso$B_0$, and MAG can independently not exceed about 3.0 percent HPLC distribution, alternatively can independently not exceed about 2.5 percent HPLC distribution, alternatively can independently not exceed about 2.0 percent HPLC distribution, alternatively can independently not exceed about 1.5 percent HPLC distribution, alternatively can independently not exceed about 1.0 percent HPLC distribution, alternatively can independently not exceed about 0.5 percent HPLC distribution, or alternatively can independently not exceed about 0.1 percent HPLC distribution.

The invention also includes methods for treating a bacterial infection comprising providing at least one of the pharmaceutical compositions described above to patient in need thereof and administering a therapeutically effective dose of sterile, stable, particle-free, clear dalbavancin to the patient. The method may further include administering a single subsequent therapeutically effective dose. The single subsequent therapeutically effective dose may be administered approximately five to ten days, or about a week, after the initial dose. The single subsequent therapeutically effective dose may also be administered approximately five to ten days, or about a week, after the initial dose, without any intervening dose of dalbavancin. In another embodiment, the method may include administering multiple subsequent doses. The multiple subsequent doses may be administered at approximately five to ten day intervals, or one week intervals. The multiple subsequent doses may also be administered at approximately five to ten day intervals, or one week intervals, without any intervening doses of dalbavancin. The method may also include the further step of monitoring the infection after administering the first dose and, optionally, adjusting the subsequent dose(s) accordingly.

The invention also includes methods for treating a bacterial infection in a patient with renal impairment comprising administering a therapeutically effective dose of sterile, stable, particle-free, clear dalbavancin to the patient. The impairment can range from mild to severe. In one embodiment, the therapeutically effective dose achieves a peak concentration in the patient ($C_{max}$) of at least 100 mg/L. In another embodiment, the therapeutically effective dose achieves a patient exposure (area under the curve) of at least 13,000 mg·h/L. The method may include administering a single dose of dalbavancin of about 300-1200 mg, alternatively about 400 mg, alternatively about 500 mg, alternatively about 600 mg, alternatively about 700 mg, alternatively about 800 mg, alternatively about 900 mg, alternatively about 1000 mg, alternatively about 1100 mg, alternatively about 1200 mg.

The method for treating a bacterial infection in a patient with renal impairment may also include administering multiple doses of dalbavancin. In one embodiment, two doses may be administered about five to about ten days apart, such as about one week apart, or alternatively about ten to about eighteen days apart, such as a bout two weeks (or 14 days apart). Alternatively, dose frequency may be, for example, twice weekly doses, thrice weekly doses, or multiple weekly doses. Alternatively, the dosing interval may be, for example, any of about 2, 3, 4, 5, 6, 7, 8, 9, 10, 11, 12, 13, 14, 15, 16, 17, 18, 19, 20, 21, 22, 23, 24, 25, or more days apart. The number of doses given, can be, for example, one, two, three, four, five, six, or more doses, each dose after the initial dose being given after the selected dosage interval.

In one embodiment, the first dose may be about 750 mg and the second (or subsequent) dose may be about 250 mg. In another embodiment, the first dose may be about 750 mg and the second (or subsequent) dose may be about 150 mg. In another embodiment, the first dose may be about 750 mg and the second (or subsequent) dose may be about 125 mg. In another embodiment, the first dose may be about 1000 mg and the second (or subsequent) dose may be about 500 mg.

In another embodiment, the first dose may be about 200 mg to about 1500 mg, alternatively about 200 mg to about 1300 mg, alternatively about 100 mg to about 1500 mg, alternatively about 200 mg to about 1400 mg, alternatively about 300 mg to about 1300 mg, alternatively about 400 mg to about 1200 mg, alternatively about 500 mg to about 1100 mg, alternatively about 600 mg to about 1000 mg, alternatively about 1000 mg, alternatively about 950 mg, alternatively about 900 mg, alternatively about 850 mg, alternatively about 800 mg, alternatively about 750 mg, alternatively about 700 mg, alternatively about 650 mg, alternatively about 600 mg, alternatively about 550 mg, or alternatively about 500 mg. The second or subsequent dose may be about 200 mg to about 1500 mg, alternatively about 200 mg to about 1300 mg, alternatively about 100 mg to about 1500 mg, alternatively about 200 mg to about 1400 mg, alternatively about 300 mg to about 1300 mg, alternatively about 400 mg to about 1200 mg, alternatively about 500 mg to about 1100 mg, or alternatively about 600 mg to about 1000 mg, alternatively about 600 mg, alternatively about 550 mg, alternatively about 500 mg, alternatively about 450 mg, alternatively about 400 mg, alternatively about 350 mg, alternatively about 300 mg, alternatively about 250 mg, alternatively about 200 mg, alternatively about 150 mg, or alternatively about 100 mg. It is to be understood that any of the above first doses may be combined with any of the above second or subsequent doses in a dosing regimen.

In a multiple dosing regimen for renal or normal patients, the ratio between the first and second (or subsequent) doses may be defined by a factor. The amount of the first dose may be greater than about 1 times the amount of the second dose. Alternatively, the first dose may be greater than about 1.5 times, greater than about 2 times, greater than about 2.5 times, greater than about 3 times, greater than about 3.5 times, greater than about 4 times, greater than about 4.5 times, greater than about 5 times, greater than about 5.5 times, or greater than about 6 times the amount of the second (or subsequent) doses.

Similarly, the amount of the second (or subsequent) dose may be about 6 times less than the amount of the first dose. Alternatively, the amount of the second (or subsequent) dose may be about 5.5 times, alternatively less than about 5.0 times, alternatively less than about 4.5 times, alternatively less than about 4.0 times, alternatively less than about 3.5 times, alternatively less than about 3.0 times, alternatively less than about 2.5 times, alternatively less than about 2.0 times, alternatively less than about 1.5 times, alternatively less than about 1.0 times the amount of the first dose.

The method for treating a bacterial infection in a patient with renal impairment may include administering a single dose of dalbavancin. The patient may have mild, moderate, severe, or end-stage renal impairment. The amount of this single dose may be about 1200 mg, alternatively about 1150 mg, alternatively about 1100 mg, alternatively about 1050 mg, alternatively about 1000 mg, alternatively about 950 mg, alternatively about 900 mg, alternatively about 850 mg, alternatively about 800 mg, alternatively about 750 mg, alternatively about 700 mg, alternatively about 650 mg, alternatively about 600 mg, alternatively about 550 mg, alternatively about 500 mg. The amount of the single dose may also be between about 250 mg to about 1300 mg, alternatively between about 300 mg to about 1200 mg, alternatively between about 350 mg to about 1100 mg, alternatively between about 400 mg to about 1000 mg, alternatively between about 450 mg to about 1000 mg, alternatively between about 500 mg to about 1000 mg, alternatively between about 550 mg to about 950 mg, alternatively between about 600 mg to about 900 mg, alternatively between about 650 mg to about 850 mg.

The invention also includes methods of making the pharmaceutical compositions described above comprising providing dalbavancin and adding a stabilizer. In one embodiment, the stabilizer is a carbohydrate or a sugar. In another embodiment, the stabilizer is mannitol, lactose, or a combination thereof.

In yet another embodiment, the method further includes the step of adjusting the pH of the composition, if necessary. In one embodiment, the pH is adjusted to about 1-7, more preferably about 2-6, more preferably about 3-5. The pH may be adjusted with a pH modifier. pH modifiers include inorganic bases of alkali and alkaline earth metals such as NaOH, $Ca(OH)_2$, KOH, and $Mg(OH)_2$. Inorganic oxides, carbonates, bicarbonates of alkali and alkaline earth metals may also be used as pH modifiers. Alkali and alkaline salts of inorganic weak acids and amphoteric acids such as phosphoric acid, boric acid, sulfuric acid, and all other sulfur-containing acids may also be used as pH modifiers. Amino acids such as lysine, meglumaine, arginine, n-methyl glucosamine, may also be used to modify the pH. Organic bases, including all amines, phenols, weak carboxylic acids, dicarboxylic acids, hydroxy carboxylic acids, and their salts, may also be utilized to modify the pH of the composition.

In another aspect, methods are provided for treating a bacterial infection in an individual in need thereof, including administering at least one unit dose of dalbavancin in an amount sufficient to provide a therapeutically effective plasma level of dalbavancin in the individual for at least five days, and a pharmaceutically acceptable carrier. A therapeutically effective plasma level of dalbavancin is generally at least about 4 mg of dalbavancin per liter of plasma. In one embodiment, the dosage amount of dalbavancin administered is an amount that is clinically effective and also has reduced adverse side effects in comparison to the standard of care with drugs such as teicoplanin and vancomycin.

Dalbavancin may be administered as a single dose or as multiple doses. In some embodiments, a single dose of about 100 mg to about 4000 mg, for example 3000 mg, of dalbavancin is administered. In various embodiments, a single dalbavancin dose may include at least about any of 0.1, 0.25, 0.5, 1, 1.5, 2, 2.5, or 3 grams.

In other embodiments, two doses are administered about five to about ten days apart, such as about one week apart. The first dose may be about 500 to about 5000 mg of dalbavancin and the second dose may be about 250 mg to about 2500 mg of dalbavancin. Often, the first dose includes about 1.5 to about 3 times, often at least about twice as much of the amount of dalbavancin contained in the second dose. For example, the first dose may be about 1000 mg and the second dose may be about 500 mg of dalbavancin. In another embodiment, the first dose may be about 1200 mg and the second dose may be about 600 mg. In methods in which two doses are administered, the plasma trough level of dalbavancin in an individual prior to administration of the second dose is generally at least about 4 mg, often at least about 10 mg, often at least about 20 mg, more often at least about 30 mg dalbavancin per liter of plasma, and still more often at least about 40 mg dalbavancin per liter of plasma.

In some embodiments, dalbavancin is administered in two therapeutically effective doses, administered about 5 to about 10 days apart. In one embodiment, dalbavancin is administered in two therapeutically effective doses administered one week apart. In another embodiment, dalbavancin is administered in at least two weekly doses.

In some embodiments, each dose is about 0.1 to about 5 g of dalbavancin. In other embodiments, the amount of the second dose is about half or less of the amount of the first dose. In one embodiment, the first dose is about 1 gram of dalbavancin and the second dose is about 0.5 gram of dalbavancin. In another embodiment, the first dose is about 0.5 gram of dalbavancin and the second dose is about 0.25 gram of dalbavancin. In a further embodiment, the first dose is about 5 grams of dalbavancin and the second dose is about 2.5 grams of dalbavancin.

Often, methods of the invention include parenteral administration, for example intravenous administration. In some embodiments, administration is intravenous with the rate of administration controlled such that administration occurs over at least about 30 minutes or longer.

Methods of the invention may be used to treat a Gram-positive bacterial infection, such as, for example, a *Staphylococcus aureus* or *Streptococcus pyogenes* skin and soft tissue infection. In some embodiments, the infection is penicillin-resistant and/or multi-drug resistant.

In another aspect, a method for preventing a bacterial infection is provided which includes administering at least one unit dose of dalbavancin in an amount sufficient to provide a prophylactically effective plasma level of dalbavancin in the individual for at least about one day, three days, five days, one week, or ten days or longer, and a pharmaceutically acceptable carrier. The dosage of dalbavancin may be, for example, about 100 mg to about 1000 mg. In some embodiments, dalbavancin is administered prior, during, or subsequent to a medical procedure or a stay in the hospital.

Therapeutic or prophylactic methods of the invention may include administration of at least one antibiotic that is not dalbavancin, preferably an antibiotic that is effective against a Gram-negative bacterium and/or an antibiotic that is effective against Gram-positive strains that dalbavancin is not effective against, such as VanA strains.

In another aspect, kits are provided that include at least one unit dose of dalbavancin in an amount sufficient to provide a therapeutically effective plasma level for at least about five days or a prophylactically effective plasma level of dalbavancin for at least about one day in an individual, and instructions for use in a method of treatment or prophylaxis of a bacterial infection. A kit may contain two unit dosages, with a first dosage including 1.5 to 3 times, often at least about twice as much of the amount of dalbavancin included in a second dosage. Kits may also include an antibiotic that is not dalbavancin, preferably effective against a Gram-negative bacterium.

In one embodiment, kits are provided that include a first container containing a dry powder (e.g., lyophilized) dalbavancin composition and a second container containing a predetermined amount of a physiologically acceptable aqueous solution for admixing with the dalbavancin composition. Such solutions are preferably sterile aqueous solutions. In one embodiment, kits include a delivery means for administering the dalbavancin composition to an individual, for example a syringe or intravenous administration means.

The present invention also provides $N^{15},N^{15}$-dialkyl antibiotic compounds with utility against infectious microbes. The compounds of the invention are useful for treating and/or preventing microbial infections, such as SSTIs and other bacterial infections.

The present invention is based, in part, on the discovery of $N^{15},N^{15}$-dialkyl antibiotic compounds having antimicrobial activity at least comparable to, or even greater than, previously known $N^{15}$-monoalkyl antibiotic compounds such as dalbavancin compounds. In addition, as described in the examples below, certain $N^{15},N^{15}$-dialkyl antibiotic compounds of the invention show activity against a broader spectrum of microbes when compared to the previously known $N^{15}$-monoalkyl antibiotic compounds such as $N^{15}$-monomethyl dalbavancin compounds.

In one aspect, the present invention provides $N^{15},N^{15}$-dialkyl antibiotic compounds according to formula (I):

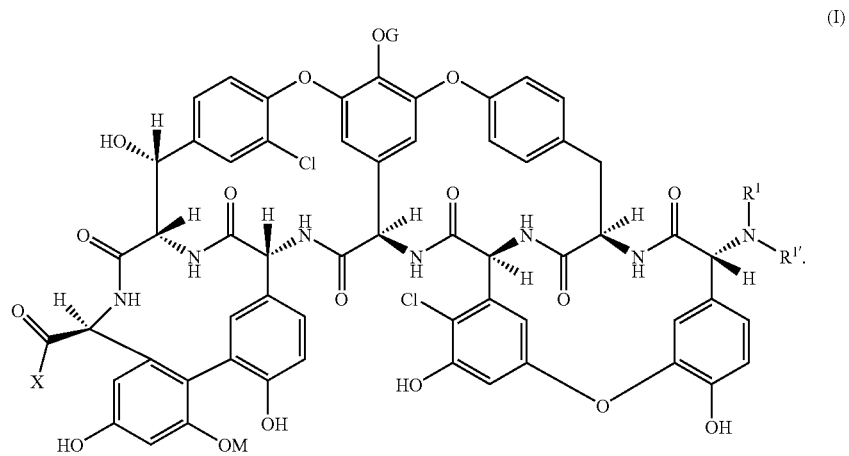

(I)

The $N^{15},N^{15}$-dialkyl antibiotic compounds of the invention (having atoms numbered according to FIG. 26) comprise two alkyl substituents on the amino terminal nitrogen. In other words, in formula (I) $R^1$ and $R^{1'}$ are alkyl. In most preferred embodiments of the invention, $R^1$ and $R^{1'}$ are methyl. The other substituents of formula (I) are described in detail below. Preferred substituents include those found on antibiotic A 40926 compounds and/or dalbavancin compounds known to those of skill in the art. For instance, in preferred embodiments G and M are glycosyl moieties such as the aminoglucuronyl and mannopyranosyl moieties described in the sections below. In certain embodiments, the aminoglucuronyl moiety is acylated, for example, with a fatty acid, and in certain embodiments, the mannopyranosyl moiety is acetylated.

In certain embodiments, X is OH while in further embodiments X is aminoalkylamino. The aminoalkylamino group can be any aminoalkylamino group known to those of skill in the art, including those described in U.S. Pat. No. 5,750,509. In preferred embodiments, X is N,N-dimethylaminopropylamino. As described in detail in the examples below, compounds according to formula (I) wherein X is aminoalkylamino show antibiotic activity comparable to or greater than corresponding dalbavancin compounds, such as those described in U.S. Pat. No. 5,750,509. Although compounds wherein X is aminoalkylamino are preferred, compounds wherein X is OH are useful, for example, for the preparation of compounds of the invention wherein X is aminoalkylamino, and they can also be useful themselves for treating and/or preventing microbial infections.

In another aspect, the present invention provides compositions comprising an $N^{15},N^{15}$-dialkyl antibiotic compound of the invention and a second compound. The second compound can be any compound known to those of skill in the art. In particular embodiments, the second compound is an antibiotic compound, for instance an antibiotic A 40926 compound or a dalbavancin compound. In further embodiments, the second compound is also an $N^{15},N^{15}$-dialkyl antibiotic compound of the invention. Exemplary compositions of the invention include mixtures of antibiotic A 40926 compounds and/or dalbavancin compounds that further comprise a compound according to formula (I). In particular embodiments, the compositions are enriched in the $N^{15},N^{15}$-dialkyl antibiotic compound of the invention. The enrichment can be relative to antibiotic A 40926 compounds and/or dalbavancin compounds of the composition, or relative to other compounds of the composition, or both. In certain embodiments, the present invention provides compositions comprising a purified $N^{15},N^{15}$-dialkyl antibiotic compound of the invention, an isolated $N^{15},N^{15}$-dialkyl antibiotic compound of the invention or a purified and isolated $N^{15},N^{15}$-dialkyl antibiotic compound of the invention.

In a further aspect, the present invention provides pharmaceutical compositions comprising a $N^{15},N^{15}$-dialkyl antibiotic compound of the invention. Preferred compositions comprise compounds according to formula (I) wherein X is aminoalkylamino The compositions can further comprise other active ingredients, including antibiotic A 40926 compounds and/or dalbavancin compounds known to those of skill in the art. In certain embodiments, the pharmaceutical compositions further comprise a pharmaceutically acceptable carrier, excipient or diluent. In particular embodiments, the present invention provides pharmaceutical unit dosages of a compound of the invention for use, for example, in the treatment and/or prevention of microbial infections.

In a further aspect, the present invention provides a dosage form comprising a sterile, stable, particle-free dalbavancin powder suitable for reconstitution with a pharmaceutically acceptable vehicle comprising dalbavancin factors $B_0$ and $B_2$. The names $B_2$, $C_2$, and $N^{15},N^{15}$-dimethyl dalbavancin $B_0$ have been used interchangeably. In one embodiment, the content of factor $B_0$ is not less than about 75 percent HPLC distribution, alternatively not less than about 80 percent HPLC distribution, alternatively not less than about 85 percent HPLC distribution, alternatively not less than about 90 percent HPLC distribution, alternatively not less than about 95 percent HPLC distribution. The content of $B_2$ is not less than about 4.0 percent HPLC distribution, alternatively not less than about 5.0 percent HPLC distribution, alternatively not less than about 6.0 percent HPLC distribution, alternatively not less than about 7.0 percent HPLC distribution, alternatively not less than about 8.0 percent HPLC distribution, alternatively not less than about 9.0 percent HPLC distribution, alternatively not less than about 10.0 percent HPLC distribution, alternatively not less than about 15.0 percent HPLC distribution, alternatively not less than about 20.0 percent HPLC distribution, alternatively not less than about 25.0 percent HPLC distribution, alternatively not less than about 30.0 percent HPLC distribution, alternatively not less than about 40.0 percent HPLC distribution. The percent HPLC distribution of particular components can be calculated by comparing the area of each single component to the total chromatography area. The dosage form may further include at least one additional factor, such as dalbavancin factor $A_0$, $A_1$, $B_1$, $C_0$, or $C_1$.

In a further aspect, the present invention provides for a pharmaceutical composition comprising dalbavancin factors $B_0$ and $B_2$. In one embodiment, the content of factor $B_0$ is not less than about 75 percent HPLC distribution. alternatively not less than about 80 percent HPLC distribution, alternatively not less than about 85 percent HPLC distribution, alternatively not less than about 90 percent HPLC distribution, alternatively not less than about 95 percent HPLC distribution. The content of $B_2$ is not less than about 3.0 percent HPLC distribution, alternatively not less than about 4.0 percent HPLC distribution, alternatively not less than about 5.0 percent HPLC distribution, alternatively not less than about 6.0 percent HPLC distribution, alternatively not less than about 7.0 percent HPLC distribution, alternatively not less than about 8.0 percent HPLC distribution, alternatively not less than about 9.0 percent HPLC distribution, alternatively not less than about 10.0 percent HPLC distribution, alternatively not less than about 15.0 percent HPLC distribution, alternatively not less than about 20.0 percent HPLC distribution, alternatively not less than about 25.0 percent HPLC distribution, alternatively not less than about 30.0 percent HPLC distribution, alternatively not less than about 40.0 percent HPLC distribution. As defined above, the percent HPLC distribution of particular components can be calculated by comparing the area of each single component to the total chromatography area. The pharmaceutical composition may further include at least one additional factor, such as dalbavancin factor $A_0$, $A_1$, $B_1$, $C_0$, or $C_1$.

In another aspect, the present invention also provides for the de-enrichment of the $B_2$ component. In one embodiment, the content of factor $B_2$ is not more than about 5.0 percent HPLC distribution, alternatively not more than about 4.5 percent HPLC distribution, alternatively not more than about 4.0 percent HPLC distribution, alternatively not more than about 3.5 percent HPLC distribution, alternatively not more than about 3.0 percent HPLC distribution, alternatively not more than about 2.5 percent HPLC distribution, alternatively not more than about 2.0 percent HPLC distribution, alternatively not more than about 1.5 percent HPLC distribution, alternatively not more than about 1.0 percent HPLC distribution, alternatively not more than about 0.5 percent HPLC distribution, alternatively not more than about 0.1 percent HPLC distribution.

In another aspect, the present invention provides methods of treating and/or preventing microbial infections in a subject in need thereof. The methods can comprise the administration of an effective amount of a $N^{15},N^{15}$-dialkyl antibiotic compound or composition of the invention to the subject. The invention encompasses the prevention or treatment of gram-positive or antibiotic-resistant bacterial infections, such as a *Bacillus, Corynebacteria, Listeria, Enterococcus, Staphylococcus, Streptococcus, Neisseria*, or *Clostridium* genus infection, in particular *Staphylococcus aureus, Staphylococcus epidermidis, Staphylococcus hemolyticus, Streptococcus pyogenes, Streptococcus pneumoniae*, Groups A and C *Streptococcus, Enterococcus faecalis, Bacillus subtilis, Neisseria gonorrhoeae*, or *Clostridium difficile*. Other infections that can be prevented or treated using the $N^{15},N^{15}$-dialkyl antibiotic compounds, compositions, and methods of the invention include gram negative bacterial infections, such as a *Bartonella, Brucella, Campylobacter, Enterobacter, Escherichia* (as well as other *Proteobacteria*), *Francisella, Helicobacter, Hemophilus, Klebsiella, Legionella, Leptospira, Morganella, Moraxella, Proteus, Providencia, Pseudomonas, Salmonella, Serratia, Shigella, Stenotrophomonas, Vibrio*, and *Yersinia* genus infection, in particular *Escherichia coli, Proteus vulgaris, Pseudomonas aeruginosas*, and yeast, such as *Candida albicans*, infections.

BRIEF DESCRIPTION OF THE DRAWINGS

FIG. 17A depicts dalbavancin in monomer-dimer equilibrium in solution, binding as monomer to two separate sites on HSA. FIG. 17B depicts ligand binding to dalbavancin dimer in solution and more weakly to dalbavancin monomers attached to HAS FIG. 18 provides mean dalbavancin plasma concentration-time profiles.

DETAILED DESCRIPTION OF THE INVENTION

Definitions

Figure 1A:
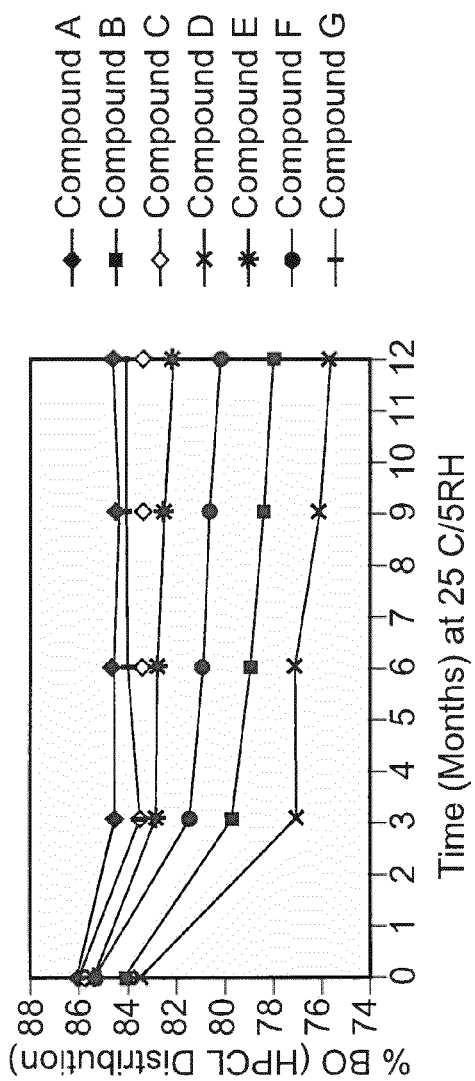
FIG. 1A depicts the amount of dalbavancin component $B_0$ versus time in various pharmaceutical compositions, with and without mannitol, at 25° C.

When describing compounds of the invention, pharmaceutical compositions containing such compounds and methods of using such compounds and compositions, the following terms have the following meanings unless otherwise indicated.

"Antibiotic A 40926 compound" refers to a glycopeptide antibiotic known to those of skill in the art. Exemplary antibiotic A 40926 compounds are described in U.S. Pat. Nos. 4,935,238, 4,868,171 and 4,782,042, the contents of which are hereby incorporated by reference in their entireties.

"Dalbavancin compound" refers to a glycopeptide antibiotic described in U.S. Pat. No. 5,750,509 and U.S. Patent Application Publication No. 2004/0142883, the contents of which are hereby incorporated by reference in their entireties. The systematic name of an exemplary dalbavancin compound known to those of skill in the art is ristomycin A aglycone, 5,31-dichloro-38-de(methoxycarbonyl)-7-demethyl-19-deoxy-56-O-(2-deoxy-2-((10-methyl-1-oxoundecyl)amino)-beta-D-glucopyranuronosyl)-38-(((3-(dimethylamino)propyl)amino)-carbonyl)-42-O-alpha-D-mannopyranosyl-$N^{15}$-methyl-. Examples include those depicted in FIGS. 26 and 27. Dalbavancin compounds include those compounds with optional sugar moieties at the 56 and 42 positions and optional acyl groups, such as fatty acids, on the sugars. Dalbavancin compounds can be derived from the natural antibiotic A-40926 known to those of skill in the art. Exemplary dalbavancin compounds include those described U.S. Patent Application Publication No. 2004/0142883 such as dalbavancin $A_0$, $A_1$, $B_0$, $B_1$, $C_0$ and $C_1$.

"$N^{15}$,$N^{15}$-dialkyl antibiotic compound," described in detail in the sections below, refers to a compound of the invention, i.e. an antibiotic compound having two alkyl groups on its $N^{15}$ nitrogen. A $N^{15}$,$N^{15}$-dialkyl antibiotic compound of the invention can be derived from an antibiotic A 40926 compound or from a dalbavancin compound such as dalbavancin $A_0$, $A_1$, $B_0$, $B_1$, $C_0$ and $C_1$.

"$N^{15}$,$N^{15}$-dimethyl antibiotic compound," described in detail in the sections below, refers to a compound of the invention, i.e. an antibiotic compound, having two methyl groups on its $N^{15}$ nitrogen.

"Acyl" refers to a radical —C(O)R, where R is alkyl.

"Alkyl" refers to monovalent saturated aliphatic hydrocarbyl groups preferably having from 1 to about 11 carbon atoms, more preferably from 1 to 8 carbon atoms, and still more preferably from 1 to 6 carbon atoms. The hydrocarbon chain may be either linear or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having from 1 to 6 carbon atoms.

"Alkylene" refers to divalent saturated aliphatic hydrocarbyl groups preferably having from 1 to 11 carbon atoms and more preferably 1 to 6 carbon atoms which can be linear or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Amino" refers to the radical —NH$_2$.

"Alkylamino" refers to the radical —NH-alkyl or —N(alkyl)$_2$.

"Aminoalkylamino" refers to a radical of the form —NR-(alkyl)-NR'R" wherein each R, R' and R" independently represent hydrogen, alkyl, substituted alkyl, aryl, substituted aryl, cycloalkyl, substituted cycloalkyl, cycloheteroalkyl, substituted cycloheteroalkyl, heteroaryl or substituted heteroaryl group. Preferred R, R' and R" groups include hydrogen and alkyl. Exemplary aminoalkylamino groups are described in U.S. Pat. No. 5,750,509, the contents of which are hereby incorporated by reference in their entirety.

"Carboxy" refers to the radical —C(O)OH.

"Dialkylamino" means a radical —NRR' where R and R' each independently represent an alkyl, substituted alkyl, aryl, substituted aryl, cycloalkyl, substituted cycloalkyl, cycloheteroalkyl, substituted cycloheteroalkyl, heteroaryl or substituted heteroaryl group as defined herein.

"Halo" or "halogen" refers to fluoro, chloro, bromo and iodo. Preferred halo groups are either fluoro or chloro.

"Percent HPLC distribution" of a particular component is calculated by comparing the area of the peak corresponding to the particular component to the total chromatographic area.

"Pharmaceutically acceptable" means approved (by a regulatory agency for investigational or commercial use) of the federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts formed with organic or inorganic acids such as hydrochloric, hydrobromic, sulfuric, nitric, phosphoric, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, and barium hydroxide, ammonia or (b) coordinates with an organic base, such as aliphatic, alicyclic, or aromatic organic amines, such as methylamine, dimethylamine, diethylamine, picoline, ethanolamine, diethanolamine, triethanolamine, N-methylglucamine and the like (see, e.g., U.S. Pat. No. 5,606,036).

Salts further include, by way of example only, sodium, potassium, calcium, magnesium, ammonium, tetraalkylammonium and the like, and when the compound contains a basic functionality, salts of non-toxic organic or inorganic acids, such as hydrochloride, hydrobromide, tartrate, mesylate, acetate, maleate, oxalate and the like. The term "pharmaceutically acceptable cation" refers to a non-toxic, pharmaceutically acceptable cationic counterion of an acidic functional group. Such cations are exemplified by sodium, potassium, calcium, magnesium, ammonium and tetraalkylammonium cations and the like.

"Pharmaceutically acceptable vehicle" refers to a diluent, adjuvant, excipient or carrier with which a compound of the invention is administered.

"Solvate" refers to a compound of the present invention or a salt thereof, that further includes a stoichiometric or non-stoichiometric amount of solvent bound by non-covalent intermolecular forces. Where the solvent is water, the solvate is a hydrate.

"Preventing" or "prevention" refers to a reduction in the risk of acquiring a disease or disorder (i.e., causing at least one of the clinical symptoms of the disease not to develop in a subject that may be exposed to or predisposed to the disease but does not yet experience or display symptoms of the disease). Preferably, prevention refers to the use of a compound or composition in a subject not yet affected by the disease or disorder or not yet exhibiting a symptom of the disease or disorder, for instance a subject not yet infected or not yet exhibiting the symptoms of infection.

"Subject" includes humans. The terms "human," "patient" and "subject" are used interchangeably herein.

"Therapeutically effective amount" means an amount of a compound or composition that, when administered to a subject for treating a disease, is sufficient to effect such treatment for the disease. A "therapeutically effective amount" can vary depending on, inter alia, the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof) that exists in a subject. In another embodiment, "treating" or "treatment" refers to ameliorating at least one physical parameter, which may be indiscernible by the subject. In yet another embodiment, "treating" or "treatment" refers to modulating the disease or disorder, either physically (e.g., stabilization of a discernible symptom) or physiologically (e.g., stabilization of a physical parameter) or both. In yet another embodiment, "treating" or "treatment" refers to delaying the onset of the disease or disorder.

It is to be understood that compounds having the same molecular formula but differing in the nature or sequence of bonding of their atoms or in the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, when it is bonded to four different groups, a pair of enantiomers is possible. An enantiomer can be characterized by the absolute configuration of its asymmetric center and is designated (R) or (S) according to the rules of Cahn and Prelog, or can be characterized by the manner in which the molecule rotates the plane of polarized light and is designated dextrorotatory or levorotatory (i.e., as (+)- or (−)-isomers, respectively). A chiral compound can exist as either individual enantiomer or as a mixture thereof. A mixture containing equal proportions of enantiomers is called a "racemic mixture".

In certain embodiments, the compounds of this invention may possess one or more asymmetric centers; such compounds can therefore be produced as the individual (R)- or (S)-enantiomer or as a mixture thereof. Unless indicated otherwise, for example by designation of stereochemistry at any position of a formula, the description or naming of a particular compound in the specification and claims is intended to include both individual enantiomers and mixtures, racemic or otherwise, thereof. Methods for determination of stereochemistry and separation of stereoisomers are well-known in the art. In particular embodiments, the present invention provides the stereoisomers of the compounds depicted herein upon treatment with base.

The present invention provides novel pharmaceutical compositions of dalbavancin, methods of making the pharmaceutical compositions, and methods of treatment of bacterial infections using these novel compositions. In particular, the invention provides stable dalbavancin compositions having bactericidal activity, which may be refrigerated or stored at room temperature for a prolonged period of time, more preferably at least one year at room temperature, more preferably at least two years at room temperature, without significant degradation of the active dalbavancin component.

The present invention also provides improved dosage regimes and novel compositions of dalbavancin, and improved methods of treatment of antibiotic-resistant bacterial infections. In particular, the invention provides dalbavancin compositions having activity against one or more antibiotic resistant strains of bacteria, such as MRSA, which may be administered in a dosing regimen of once every 5-7 days or longer.

Dalbavancin, which is also referred to in the scientific literature as BI 397 or VER001, is a semi-synthetic glycopeptide mixture, the properties of which have been reported in U.S. Pat. Nos. 5,606,036, 5,750,509, 5,843,679, and 5,935,238.

As used herein, the term "dalbavancin" refers to compositions comprising one or more, preferably two or more, in some cases three or more, in some cases four or more, in some cases five or more closely related homologs, termed "$A_0$," "$A_1$," "$B_0$," "$B_1$," "$C_0$," "$C_1$," "$B_2$" or "$C_2$," "$D_0$" and "$D_1$," as described below, or monomers, multimers (i.e., dimer or higher order multimer), tautomers, esters, solvates, or pharmaceutically acceptable salts thereof. As used herein, 1"dimer" or "multimer" refers to either a homodimer or homomultimer, i.e., a dimer or multimer composed of monomers of the same dalbavancin homolog, or a heterodimer or heteromultimer, i.e., a dimer or multimer composed of monomers of at least two different dalbavancin homologs. The factors differ in the structures of the fatty acid side chains of the N-acylaminoglucuronic acid moiety, with the exception of $C_2$ (a.k.a. $B_2$). Mass spectrometry of the $C_2$ component has indicated the presence of an additional methylene group on the terminal amino group. Dalbavancin often includes "MAG," a non-homolog variant described below that lacks the acylglucuronamine moiety. Individually, dalbavancin homologs and MAG are sometimes referred to herein as "dalbavancin components."

Dalbavancin is prepared by chemical modification of the natural glycopeptide complex A-40,926 as described in Malabarba and Donadio (1999) *Drugs of the Future* 24(8):839-846. The predominant component of dalbavancin is Factor $B_0$, which accounts for >75% of the whole complex.

The amount of each of the components present in a dalbavancin composition is dictated by a variety of factors, including, for example, the fermentation conditions employed in the preparation of the natural glycopeptide complex A-40926, which is the precursor to dalbavancin (see, e.g., U.S. Pat. No. 5,843,679), the conditions employed to recover A-40926 from the fermentation broth, the chemical reactions employed to selectively esterify the carboxyl group of the sugar moiety of A-40926, the conditions employed to amidate the peptidyl carboxyl group, the conditions employed to saponify the ester of the carboxyl group of the N-acylaminoglucuronic acid function, the conditions employed to recover dalbavancin from the synthetic mixture, and the like.

In preferred embodiments, dalbavancin compositions comprise at least about 80 to about 98% by weight of the $B_0$ component. In particularly preferred embodiments, dalbavancin comprises the following amounts of $B_0$:

TABLE 1

Preferred Amounts of $B_0$ Component in Dalbavancin Composition

| Preferred[1] | More Preferred[1] | Even More Preferred[1] |
|---|---|---|
| 80-98 | 80-97 | 80-96 |
| 81-98 | 81-97 | 81-96 |
| 82-98 | 82-97 | 82-96 |
| 83-98 | 83-97 | 83-96 |
| 84-98 | 84-97 | 84-96 |
| 85-98 | 85-97 | 85-96 |
| 86-98 | 86-97 | 86-96 |
| 87-98 | 87-97 | 87-96 |
| 88-98 | 88-97 | 88-96 |
| 89-98 | 89-97 | 89-96 |
| 90-98 | 90-97 | 90-96 |

[1]each range represents the mole % of $B_o$ relative to the total dalbavancin_components present in the dalbavancin composition including MAG In one embodiment, the dalbavancin composition or formulation contains a minimal amount, if any, of Components $C_0$, $C_1$, and $C_2$ ($B_2$). In another embodiment, the dalbavancin composition or formulation does not contain any of Components $C_0$, $C_1$, and $C_2$ ($B_2$).

Individual dalbavancin factors have previously been purified by HPLC and characterized by NMR. In U.S. Pat. No. 5,750,509, Malabarba et al. described the antibiotic A 40926 derivative, which was characterized as having a carboxy, ($C_1$-$C_4$) alkoxy-carbonyl, aminocarbonyl, ($C_1$-$C_4$) alkylaminocarbonyl or hydroxymethyl substituent on the N-acylaminoglucuronyl moiety and a hydroxyl or a polyamine substituent in position 63 of the molecule. The compounds of the invention were found to have high in vitro activity against glycopeptide resistant Enterococci and Staphylococci. Malabarba et al., however, neither recognized combinations of factors that were pharmaceutically beneficial nor identified or characterized the degradation product that lacks the acylglucuronamine moiety. Malabarba et al. never monitored for MAG or produced a sterile form. Malabarba et al. only purified a small amount by HPLC and did not do quantitative mass analysis.

The chemical structure of several of the dalbavancin components is depicted in Formula II below:

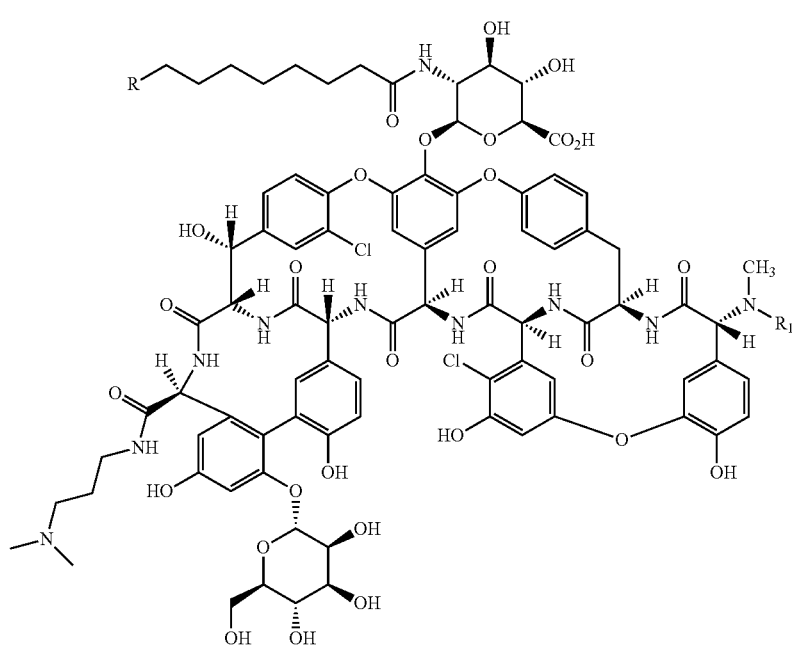

II

| Dalbavancin Component | R | $R_1$ | Molecular Weight |
|---|---|---|---|
| $A_0$ | —CH(CH$_3$)$_2$ | H | 1802.7 |
| $A_1$ | —CH$_2$CH$_2$CH$_3$ | H | 1802.7 |
| $B_0$ | —CH$_2$CH(CH$_3$)$_2$ | H | 1816.7 |
| $B_1$ | —CH$_2$CH$_2$CH$_2$CH$_3$ | H | 1816.7 |
| $B_2$ or $C_2$ | —CH$_2$CH(CH$_3$)$_2$ | CH$_3$ | 1830.74 |
| $C_0$ | —CH$_2$CH$_2$CH(CH$_3$)$_2$ | H | 1830.7 |
| $C_1$ | —CH$_2$CH$_2$CH$_2$CH$_2$CH$_3$ | H | 1830.7 |
| $D_0$ | —(CH$_3$)$_2$ | H | 1788.66 |
| $D_1$ | —CH$_2$CH$_3$ | H | 1788.66 |
| MAG | — | H | 1459.27 |

All of the above dalbavancin components are bactericidally active against a number of Gram-positive bacteria. However, one non-homologous dalbavancin component, termed "MAG," which lacks an acylglucoronamine moiety present in other components, is less bactericidally effective, both in vivo and in vitro, than other dalbavancin components. (See Tables 2 and 3). MAG is thought to be a decomposition product of one or more of the other dalbavancin components. Accordingly, in a preferred embodiment, the amount of MAG in dalbavancin is less than about 4, 3.5, 3, 2.5, 2, 1.5, 1, or 0.5 mole percent of all dalbavancin components present, including MAG.

TABLE 2

$ED_{50}$s of MAG in comparison with dalbavancin and vancomycin against *Staph. aureus* murine septicaemias

| Microorganism | Compound | MIC (µg/mL) | $ED_{50}$ (mg/kg) |
|---|---|---|---|
| MSSA *Staph. aureus* Smith 819 | MAG | 0.5 | 0.3 |
|  | Dalbavancin | 0.06 | 0.05 |
|  | Vancomycin | 0.5 | 1.7 |
| MRSA *Staph. aureus* 3817 | MAG | 0.5 | 1.6 |
|  | Dalbavancin | ≦0.03 | 0.7 |
|  | Vancomycin | 0.5 | 1.0 |

** Treatment: once within 10 min from infection by sc route

TABLE 3

Microbiological Activity

| | MIC µg/ml | |
|---|---|---|
| Microorganism | MAG | Dalbavancin |
| L 819 *S aureus* Smith | 0.5-0.5-0.25 | <0.13-0.06-<0.03 |
| L 819 *S aureus* Smith 50% serum | 1-1-1 | 1-2-2 |
| L 613 *S aureus* clin. isolate | 1-0.5-0.5 | 0.5-0.06-<0.03 |
| 3797 *S aureus* clin. Isolate GISA | 0.5-0.5 | 2-2 |
| 3817 *S aureus* clin. Isolate | 0.5 | <0.03 |
| L 147 *S epidermidis* | 0.25-0.13-0.13 | <0.13-<0.03-<0.03 |
| L 49 *S pyogenes* C203 | 0.5-0.5-0.25 | <0.13-<0.03-<0.03 |
| L 44 *S pneumoniae* UC41 | 1-0.5-0.5 | 0.25-0.03-<0.03 |
| L 602 *S haemolyticus* clin. isolate | >32-32 | >32->32 |
| L 149 *E faecalis* | 0.25-0.5-0.5 | 0.06-0.06 |
| L 562 *E faecalis* clin. isolate | 32->32->32 | >32->32->32 |
| L 1666 *E. faecium* Van-A | >32->32->32 | >32->32->32 |
| L 102 *B subtilis* ATCC | 0.13-0.13 | <0.03-<0.03 |
| L 47 *E coli* SKF12140 | >32->32->32 | >32->32->32 |
| G 16440 *E coli* iperperm | 8-8-16 | 16-8-16 |
| L 79 *P vulgaris* | >32->32->32 | >32->32->32 |
| L 4 *P aeruginosas* ATCC10145 | >32->32->32 | >32->32->32 |
| L 145 *C albicans* SKF2270 | >32->32->32 | >32->32->32 |

Additional modifications in the final drug substance originate from the fermentation process, the subsequent chemical steps, or drying. IsoB$_0$ (RRT 0.76) is a diastereomer of dalbavancin B$_0$ resulting from epimerization of a labile proton in the dalbavancin core structure. It originates during the deacetylation of the precursor A-40926 with base, forming the diastereomer of A-40,926. This diastereomer is subsequently converted to IsoB$_0$ in the chemical modification steps that follow. IsoB$_0$ is well resolved in the HPLC release method and is the only stereoisomer detected in the API. Laboratory data has demonstrated that IsoB$_0$ is not formed during the basic hydrolysis procedure that converts the ester form (MA-A-1) to dalbavancin. IsoB$_0$ has been characterized by NMR and MS and has demonstrated in vivo biological activity that is comparable to that of dalbavancin B$_0$.

The level of IsoB$_0$ in a dalbavancin composition is less that about 3.5%, alternatively less than about 3.0%, alternatively less than about 2.5%, alternatively less than about 2.0%, alternatively less than about 1.5%, alternatively less than about 1.0%, alternatively less than about 0.5%, alternatively less than about 0.4%, alternatively less than about 0.3%, alternatively less than about 0.2%, or alternatively less than about 0.1%.

The level of IsoB$_0$ in a dalbavancin composition may alternatively be between about 0.5% of about 3.0%, alternatively between about 0.5% to about 2.8%, alternatively between about 0.5% to about 2.5%, alternatively between about 0.5% to about 2.3%, alternatively between about 0.5% to about 2.0%, alternatively between about 0.5% to about 1.8%, alternatively between about 0.5% to about 1.5%, alternatively between about 0.5% to about 1.3%, or alternatively between about 0.5% to about 1.0%, or alternatively between about 0.1% to about 0.5%.

The level of IsoB$_0$ in a dalbavancin composition is alternatively not less than about 1.0%, alternatively not less than about 1.5%, alternatively not less than about 2.0%, alternatively not less than about 2.5%, alternatively not less than about 3.0%, alternatively not less than about 3.5%, alternatively not less than about 4.0%, alternatively not less than about 4.5%, or alternatively not less than about 5.0%.

Dalbavancin is thought to inhibit the biosynthesis of the bacterial cell wall by binding to D-alanyl-D-alanine-terminating precursors of peptidoglycans. Dimeric or higher order multimers of dalbavancin may possess further antibacterial properties by interaction of the lipophilic side chains with the cytoplasmic membrane of bacteria. See, for example, Malabarba and Ciabatti, et al. (2001) *Current Medicinal Chemistry* 8:1759-1773. A further elaboration on dalbavancin multimers may be found in U.S. Ser. No. 10/714,166, entitled "DALBAVANCIN COMPOSITIONS FOR TREATMENT OF BACTERIAL INFECTIONS," filed on Nov. 14, 2003, the disclosure of which is hereby incorporated by reference in its entirety.

In vitro, nonclinical, and clinical data indicate dalbavancin to be of benefit for the treatment of serious Gram-positive infections caused by MRSA and CoNS, and all streptococcal and non-VanA enterococcal species, including VanB and VanC phenotypes poorly susceptible or resistant to vancomycin.

Dalbavancin is more active in vitro against staphylococci (including some teicoplanin-resistant strains) than teicoplanin and vancomycin. Dalbavancin has better activity against streptococci, including penicillin-resistant strains, than teicoplanin or vancomycin. Dalbavancin is active in vitro and in vivo against a number of Gram-positive bacteria, including most drug resistant strains.

Dalbavancin is typically administered to an individual as a dalbavancin composition. As used herein, the term "dalbavancin composition" or "dalbavancin formulation" refers to a composition, typically a pharmaceutical composition comprising dalbavancin, as defined above, and one or more other non-dalbavancin components such as, for example, a pharmaceutically acceptable carrier, a stabilizer, a buffers, or other similar components.

As shown in Example 1, dalbavancin is effective at dose intervals of one week. Thus, an advantage of dalbavancin versus other treatment options is the ability to administer this antibiotic on a once-weekly basis, thereby maximizing patient compliance and potentially minimizing the need for or decreasing the length of a hospital stay for parenteral antibiotic administration. Less frequent dosing often permits treatment on an out-patient basis, thus decreasing treatment costs. As further shown in Example 1, a second dose of dalbavancin approximately one week after administration of the first dosage, where the second dose is approximately one-half the first dose, unexpectedly provides significant improvement in the efficacy of treatment.

Methods of Use

Previously, various dosing regimens, including single dose and multiple dose regimens, for dalbavancin have been reported. Leighton et al. reported a multi-dose administration with an optimal dose ratio (loading dose (LD)/maintenance dose (MD)) of 10:1. In this study, dose escalation proceeded to 1120 mg single dose (SD) and a multiple dose regimen up to 500 mg BID Day 1 followed by 100 mg daily for 6 successive days. Leighton et al. "Dalbavancin: Phase I Single and Multiple-Dose Placebo Controlled Intravenous Safety, Pharmacokinetic Study in Healthy Volunteers," $41^{st}$ ICAAC Abstracts, Chicago, Ill., Sep. 22-25 2001, Abstract No. 951, p. 25, Leighton et al. also described other single and multiple dose administrations. In the single dose studies, reported dose escalation proceeded via a series of 140 mg, 220 mg, 350 mg, 500 mg, 630 mg, 840 mg, and 1120 mg. In the multiple dose phase, the dosing consisted of a loading dose, administered as two equal doses given 12 hours apart, followed by maintenance doses. The starting regimen was a loading dose of 150 mg BID followed by a maintenance dose of 30 mg per day for 6 days. Dose escalation proceeded as follows: 200 mg BID/40 mg, 300 mg BID/60 mg; 400 mg BID/80 mg, and 500 mg BID/100 mg. Leighton et al. "Dalbavancin: Phase I Single and Multiple-dose Placebo Controlled Intravenous Safe Pharmacokinetic Study in Healthy Volunteers." $41^{st}$ ICAAC, Chicago, Ill., December 2001, Poster No. 951.

White et al. reported dosing regimens of single 0.5 hour intravenous infusion of 70 mg, 140 mg, 220 mg, or 360 mg. The multi-dose regimen consisted of 70 mg administered daily for 7 days. White et al. "V-Glycopeptide: Phase 1 Single and Multiple-Dose Placebo Controlled Intravenous Safety, Pharmacokinetic, and Pharmacodynamic Study in Healthy Subjects." $40^{th}$ ICAAC, Toronto, Canada, Sep. 17-20, 2000, Poster No. 2196 and Abstract No. 2196. All of the above-mentioned references are hereby expressly incorporated by reference in their entirety.

Novel methods are provided for administration of dalbavancin to an individual in need of treatment for a bacterial infection. Treatment can include prophylaxis, therapy, or cure. Methods include administration of one or more unit doses of dalbavancin in a therapeutically or prophylactically effective amount.

As used herein, "therapeutically effective amount" refers to the amount of dalbavancin that will render a desired therapeutic outcome (e.g., reduction or elimination of a bacterial infection). A therapeutically effective amount may be administered in one or more doses. A "prophylactically effective amount" refers to an amount of dalbavancin sufficient to prevent or reduce severity of a future bacterial infection when administered to an individual who is susceptible to and/or who may contract a bacterial infection, e.g., by virtue of a medical procedure or stay in the hospital, or exposure to an individual with a bacterial infection. Dalbavancin is generally administered in a pharmaceutically acceptable carrier.

Dalbavancin is often provided as a hydrochloride salt, which is freely soluble in water.

Typically, dalbavancin is administered as a "unit dose" in a dalbavancin formulation which includes an amount of dalbavancin sufficient to provide a therapeutically or prophylactically effective plasma level of dalbavancin for several days, often at least about 5 days, one week, or 10 days, when administered to an individual.

As used herein, "individual" refers to a vertebrate, typically a mammal, often a human.

All homologs of dalbavancin described above exhibit a prolonged half-life in plasma, often 9 days or more, although MAG is thought to have a shorter half-life than other homologs. The long half-life permits longer intervals between dosages than vancomycin or teicoplanin. As described in Example 1, weekly dosing of dalbavancin is effective for control of bacterial infections, in contrast to the twice daily dosing schedule which is often used for vancomycin or the once daily schedule generally used for teicoplanin. Less frequent dosing of dalbavancin offers significant treatment advantages over vancomycin and teicoplanin, particularly with regard to improved convenience and patient compliance with the treatment regimen. Surprisingly high doses (i.e., resulting in surprising high and long-lasting serum levels) can be administered, and with less frequency than other available treatment options. The novel dosage regimen available for dalbavancin results in improved efficacy because at concentrations required to effect less frequent dosing, dalbavancin exhibits minimal adverse effects in vivo, evidencing a large pharmaceutical window, and further because blood levels of dalbavancin are maintained above minimum bactericidal levels for the entire treatment protocol, evidencing a prolonged serum half-life for dalbavancin. The combination of the large pharmaceutical window coupled with prolonged serum half-life permits less frequent dosing of dalbavancin.

In addition, dalbavancin is preferably formulated with a stabilizer which inhibits degradation of one or more of the components of dalbavancin. In one preferred embodiment, dalbavancin is formulated with a 1:2 weight ratio of mannitol:dalbavancin. In another preferred embodiment, dalbavancin is formulated with a 1:1:4 weight ratio of mannitol:lactose:dalbavancin.

In some embodiments, a dalbavancin formulation is administered at a dosage that results in therapeutically effective (i.e., bactericidal) plasma levels of the drug for several days, often at least about 5 to about 10 days, often at least about one week. Generally, dalbavancin is maintained in plasma at or above the minimum bactericidal concentration of about 4 mg/l for at least 5 days. Often, dalbavancin is maintained at a plasma level of at least about 5 mg/l, often at least about 10 mg/l, often at least about 20 mg/l, often at least about 30 mg/l, often at least about 40 mg/l, for at least 5 days, often at least about one week or longer. Plasma levels of dalbavancin may be measured by methods that are well known in the art, such as liquid chromatography, mass spectrometry, or microbiological bioassay. An example of a method for quantitating dalbavancin in plasma is provided in Example 5.

Upper limits for dalbavancin plasma concentration levels are generally dictated by dosages which inhibit unacceptable adverse effects in the patient population treated.

Dalbavancin compositions may be administered in a single dose or in multiple doses. When administered as a single dose, the dalbavancin composition is preferably formulated to contain sufficient amounts of dalbavancin to effect antibacterial properties in vivo for at least 5 days, preferably at least 7 days, and more preferably at least 10 days.

When multiple doses are employed, dalbavancin can be administered weekly for two or more weeks. In one embodiment, dalbavancin is administered in at least two doses, often in two doses about 5 to about 10 days apart, more often once a week for two weeks. As shown in Example 1, such a dosing regimen provides significant advantages over conventional antibiotic treatment protocols.

Dalbavancin compositions also may be administered in multiple doses two or more days or at least one week apart or in one or more biweekly doses. In some embodiments, a dalbavancin composition is administered weekly, followed by biweekly, or monthly administration. In some embodiments, dalbavancin is administered at weekly intervals for 2, 3, 4, 5, 6, or more weeks.

Most advantageously, daily dosing is not required because higher, less frequent doses are used. Single or multiple doses may range, for example, from about 0.1 to about 5 grams. A single dose of about 0.1 to about 4 grams, e.g., about 3 grams, may be administered for various infection treatments. Where multiple doses are administered, for example, weekly, each dose may range, for example, from about 0.25 to about 5.0 grams.

For embodiments in which a single dose is administered to treat an infection, the amount of the dose may be, for example, about 0.1 to about 5 grams, or about 0.5 to about 4 grams, or about 1 to about 3.5 grams, or about 2 to about 3 grams e.g., about 3 grams. In some embodiments, a single dose of about 1, 1.5, 2, 2.5, or 3 grams is administered for treatment of a bacterial infection. For embodiments in which a single dose is administered for prophylaxis, the amount of the dose may be, for example, about 0.1 to about 3 grams, or about 0.1 to about 1 gram, e.g., about 0.5 or about 0.25 gram.

In dosing schemes that include multiple dosages, the individual dosages may be the same or different. In some embodiments, a first, higher dose is administered, that is, for example, about 1.5 to 10 times higher, in certain cases 9 times higher, in other cases 8 times higher, in other cases 7 times higher, in other cases 6 times higher, in other cases 5 times higher, in other cases 4 times higher, in other cases 3 times higher, in other cases 2 times higher, than one or more subsequent doses. For example, the first dose may be about 0.5 grams to about 5 grams and the second dose about 0.25 grams to about 2.5 grams, the first dose may be about 0.8 to about 2 g and the second dose about 0.4 to about 1 gram, or the first dose may be about 0.4 to about 3 g and the second dose about 0.2 to 1.5 g.

In some embodiments, at least two dosages are administered wherein the first dosage includes about twice as much dalbavancin as subsequent dosages. In one embodiment, a first dosage includes about 1 gram of dalbavancin and a subsequent dosage includes about 0.5 gram. In another embodiment, a first dosage includes about 0.5 gram of dalbavancin and a subsequent dosage includes about 0.25 gram.

In some embodiments, a dalbavancin composition is administered in two doses of equal or different amount two or more days or at least about one week apart. Often, two doses of about 0.2 to about 1.5 grams of dalbavancin are administered about 5 to about 10 days apart, more often about 1 week apart. In one embodiment, a first dosage of about 1 gram of dalbavancin and a second dosage of about 0.5 gram of dalbavancin are administered about 1 week apart.

In a multiple dosing regimen, the time between doses may range, for example, from about 5 to about 10 days, often about one week, alternatively about two weeks. Dose frequency may be, for example, two weekly doses, or multiple weekly doses. The dosing interval, or time between doses, can be, for example, any of about 2, 3, 4, 5, 6, 7, 8, 9, 10, 11, 12, 13, 14, 15, 16, 17, 18, 19, 20, 21, 22, 23, 24, 25, or more days. The number of doses given, can be, for example, one, two, three, four, five, six or more doses, each dose after the initial dose being given after the selected dosage interval.

In a multiple dosing scheme, often the "trough level," or the level of dalbavancin in plasma after a first dose of dalbavancin and just prior to administration of a second dose, is at least about 4 mg/l. Preferably, the trough level at the end of a dosing interval such as about one week is at least about 20 mg/l, more preferably at least about 30 mg/l, and even more preferably at least about 40 mg/l.

Dalbavancin can be administered parenterally, e.g., intramuscularly (i.m.), intravenously (i.v.) (bolus or slow infusion), subcutaneously (s.c.), intraperitoneally (i.p.), or intrathecally (i.t.). The dosing schedule and actual dosage administered may vary depending on such factors as the nature and severity of the infection, the age, weight, and general health of the patient and the tolerance of a particular patient to dalbavancin, but will be ascertainable to health professionals. In one embodiment, a one gram intravenous dose of dalbavancin is followed by a 0.5 gram intravenous dose one week later.

Administration and delivery of the drug to the patient, e.g., intravenously, can be done at a controlled rate, so that the concentration in the blood does not increase too quickly or cause precipitation to occur. In some embodiments, dalbavancin is administered at an appropriate rate such that the drug forms a complex with endogenous protein(s) in the bloodstream. Without intending to be bound to a particular theory, it is believed that endogenous protein, such as human serum albumin, can form a complex in vivo with one or two molecules of dalbavancin homolog monomers. When a sufficient amount of dalbavancin is present, it is believed that up to two molecules of dalbavancin homolog will bind to the endogenous protein and it is further believed that this complex is formed by binding of separate homolog molecules of dalbavancin at two different binding sites. Alternatively, it is possible that dimeric dalbavancin is binding to a single binding site on the endogenous protein. A further elaboration on the dalbavancin-endogenous protein complexes discussed above may be found in U.S. Ser. No. 10/713,924, entitled "COMPOSITIONS AND METHODS FOR TREATING BACTERIAL INFECTIONS WITH PROTEIN-DALBAVANCIN COMPLEXES," filed on Nov. 14, 2003, the disclosure of which is hereby incorporated by reference in its entirety.

The infusion duration can be, for example, about 1 minute to about 2 hours, or alternatively, from about 15 minutes to about 2 hours. For example, an infusion duration of about 30 minutes may be used where the dose is about 0.5 to about 1 gram. Intravenous administration under controlled rate conditions can generate concentrations of dalbavancin in the body that are in great excess of what can be achieved in the solution phase at physiological pH in vitro. Although not wishing to be limited by theory, this may be due to the formation of a complex of dalbavancin with endogenous protein(s) such as serum albumin, which may increase the solubility of dalbavancin in plasma as compared to in vitro studies.

Formation of a dalbavancin complex in vitro or ex vivo may permit faster administration, such as at least about 1 minute, at least about 10 minutes or at least about 20 minutes. Such a complex can be achieved by mixing human serum albumin and/or another endogenous protein with dalbavancin, thereby forming the complex in vitro or ex vivo, and then administering this complex to the treated patient. Alternatively, the human serum albumin or other endogenous protein may be obtained from autologous sources or by expression from a microorganism modified to contain the gene for the protein.

The amount of dalbavancin administered may be any of the dosages disclosed herein. The dalbavancin dose is generally chosen such that the drug will remain at a therapeutically or prophylactically effective (i.e., bactericidal) plasma level for an extended period of time, often at least 5 days, more often about one week or longer. Administration of a dose of dalbavancin which produces and maintains bactericidal concentrations for at least about one week (or about 5 to about 10 days) is preferred. A bactericidal concentration is defined as the concentration of dalbavancin required to kill at least 99% of the bacteria present at the initiation of an in vitro experiment over a 24 hour period. A minimum bactericidal concentration of dalbavancin in plasma is typically about 4 mg/l.

Examples of indications that can be treated include both complicated and uncomplicated skin and soft tissue infections (SSTI) (also known as complicated and uncomplicated skin and skin structure infections (SSSI)), blood stream infections (BSI), catheter-related blood stream infections (CRBSI), osteomyelitis, prosthetic joint infections, surgical prophylaxis, endocarditis, hospital or community acquired pneumonia, pneumococcal pneumonia, empiric treatment of febrile neutropenia, joint space infections, and device infections (e.g., pace makers and internal cardiac defibrillators). Gram-positive or antibiotic-resistant bacterial infections may be treated, such as a *Staphylococcus, Streptococcus, Neisseria*, or *Clostridium* genus infection, in particular *Staphylococcus aureus, Staphylococcus epidermidis, Staphylococcus hemolyticus, Streptococcus pyogenes*, Groups A and C *Streptococcus, Neisseria gonorrhoeae*, or *Clostridium difficile*.

The invention provides methods for treatment of skin and soft tissue infections (SSTIs). Patients who may benefit from this treatment may have either deep or superficial infections. SSTI may involve deeper soft tissue and/or require significant surgical intervention, such as for example a major abscess, infected ulcer, major burn, or deep and extensive cellulitis. Infected surgical wounds may also be treated. The effectiveness of dalbavancin treating the skin is an unexpected and surprising result because dalbavancin complexes with proteins in vivo (see Example 5).

The clinical presentation of skin and skin structure infection may vary from mild folliculitis to severe necrotizing fasciitis. The mode of acquisition may also vary with community-acquired skin and skin structure infections, which are often preceded by injuries resulting from occupational exposure or recreational activities, and are usually associated with a greater diversity of pathogens. Hospital-acquired skin and skin structure infections are generally associated with surgical procedures, the development of pressure sores, and catheterization. Post-surgical infections are the third most frequent nosocomial infection and account for 17% of all nosocomial infections reported to the National Nosocomial Infection Surveillance System (NNIS). The most frequent source of infection is the patient's endogenous flora. *Staphylococcus aureus*, coagulase-negative staphylococci, and *Enterococcus* spp. are the pathogens most frequently isolated from SSTIs.

Symptoms of SSTI infections may include erythema, tenderness or pain, heat or localized warmth, drainage or discharge, swelling or induration, redness, or fluctuance. Patients that may benefit from treatment with the methods of the invention include those with deep or complicated infections or infections that require surgical intervention, or patients with underlying diabetes mellitus or peripheral vascular disease. These infections are often caused by Gram-positive bacteria such as *Staphylococcus* or *Streptococcus* species, such as *Staphylococcus aureus* or *Streptococcus pyogenes*. Methods for treatment of a skin or soft tissue bacterial infection include administering a therapeutically effective amount of dalbavancin to an individual in need of treatment, in an amount and according to a dosing regime as discussed above. In some embodiments, a dalbavancin composition is administered intravenously in two doses, often about 5 to about 10 days apart, more often about 1 week apart. In some embodiments, the first dosage includes at least twice as much dalbavancin as the second dosage. In one embodiment, the first dosage is about 1000 mg and the second dosage is about 500 mg. In another embodiment, the first dose may be about 1200 mg and the second dose may be about 600 mg.

The invention also provides methods for prophylactic prevention of the onset of a bacterial infection, for example an infection caused by *Staphylococcus aureus*, or by a *Neisseria* or *Clostridium* genus bacterium. In a prophylactic method of the invention, a prophylactically effective amount of dalbavancin is administered to an individual who may be susceptible to contracting a bacterial infection, for example, through a medical procedure. Often, dalbavancin is administered in an amount sufficient to provide a prophylactically effective plasma level for at least about 1 day, at least about 3 days, at least about 5 days, or at least about one week or longer. Dalbavancin compositions may be administered, for example, parenterally, e.g., via intramuscular (i.m.), intravenous (i.v.), intraperitoneal (i.p.), subcutaneous (s.c.), or intrathecal (i.t.) injection, prior or subsequent to surgery as a preventative step against infection. Dalbavancin compositions may be administered immediately prior or subsequently to, 1 or more days or about one week prior or subsequently to, or during an invasive medical procedure such as surgery or a stay in a medical care facility such as a hospital to prevent infection. A prophylactic method may be used in any situation in which it is possible or likely that an individual may contract a bacterial infection, including situations in which an individual has been exposed to or is likely to be exposed to a bacterially infected individual. For prophylactic methods, dalbavancin compositions may be administered as either a single dose or as two or more doses of equal or different amount that are administered several days to about one week apart. In one embodiment, a dalbavancin composition may be administered prior to or simultaneously with insertion of an intravenous catheter in order to prevent a bloodstream related infection.

For prophylactic methods, dalbavancin compositions may be administered in a single dose or in multiple doses, according to any of the dosing schemes described above. Often, a dalbavancin composition is administered as a single dose comprising about 0.1 to about 3 grams, or about 0.1 to about 1 gram, e.g., about 0.25 gram or about 0.5 gram. In one embodiment, a single dose of about 0.25 gram is administered intravenously over a time frame of about 2 minutes to about 1 hour, e.g., about 30 minutes. In another embodiment, the dalbavancin composition is administered intravenously simultaneously with administration of another pharmaceutical (e.g., antibiotic) treatment.

In any of the therapeutic or prophylactic methods described above, the dalbavancin composition may be administered either simultaneously or sequentially with at least one other antibiotic. In some embodiments, at least one other antibiotic that is effective (e.g., bactericidal) against one or more Gram-negative bacterial species and/or a Gram-positive bacterial strain against which dalbavancin is not effective is administered in addition to dalbavancin. In some embodiments, dalbavancin and at least one antibiotic that is effective (e.g., bactericidal) against at least one Gram-negative bacterial species is administered as a mixture in the dalbavancin composition.

Pharmacokinetics

Animal studies of dalbavancin were conducted using mice, rats, rabbits, dogs, and minipigs.

Various validated methods were used to quantify dalbavancin. Dalbavancin API consists of 5 homologues ($A_0$, $A_1$, $B_0$, $B_1$, and $B_2$). Methods based on antibacterial activity measured all microbiologically active dalbavancin components. With chromatographic methods, the major component $B_0$ was measured in combination with component $B_1$ (together 90% to 95% of dalbavancin) and the result reported in terms of total dalbavancin. Liquid scintillation counting (LSC) and liquid chromatography with radiochemical detection (LC/RC) allowed for the measurement of dalbavancin and metabolites in plasma, urine, and feces of animals given radiolabeled drug. Whenever both dalbavancin and drug-derived radioactivity were quantified in the plasma of animals given clinically relevant doses, the concentration-time curves for drug and radioactivity were superimposable. This indicates that virtually all of the drug-derived radioactivity in plasma was intact drug.

The drug was widely distributed throughout the body into all tested organs and tissues after IV dose administration. Dalbavancin penetrated into the skin of rats and minipigs. Dalbavancin kinetics behaved in a predictable manner across species. Plasma clearance (CL) was found to be proportional to species body weight. Additionally, dalbavancin crossed the rat placenta and was found in fetal rat plasma.

Dalbavancin is not a substrate, inhibitor, or inducer of hepatic cytochrome P450 isoenzymes. The drug is not metabolized in vitro by rat, dog, or human hepatic microsomes; rat, dog, or human hepatocytes; or human kidney microsomes. Dalbavancin did not affect the metabolism of marker substrates by isolated human hepatic microsomes. Administration of dalbavancin to rats did not induce any P450 activity.

Similar dalbavancin metabolite profiles are observed across species. Two (2) metabolites (OH-dalbavancin and MAG) have been observed in the urine of rats, dogs, and humans. Both metabolites are either undetectable or close to the limit of detection (<0.4 mg/L) in human plasma, have less antibacterial activity than dalbavancin, and contribute little (if anything) to in vivo activity. With clinically relevant doses, similar results were generally observed in animal plasma.

The drug has dual routes (renal and fecal) of excretion and is excreted as intact drug and metabolites. Dalbavancin is excreted in the urine and feces of rats, dogs, and humans. Most of the dose is excreted as intact drug in the urine. OH-dalbavancin and MAG are found in the urine as well. Some intact drug is found in animal feces along with trace quantities of metabolites. Human feces contained microbiologically active dalbavancin components. Dalbavancin is also excreted into rat milk. Therefore, dalbavancin is eliminated from the body via metabolism, urinary excretion, and fecal excretion. This would predict that little if any dose adjustments would be required based on patient demographics. Surprisingly, patients with severe renal failure (creatinine clearance $CL_{CR}$ less than 30 mL/min) achieved higher levels than normal renal patients (creatinine clearance $CL_{CR}$ greater than 80 mL/min). The severe patients with a 1 g dose on Day 1 appeared similar to the levels for a normal patient who received 100 mg on Day 1 and 500 mg on Day 8.

Pharmaceutical Compositions

The invention provides pharmaceutical compositions formulated for administration of dalbavancin according to the methods described above. Pharmaceutical compositions of the invention may be in the form of a unit dose of dalbavancin that includes an amount of dalbavancin sufficient to provide a therapeutically or prophylactically effective plasma level of dalbavancin for several days, often at least about 3 days, at least about 5 days, or at least about one week or longer when the composition is administered to an individual, and a pharmaceutically acceptable carrier. Generally, a therapeutically or prophylactically effective plasma level of dalbavancin is at least about 4 mg per liter of plasma. Plasma levels of dalbavancin may be measured by well known methods in the art, such as those described above.

Dalbavancin may optionally be in a pharmaceutically acceptable form for administration to an individual, optionally as a pharmaceutically acceptable, non-toxic salt.

Examples of suitable salts of dalbavancin include salts formed by standard reaction with both organic and inorganic acids such as, for example, hydrochloric, hydrobromic, sulfuric, phosphoric, acetic, trifluoroacetic, trichloroacetic, succinic, citric, ascorbic, lactic, maleic, glutamic, camphoric, glutaric, glycolic, phthalic, tartaric, lauric, stearic, salicylic, methanesulfonic, benzenesulfonic, sorbic, picric, benzoic, cinnamic, and the like acids. Representative examples of bases that can form salts with dalbavancin include alkali metal or alkaline earth metal hydroxides such as sodium, potassium, calcium, magnesium, and barium hydroxide, ammonia and aliphatic, alicyclic, or aromatic organic amines such as methylamine, dimethylamine, diethylamine, ethanolamine, and picoline. (See, for example, U.S. Pat. No. 5,606,036.)

In some embodiments, a pharmaceutically acceptable aqueous formulation of dalbavancin is provided that is suitable for parenteral administration, such as, for example, intravenous injection. For preparing such an aqueous formulation, methods well known in the art may be used, and any pharmaceutically acceptable carriers, diluents, excipients, or other additives normally used in the art may be used. In one embodiment, a pharmaceutically acceptable aqueous formulation for intravenous injection includes 5% dextrose.

Dalbavancin may be administered parenterally, i.e., the route of administration is by injection under or through one or more layers of the skin or mucous membranes. Since this route circumvents these highly efficient protective barriers of the human body, exceptional purity of a parenteral dosage form free of microorganisms and insoluble particulates must be achieved. The process used in preparing such a dosage form must embody good manufacturing practices that will produce and maintain the required quality of the product in terms of sterility and therapeutic effectiveness. In addition, the form should be stable when stored at room temperature for a practical and convenient dosage form.

There are several conventional methods generally available for converting bulk drug materials into a dosage form suitable for parenteral administration. These methods are generally outlined in Remington's Pharmaceutical Sciences, eighteenth edition, 1990 ("Remington").

Steam Sterilization

The USP defines steam sterilization as employing saturated steam under pressure for at least 15 minutes at a minimum of 121° C. in a pressurized vessel. A drug in its solid form may be placed in an autoclave to affect the steam sterilization. A drug in its solution form may be placed directly in an autoclave or contained in a sealed container and placed in an autoclave to affect the same kind of steam sterilization.

Dry Heat Sterilization

In dry heat sterilization, a bulk drug material is subjected to elevated temperatures at relatively low humidity. Because dry heat is less efficient than moist heat for sterilization, longer exposure times and higher temperatures than those used in steam sterilization is required. The objective is to kill microorganisms by an oxidation process. While establishing exact and correct time-temperature cycles is not routine, typical temperatures used are 140-170° C. from 1 to 3 hours.

Sterilization by Radiation

Sterilization by radiation may employ either electromagnetic radiation or particle radiation. Electromagnetic radiation, comprised of photons of energy, includes ultraviolet, gamma, x-ray, and cosmic radiation. Gamma radiation, emitted from radioactive materials such as cobalt-60 or cesium-137, is the most frequently used source of electromagnetic sterilization. The particle radiation most widely employed for sterilization is the beta particle or electron radiation.

Sterilizing Filtration

Sterilizing filtration is a process that removes, but does not destroy, microorganisms from a fluid stream. Such filtration is the method of choice for solutions that are unstable to other types of sterilizing processes.

Sterile Freeze-Drying (Lyophilization)

This method employs sterilizing filtration with the subsequent step of separating the sterilized drug from solution by sublimating the solution after the solution is frozen, leaving behind the drug substance. The method typically comprises the following steps:
 1) dissolve bulk drug in aqueous solution
 2) sterilize the solution by membrane filtration
 3) fill the sterilized solution in opened, pre-sterilized vials and place in freeze-drying chamber
 4) freeze the solution in the vials
 5) evacuate the chamber to sublime the ice under low temperature
 6) increase the temperature to room temperature or above to remove the residual water.

Sterile Freeze-Drying (Lyophilization) with Addition of Sterile Water (Steam)

This method employs sterilizing filtration with the subsequent steps of separating the sterilized drug from the solution by freeze-drying (lyophilization), and adding sterile water in the form of steam.

Sterile Precipitation

This method employs sterilizing filtration with the subsequent step of precipitating the sterilized drug from solution. More specifically, a bulk drug is first dissolved in water at an elevated temperature (above room temperature), the heated solution is then filtered under aseptic conditions to remove any microorganisms, and the filtered solution is then cooled in order to precipitate the drug from solution. The precipitated drug is then separated from the solution by filtration or centrifugation, and filled into containers by powder filling under aseptic conditions. For such powder filling to be practical, the drug must have good flow properties—the powder should generally be granular, non-crystalline and of uniform particle size.

A pharmaceutical composition for parenteral administration includes dalbavancin and a physiologically acceptable diluent such as sterile or deionized water, for injection, physiological saline, 5% dextrose, water miscible solvent (e.g., ethyl alcohol, polyethylene glycol, propylene glycol, etc.), non-aqueous vehicle (e.g., oil such as corn oil, cottonseed oil, peanut oil, and sesame oil), or other commonly used diluent. The formulation may additionally include a solubilizing agent such as polyethylene glycol, polypropylene glycol, or other known solubilizing agent, buffers for stabilizing the solution (e.g., citrates, acetates, and phosphates) and/or antioxidants (e.g., ascorbic acid or sodium bisulfite). (See, for example, U.S. Pat. No. 6,143,739.) Other suitable pharmaceutical carriers and their formulations are described in "Remington's Pharmaceutical Sciences" by E. W. Martin. As is known in the art, pharmaceutical preparations of the invention may also be prepared to contain acceptable levels of particulates (e.g., particle-free) and to be non-pyrogenic (e.g., meeting the requirements of an injectable in the U.S. Pharmacopeia).

In one embodiment, a pharmaceutical composition is provided by dissolving a dried (e.g., lyophilized) dose of dalbavancin, often containing a stabilizer or mixture of stabilizers, in an amount of water and preferably deionized water in a volume sufficient for dissolving the lyophile. Typically, the amount of water sufficient for dissolution is approximately 10 mL and the resulting pH of the dalbavancin solution is above 3.0, and about 3.5 to 4.5. This solution is further diluted in a secondary diluent, often containing 5% dextrose, such as an amount contained in a drip bag for intravenous administration, raises the pH of the dalbavancin solution to about 5 to 5.5. In another embodiment, the pH of the dalbavancin solution in a drip bag is about 4.5. The secondary diluent may be deionized and sterile water for injection. In one embodiment, the aqueous diluent is 5% dextrose.

Pharmaceutical compositions for parenteral administration may be made up in sterile vials containing one or more unit doses of dalbavancin in a therapeutically or prophylactically effective amount as described above, optionally including an excipient, under conditions in which bactericidal effectiveness of dalbavancin is retained. The composition may be in the form of a dry (e.g., lyophilized) powder. Prior to use, the powder is reconstituted with a physiologically acceptable diluent and then withdrawn via syringe for administration to a patient. A pharmaceutical formulation as described above may be sterilized by any acceptable means including, for example, e-beam or gamma sterilization methods, or by sterile filtration.

A typical formulation for parenteral administration may include dalbavancin at a concentration such as about 0.1 to about 100 mg, about 0.5 to about 50 mg, about 1 to about 10 mg, or about 2 to about 4 mg of dalbavancin per ml of final preparation.

In some embodiments, a pharmaceutical composition in accordance with the invention includes a mixture of dalbavancin and one or more additional antibiotics. Preferably, at least one non-dalbavancin antibiotic in the mixture is effective (e.g., bactericidal) against one or more species of Gram-negative bacteria, such as, for example, azthreonam, and/or against one or more Gram-positive bacterial strains against which dalbavancin is not effective, such as, for example, linezolide or daptomycin. The mixture may also include a pharmaceutically acceptable carrier as described above.

In some embodiments, pharmaceutical compositions of the invention include one or more stabilizing substances which inhibit degradation of one or more of the components of dalbavancin to less active or inactive materials, homologs, or related materials, for example, MAG. As used herein, "stabilizing substance" or "stabilizer" refers to a substance that stabilizes the level of one or more of the constituent components of dalbavancin, for example, $B_0$, in the composition. A "stabilizing effective amount" refers to an amount of a stabilizer sufficient to enhance long-term stability of one or more components of a dalbavancin composition. In some embodiments, a stabilizing effective amount may be provided by a mixture of two or more stabilizing substances, each of which alone is not present in an amount sufficient to provide a stabilizing effect.

Examples of stabilizers include, for example, nonionic substances such as sugars, e.g., mono-, di-, or polysaccharides, or derivatives thereof, sugar alcohols, or polyols. Such stabilizing substances include, for example, mannitol, lactose, sucrose, sorbitol, glycerol, cellulose, trehalose, maltose, raffinose, dextrose, low and high molecular weight dextrans, or mixtures thereof.

In addition to sugars, stabilizers may also be amino acids. Amino acid stabilizers include natural and synthetic amino acids and amino acid derivatives. In a preferred embodiment, the amino acids are glycine, alanine, valine, leucine, isoleucine, phenylalanine, tryptophan, and asparagine. Stabilizers may also be cyclodextrins, cyclic amides such as niacinamide and benzamide, salicylic acid, and its ortho-, meta-, para-substituted hydroxyl acids and esters.

In addition to adding stabilizers, adjusting the pH of the compounds was found to increase the stability of the composition. The particular pH of the composition that increases or maximizes the stability depends on the type and amount of stabilizer added. The pH may be preferably about 1-7, more preferably 2-6, more preferably 3-5, more preferably 4-5, more preferably approximately 4.5.

In one embodiment, the pharmaceutical composition includes a weight ratio of 1:2 mannitol:dalbavancin. In another embodiment, the pharmaceutical composition includes a weight ratio of 1:1:4 mannitol:lactose:dalbavancin. Surprisingly, it has been found that a combination of mannitol and lactose provides a greater stabilizing effect than either substance alone. Often, the pH of a pharmaceutical composition of the invention is, for example, about 3 to about 5, for example about 3.5 or about 4.5.

In some embodiments, one or more procedures may be employed to reduce formation of MAG. For example, freeze drying of dalbavancin in the presence of a stabilizing substance, such as mannitol and/or lactose, may be employed to reduce the amount of MAG formed.

Storage of dalbavancin compositions is often at lower than ambient temperature, such as at about 5° C., to enhance stability.

Drying

Acetone removal from high molecular weight natural products can be quite difficult because of it can form adducts with them. Its removal can be accomplished in presence of water that replaces acetone in the solid product. Moreover, the process of drying dalbavancin is more delicate due to the possibility of forming MAG, which depends on pH, temperature, vacuum, and time. In order to minimize MAG formation and speed up the drying process, low endotoxin water is added or sprayed on the product during the drying process to replace acetone. The excess water is later reduced with additional hours of drying.

Drying is carried out under vacuum (internal temperature at <25° C.). When most of the acetone has been removed from the product, about 20% (w/w) of low endotoxin water is sprayed on the solid product and drying is continued at the same conditions. To follow the drying process, acetone and Karl Fischer (K.F.) analyses are performed, and additional water is sprayed on the solid product until the residual acetone is less than 1.5%.

Study 25

Drying at 20-30° C. at 50 mbar.

This procedure was first simulated in the laboratory using a rotary evaporator. Dalbavancin batch 027 was dried at 30° C. without adding water giving a product which contained 6.4% of MAG and 3.2% of acetone. 126 g of this dried dalbavancin batch (batch 027, HCl/Dalba ratio 1.7 mols/mol) was charged in a 1 L round bottomed flask and the solid was sprayed with 25 mL of water every two hours, maintaining the temperature of the water bath at 20-30° C. and the vacuum at 50 mbar. Samples of the dalbavancin were taken at specific times and analyzed for acetone, K.F., and MAG analyses. The data obtained are reported in Table 4A. All of the percentages of MAG reported in this table are the difference between the actual amount and the starting amount.

TABLE 4A

| Time h | T ° C. | P mbar | water % | Acetone % | Delta MAG % | water sprayed % |
|---|---|---|---|---|---|---|
| 0 | — | — | 1.6 | 3.2 | — | 20 |
| 2 | 20-25 | 50 | 8.3 | 2.8 | 0 | 20 |
| 4 | 20-25 | 50 | 15.6 | 1.9 | 0 | 20 |
| 6 | 20-25 | 50 | 23.3 | 0.9 | 0 | — |
| 8 | 30 | 50 | 22.6 | 0.56 | — | — |
| 10 | 30 | 50 | 21.8 | 0.43 | 0 | — |
| 12 | 30 | 50 | 20.8 | 0.22 | 0 | — |

This experiment was completed with some additional hours of drying at the same conditions, reducing the water content below 15%.

Drying at 30° C. at 10 mbar.

125 g of Dalbavancin batch 027, MAG 6.4% (HPLC area %), was dried at 30° C. and 10 mbar for 24 hours by using the same equipment of the previous experiment. The results obtained are reported in Table 4B.

TABLE 4B

| Time h | T ° C. | P mbar | KF % | Acetone % | Delta MAG % | water sprayed % |
|---|---|---|---|---|---|---|
| 0 | — | — | 1.6 | 3.21 | — | 20 |
| 2 | 30 | 10 | 13.0 | 1.09 | 0 | 20 |
| 4 | 30 | 10 | 15.08 | 1.18 | 0 | 20 |
| 6 | 30 | 10 | 16.8 | 0.02 | 0 | — |
| 24 | 30 | 10 | 8.89 | 0.02 | 0 | — |

From these laboratory experiments, it can be concluded that the drying process can be simplified by adding water to the solid product. These results were unexpected since the degradation of dalbavancin to MAG is a hydrolysis step, one would expect that the increase in water would increase the degradation process. In this way, acetone is rapidly removed from the product, thereby reducing the drying time and avoiding the formation of additional MAG. Moreover, it can be observed (Table 4B) that a lower residual pressure gave a significant reduction of the drying process. It is also surprising that the acetone level was reduced in the presence of a large amount of water.

Drying of Dalbavancin in Tumble Drier

Wet dalbavancin was put into a tumble drier, DR 216, and dried at 29-32° C. (external temperature) with maximum vacuum (<50 mbar). At the beginning, the internal temperature decreased from 30 to 17-18° C. and then, when it began to increase, a sample of product was taken for analysis (water 17.2% and acetone 9.5%). At this point, low endotoxin water (about 20%, w/w) was sprayed into the drier on the stirred product and additional samples were taken on time for analysis. After two hours, low endotoxin water was sprayed again until the amount of acetone was lower than 0.5%, (Table 4C).

TABLE 4C

External temperature 29-30° C.
Pressure = 10-15 mbar

| Time h | weight Kg | Int. Temp. | Water added mL (*) | analysis # | water % | Acetone % | MAG area % |
|---|---|---|---|---|---|---|---|
| 0 | | 19.1 | | | | | 0.11 |
| 1 | | 17.4 | | | | | ** |
| 2 | | 18.3 | | | | | ** |
| 3 | | 23.5 | | 200201019 | 17.27 | 9.52 | ** |
| 4.5 | | 26.8 | 500 | " | 13.59 | 4.10 | 0.13 |
| 6.5 | | 28.1 | 500 | " | 19.60 | 0.61 | 0.16 |
| 8.5 | | 28.1 | | " | 22.38 | 0.13 | 0.12 |
| 9.5 | | 28.5 | | " | 19.86 | 0.12 | 0.13 |
| 11.5 | | 21.9 | | " | 17.68 | 0.09 | 0.31 |
| 15 | | 29.5 | | " | 14.11 | n.d. | 0.38 |

Final weight 2592 g,
An. # 200201027: water (K.F.) 13.93%,
acetone 0.12%,
MAG 0.38%.
(*) water was sprayed in the tumble drier after sampling Comparison of Drying in the Presence and Absence of Water This study is a comparison between dalbavancin batch 027 and 027/R drying processes carried out in the absence (batch 027) and in the presence of water (027/R). Dalbavancin batches 027 (14.6 Kg) and 027/R (8.3 Kg) were dried under vacuum at 25-35° C. (internal temperature) using a tumble drier (DR 216). Batch 027 was dried without adding water. In contrast, four additions of 400 mL each of low endotoxin water were sprayed on batch 027/R. During each drying, samples of dalbavancin were taken at specific times for analysis. The results are reported in Table 5. For batch 027, MAG was only determined at the end of the drying process.

TABLE 5

| | Lot 027 | | | | | Lot 027/R | | | | | |
|---|---|---|---|---|---|---|---|---|---|---|---|
| hours | temp. (° C.) | Press mbar | KF (%) | Acetone (%) | MAG (%) | temp. (° C.) | Press mbar | KF (%) | Acetone (%) | MAG (%) | Water added (mL) |
| 0 | 32 | 280 | | | 0.52 (*) | 30 | 171 | | | 0.22 (°) | |
| 2 | 29 | 32 | | | | | | | | | |
| 3 | — | — | | | | 23 | 57 | 16 | 6.7 | 0.23 | |
| 7 | — | — | | | | 29 | 1 | 7.4 | 3.94 | 0.44 | 400 |
| 9 | — | — | | | | 28.4 | 2 | 8 | 2.6 | 0.48 | 400 |
| 11 | — | — | | | | 28 | 4 | 10 | 1.5 | 0.59 | 400 |
| 12.5 | — | — | | | | 27 | 12 | 13.9 | 1 | 0.74 | 400 |
| 15 | — | — | | | | 27.3 | 9 | 12 | 0.45 | 0.88 | — |
| 17 | 35 | 0 | 5.5 | 2.9 | | | | | | | |
| 18 | — | — | — | — | | 27.5 | 8 | 11.5 | 0.26 | 0.96 | — |
| 26 | 37.8 | — | — | — | | | | | | | |
| 65 | 35.7 | 0 | 1.6 | 3.1 | n.a. | | | | | | |
| Analysis # | | | 200101408 | | | Analysis # | | | 200101944 | | |
| MAG. | | | 6.46% | | | MAG | | | 1.81% | | |
| K.F | | | 1.63% | | | KF | | | 11.86% | | |
| Acetone | | | 3.14% | | | Acetone | | | 0.27% | | |

(*) An. # 200101392
(°) An. # 200101913

Full Scale Production Data

Below in Table 6 is a summary of the process and MAG levels between the full scale campaigns of 2002 and 2004.

TABLE 6

| | Campaign | | | | | |
|---|---|---|---|---|---|---|
| | 2002 | | | 2004 | | |
| | Lot | | | | | |
| | 020004/R | 020005/R | 020006 | DA204001 | DA2040002 | DA2040003 |
| % MAG | 2.3 | 0.8 | 1.7 | 0.4 | 0.3 | 0.3 |

In the 2002 Process, the dalbavancin product is dried under vacuum at less than 30° C. At various times, low endotoxin water is sprayed on the product. Drying is continued until the acetone content is less than 0.5%.

In the 2004 process, dalbavancin API is recovered by centrifugation, washed with cold acetone (0-10° C.), and dried under vacuum (internal temperature at <25° C.). MAG is the primary degradant of dalbavancin and its formation is dependent on temperature. During the drying process, water is added in order to displace the acetone to ultimately achieve an acetone content of less than 1.5% (GC). As apparent from Table 5, drying at low temperature in the presence of water led to an unexpectedly lower amount of acetone present (compare 0.27% in Lot 027/R to 3.14% in Lot 027) and an unexpectedly low amount of MAG degradation product (compare 1.81% in Lot 027/R to 6.46% in Lot 027).

Therefore, a method for drying dalbavancin includes the steps of adding water to the dalbavancin product in order to displace the acetone. A preferred amount of water to be added is about 20% of the assumed final dry product. Alternatively, the amount of water may be about 15%, alternatively about 25%, alternatively about 30%, alternatively about 40%, alternatively about 45%, alternatively about 50% of the assumed final dry product.

A method for drying dalbavancin may include the steps of drying the dalbavancin product for about 2 hours without the addition of any water at about 100 torr and at a temperature of less than about 25° C. Low endotoxin water is then sprayed on the product and the product is then dried for about two more hours. The level of acetone is then sampled and checked. If the level is more than about 1.5%, the additional water is sprayed on the product and the product is again dried until the acetone level is less than about 1.5%.

Manufacture

All bulk solution manufacturing operations take place in a class 100,000. (Grade D) area. Aseptic filling takes place in a class 100 (Grade A) laminar airflow area.

A suitable manufacturing vessel is charged with about 80% of the Water for Injections theoretical batch volume. The solution is mixed and the temperature is maintained between 15-30° C. The dalbavancin is added and mixed until it is dissolved. At least one stabilizer is added to the solution and mixed until dissolved. Water for injection is added to bring the solution up to final volume and the pH is adjusted, if necessary, with either 0.1N HCl or 1.0N NaOH to an appropriate pH. The bulk solution is sterilized by filtration through two 0.2 micron sterilizing filters in series into a sterilized receiving vessel. (A prefilter can be used if necessary to aid in filter clarity or to reduce particle load to the sterilizing filters). The solution is aseptically filled into sterile/depyrogenated Type I glass vials. Sterile siliconised lyophilisation stoppers are partially inserted to the lyophilisation position and the vials are transferred to the lyophilisation chamber.

The lyophilisation process is monitored by the use of thermocouple probes for representative vials. Vials are frozen at −45° C. and held for 3 hours, after which vacuum is applied. The shelf temperature is adjusted to −25° C. When all thermocouples are −29° C. or warmer the shelf temperature is adjusted to 0° C. When all thermocouples are −5° C. or warmer the shelf temperature is adjusted to +30° C. When all thermocouples are +27° C. or warmer the vials are held for 14±2 hours. The chamber is restored to atmospheric pressure by the introduction of sterile nitrogen which has been filtered through a 0.2 micron filter and the vials are then sealed by collapsing the lyophilisation shelves. Vials are then removed from the chamber and the aluminum seals are applied All components and equipment are sterilized by appropriate processes. Vials are washed and sterilized in a hot air oven at a temperature not less than 255° C. for not less than 3 hours. Stoppers are steam autoclaved at a temperature of 123-125° C. and a chamber pressure of about 33 psi. The dwell time in the sterile range is typically 50-60 minutes.

Validation of sterilization processes uses the "overkill" approach for both steam and dry heat sterilization cycles. All sterilization cycles provide a sufficient lethality to provide at least a $10^{-6}$ probability of microbial survival regardless of the naturally occurring microorganisms. All cycles are designed with lethalities sufficient to provide not less than 12 log reductions. Dry heat cycles will provide a minimum of a 3 log endotoxin reduction.

Stability Studies

Dalbavancin was found to decompose during the freeze drying process. The addition of a stabilizer was found to decrease the amount of decomposition of the active component $B_0$ during the stability studies.

The stability of various lyophilized formulations of dalbavancin at 25° C. and 40° C. over time is shown in FIGS. 1-4. Under FDA guidelines, a product that is stable for three to six months at 40° C. is assumed to be stable for two years at room temperature. FIGS. 1A, 2A, 3A, and 4A show the decrease in amount of dalbavancin component $B_0$, which is one of the bactericidally active dalbavancin components. As discussed above, component $B_0$ is also one of the major components of most dalbavancin compositions. FIGS. 1B, 2B, 3B, and 4B show the increase in the amount of MAG, a less active component thought to be a decomposition product of one or more of the other dalbavancin components. Table 7 lists the compositions for each of the formulations used in the stability studies, the results of which are shown in FIGS. 1-4. Any of these compositions could be used to produce a stable, sterile, particle free dosage form.

TABLE 7

Compositions of Various Dalbavancin Formulations

| Composition | Dalbavancin (mg/vial) | Mannitol (mg/vial) | Lactose (mg/vial) | pH |
|---|---|---|---|---|
| A | 250 | 62.5 | — | 3.4 |
| B | 250 | — | — | 3.69 |
| C | 250 | 62.5 | — | 3.80 |
| D | 250 | — | — | 3.01 |
| E | 250 | 62.5 | — | 3.01 |
| F | 250 | — | — | 4.5 |
| G | 250 | 62.5 | — | 4.5 |
| H | 250 | 62.5 | — | 5.3 |
| I | 250 | 125 | — | 5.0 |
| J | 250 | 62.5 | — | 5.0 |
| K | 250 | 125 | — | 4.5 |
| L | 250 | 62.5 | — | 4.5 |
| M | 250 | 62.5 | 62.5 | 4.5 |
| N | 250 | — | 125 | 4.5 |
| O | 250 | 125 | — | 3.3 |

Figure 1B:
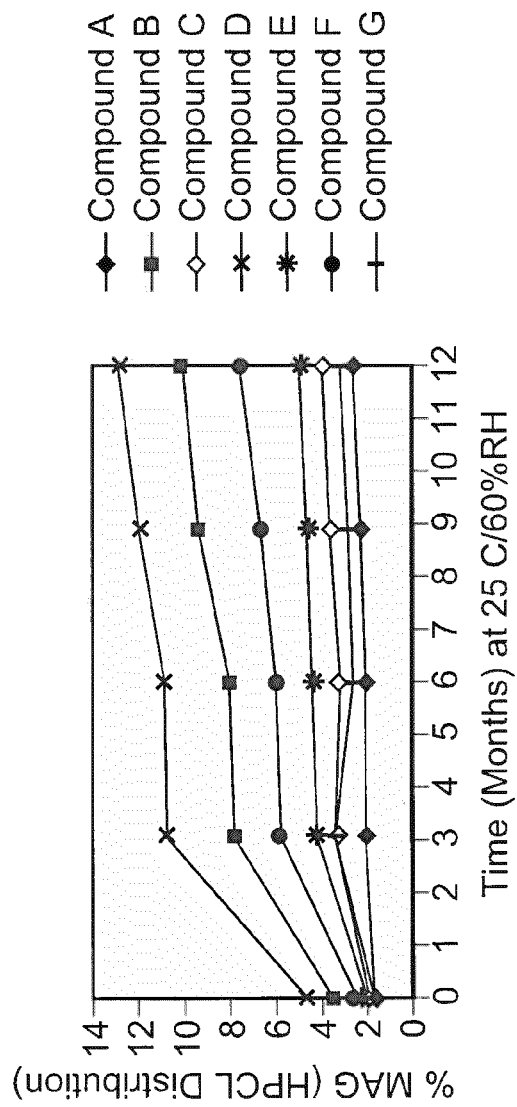
FIG. 1B depicts the amount of MAG versus time in various pharmaceutical compositions, with and without mannitol, at 25° C.
Figure 2A:
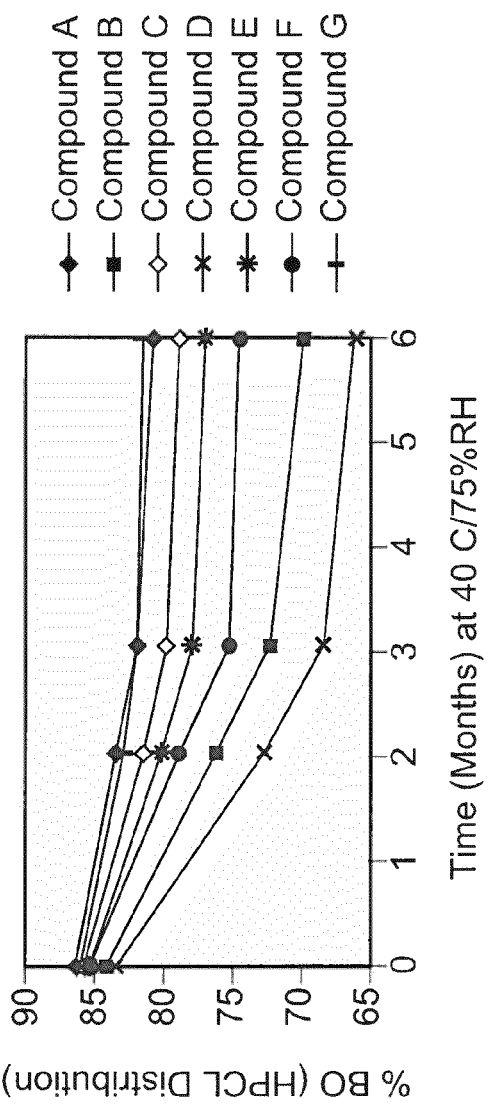
FIG. 2A depicts the amount of dalbavancin component $B_0$ versus time in various pharmaceutical compositions, with and without mannitol, at 40° C.
Figure 2B:
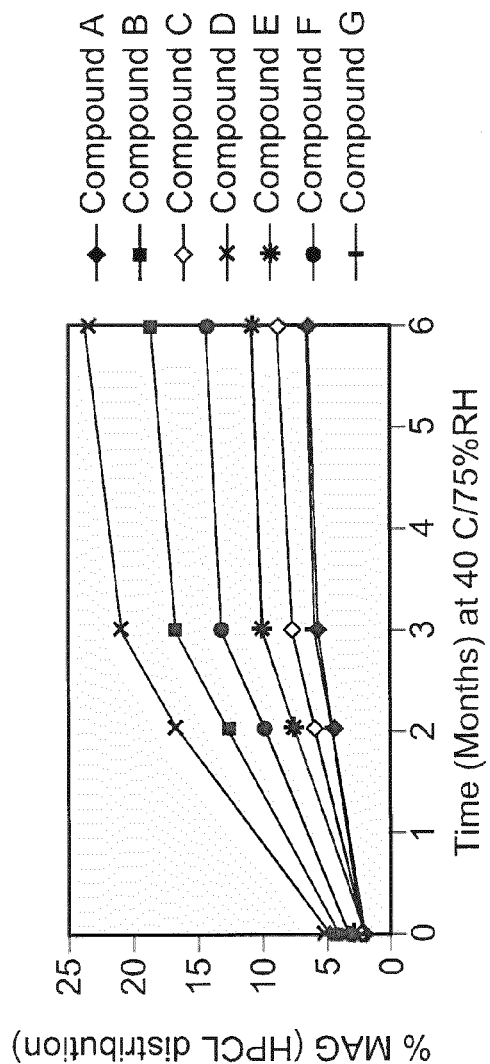
FIG. 2B depicts the amount of MAG versus time in various pharmaceutical compositions, with and without mannitol, at 40° C.

As seen in FIGS. 1B and 2B, at T=0, there is already a significant amount (greater than 4%) of MAG present for Composition D, which contains dalbavancin with no other non-dalbavancin components and which has not been pH adjusted (pH about 3.01), at 25° C. and 40° C., respectively. At the higher temperature, the formation of MAG increased at a far greater rate. After 3 and 6 months at 40° C., Composition D had 21.0% MAG and 23.7% MAG, respectively (see FIG. 2B). This implies that pure dalbavancin is highly unstable, and that merely freeze-drying the dalbavancin results in significant degradation. In addition, normal drying also results in formation of the MAG degradation product. Storage at −20° C. is required for some formulations of dalbavancin.

When the pH is increased, without the addition of any other non-dalbavancin components, the stability increased. Composition D was not pH adjusted and had a pH of about 3.01. Composition B was adjusted to pH 3.69. Composition F was adjusted to pH 4.5. As seen in FIGS. 1A and 2A, as the pH was increased, there was less initial degradation of $B_0$ and less overall degradation over time. Analogously, in FIGS. 1B and 2B, there was less MAG formation in the compositions that were adjusted to a higher pH, both initially and over time at both temperatures.

The addition of mannitol was also shown to increase the stability of dalbavancin significantly. The degradation of factor $B_0$ and increase in MAG over time was also reduced significantly in comparison with Composition D, which was also not pH adjusted but contained no mannitol. As seen in Composition E (62.5 mg mannitol, about pH 3.01), even without any pH adjustment, there was significant improvement in stability, both in the initial freeze-drying process and over time. At time T=0, there is approximately 2% of MAG present at T=25° C. (see FIG. 1A) and T=40° C. (see FIG. 2A), which is less than half the amount of MAG present in Composition D at T=0.

As the pH was increased and the amount of mannitol was held constant, the stability of the dalbavancin also increased. A comparison of Compositions E, C, and G illustrate that, as the pH was increased from about 3.01 to 3.8 to 4.5, the amount of degradation of dalbavancin also decreased. As seen in FIGS. 1A and 2A, as the pH was increased, there was less initial degradation of $B_0$ and less overall degradation over time. Analogously, in FIGS. 1B and 2B, there was less MAG formation in the compositions that were adjusted to a higher pH, both initially and over time.

Increasing the amount of mannitol, while keeping the pH constant, also resulted in an increase in stability. For instance, although Compounds L and K, which contain 62.5 mg and 125 mg of mannitol at pH 4.5, respectively, have similar amounts of $B_0$ at T=0, the change in the percentage of $B_0$ after 12 months was significantly less for Compound K. A similar pattern can be seen for Compound J and I, which contain 62.5 mg and 125 mg of mannitol at pH 5.0, respectively.

Although changing the pH of the compositions containing only mannitol did result in changes in the amount of degradation of $B_0$, there was no predictable trend. Compounds L, J, and H contain 62.5 mg of mannitol at pH 4.5, 5.0, and 5.3, respectively. The changes in the percentage of $B_0$ after 12 months was 1.0, 1.2, and 0.7, respectively, at 25° C. Compounds O, K, and I contain 125 mg of mannitol at pH 3.3, 4.5, and 5.0, respectively. The changes in the percentage of $B_0$ for these compositions after 12 months was 0.5, 0.1, and 0.3, respectively, at 25° C. Notably, after 2 months at 40° C., the amount of component $B_0$ only decreased by 1.9% in Compound O and 1.0% in Compound M (See FIG. 4A).

Figure 3A:
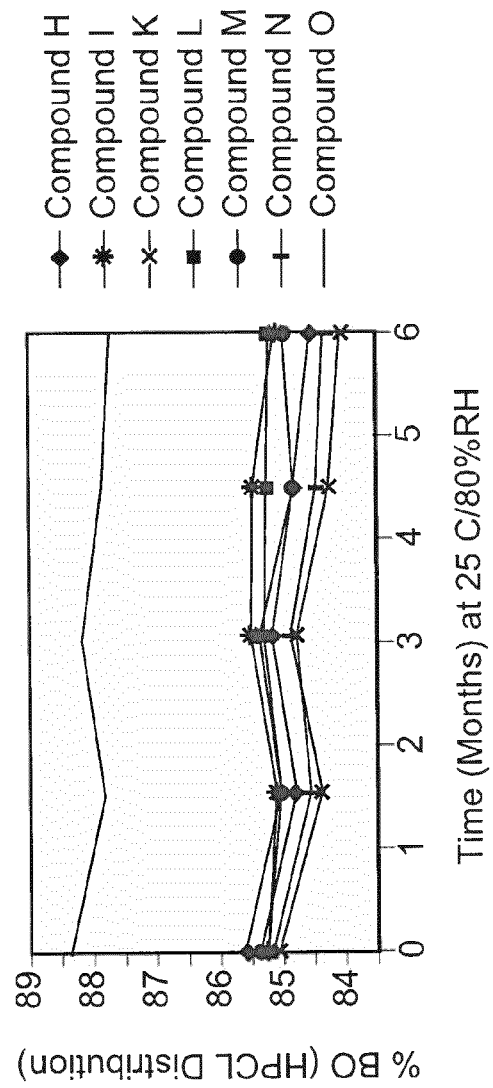
FIG. 3A depicts the amount of dalbavancin component $B_0$ versus time in various pharmaceutical compositions containing mannitol and/or lactose at 25° C.
Figure 3B:
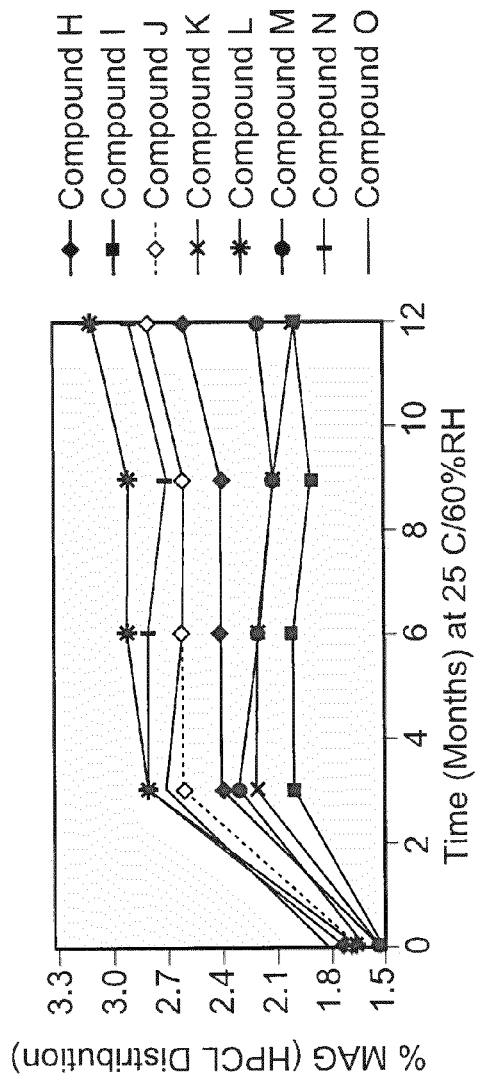
FIG. 3B depicts the amount of MAG versus time in various pharmaceutical compositions containing mannitol and/or lactose at 25° C.

Although the change in the percentage of $B_0$ for Compound O (125 mg of mannitol, pH 3.3) is similar to the other differences found for the compositions containing 125 mg of mannitol (see Compositions I and K), as seen in FIG. 3A, the amount of initial degradation of $B_0$ at T=0 is significantly less for Compound O (88.3% $B_0$). This is especially the case when compared with Compound K (pH 4.5) and Compound I (pH 5.0), which had 85.3% $B_0$ and 85.5% $B_0$, respectively. The differences between the amount of $B_0$ present and the amount of MAG present in Compound O (see FIGS. 3A and 3B) can most likely be explained by the fact that, as explained previously, $B_0$ is not the only dalbavancin component that degrades to form MAG.

Lactose also appears to be a suitable stabilizer for dalbavancin. For Compound N, which contains 125 mg of lactose at pH 4.5, the change in percentage of $B_0$ over 12 months was only 0.6 at 25° C. After 2 months at 40° C., the change in percentage of $B_0$ was only 1.4. Lactose alone, however, does not appear to stabilize the dalbavancin as well as mannitol. At pH 4.5, the $B_0$ component of Compound K (125 mg of mannitol) only decreased by 1.0 after 2 months at 40° C.

Figure 4A:
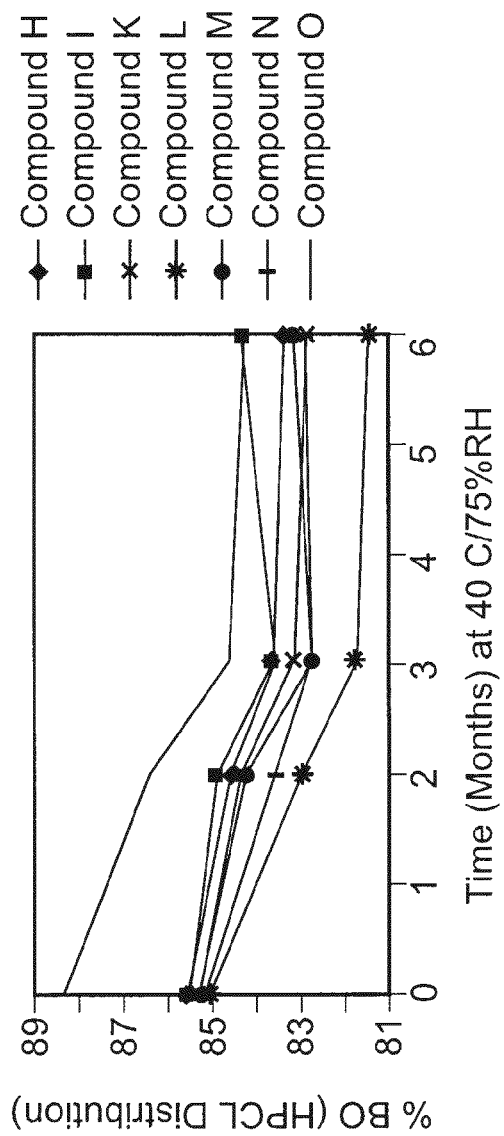
FIG. 4A depicts the amount of dalbavancin component $B_0$ versus time in various pharmaceutical compositions containing mannitol and/or lactose at 40° C.
Figure 4B:
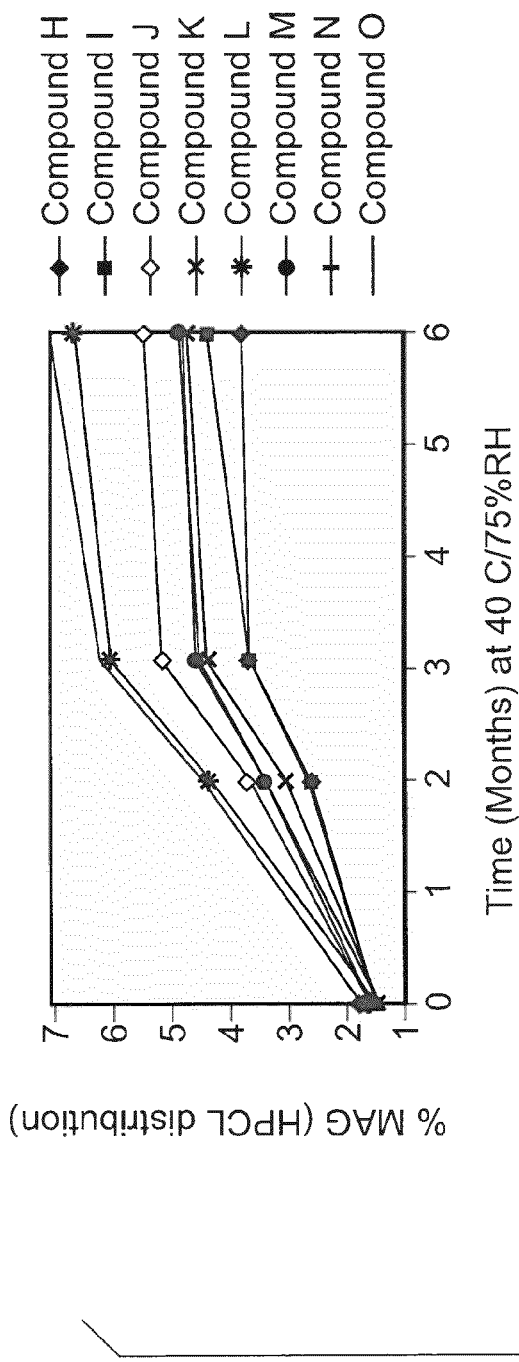
FIG. 4B depicts the amount of MAG versus time in various pharmaceutical compositions containing mannitol and/or lactose at 40° C.

The combination of mannitol and lactose also appears to stabilize dalbavancin and is particularly preferred. Mannitol and lactose have similar stabilizing properties. Mannitol, however, is a diuretic. Therefore, in a preferred embodiment, the amount of mannitol is minimized. Compound M contains 62.5 mg each of mannitol and lactose. As seen in FIG. 3A, the change in percentage of MAG over 12 months at 25° C. was only 0.6. In addition, as seen in FIG. 4A, the amount of MAG only increased by 2.1% after 3 months at 40° C. This is less degradation than that seen for Compounds N (125 mg lactose) and K (125 mg mannitol), which both showed an increase in the amount of MAG of 2.9% after 3 months at 40° C. It was unexpected that a combination of half of each of the amounts of mannitol and lactose used in other formulations would lead to a greater increase in dalbavancin stability.

Additional stability data for dalbavancin stabilized with mannitol and lactose at approximately pH 4.5 is reported in Tables 8A-D below for various temperatures.

TABLE 8A

Stability of Dalbavancin for Injection Lot 554399 at 40° C./75% TH (500 mg vial, mannitol and lactose, pH 4.5)

| TEST | TIME (MONTHS) | | | |
| --- | --- | --- | --- | --- |
| | 0 | 1 | 3 | 6 |
| Physical Appearance | White to off white to pale yellow solid | White to off white to pale yellow solid | White to off white to pale yellow solid | White to off white to pale yellow solid |
| HPLC Assay | 95.4 | 95.7 | 92.2 | 91.6 |
| Component Distribution | | | | |
| $(A_0 + A_1)$ | 2.6 | 2.5 | 2.4 | 2.5 |
| $B_0$ | 87.0 | 86.0 | 85.4 | 84.9 |
| $(B_1 + B_2)$ | 5.8 | 6.2 | 6.3 | 6.4 |

TABLE 8A-continued

Stability of Dalbavancin for Injection Lot 554399 at 40° C./75% TH (500 mg vial, mannitol and lactose, pH 4.5)

| | TIME (MONTHS) | | | |
|---|---|---|---|---|
| TEST | 0 | 1 | 3 | 6 |
| Degradants | | | | |
| MAG | 1.0 | 1.5 | 1.9 | 2.2 |
| Maximum Individual Unspecified | n.d. | n.d. | n.d. | n.d. |
| Total Degradants | 1.0 | 1.5 | 1.9 | 2.2 |
| Reconstitution Time | 115 | 57 | 47 | 55 |
| Appearance of Solution | Clear to pale yellow solution | Clear to pale yellow solution | Clear to pale yellow solution | Clear to pale yellow solution |
| Particulate Matter | | | | |
| Particles ≧10 microns | Meets USP | — | — | — |
| Particles ≧25 microns | Meets USP | — | — | — |
| Moisture | 0.4 | 0.5 | 0.5 | 0.6 |
| pH of Reconstituted Solution | 4.3 | 4.6 | 4.5 | 4.5 |
| Sterility | Meets USP | — | — | — | n.d. not detected
— not tested at this time point, per stability protocol

TABLE 8B

Stability of Dalbavancin for Injection Lot 554399 at 30° C./65% RH (500 mg vial, mannitol and lactose, pH 4.5)

| | TIME (MONTHS) | | | | | |
|---|---|---|---|---|---|---|
| TEST | 0 | 1 | 3 | 6 | 9 | 12 |
| Physical Appearance | White to off white to pale yellow solid | White to off white to pale yellow solid | White to off white to pale yellow solid | White to off white to pale yellow solid | White to off white to pale yellow solid | White to off white to pale yellow solid |
| HPLC Assay | 95.4 | 97.3 | 94.2 | 93.7 | 94.0 | 93.8 |
| Component Distribution | | | | | | |
| $(A_0 + A_1)$ | 2.6 | 2.5 | 2.5 | 2.5 | 2.4 | 2.4 |
| $B_0$ | 87.0 | 86.2 | 85.8 | 85.3 | 86.7 | 85.9 |
| $(B_1 + B_2)$ | 5.8 | 6.2 | 6.4 | 6.5 | 5.5 | 6.4 |
| Degradants | | | | | | |
| MAG | 1.0 | 1.1 | 1.3 | 1.5 | 1.7 | 1.7 |
| Maximum Individual Unspecified | n.d. | n.d. | n.d. | n.d. | 0.1 | n.d. |
| Total Degradants | 1.0 | 1.1 | 1.3 | 1.5 | 1.8 | 1.7 |
| Reconstitution Time | 115 | 146 | 53 | 40 | 37 | 49 |
| Appearance of Solution | Clear to pale yellow solution | Clear to pale yellow solution | Clear to pale yellow solution | Clear to pale yellow solution | Clear to pale yellow solution | Clear to pale yellow solution |
| Particulate Matter | | | | | | |
| Particles ≧10 microns | Meets USP | — | — | — | — | — |
| Particles ≧25 microns | Meets USP | — | — | — | — | — |
| Moisture | 0.4 | 0.4 | 0.4 | 0.5 | 0.6 | 0.5 |
| pH of Reconstituted Solution | 4.3 | 4.5 | 4.5 | 4.4 | 4.5 | 4.5 |
| Sterility | Meets USP | — | — | — | — | — | n.d. Not detected
— Not tested at this time point, per stability protocol.

TABLE 8C

Stability of Dalbavancin for Injection Lot 554399 at 25° C./60% RH
(500 mg vial, mannitol and lactose, pH 4.5)

| TEST | TIME (MONTHS) | | | | |
|---|---|---|---|---|---|
| | 0 | 3 | 6 | 9 | 12 |
| Physical Appearance | White to off white to pale yellow solid | White to off white to pale yellow solid | White to off white to pale yellow solid | White to off white to pale yellow solid | White to off white to pale yellow solid |
| HPLC Assay | 95.4 | 94.6 | 93.2 | 93.9 | 92.6 |
| Component Distribution | | | | | |
| $(A_0 + A_1)$ | 2.6 | 2.5 | 2.5 | 2.5 | 2.4 |
| $B_0$ | 87.0 | 86.0 | 85.9 | 87.0 | 86.2 |
| $(B_1 + B_2)$ | 5.8 | 6.4 | 6.3 | 5.7 | 6.4 |
| Degradants | | | | | |
| MAG | 1.0 | 1.2 | 1.2 | 1.4 | 1.4 |
| Maximum Individual Unspecified | n.d. | n.d. | n.d. | n.d. | n.d. |
| Total Degradants | 1.0 | 1.2 | 1.2 | 1.4 | 1.4 |
| Reconstitution Time | 115 | 55 | 68 | 54 | 50 |
| Appearance of Solution | Clear to pale yellow solution | Clear to pale yellow solution | Clear to pale yellow solution | Clear to pale yellow solution | Clear to pale yellow solution |
| Particulate Matter | | | | | |
| Particles ≧10 microns | Meets USP | — | — | — | Meets USP |
| Particles ≧25 microns | Meets USP | — | — | — | Meets USP |
| Moisture | 0.4 | 0.3 | 0.4 | 0.4 | 0.5 |
| pH of Reconstituted Solution | 4.3 | 4.5 | 4.5 | 4.6 | 4.6 |
| Sterility | Meets USP | — | — | — | Meets USP | n.d. Not detected
— Not tested at this time point, per stability protocol.

TABLE 8D

Stability of Dalbavancin for Injection Lot 554399 at 5° C.
(500 mg vial, mannitol and lactose, pH 4.5)

| TEST | TIME (MONTHS) | | | | |
|---|---|---|---|---|---|
| | 0 | 3 | 6 | 9 | 12 |
| Physical Appearance | White to off white to pale yellow solid | White to off white to pale yellow solid | White to off white to pale yellow solid | White to off white to pale yellow solid | White to off white to pale yellow solid |
| HPLC Assay | 95.4 | 94.7 | 92.7 | 93.7 | 93.4 |
| Component Distribution | | | | | |
| $(A_0 + A_1)$ | 2.6 | 2.5 | 2.5 | 2.5 | 2.4 |
| $B_0$ | 87.0 | 86.2 | 86.1 | 87.6 | 86.9 |
| $(B_1 + B_2)$ | 5.8 | 6.4 | 6.3 | 5.7 | 6.4 |
| Degradants | | | | | |
| MAG | 1.0 | 0.9 | 0.9 | 1.0 | 0.9 |
| Maximum Individual Unspecified | n.d. | n.d. | n.d. | n.d. | n.d. |
| Total Degradants | 1.0 | 0.9 | 0.9 | 1.0 | 0.9 |
| Reconstitution Time | 115 | 90 | 88 | 75 | 72 |
| Appearance of Solution | Clear to pale yellow solution | Clear to pale yellow solution | Clear to pale yellow solution | Clear to pale yellow solution | Clear to pale yellow solution |

TABLE 8D-continued

Stability of Dalbavancin for Injection Lot 554399 at 5° C.
(500 mg vial, mannitol and lactose, pH 4.5)

| TEST | TIME (MONTHS) | | | | |
|---|---|---|---|---|---|
| | 0 | 3 | 6 | 9 | 12 |
| Particulate Matter | | | | | |
| Particles ≧10 microns | Meets USP | — | — | — | Meets USP |
| Particles ≧25 microns | Meets USP | — | — | — | Meets USP |
| Moisture | 0.4 | 0.3 | 0.3 | 0.4 | 0.4 |
| pH of Reconstituted Solution | 4.3 | 4.5 | 4.5 | 4.5 | 4.6 |
| Sterility | Meets USP | — | — | — | Meets USP | n.d. Not detected
— Not tested at this time point, per stability protocol.

Data from further long-term stability studies are listed in Tables 9-11. Samples were analyzed by reverse-phase HPLC utilizing binary mobile phase gradient and a UV detection system to determine the stability of the dalbavancin formulation. Dalbavancin content was determined using an external reference standard. The percentage distribution of dalbavancin components was calculated by comparing the area of each single component to the total area of all of the major drug components. The percentage distribution of impurities was calculated by comparing each the area of individual impurity to the total chromatographic area.

Samples were tested for HPLC assay, bioassay, water content, microbial limits, pH, HPLC distribution, or total impurities. The results are shown in Tables 9-11. Stability data for Batch 025 is shown in Tables 9A, 10A, and 11A, which has 1.5% MAG at T=0, Stability data for Batch 020005/R is shown in Tables 9B, 10B, and 11B, which has 0.8% MAG at T=0, as a result of a different drying process described that is described below.

Dalbavancin demonstrated good stability during storage at −20° C. (see Tables 9A-B) with no significant changes in bioassay, HPLC assay, HPLC distribution, or total impurities. The pH remained unchanged and a slight increase in water content was observed.

Degradation was observed over 36 months at 5° C. (see Table 10A) as evidenced by an increase in MAG content by about 2.9% and a corresponding decrease in Factor $B_0$ by about 3.6%. No trend in total impurities was observed and bioassay and pH remain essentially unchanged. Similar results are seen for Batch 020005 (see Table 10B).

More extensive degradation was observed during storage at 25° C. over 12 months (see Table 11A) with an increase in MAG of about 10.2% and a decrease in factor $B_0$ of approximately 8.5%. Levels of other factors, related substances, and pH remained unchanged. The water content increased by about 1.6%.

TABLE 9A

Stability Data for Unformulated Dalbavancin Batch 025 at −20° C. (pH 3.5)

| TEST | TIME (MONTHS) | | | | | | | |
|---|---|---|---|---|---|---|---|---|
| | 0 | 3 | 6 | 9 | 12 | 18 | 24 | 36 |
| Physical Appearance | — | — | — | — | — | — | — | — |
| HPLC Assay (anhydrous, free base, % w/w) | 92.0 | 93.3 | 90.1 | 88.6 | 88.4 | 91.1 | 89.6 | 90.3 |
| Component Distribution | | | | | | | | |
| (HPLC % AUC) | | | | | | | | |
| $A_0 + A_1$ | 4.0 | 4.0 | 4.0 | 4.0 | 3.9 | 3.9 | 3.9 | 3.8 |
| $B_0$ | 83.4 | 83.5 | 82.1 | 82.9 | 84.4 | 83.8 | 83.5 | 82.7 |
| $B_1 + B_2$ | 7.5 | 7.4 | 8.1 | 8.0 | 7.4 | 7.3 | 7.5 | 7.9 |
| Related Substances | | | | | | | | |
| (HPLC % AUC) | | | | | | | | |
| MAG | 1.5 | 1.5 | 1.3 | 1.6 | 1.3 | 1.5 | 1.4 | 1.2 |
| Maximum Individual Unspecified | 0.2 | 0.2 | 0.2 | 0.2 | 0.2 | 0.2 | 0.2 | 0.2 |
| Total Impurities | 5.1 | 5.1 | 5.8 | 5.2 | 4.3 | 4.9 | 5.2 | 5.6 |
| Moisture (% w/w) | 11.0 | 13.3 | 12.1 | 12.6 | 12.1 | 12.8 | 12.2 | 14.2 |
| pH | 3.0 | 2.9 | 3.0 | 2.9 | 2.9 | 2.9 | 2.9 | 2.8 |
| Microbial Limits* | <10, <10 cfu/g | — | — | — | — | — | — | — |

— Not tested at this time point, per stability protocol.
*Total aerobic count, total combined molds and yeast count

TABLE 9B

Stability Data for Unformulated Dalbavancin Batch 020005/R at −20° C.

| TEST | TIME (MONTHS) | | | | | |
|---|---|---|---|---|---|---|
| | 0 | 3 | 6 | 9 | 12 | 18 |
| Physical Appearance | White to tan powder | White to tan powder | White to tan powder | White to tan powder | White to tan powder | White to tan powder |
| HPLC Assay (anhydrous, free base, % w/w) | 92.0 | 94.4 | 92.5 | 94.6 | 91.0 | 92.1 |
| Component Distribution (HPLC % AUC) | | | | | | |
| $A_0 + A_1$ | 2.5 | 2.5 | 2.5 | 2.5 | 2.4 | 2.5 |
| $B_0$ | 87.1 | 87.5 | 86.7 | 86.6 | 86.5 | 87.3 |
| $B_1 + B_2$ | 6.2 | 5.6 | 6.2 | 6.2 | 6.6 | 5.9 |
| Related Substances (HPLC % AUC) | | | | | | |
| MAG | 0.8 | 0.9 | 0.9 | 0.8 | 0.9 | 0.9 |
| Maximum Individual Unspecified | 0.2 | 0.2 | 0.2 | 0.3 | 0.2 | 0.2 |
| Total Impurities | 4.3 | 4.5 | 4.6 | 4.7 | 4.4 | 4.4 |
| Moisture (% w/w) | 18.2 | 20.1 | 20.1 | 20.3 | 20.0 | 19.6 |
| pH | 2.4 | 2.5 | 2.4 | 2.5 | 2.5 | 2.6 |
| Microbial Limits* | 2, 1 cfu/g | — | — | — | — | — |

— Not tested at this time point, per stability protocol.
*Total aerobic count, total combined molds and yeast count

TABLE 10A

Stability Data for Unformulated Dalbavancin Batch 025 at 5° C.)

| TEST | TIME (MONTHS) | | | | | | | |
|---|---|---|---|---|---|---|---|---|
| | 0 | 3 | 6 | 9 | 12 | 18 | 24 | 36 |
| Physical Appearance | — | — | — | — | — | — | — | — |
| HPLC Assay (anhydrous, free base, % w/w) | 92.0 | 91.0 | 90.3 | 91.8 | 90.5 | 89.3 | 88.2 | 87.3 |
| Component Distribution (HPLC % AUC) | | | | | | | | |
| $A_0 + A_1$ | 4.0 | 4.0 | 3.9 | 3.9 | 3.8 | 3.9 | 3.8 | 3.7 |
| $B_0$ | 83.4 | 83.1 | 81.3 | 81.8 | 83.3 | 82.2 | 81.3 | 79.8 |
| $B_1 + B_2$ | 7.5 | 7.4 | 7.9 | 7.7 | 7.2 | 7.2 | 7.2 | 7.5 |
| Related Substances (HPLC % AUC) | | | | | | | | |
| MAG | 1.5 | 1.8 | 2.0 | 2.5 | 2.8 | 3.3 | 3.8 | 4.4 |
| Maximum Individual Unspecified | 0.2 | 0.3 | 0.3 | 0.2 | 0.2 | 0.2 | 0.2 | 0.3 |
| Total Impurities | 5.1 | 5.5 | 6.9 | 6.5 | 5.7 | 6.7 | 7.7 | 9.0 |
| Moisture (% w/w) | 11.0 | 12.3 | 11.8 | 13.2 | 15.0 | 14.8 | 14.9 | 17.6 |
| pH | 3.0 | 3.0 | 3.0 | 2.9 | 2.9 | 2.9 | 2.9 | 2.8 |
| Microbial Limits* | <10, <10 cfu/g | — | — | — | <1, 3 cfu/g | — | <1, 1 cfu/g | <1, <1 cfu/g |

— Not tested at this time point, per stability protocol.
*Total aerobic count, total combined molds and yeast count

TABLE 10B

Stability Data for Unformulated Dalbavancin Batch 020005/R at 5° C.

| TEST | TIME (MONTHS) | | | | | |
|---|---|---|---|---|---|---|
| | 0 | 3 | 6 | 9 | 12 | 18 |
| Physical Appearance | White to tan powder | White to tan powder | White to tan powder | White to tan powder | White to tan powder | White to tan powder |
| HPLC Assay (anhydrous, free base, % w/w) | 92.0 | 92.0 | 91.7 | 91.8 | 89.2 | 89.7 |

TABLE 10B-continued

Stability Data for Unformulated Dalbavancin Batch 020005/R at 5° C.

| TEST | TIME (MONTHS) | | | | | |
|---|---|---|---|---|---|---|
| | 0 | 3 | 6 | 9 | 12 | 18 |
| Component Distribution (HPLC % AUC) | | | | | | |
| $A_0 + A_1$ | 2.5 | 2.5 | 2.5 | 2.4 | 2.4 | 2.3 |
| $B_0$ | 87.1 | 87.1 | 85.6 | 85.3 | 84.6 | 84.3 |
| $B_1 + B_2$ | 6.2 | 5.6 | 6.2 | 6.1 | 6.4 | 5.5 |
| Related Substances (HPLC % AUC) | | | | | | |
| MAG | 0.8 | 1.5 | 1.9 | 2.1 | 2.6 | 4.1 |
| Maximum Individual Unspecified | 0.2 | 0.2 | 0.2 | 0.2 | 0.2 | 0.3 |
| Total Impurities | 4.3 | 4.9 | 5.8 | 6.3 | 6.6 | 7.9 |
| Moisture (% w/w) | 18.2 | 17.4 | 17.2 | 16.4 | 15.4 | 14.2 |
| pH | 2.4 | 2.5 | 2.4 | 2.5 | 2.5 | 2.5 |
| Microbial Limits* | 2, 1 cfu/g | — | — | — | <1, <1 cfu/g | — |

— Not tested at this time point, per stability protocol.
*Total aerobic count, total combined molds and yeast count

TABLE 11A

Stability Data for Unformulated Dalbavancin Batch 025 at 25° C./60% RH

| TEST | TIME (MONTHS) | | | | |
|---|---|---|---|---|---|
| | 0 | 1 | 3 | 6 | 12 |
| Physical Appearance | — | — | — | — | — |
| HPLC Assay (anhydrous, free base, % w/w) | 92.0 | 90.9 | 87.0 | 85.2 | 78.8 |
| Component Distribution (HPLC % AUC) | | | | | |
| $A_0 + A_1$ | 4.0 | 3.9 | 3.8 | 3.7 | 3.4 |
| $B_0$ | 83.4 | 81.6 | 79.5 | 76.3 | 74.9 |
| $B_1 + B_2$ | 7.5 | 7.4 | 7.0 | 7.3 | 6.3 |
| Related Substances (HPLC % AUC) | | | | | |
| MAG | 1.5 | 3.6 | 6.0 | 8.1 | 11.7 |
| Maximum Individual Unspecified | 0.2 | 0.2 | 0.2 | 0.4 | 0.3 |
| Total Impurities | 5.1 | 7.1 | 9.6 | 12.7 | 15.4 |
| Moisture (% w/w) | 11.0 | 11.3 | 12.1 | 12.9 | 12.6 |
| pH | 3.0 | 3.0 | 3.0 | 3.0 | 3.0 |
| Microbial Limits* | <10, <10 cfu/g | — | — | — | 1, <1 cfu/g |

— Not tested at this time point, per stability protocol.
*Total aerobic count, total combined molds and yeast count

TABLE 11B

Stability Data for Unformulated Dalbavancin Batch 020005/R at 25° C./60% RH.

| TEST | TIME (MONTHS) | | | |
|---|---|---|---|---|
| | 0 | 1 | 3 | 6 |
| Physical Appearance | White powder | White powder | White powder | White powder |
| HPLC Assay (anhydrous, free base, % w/w) | 92.0 | 91.2 | 87.2 | 83.3 |
| Component Distribution (HPLC % AUC) | | | | |
| $A_0 + A_1$ | 2.5 | 2.5 | 2.3 | 2.3 |
| $B_0$ | 87.1 | 84.9 | 82.3 | 78.7 |
| $B_1 + B_2$ | 6.2 | 5.3 | 5.3 | 5.8 |
| Related Substances (HPLC % AUC) | | | | |
| MAG | 0.8 | 3.6 | 6.1 | 8.2 |
| Maximum Individual Unspecified | 0.2 | 0.2 | 0.3 | 0.7 |
| Total Impurities | 4.3 | 7.3 | 10.1 | 13.2 |
| Moisture (% w/w) | 18.2 | 15.2 | 13.8 | 12.6 |
| pH | 2.4 | 2.6 | 2.5 | 2.5 |
| Microbial Limits* | 2, 1 cfu/g | — | — | — |

— Not tested at this time point, per stability protocol.
*Total aerobic count, total combined molds and yeast count Stability tests of the sterilized product were also conducted. Samples were tested for appearance of cake and solution, reconstitution time, pH, HPLC assay, bioassay, water content, sterility, HPLC distribution, and related substances. Results are shown in Tables 12-14.

The lyophilized product shows good stability when stored at 5° C. with only minor changes in HPLC assay or HPLC distribution. (see Tables 12A and B). As temperature increases (See Tables 13 and 14), there is a decrease in Factor $B_0$ with a corresponding increase in MAG. The other factors do not appear to be affected by temperature. The product appearance and pH do not appear to be affected by temperature. It is also not possible to determine a clear trend in reconstitution time, considering that the visual inspection of the solubilized product can require some seconds.

TABLE 12A

Stability of Dalbavancin for Injection Lot 149570 at 5° C.
(lyophilized, mannitol, pH 3.5)

| TEST | TIME (MONTHS) | | | | | | | |
| --- | --- | --- | --- | --- | --- | --- | --- | --- |
| | 0 | 3 | 6 | 9 | 12 | 18 | 24 | 36 |
| Physical Appearance | White to off white to pale yellow solid | White to off white to pale yellow solid | White to off white to pale yellow solid | White to off white to pale yellow solid | White to off white to pale yellow solid | White to off white to pale yellow solid | White to off white to pale yellow solid | White to off white to pale yellow solid |
| HPLC Assay | 97.3 | 99.8 | 100.7 | 100.2 | 100.0 | 100.2 | 99.3 | 104.4 |
| Component Distribution | | | | | | | | |
| $(A_0 + A_1)$ | 3.6 | 3.6 | 3.6 | 3.7 | 3.6 | 3.6 | 3.7 | 3.7 |
| $B_0$ | 79.4 | 79.6 | 80.3 | 80.1 | 80.0 | 80.1 | 80.0 | 81.3 |
| Post $B_0$* Degradants | 12.8 | 12.3 | 11.3 | 11.6 | 11.6 | 11.7 | 11.6 | 10.6 |
| MAG | 0.6 | 0.6 | 0.7 | 0.6 | 0.7 | 0.7 | 0.7 | 0.7 |
| Reconstitution Time | 90 | 45 | 40 | 45 | 40 | 40 | 41 | 66 |
| Appearance of Solution | Clear to pale yellow solution | Clear to pale yellow solution | Clear to pale yellow solution | Clear to pale yellow solution | Clear to pale yellow solution | Clear to pale yellow solution | Clear to pale yellow solution | Clear to pale yellow solution |
| Particulate Matter | | | | | | | | |
| Particles ≧10 microns | — | — | — | — | — | — | — | — |
| Particles ≧25 microns | — | — | — | — | — | — | — | — |
| Moisture | 0.8 | 1.4 | 1.2 | nd | 1.1 | 1.6 | 1.5 | 1.3 |
| pH of Reconstituted Solution | 3.7 | 3.5 | 3.5 | 3.5 | 3.5 | 3.4 | 3.4 | 3.5 |
| Sterility | Sterile | — | — | — | Sterile | — | Sterile | Sterile |

— Not tested at this time point, per stability protocol.

*Analysis performed with development HPLC method. Dalbavancin $B_1$ and $B_2$ were not resolved with this method.

TABLE 12B

Stability of Dalbavancin for Injection Lot 442378 at 5° C. (lyophilized, mannitol, pH 3.5)

| TEST | TIME (MONTHS) | | | | | |
| --- | --- | --- | --- | --- | --- | --- |
| | 0 | 3 | 6 | 9 | 12 | 18 |
| Physical Appearance | White to off white to pale yellow solid | White to off white to pale yellow solid | White to off white to pale yellow solid | White to off white to pale yellow solid | White to off white to pale yellow solid | White to off white to pale yellow solid |
| HPLC Assay | 101.8 | 102.9 | 100.8 | 99.9 | 101.4 | 99.4 |
| Component Distribution | | | | | | |
| $(A_0 + A_1)$ | 2.5 | 2.5 | 2.5 | 2.5 | 2.5 | 2.5 |
| $B_0$ | 85.7 | 85.5 | 85.6 | 85.3 | 85.3 | 85.5 |
| $(B_1 + B_2)$ | 5.5 | 5.8 | 5.6 | 5.7 | 6.2 | 5.7 |
| Degradants | | | | | | |
| MAG | 1.7 | 1.8 | 1.6 | 1.7 | 1.7 | 1.9 |
| Maximum Individual Unspecified | n.d. | n.d. | 0.1 | n.d. | n.d. | n.d. |
| Total Degradants | 1.7 | 1.8 | 1.8 | 1.7 | 1.7 | 1.9 |
| Reconstitution Time | 75 | 46 | 43 | 43 | 32 | 32 |
| Appearance of Solution | Clear to pale yellow solution | Clear to pale yellow solution | Clear to pale yellow solution | Clear to pale yellow solution | Clear to pale yellow solution | Clear to pale yellow solution |
| Particulate Matter | | | | | | |
| Particles ≧10 microns | Meets USP | — | — | — | Meets USP | — |

TABLE 12B-continued

Stability of Dalbavancin for Injection Lot 442378 at 5° C. (lyophilized, mannitol, pH 3.5)

| TEST | 0 | 3 | 6 | 9 | 12 | 18 |
|---|---|---|---|---|---|---|
| Particles ≧25 microns | Meets USP | — | — | — | Meets USP | — |
| Moisture | 0.3 | 0.3 | 0.4 | 0.7 | 0.4 | 0.6 |
| pH of Reconstituted Solution | 3.4 | 3.4 | 3.4 | 3.2 | 3.4 | 3.3 |
| Sterility | Sterile | — | — | — | Sterile | — | n.d. Not detected
— Not tested at this time point, per stability protocol.

TABLE 13A

Stability of Dalbavancin for Injection Lot 149570 at 25° C./60% RH (lyophilized, mannitol, pH 3.5)

| TEST | 0 | 1 | 3 | 6 | 9 | 12 |
|---|---|---|---|---|---|---|
| Physical Appearance | White to off white to pale yellow solid | White to off white to pale yellow solid | White to off white to pale yellow solid | White to off white to pale yellow solid | White to off white to pale yellow solid | White to off white to pale yellow solid |
| HPLC Assay | 97.3 | 99.4 | 98.3 | 100.3 | 99.7 | 98.7 |
| Component Distribution | | | | | | |
| $(A_0 + A_1)$ | 3.6 | 3.7 | 3.6 | 3.6 | 3.6 | 3.7 |
| $B_0$ | 79.4 | 81.0 | 79.3 | 80.0 | 79.7 | 78.9 |
| Post $B_0$* Degradants | 12.8 | 10.6 | 12.1 | 11.1 | 10.9 | 11.6 |
| MAG | 0.6 | 0.8 | 1.1 | 1.3 | 1.8 | 1.8 |
| Reconstitution Time | 90 | 50 | 45 | 45 | 30 | 40 |
| Appearance of Solution | Clear to pale yellow solution | Clear to pale yellow solution | Clear to pale yellow solution | Clear to pale yellow solution | Clear to pale yellow solution | Clear to pale yellow solution |
| Particulate Matter | | | | | | |
| Particles ≧10 microns | — | — | — | — | — | — |
| Particles ≧25 microns | — | — | — | — | — | — |
| Moisture | 0.8 | nd | 1.6 | 1.4 | nd | 1.6 |
| pH of Reconstituted Solution | 3.7 | 3.6 | 3.6 | 3.5 | 3.5 | 3.5 |
| Sterility | Sterile | — | — | — | — | Sterile |

— Not tested at this time point, per stability protocol.
*Analysis performed with development HPLC method. Dalbavancin $B_1$ and $B_2$ were not resolved with this method.

TABLE 13B

Stability of Dalbavancin for Injection Lot 442378 at 25° C./60% RH (lyophilized, mannitol, pH 3.5)

| TEST | 0 | 3 | 6 | 9 | 12 | 18 |
|---|---|---|---|---|---|---|
| Physical Appearance | White to off white to pale yellow solid | White to off white to pale yellow solid | White to off white to pale yellow solid | White to off white to pale yellow solid | White to off white to pale yellow solid | White to off white to pale yellow solid |
| HPLC Assay | 101.8 | 103.9 | 100.2 | 98.6 | 100.7 | 98.0 |
| Component Distribution | | | | | | |
| $(A_0 + A_1)$ | 2.5 | 2.5 | 2.4 | 2.5 | 2.4 | 2.5 |
| $B_0$ | 85.7 | 85.0 | 85.5 | 84.4 | 84.3 | 83.9 |
| $(B_1 + B_2)$ | 5.5 | 5.8 | 5.4 | 5.7 | 6.1 | 5.6 |

TABLE 13B-continued

Stability of Dalbavancin for Injection Lot 442378 at 25° C./60% RH (lyophilized, mannitol, pH 3.5)

| TEST | TIME (MONTHS) | | | | | |
|---|---|---|---|---|---|---|
| | 0 | 3 | 6 | 9 | 12 | 18 |
| Degradants | | | | | | |
| MAG | 1.7 | 2.3 | 2.4 | 2.8 | 2.9 | 3.5 |
| Maximum Individual Unspecified | n.d. | n.d. | 0.2 | n.d. | n.d. | 0.1 |
| Total Degradants | 1.7 | 2.3 | 2.5 | 2.8 | 2.9 | 3.6 |
| Reconstitution Time | 75 | 45 | 38 | 33 | 25 | 31 |
| Appearance of Solution | Clear to pale yellow solution | Clear to pale yellow solution | Clear to pale yellow solution | Clear to pale yellow solution | Clear to pale yellow solution | Clear to pale yellow solution |
| Particulate Matter | | | | | | |
| Particles ≧10 microns | Meets USP | — | — | — | Meets USP | — |
| Particles ≧25 microns | Meets USP | — | — | — | Meets USP | — |
| Moisture | 0.3 | 0.7 | 0.6 | 0.7 | 0.7 | 0.8 |
| pH of Reconstituted Solution | 3.4 | 3.4 | 3.4 | 3.3 | 3.4 | 3.4 |
| Sterility | Sterile | — | — | — | Sterile | — | n.d. Not detected
— Not tested at this time point, per stability protocol.

TABLE 13C

Stability of Dalbavancin for Injection Lot 442378 at 30° C./65% RH (lyophilized, mannitol, pH 3.5)

| TEST | TIME (MONTHS) | | | | | |
|---|---|---|---|---|---|---|
| | 0 | 1 | 3 | 6 | 9 | 12 |
| Physical Appearance | White to off white to pale yellow solid | White to off white to pale yellow solid | White to off white to pale yellow solid | White to off white to pale yellow solid | White to off white to pale yellow solid | White to off white to pale yellow solid |
| HPLC Assay | 100.0 | 98.5 | 99.7 | 100.0 | 95.3 | 96.8 |
| Component Distribution | | | | | | |
| $(A_0 + A_1)$ | 2.5 | 2.4 | 2.4 | 2.4 | 2.4 | 2.4 |
| $B_0$ | 86.3 | 85.6 | 84.7 | 84.3 | 83.2 | 83.0 |
| $(B_1 + B_2)$ | 5.5 | 5.5 | 5.7 | 5.9 | 6.3 | 5.6 |
| Degradants | | | | | | |
| MAG | 1.7 | 2.1 | 2.5 | 3.0 | 3.5 | 4.2 |
| Maximum Individual Unspecified | 0.1 | 0.1 | 0.2 | 0.2 | 0.2 | 0.2 |
| Total Degradants | 1.8 | 2.3 | 2.9 | 3.3 | 3.8 | 4.5 |
| Reconstitution Time | 45 | 55 | 31 | 27 | 46 | 26 |
| Appearance of Solution | Clear to pale yellow solution | Clear to pale yellow solution | Clear to pale yellow solution | Clear to pale yellow solution | Clear to pale yellow solution | Clear to pale yellow solution |
| Particulate Matter | | | | | | |
| Particles ≧10 microns | Meets USP | — | — | — | — | — |
| Particles ≧25 microns | Meets USP | — | — | — | — | — |
| Moisture | 0.5 | 0.7 | 0.9 | 0.7 | 0.9 | 0.9 |
| pH of Reconstituted Solution | 3.5 | 3.6 | 3.3 | 3.4 | 3.3 | 3.3 |
| Sterility | Sterile | — | — | — | — | — |

— Not tested at this time point, per stability protocol.

TABLE 14A

Stability of Dalbavancin for Injection Lot 149570 at 40° C./75% RH (lyophilized, mannitol, pH 3.5)

| TEST | TIME (MONTHS) | | | |
|---|---|---|---|---|
| | 0 | 1 | 3 | 6 |
| Physical Appearance | White to off white to pale yellow solid | White to off white to pale yellow solid | White to off white to pale yellow solid | White to off white to pale yellow solid |
| HPLC Assay | 97.3 | 98.6 | 94.7 | 95.1 |
| Component Distribution | | | | |
| $(A_0 + A_1)$ | 3.6 | 3.7 | 3.5 | 3.5 |
| $B_0$ | 79.4 | 79.8 | 77.1 | 76.5 |
| Post $B_0$* | 12.8 | 10.5 | 11.9 | 10.7 |
| Degradants | | | | |
| MAG | 0.6 | 2.0 | 3.7 | 5.5 |
| Reconstitution Time | 90 | 55 | 45 | 40 |
| Appearance of Solution | Clear to pale yellow solution | Clear to pale yellow solution | Clear to pale yellow solution | Clear to pale yellow solution |
| Particulate Matter | | | | |
| Particles ≧10 microns | — | — | — | — |
| Particles ≧25 microns | — | — | — | — |
| Moisture | 0.8 | n.d. | 2.0 | 1.7 |
| pH of Reconstituted Solution | 3.7 | 3.5 | 3.6 | 3.5 |
| Sterility | Sterile | — | — | — |

— Not tested at this time point, per stability protocol.
*Analysis performed with development HPLC method. Dalbavancin $B_1$ and $B_2$ were not resolved with this method.

TABLE 14B

Stability of Dalbavancin for Injection Lot 442378 at 40° C./75% RH (lyophilized, mannitol, pH 3.5)

| TEST | TIME (MONTHS) | | | |
|---|---|---|---|---|
| | 0 | 1 | 3 | 6 |
| Physical Appearance | White to off white to pale yellow solid | White to off white to pale yellow solid | White to off white to pale yellow solid | White to off white to pale yellow solid |
| HPLC Assay | 101.8 | 101.5 | 98.6 | 91.8 |
| Component Distribution | | | | |
| $(A_0 + A_1)$ | 2.5 | 2.4 | 2.4 | 2.2 |
| $B_0$ | 85.7 | 84.2 | 82.0 | 80.6 |
| $(B_1 + B_2)$ | 5.5 | 5.8 | 5.6 | 5.2 |
| Degradants | | | | |
| MAG | 1.7 | 3.2 | 5.3 | 6.6 |
| Maximum Individual Unspecified | n.d. | 0.3 | 0.2 | 0.5 |
| Total Degradants | 1.7 | 3.8 | 5.6 | 7.4 |
| Reconstitution Time | 75 | 46 | 46 | 41 |
| Appearance of Solution | Clear to pale yellow solution | Clear to pale yellow solution | Clear to pale yellow solution | Clear to pale yellow solution |
| Particulate Matter | | | | |
| Particles ≧10 microns | Meets USP | — | — | — |
| Particles ≧25 microns | Meets USP | — | — | — |
| Moisture | 0.3 | 0.6 | 0.8 | 0.8 |
| pH of Reconstituted Solution | 3.4 | 3.4 | 3.4 | 3.4 |
| Sterility | Sterile | — | — | — | n.d. Not detected
— Not tested at this time point, per stability protocol.

Photostability

Dalbavancin for injection (500 mg vials) were also evaluated for photostability in labeled vials. Ten labeled vials were introduced into a photostability chamber, along with a dark control consisting of ten labeled vials wrapped with aluminum foil. The test samples were exposed to not less than 1.2 million lux hours and an integrated near ultraviolet energy of not less that 200 watt hours/meter$^2$. Samples were evaluated for appearance, appearance of solution, pH, moisture, and HPLC assay. Results of this evaluation are presented in Table 15.

TABLE 15

Immediate Pack Photostability Results for 500 mg/vial Drug Product

| Test | Results | |
|---|---|---|
| | Light Exposed | Dark Control |
| Appearance | White to off-white solid | White to off-white solid |
| Appearance of Solution | Pale yellow solution | Pale yellow solution |
| Assay (anhydrous, free base) | 91.8% | 92.8% |
| Moisture Content | 0.3% | 0.3% |
| pH | 4.5 | 4.5 |
| Reconstitution Time (sec) | 43 | 68 |
| Component Distribution (% AUC) | | |
| $A_0$ | 0.7% | 0.7% |
| $A_1$ | 1.7% | 1.8% |
| $B_0$ | 86.0% | 86.2% |
| $B_1$ | 4.2% | 4.3% |
| $B_2$ | 1.9% | 2.0% |
| Related Substances (% AUC) | | |
| $C_0$ | 0.3% | 0.3% |
| $C_1$ | 0.1% | 0.1% |
| $D_0$ | 0.2% | 0.2% |
| $D_1$ | 0.3% | 0.3% |
| $IsoB_0$ | 0.9% | 1.0% |
| MAG | 1.2% | 1.1% |
| Trichloro | 0.5% | 0.5% |
| RRT 0.85 | 0.1% | n.d. |
| Total Impurities (% AUC) | 5.4% | 5.0% | n.d. not detected

Comparison of the light exposed and dark control samples shows that the light exposed samples remain comparable, with slight changes in potency, API component levels, and total impurities.

The light exposed samples demonstrated the presence of a very low level of an unspecified impurity at RRT 0.85, which was not detected in the dark control samples. Evaluation of this component by HPLC/MS has indicated that it is the mono-chlorinated derivative of the dalbavancin B homologues.

Based on these results, Dalbavancin for Injection is considered photostable in its immediate pack.

Improved Efficacy and Reduced Side Effects

Weekly dosing of dalbavancin at high dosage levels (i.e., resulting in surprising high and long-lasting serum levels) shows a surprisingly good safety profile, similar to, or better than, that observed with the standard therapy of lower doses of conventional antibiotics administered daily or even 2-4 times daily, as demonstrated by the Examples herein. A surprisingly high dosage (i.e., resulting in surprising high and long-lasting serum levels) of dalbavancin may be administered, with less frequency than other antibiotics, and without adverse side effects, enabling improved efficacy and patient compliance.

As discussed in Example 1, treatment with dalbavancin results in a low incidence of adverse events. Serious adverse events include any adverse drug experience occurring at any dose that results in death, is life-threatening, results in hospitalization or prolongation of existing hospitalization, or persistent or significant disability or incapacity. In the Phase II trial described in Example 1, 90% of adverse reactions, such as diarrhea, nausea, hyperglycemia, limb pain, vomiting, and constipation, were mild to moderate in severity. Use of dalbavancin in the trial in Example 1 resulted in no serious adverse events related to study drug treatment.

Kits

The invention also provides kits for use in methods of treatment or prophylaxis of bacterial infections. The kits include a pharmaceutical composition of the invention, for example including at least one unit dose of dalbavancin, and instructions providing information to a health care provider regarding usage for treating or preventing a bacterial infection. Instructions may be provided in printed form or in the form of an electronic medium such as a floppy disc, CD, or DVD, or in the form of a website address where such instructions may be obtained. Often, a unit dose of dalbavancin includes a dosage such that when administered to an individual, a therapeutically or prophylactically effective plasma level of dalbavancin is maintained in the individual for at least 5 days. In some embodiments, a kit includes two unit dosages to be administered at least 5 days apart, often about one week apart, often including a first dosage of dalbavancin that is about 1.5 to about 3 times higher than the second dosage. Dalbavancin is often included as a sterile aqueous pharmaceutical composition or dry powder (e.g., lyophilized) composition.

Suitable packaging is provided. As used herein, "packaging" refers to a solid matrix or material customarily used in a system and capable of holding within fixed limits a dalbavancin composition suitable for administration to an individual. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Kits may also optionally include equipment for administration of dalbavancin, such as, for example, syringes or equipment for intravenous administration, and/or a sterile solution, e.g., a diluent such as 5% dextrose, for preparing a dry powder (e.g., lyophilized) composition for administration.

Kits of the invention may include, in addition to dalbavancin, a non-dalbavancin antibiotic or mixture of non-dalbavancin antibiotics, for use with dalbavancin as described in the methods above.

In the examples below, the following abbreviations have the following meanings. If an abbreviation is not defined, it has its generally accepted meaning.

| | |
|---|---|
| AcOH = | acetic acid |
| AcONa = | sodium acetate |
| aq. = | aqueous |
| AST = | aspartate amino transferase |
| ALT = | alanine amino transferase |
| BV = | bed volume |
| CV = | coefficient of variation |
| d = | diameter |
| D = | dalton |
| DCC = | dicyclohexylcarbodiammide |

-continued

| | |
|---|---|
| DMEPA = | 3-(dimethylamino)-propylamine |
| DMSO = | dimethyl sulfonamide |
| eq = | equivalents |
| EU = | endotoxin units |
| g = | gram |
| GC = | gas chromatography |
| HCl = | hydrochloric acid |
| $H_2O$ = | water |
| HOBT = | 1-hydroxybenzothiazole hydrate |
| HPLC = | high performance liquid chromatography |
| $H_2SO_4$ = | sulfuric acid |
| IPA = | isopropylamine |
| IU = | international unit |
| KF = | potassium fluoride |
| Kg = | kilogram |
| L = | liter |
| LC/MS/MS = | liquid chromatography/mass spec/mass spec |
| LDH = | lactate dehydrogenase |
| LSC = | liquid scintillation counting |
| $m^3$ = | cubic meter |
| MeOH = | methanol |
| mg = | milligram |
| mL = | milliliter |
| mol = | molar |
| MW = | molecular weight |
| N = | normal |
| NaOH = | sodium hydroxide |
| NMP = | N-methyl-2-pyrrolidone |
| QTD = | quantitative tissue distribution |
| Rt = | retention time |
| sd = | standard deviation |
| TEA = | triethylamine |

The following examples are intended to illustrate but not limit the invention.

EXAMPLES

Example 1

Efficacy and Safety of Once Weekly Dalbavancin in Deep Skin and Soft Tissue Infections This randomized, controlled study evaluated the safety and efficacy of two dose regimens of dalbavancin. Adult patients with skin and soft tissue infections (SSTI) involving deep skin structures or requiring surgical intervention were randomized to three groups: Study arm 1 received 1100 mg of dalbavancin via intravenous injection (IV) on day 1; Study arm 2 received 1 g of dalbavancin IV on day 1 and 500 mg of dalbavancin IV on day 8; Study arm 3 received "standard of care." Clinical and microbiological response and adverse events were assessed.

Populations for Analysis

There were 62 patients randomized into the study; all received at least one dose of study medication. Four study populations were evaluated for safety and efficacy and were defined as follows: The intent-to-treat (ITT) population included all patients who received at least one dose of study drug (all randomized study subjects). The microbiological intent-to-treat (MITT) population were all ITT patients who had a culture-confirmed Gram-positive pathogen at baseline. The clinically-evaluable population were defined as those who 1) fulfilled all study entry criteria, 2) had no change in antimicrobial therapy for Gram-positive infection following Day 4, except for oral step-down therapy (only applied to standard of care group), 3) returned for the follow-up (FU) assessment visit (unless a treatment failure), and 4) did not receive a non-protocol approved concomitant antimicrobial (unless a treatment failure). The microbiologically-evaluable population was the subset of clinically-evaluable patients who had a culture-confirmed Gram-positive pathogen at baseline.

The study populations are shown in Table 16.

TABLE 16

Study Populations for Dalbavancin SSTI Treatment

| Populations | Study arm 1 Dalbavancin 1100 mg day 1 | Study arm 2 Dalbavancin 1000 mg day 1, 500 mg day 8 | Study arm 3 "Standard of care" |
|---|---|---|---|
| Randomized ITT | 20 | 21 | 21 |
| Treated | 20 (100%) | 21 (100%) | 21 (100%) |
| Completed Study | 18/20 (90%) | 20/21 (95.2%) | 21/21 (100%) |
| Clinically eval at EOT | 16/20 (80%) | 17/21 (81%) | 21/21 (100%) |
| Clinically eval at FU | 13/20 (65%) | 17/21 (81%) | 21/21 (100%) |
| MITT | 14/20 (70%) | 13/21 (61.9%) | 14/21 (66.7%) |
| Micro eval at EOT | 13/20 (65%) | 11/21 (52.4%) | 14/21 (66.7%) |
| Micro eval at FU | 11/20 (55%) | 11/21 (52.4%) | 14/21 (66.7%) |

ITT—intent-to-treat
MITT—subset of ITT population with culture confirmed Gram-positive infection
EOT—end of treatment
FU—follow up The median age of the subjects was 50-55 years (range 18-86 years). There were no apparent differences in age across the treatment arms. There were differences in gender across treatment arms, but overall the study enrolled equal numbers of men and women. The patient population was predominantly Caucasian. These results were consistent for both the ITT and clinically evaluable populations.

62 patients were enrolled, 20 in Study arm 1 and 21 each in Study arms 2 and 3. The most common comparators for standard of care were clindamycin, ceftriaxone, vancomycin and cefazolin. Mean duration of treatment in Study arm 3 was 15 days.

Baseline Pathogens and Susceptibility

Of the 62 ITT patients, 66% (14 single-dose dalbavancin, 13 two-dose dalbavancin, 14 standard of care) had a pre-therapy Gram-positive pathogen isolated (MITT population). The most common pathogen was *S. aureus*. The distribution of pathogens at baseline is shown in Table 17.

TABLE 17

Baseline Gram-positive Pathogens and Dalbavancin MIC Range for the MITT Population

| Number with Pathogen (MIC) | Single dose Dalbavancin (1100 mg) (N = 14) | Two-dose Dalbavancin (1000/500 mg) (N = 13) | Standard of Care Regimens (N = 14) |
|---|---|---|---|
| All *S. aureus* | 13 (0.12) | 11 (0.12) | 10 (0.016-0.25) |
| Methicillin-sensitive | 7 | 6 | 8 |
| Methicillin-resistant | 6 | 5 | 2 |
| Group B *streptococcus* | 0 | 2 (0.016) | 2 (0.016) |
| *Streptococcus pyogenes* | 0 | 1 (0.016) | 1 (0.016) |

TABLE 17-continued

Baseline Gram-positive Pathogens and Dalbavancin MIC Range for the MITT Population

| Number with Pathogen (MIC) | Single dose Dalbavancin (1100 mg) (N = 14) | Two-dose Dalbavancin (1000/500 mg) (N = 13) | Standard of Care Regimens (N = 14) |
|---|---|---|---|
| Miscellaneous *Streptococcus* and nontypeable strains | 3 (0.016) | 2 (0.016) | 4 (0.016) |

Clinical and Microbiological Responses

The effectiveness of the three treatment regimens was determined by assessing the patients' clinical response and the documented or presumed microbiological responses. The primary efficacy endpoint was clinical response at the follow-up visit for the clinically evaluable population. Clinical response, for both EOT and FU visits, was categorized as success (cure or improvement) or failure (including indeterminate results). Patients classified as successes must not have received additional systemic antibacterial treatment for their infection. Failure was defined as persistence of one or more local or systemic signs and symptoms of SSTI such that treatment with new or additional systemic antibacterial agents was required for the SSTI.

Microbiological outcome, a secondary efficacy variable, was assessed in the subpopulation of patients who had microbiologically documented SSTI (i.e., at least one identified baseline pathogen). A microbiologic response was assessed for each Gram-positive pathogen identified at baseline (i.e., eradication, presumed eradication, persistence, presumed persistence). For patients for whom follow-up cultures were not performed, the microbiologic responses for baseline pathogens were presumed on the basis of the clinical response. Microbiologic response by patient at the EOT and FU visits was graded as success (i.e., all Gram-positive organisms eradicated or presumed eradicated) or failure (i.e., at least one Gram-positive organism persisted or presumed to have persisted, multiple pathogens with partial eradication). At both the EOT and FU visits, colonization and superinfection were assessed. At the FU visit, a patient's bacteriological response could also include recurrence.

Clinical Efficacy

Clinical success rates are shown in Table 18. In the clinically-evaluable population, 61.5% of patients in the single-dose dalbavancin, 94.1% in the two-dose dalbavancin, and 76.2% in the standard of care group were classified as successes at the time of the FU assessment. In an exploratory subanalysis of those patients categorized with deep or complicated SSTI at baseline, two-dose dalbavancin therapy also provided a higher clinical success rate (93.8%), compared with the single-dose dalbavancin and standard of care therapies, 58.3% and 73.7%, respectively.

Similar success rates at both the EOT and FU assessments were found in the supportive ITT and microbiologically-evaluable populations with a consistent trend towards a more favorable response following treatment with two-dose dalbavancin (Table 17). For the MITT population, clinical success rates at the FU assessment for those with methicillin-resistant *S. aureus* (MRSA) were 50% (3/6) for single-dose dalbavancin, 80% (4/5) for two-dose dalbavancin, and 50% (1/2) for patients treated with a standard of care regimen.

TABLE 18

Clinical Success Rates by Analysis Population and Treatment Group

| Population | Single-dose (1100 mg) Dalbavancin | Two-dose (1000/500 mg) Dalbavancin | Standard of Care Regimens |
|---|---|---|---|
| ITT at EOT | 15/20 (75.0) | 19/21 (90.5) | 17/21 (81.0) |
| ITT at FU | 12/20 (60.0) | 19/21 (90.5) | 16/21 (76.2) |
| MITT at EOT | 10/14 (71.4) | 12/13 (92.3) | 10/14 (71.4) |
| MITT at FU | 7/14 (50.0) | 12/13 (92.3) | 9/14 (64.3) |
| Clinically evaluable at EOT | 13/16 (61.5) | 16/17 (94.1) | 17/21 (81.0) |
| Clinically evaluable at FU | 8/13 (61.5) | 16/17 (94.1) | 16/21 (76.2) |
| Microbiologically evaluable at EOT | 10/13 (76.9) | 10/11 (90.9) | 10/14 (71.4) |
| Microbiologically evaluable at FU | 6/11 (54.5) | 10/11 (90.9) | 9/14 (64.3) |

Microbiologic Efficacy

The success rates of the different treatment regimes with respect to different pathogens is shown in Table 19. For the microbiologically-evaluable population, eradication/presumed eradication rates at the FU assessment for all organisms were 58.3% (7/12) for single-dose dalbavancin, 92.3% (12/13) for two-dose dalbavancin, and 70.6% (12/17) for patients in the standard of care group. For isolates that persisted, there was no change in dalbavancin MIC. At FU, *S. aureus* eradication rates were higher for the two-dose dalbavancin group (90%) compared with single-dose dalbavancin (50%) and standard of care (60%) treatments. Similar findings were observed for the MITT population; two-dose dalbavancin eradicated 80% of MRSA isolates (Table 19).

TABLE 19

Success Rates by Pathogen for Microbiologically ITT Population at FU Assessment

| | Single-dose (1100 mg) Dalbavancin | Two-dose (1000/500 mg) Dalbavancin | Standard of Care Regimens |
|---|---|---|---|
| Total organisms | 7/16 (43.8%) | 14/16 (87.5%) | 12/17 (70.6%) |
| All *S. aureus* | 5/13 (38%) | 9/11 (82%) | 6/10 (60%) |
| Methicillin-sensitive | 2/7 (29%) | 5/6 (83%) | 5/8 (63%) |
| Methicillin-resistant | 3/6 (50%) | 4/5 (80%) | 1/2 (50%) |
| Miscellaneous *streptococcus* species | 2/3 (67%) | 4/4 (100%) | 5/7 (71%) |

For the microbiologically-evaluable and MITT populations, the microbiological success rates at EOT and FU are summarized in Table 20. Comparable microbiologic success rates were reported at both visits for patients treated with two-dose dalbavancin and standard of care regimens (approximately 64% to 77%), whereas those given a single dose of dalbavancin had lower rates of success (<40%). The microbiologic success rates at EOT/FU in the microbiologically-evaluable population paralleled clinical response findings: 38.5%/27.3% for single-dose dalbavancin, 72.7%/72.7% for two-dose dalbavancin, and 71.4%/64.3% for standard of care therapy. Similar findings were observed for the MITT population (data not shown).

TABLE 20

Microbiologic Success Rates

|  | Single-dose (1100 mg) Dalbavancin | Two-dose (1000/500 mg) Dalbavancin | Standard of Care Regimens |
|---|---|---|---|
| MITT population | | | |
| EOT | 5/14 (35.7) | 10/13 (76.9) | 10/14 (71.4) |
| FU | 3/14 (21.4) | 9/13 (69.2) | 9/14 (64.3) |
| Microbiologically evaluable population | | | |
| EOT | 5/13 (38.5) | 8/11 (72.7) | 10/14 (71.4) |
| FU | 3/11 (27.3) | 8/11 (72.7) | 9/14 (64.3) |

Pharmocokinetic Analysis

For patients randomized to the dalbavancin treatment groups, 5 ml of blood was obtained on Day 8 for determination of dalbavancin plasma concentrations. For patients randomized to receive a 500 mg dalbavancin dose on Day 8, blood was obtained just prior to administration of the second dose. Additional 5 ml blood samples were obtained on Days 10 and 24 for patients were randomized to the single-dose dalbavancin group and on Days 20 and 34 for those who received two doses of dalbavancin.

Dalbavancin plasma concentrations were determined using validated liquid chromatography and mass spectrophotometer methods. The lower limit of quantitation was 500 ng/ml for plasma.

Mean dalbavancin concentrations collected on Study days 8, 10, and 24 in the single-dose regimen were 31.1±7.1, 25.2±4.8, and 10.2±3.5 mg/l (mean±SD), respectively. Dalbavancin concentrations following the two-dose regimen on Study days 8 (prior to the second dose), 20, and 34 were 30.4±8.2, 21.2±10.0, and 9.0±4.4 mg/l, respectively. As expected, all patients had dalbavancin concentrations of greater than 20 mg/l through the first week following the first dose, and levels above 20 mg/l were maintained for an additional week with an additional dose of 500 mg IV on day 8. Generally, minimum bactericidal concentrations are about 4 to 10 mg/l.

Safety Evaluation

Each patient who received at least one dose of study drug (ITT population) was evaluated for drug safety through monitoring of adverse events (AE), including abnormal clinical laboratory test results and vital signs. AE were rated by the investigator as to their severity (mild, moderate, severe, life-threatening), and by the relationship to the study drug (not related, unlikely related, possibly related, or probably related).

A summary of the AE data is presented in Table 21. The majority of adverse reactions (90%) were considered mild to moderate in severity. All serious adverse reactions (8 events in 5 patients) were unrelated to study drug treatment. Approximately 59% of all patients who reported at least one treatment-emergent AE (19 single-does dalbavancin, 16 two-dose dalbavancin, 21 standard of care) experienced an event that was categorized by the investigator as possibly or probably related to study drug. Specifically, drug-related AEs were reported in 11 (55%) single-dose dalbavancin, 10 (48%) two-dalbavancin, and 12 (57%) standard of care patients. The most frequently reported drug-related AE in both the dalbavancin and standard of care treatment groups were diarrhea and nausea. A summary of types of AEs observed for the different treatment groups is presented in Table 22.

No dalbavancin-treated patient discontinued treatment prematurely due to an AE. Three of 21 (14%) patients on a standard of care regiment discontinued treatment prematurely due to an AE, including one patient who developed urticaria on Day 1 which was probably drug related and two patients who had AE unrelated to study drug (superinfection with *P. aeruginosa* and elevated vancomycin trough level).

TABLE 21

Summary of Adverse Event (AE) Data

|  | Single-dose dalbavancin (N = 20) | Two-dose dalbavancin (N = 21) | Standard of care (N = 21) |
|---|---|---|---|
| ≧1 AE | 95% | 76.2% | 100% |
| % AE severe | 15% | 9.5% | 4.8% |
| ≧1 AE possibly/probably related to treatment | 55% | 48% | 57% |
| AE leading to discontinuation of study medication | 0 | 0 | 14.3% |
| ≧1 severe AE | 2 (10%) | 2 (9.5%) | 1 (4.8%) |

TABLE 22

Most Common Adverse Events

|  | Single-dose dalbavancin (N = 20) | Two-dose dalbavancin (N = 21) | Standard of care (N = 21) |
|---|---|---|---|
| Diarrhea | 20% | 9.5% | 28.6% |
| Nausea | 10% | 28.6% | 9.5% |
| Hyperglycemia | 5% | 14.3% | 19% |
| Limb Pain | 10% | 9.5% | 9.5% |
| Vomiting | 10% | 14.3% | 4.8% |
| Constipation | 5% | 4.8% | 14.3% |

Discussion

This open-label, randomized Phase II trial shows that dalbavancin is effective for the treatment of adults with SSTI. The majority of enrolled patients had deep or complicated infections (>90%) and infections that required surgical intervention (~70%), while approximately 45% had underlying diabetes mellitus.

Two weekly doses of dalbavancin had a numerically higher clinical response rate than either a single-dose of dalbavancin or the standard of care regimen. Data from both ITT and clinically-evaluable populations suggests that a regimen of two sequential weekly injectable doses of dalbavancin (1000 mg, 500 mg weekly) is effective in the treatment of SSTIs. The standard of care group was treated for a median duration of 13 days. At follow-up, 94% of clinically-evaluable patients treated with two-dose dalbavancin were considered clinical successes versus 76% of those given a standard of care regimen and 61.5% of patients receiving single-dose dalbavancin.

*S. aureus* was the most frequently isolated organism at baseline. In this trial, approximately 83% of patients were infected with *S. aureus* and 38% of all *S. aureus* strains were MRSA. Most infections (80%) were caused by a single pathogen. The MICs for dalbavancin against Gram-positive isolates, including MRSA, ranged from 0.016 to 0.25 mg/L.

Microbiological success rates paralleled those of clinical response for the clinically-evaluable population. For all organisms combined, treatment with the two-dose weekly dalbavancin regimen provided higher eradication rates at the 2 week post-therapy assessment (92%) compared with single-dose dalbavancin (58%) and standard of care therapies (71%). Overall, rates of *S. aureus* eradication were observed in 90%, 50%, and 60% of patients, respectively. For the MITT population, rates of eradication for MRSA were 80% for the two-dose dalbavancin regimen versus 50% for both the single-dose dalbavancin and standard of care therapies.

Concentrations of dalbavancin obtained at the end of the single-dose and two-dose weekly treatment periods (Day 10 or Day 20, respectively) were similar suggesting little drug accumulation following the second weekly dose. The higher rate of clinical success observed with the two-dose regimen is suggestive of time-dependent killing wherein sustained levels of drug or drug exposure were provided with two doses of dalbavancin separated by one week. Dalbavancin plasma levels measured at the end of the weekly dosing interval were substantially greater than the reported $MIC_{90}$ for pathogens responsible for the majority of SSTIs (<0.03 to 0.5 mg/L), including those found in this trial. These levels were also above the minimum bactericidal concentrations of 4 to 10 mg/l.

The overall rate of adverse reactions was similar for both dalbavancin regimens and the standard of care group. Gastrointestinal drug-related adverse events (i.e., diarrhea and nausea) were most commonly reported across the three treatment groups. The majority of these events were mild and self-limited. No dalbavancin-treated patient was withdrawn from the study early due to an adverse reaction, nor were any serious adverse events attributable to the glycopeptide reported, yet 14% of the standard of care group withdrew due to adverse effects. The novel dosage regimen thus had reduced adverse side effects in comparison to the standard of care. The data from this trial found no evidence that dalbavancin induces any degree of clinically significant hepatotoxicity or nephrotoxicity.

The two-dose dalbavancin regimen appears effective for treatment of patients with complicated SSTIs. Dalbavancin at both doses was well tolerated in this clinical trial, with an adverse event profile similar to that of the standard of care group.

Example 2

Efficacy and Safety of Once Weekly Dalbavancin in the Treatment of Catheter-Related Blood Stream Infection (CR-BSI)

This study evaluated the safety and efficacy (clinical and microbiological) of a weekly dosing regimen of dalbavancin in the treatment of adults with catheter-related blood stream infection (CR-BSI) due to gram-positive bacterial pathogens, relative to the standard care of treatment, vancomycin.

Methodology

Patients with CR-BSI due to suspected or known Gram-positive pathogen(s) who met the inclusion/exclusion criteria were randomized to one of two treatment arms in this open-label, comparative, multi-center study. Dalbavancin was administered once weekly in weekly dalbavancin and comparator (vancomycin) was administered daily in vancomycin. Catheter removal was required for patients with *Staphylococcus aureus* infection; catheter management was left to the Investigator's discretion for patients with coagulase-negative staphylococci (CoNS) infection. Efficacy was clinically based on the improvement or resolution of clinical signs and symptoms of CR-BSI such that no additional antibacterials were warranted, and microbiologically on the eradication or presence of the baseline or other pathogens. Safety and dalbavancin plasma concentrations were also evaluated.

Population for Analysis

Approximately 80 patients were planned (40 each for treatment arms 1 and 3); 67 patients were analyzed (33 in weekly dalbavancin and 34 in vancomycin). Seven (7) patients from daily dalbavancin were included in safety analyses only. Seventy-five (75) patients were randomized and 74 were treated at 13 sites in the United States; 64 patients completed the study. Demographic characteristics were generally similar across study arms. Mean age for patients in weekly dalbavancin was 54 years (range 20-78 years) and in vancomycin was 57 years (range 19-85 years). Males and females were equally represented overall; there were slightly more males in weekly dalbavancin and more females in vancomycin. Most patients were Caucasian (>65%), were categorized as having probable CR-BSI, and had non-tunneled catheters. For the microbiological ITT population, the most common pathogens for both treatment arms were CoNS and *S. aureus*. Of the *S. aureus* isolates, 5/11 (45.4%) and 9/12 (75.0%) were identified as methicillin-resistant (MRSA) for study arms 1 and 3, respectively.

Diagnosis and Main Criteria for Inclusion

Patients with documented Gram-positive bacteremia defined as at least one blood culture positive for *S. aureus*, or at least two positive blood cultures for all other organisms (with at least one of the cultures from a percutaneously drawn sample) were included. In addition, patients were also enrolled who met all other inclusion criteria, and also met each of the two conditions listed below:

1. At least two of the following signs of bacteremia: core temperature>38.0° C. or <36.0° C., measured rectally, orally (added 0.5° C. to the measured temperature), tympanically or via a central catheter; WBC count>12,000/$mm^3$ or <4,000/$mm^3$ or differential count showing>10% band forms; tachycardia (pulse rate>100 bpm); tachypnea (respiratory rate>20. breaths/minute); transient hypotension (systolic blood pressure<90 mm Hg)
2. No apparent source for the clinical manifestation of bacteremia other than the catheter (may have local signs and symptoms at the catheter site).

Treatment

The treatment lasted for 14 days for patients with *S. aureus* infection, and 7 to 14 days for all other pathogens. Because of the long half-life of dalbavancin, the duration of study drug therapy was assumed to be 7 days for each dose of dalbavancin given in weekly dalbavancin. Dalbavancin was administered intravenously with a 1000 mg loading dose on Day 1 and a 500 mg dose on Day 8. Vancomycin was administered intravenously with a 1000 mg dose every 12 hours (or dose-adjusted based on drug levels).

Criteria for Evaluation

Efficacy was evaluated based on clinical and microbiological responses. The primary outcome parameter was overall response at the test-of-cure (TOC) visit in the microbiological intent-to-treat (ITT) population. Safety was evaluated by the collection and analysis of data on adverse events (AEs), clinical laboratory tests, physical examinations, vital signs, and ECGs. Dalbavancin plasma concentrations were determined on up to seven occasions (prior to and after the first dose on Day 1, on Day 4±2 days, before and after the second dose on Day 8, at end of treatment (EOT) and at TOC. Due to the elimination of arm 2 during the study, only demographic data and safety data from those patients are described; efficacy was not evaluated.

Statistical Methods

Efficacy, safety, and dalbavancin concentration data are presented using descriptive statistics. For the primary efficacy analysis, 95% confidence intervals were also determined, and for prognostic factor analyses using the primary efficacy variable, logistic regression was used.

Efficacy Results

For the primary efficacy analysis, overall response in the microbiological ITT population at TOC, patients who received dalbavancin in weekly dalbavancin (87.0%, 95% CI: 73.2, 100.0) had a higher success rate than patients who received vancomycin (50.0%, 95% CI: 31.5, 68.5).

For the secondary efficacy analyses, overall success, clinical success, and overall and clinical success by pathogen, by category of infection, by catheter status at baseline, and by type of catheter for the microbiological ITT and evaluable populations at EOT and TOC were higher in the dalbavancin study arm compared with the vancomycin study arm. By-patient microbiological success was similar for the treatment arms at EOT, but was higher for the dalbavancin study arm at TOC. For CoNS, by-pathogen microbiological success was greater in the dalbavancin study arm at both EOT and TOC. By EOT, most signs and symptoms at the catheter site were resolved for both study arms.

Safety Results

Adverse events (AEs) were reported by 71 patients (95.9%). The number of patients reporting AEs was similar across study arms, although more AEs were reported in the dalbavancin groups than in the vancomycin group. The most common AEs were diarrhea, constipation, anemia, and hypotension. Most AEs were considered by the Investigator to be mild or moderate in intensity. Adverse events considered to be related (possibly or probably) to study drug were evenly distributed across study arms. One (1) patient (3%) in the dalbavancin study arm had an unrelated, non-serious AE that led to discontinuation of dalbavancin; no AEs led to withdrawal from the study. Three (3) patients (8.8%) in the vancomycin study arm had AEs that led to discontinuation of comparator; 2 AEs led to withdrawal from the study. The distribution of SAEs was similar among treatment groups; no SAE in the dalbavancin study arm and one SAE in the vancomycin study arm was considered to be related to study drug. There were 5 deaths in this study. All AEs that resulted in death were unrelated to study medication. There were no clinically meaningful laboratory abnormalities in any study arm. Few laboratory values were reported as AEs. None were SAEs or led to discontinuation of study drug.

Increased diastolic blood pressure was the most common abnormal clinically significant change across all treatment groups. Hypertension was reported as an AE for 3/74 patients (4.1%, 2 patients on dalbavancin, 1 patient on vancomycin); only 1 patient (receiving dalbavancin) had increased blood pressure as an AE considered related to study medication. Dalbavancin did not exhibit any impact on heart rate, atrio-ventricular conduction or intra-ventricular conduction. The average difference of effect on QTc values was 7 msec greater for the dalbavancin group in comparison with the vancomycin group. No significant difference was observed between treatments for frequency of outliers during drug therapy.

Therefore, dalbavancin given as an initial IV dose of 1000 mg followed 1 week later by a second IV dose of 500 mg appears well tolerated and highly effective for the treatment of CR-BSI caused by Gram-positive pathogens, with superior response rates to vancomycin Example 3

Pharmacokinetics and Renal Excretion of Dalbavancin in Healthy Subjects

The primary objectives of this study were to characterize the pharmacokinetics of dalbavancin and to calculate the extent of renal excretion in healthy subjects receiving a therapeutic dose of the drug. This was an open label, non-comparative, study.

Study Drug Treatment

Healthy male or female subjects between 18 and 65 years of age were administered a single 1000 mg IV dose of dalbavancin infused over 30 minutes.

Six subjects, one female and five male, were enrolled, received study medication, and completed all aspects of the study. Three subjects were Caucasian and three subjects were African-American. Mean age was 29.8 years (range 22 to 63). Mean height was 68.6 inches (range 63 to 75) and mean weight was 179.6 lbs (140 to 244).

Pharmacokinetics

Blood and urine (24-hr collections) were collected on study days 1, 2, 3, 4, 5, 6, 7, 14, 21, 28, and 42. Blood samples were drawn into heparinized tubes and centrifuged. Plasma was separated and stored frozen at −20° C. until time of assay. Plasma and urine samples were assayed for dalbavancin using validated LC/MS/MS methods. The lower limit of quantitation of the assay was 500 ng/mL for urine and plasma.

Dalbavancin pharmacokinetic parameters were estimated by non-compartmental methods using the WinNonlin™ software (Pharsight Corporation). The peak concentration ($C_{max}$) values were obtained directly from the observed data. The area under the plasma concentration-time curve (AUC) was calculated using the linear trapezoidal rule. Clearance (CL) was computed as dose/AUC. The elimination half life ($t_{1/2}$) was estimated by linear regression of the log-linear portion of the log concentration versus time curve. Estimates of the volume of distribution ($V_z$) was calculated using the regression parameters, while the volume of distribution at steady state ($V_{SS}$) was calculated from the area under the first moment curve (AUMC) multiplied by the dose and divided by AUC. The cumulative amount of dalbavancin excreted in urine was determined as the integrand of the urine excretion rate (AURC). $CL_R$, or renal clearance, was calculated as the ratio: $CL_R=AURC/AUC$.

Figure 5:
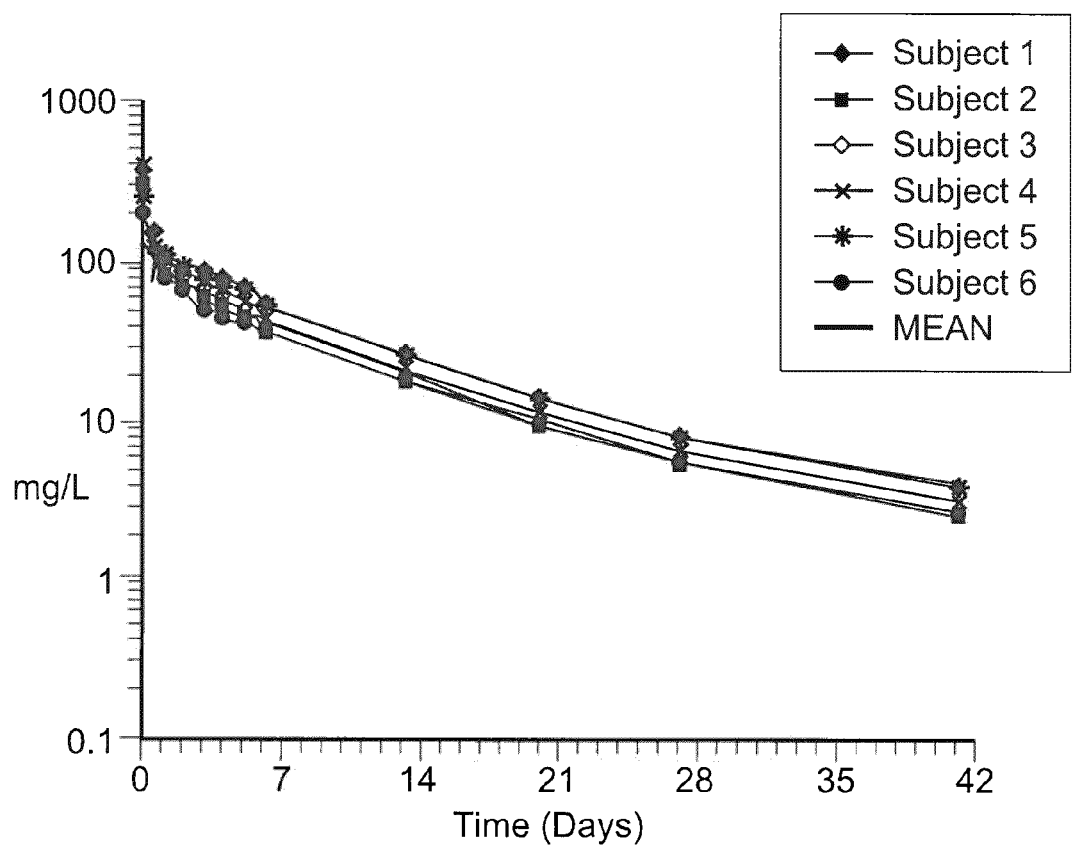
FIG. 5 depicts dalbavancin plasma concentration versus time following a single 1000 mg intravenous infusion of dalbavancin.

Plasma concentrations of dalbavancin versus time are shown for all subjects in FIG. 5. Pharmacokinetic parameters are presented in Table 23. Concentrations were similar across all subjects. Peak plasma concentrations were approximately 300 mg/L and were achieved immediately following the end of infusion. Dalbavancin shows an apparent volume of distribution of more than 10 L and is assumed to be well distributed in the extracellular fluid.

Dalbavancin was slowly eliminated with a $t_{1/2}$ of 9-12 days. The total drug clearance was 0.0431±0.0074 L/hr. The estimated fraction of drug excreted unchanged into urine was 42% of the administered dose, and renal clearance was estimated as 0.018 L/h. The variability observed across subjects was low with a coefficient of variation of less than 22% across all pharmacokinetic parameters.

TABLE 23

Pharmacokinetic parameters

|  | Cmax mg/L | $t_{1/2}$ h | AUC mg·h/L | $V_Z$ L | CL L/h | $V_{SS}$ L | AURC mg | % Renal Excretion | $CL_R$ L/h |
|---|---|---|---|---|---|---|---|---|---|
| Mean | 301 | 257 | 23843 | 16.0 | 0.0431 | 11.5 | 419 | 41.9 | 0.0181 |
| Sd | 65 | 21 | 4526 | 3.1 | 0.0074 | 2.13 | 27 | 2.7 | 0.0036 |
| CV % | 21.6 | 8.1 | 19.0 | 19.5 | 17.1 | 18.6 | 6.4 | 6.4 | 20.1 |
| Min | 243 | 227 | 19844 | 11.7 | 0.0332 | 8.58 | 379 | 37.9 | 0.0130 |
| Max | 394 | 282 | 30100 | 19.6 | 0.0504 | 13.9 | 448 | 44.8 | 0.0226 |

Safety Assessments

Adverse events were recorded and assessed for severity and relationship to study drug. Laboratory data (chemistry panel, CBC with differential, urinalysis) were collected and assessed for changes from baseline and out-of-range values. ECG, physical examination, and vital signs were obtained, and changes from baseline were assessed.

Dalbavancin was well-tolerated in this study. No subject deaths or serious adverse events were reported during this study and no subject was prematurely withdrawn from study due to an AE.

All volunteers reported at least one AE, all of mild intensity. Three volunteers reported AEs that were possibly related to study medication: elevated ALT (value 46 IU/L, upper limit of normal 40 IU/L) in one subject; eosinophilia (value 0.5× $10^3$/mL, upper limit of normal 0.4×$10^3$/µL), elevated LDH (value 303 IU/L, upper limit of normal 90 IU/L), elevated ALT (value 54 IU/L, upper limit of normally 40 IU/L), elevated AST (value 42 IU/L, upper limit of normal 40 IU/L) all in one subject; and tinnitus in one subject.

No trends were seen for post-baseline hematology, chemistry, vital signs, and ECG results.

Discussion

A single 1000 mg IV dose of dalbavancin was well-tolerated. Following a single intravenous infusion of 1000 mg, plasma concentrations of dalbavancin above 45 mg/l are maintained for at least seven days. This is above concentrations known to be bactericidal (4-32 mg/l). This supports the use of dalbavancin as a once-weekly regimen. The urinary elimination profile indicates that renal excretion is an important elimination pathway, with approximately 40% excreted in urine. This finding is consistent with observations in animals. Since the kidneys are not the exclusive elimination route, a dosing adjustment for dalbavancin may not be necessary in renally impaired patients.

Example 4

Pharmacokinetics of Dalbavancin Subjects with Renal Impairment

These were open label studies conducted to examine the safety and pharmacokinetics of intravenous dalbavancin when administered to subjects with mild, moderate and severe renal impairment.

Study Drug Treatment

Male and female subjects between ages 18 and 80 were eligible for enrollment. Subjects had to be within −10% to +50% of ideal body weight for their sex, height, and body frame.

Pharmacokinetics

Serial blood samples were collected before the dose and through at least 2 weeks after the end of infusion and assayed for dalbavancin using a validated LC-MS/MS method.

Dalbavancin pharmacokinetic parameters were estimated by non-compartmental methods. The peak concentrations ($C_{max}$) were obtained directly from the observed data. The area under the plasma concentration-time curve (AUC) were calculated using the linear trapezoidal rule.

Pharmacokinetic parameters of subjects with healthy renal impairment and subjects with the most severe renal impairment (Severe RI) are presented in Table 24.

TABLE 24

Pharmacokinetic parameters

| | Dosing Regimen | | | | |
|---|---|---|---|---|---|
| Pharmacokinetic Parameter | 1000 mg | 1120 mg | 1000 mg + 500 mg | 500 mg Severe RI^ | 1000 mg Severe RI* |
| AUC (mg · h/L) | 24453 +/− 3711 | 25790 +/− 2447 | 33000` | 24376 +/− 6615 | ~48000` |
| AUC7 (mg · h/L) | 13412 +/− 2120 | 13644 +/− 1305 | 12000` | 6860 +/− 1613 | ~14000` |
| AUC14 (mg · h/L) | 17737 +/− 2325 | 20207 +/− 2122 | 23000` | 10986 +/− 2817 | ~22000` |
| AUC42 (mg · h/L) | 23137 +/− 3326 | | 33000` | | ~38000` |
| Cmax (mg/L) | 340 +/− 68 | 325 +/− 41 | 300` | 137 +/− 22 | ~300` |
| C7 day (mg/L) | 40.9 +/− 5.2@ | 55.4 +/− 8.1 | 40` | ~30-40 | ~57` |
| C14 day (mg/L) | 21.3 +/− 2.5@ | 22.8 +/− 1.9 | 40` | | ~40` |

^Preliminary clinical data
*Estimated using parameters directly referenced, or extrapolated from plots
`Based on simulated data or extrapolated based on another study; not directly referenced in an abstract
AUC = drug exposure as estimated by the area under the plasma concentration-time curve;
AUC7 = drug exposure through 7 days post-dose or through treatment period;
AUC14 = drug exposure through 14 days post-dose or through treatment period;
AUC42 = drug exposure through 42 days post-dose or through treatment period;
$C_{max}$ = maximum observed drug concentration in plasma;
C7 = drug concentration 7-days post-dose, prior to administration of another possible dose;
C14 = drug concentration 14 days post-dose, prior to administration of another possible dose.

Discussion

For patients with severe renal impairment, a single dose of 500 or 1000 mg of dalbavancin is administered to the subject. As apparent from Table 24, after 14 days, a patient with severe renal impairment given a single dose of 1000 mg has a AUC 14 (mg·h/L) of approximately 22000, which is unexpectedly very similar to normal patients on the two dose regimen of 1000 mg+500 mg (AUC14 mg·h/L of 23000).

For patients with mild renal insufficiency, no dosage adjustment of dalbavancin was required. Dalbavancin concentrations and pharmacokinetic parameters were similar in subjects with mild renal impairment and subjects with normal renal function. In addition, dalbavancin was well-tolerated in subjects with normal or mildly impaired renal function. See Dowell, J. et al. "Dalbavancin Dosage Adjustments Not Required for Patients with Mild Renal Impairment" presented at the 2003 ECCMID Meeting, Glasgow (Clinical Microbiology and Infection, Volume 9 (Supplement 1) page 291; 2003) and Stogniew, M. et al. "Pharmacokinetic Attributes of Dalbavancin: Well Distributed and Completely Eliminated with Dual Routes of Elimination" Presented at the 2003 ECCMID Meeting, Glasgow (Clinical Microbiology and Infection, Volume 9 (Supplement 1) page 291-292; 2003) both of which are hereby expressly incorporated by reference in their entirety.

Example 5

Renal Impairment and End-Stage Renal Disease

A major pathway for dalbavancin elimination is the excretion of both intact and OH-dalbavancin into urine, and it is likely that the drug will be used in patients with various degrees of renal impairment. Because of this, the safety and pharmacokinetics of dalbavancin in subjects with various degrees of renal impairment was examined in Clinical Studies VER001-3, VER001-11 and VER001-13.

Clinical Study VER001-3 was terminated early (5 subjects enrolled; 3 subjects received dalbavancin) when it was determined that the dosage being examined (70 mg) was too low compared to the larger weekly dosage that was being proposed for clinical study. Clinical Study VER001-13 examined subjects with mild and moderate renal impairment and Clinical Study VER001-1 examined subjects with severe renal impairment and subjects with end-stage renal disease (ESRD). Matched control subjects were enrolled in all studies. Renal impairment was defined by estimated creatinine clearance: mild=51-79 mL/min, moderate=31-50 mL/min, and severe≦30 mL/min. Subjects with ESRD were dependent on dialysis through the course of the study (3 times weekly). Single doses of 1000 mg IV dalbavancin were examined in subjects with mild and moderate renal impairment, doses of 500 mg dalbavancin were studied in subjects with ESRD, and single doses of 500 and 1000 mg were studied in subjects with severe renal impairment.

Dalbavancin was well tolerated in each of these renal impairment studies. Similar percentages of subjects reporting adverse events were observed in each of the study groups. The majority of the reported adverse events were mild or moderate in severity and unrelated to study medication. There were no clinically meaningful laboratory derangements in any of the study subjects while receiving dalbavancin.

Figure 18:
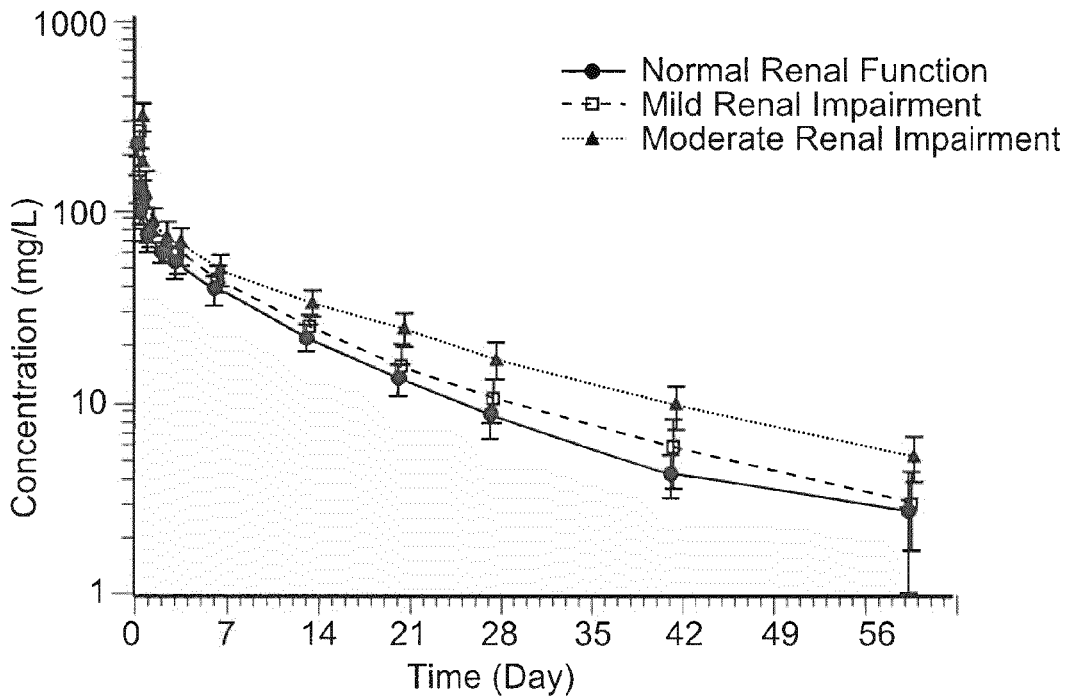

In Clinical Study VER001-13, dalbavancin administration to subjects with normal renal function and subjects with mild renal impairment resulted in comparable concentration-time profiles over the 60 day sampling interval. Through the relative treatment period, 7-days postdose, concentration-time profiles were comparable among subjects with normal renal function, and subjects with either mild or moderate renal impairment. A small increase in concentrations was observed in subjects with moderate renal impairment beyond Day 14, when concentrations were relatively low and below 40 mg/L. Dalbavancin plasma concentration-time profiles in these subjects following 1000 mg dalbavancin are shown in FIG. 18. Dalbavancin pharmacokinetic parameters are shown in Table 25. No dosage adjustment is required for patients with mild or moderate renal impairment ($CL_{CR}$>30 mL/min). The findings from this study are consistent with patients studied in the population pharmacokinetic analysis ($CL_{CR}$>50 mL/min).

Figure 19:
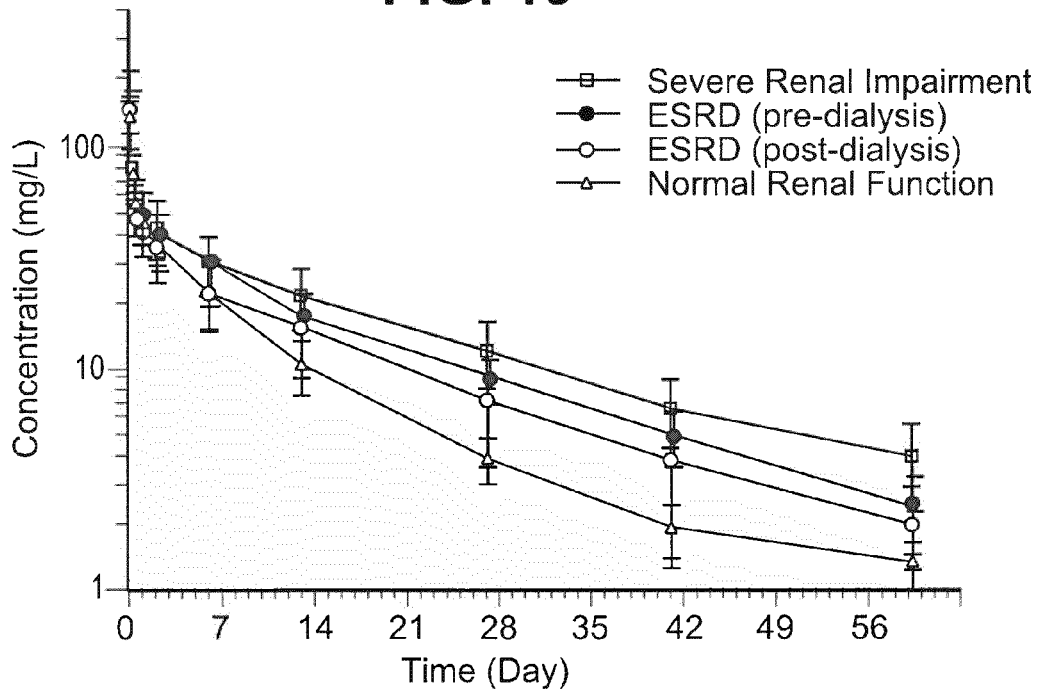
FIG. 19 provides mean dalbavancin plasma concentration-time profiles.

Dalbavancin was administered to subjects with normal renal function, subjects with severe renal impairment, and ESRD subjects in Clinical Study VER001-11. Dalbavancin concentration-time profiles observed in this study are shown in FIG. 19. Concentrations were similar among subjects with normal renal function and subjects with either severe renal impairment or ESRD through the first 12 hours, but a small and gradually increasing difference was observed in subjects with severe renal impairment. Concentrations were increased by ≦40% through the first week post-dose, and differences continued to increase through the remainder of the profile. Subjects with ESRD were divided into subjects receiving dalbavancin before or after their first dialysis session. No difference in concentration-profiles was noted between these two subgroups. Concentrations in subjects with ESRD were, however, similar to subjects with normal renal function, indicating compensation in renal insufficiency due to regularly scheduled dialysis (3-times/week). Levels in dialysate corresponding to this level of drug dialysis were too small to measure.

Figure 20:
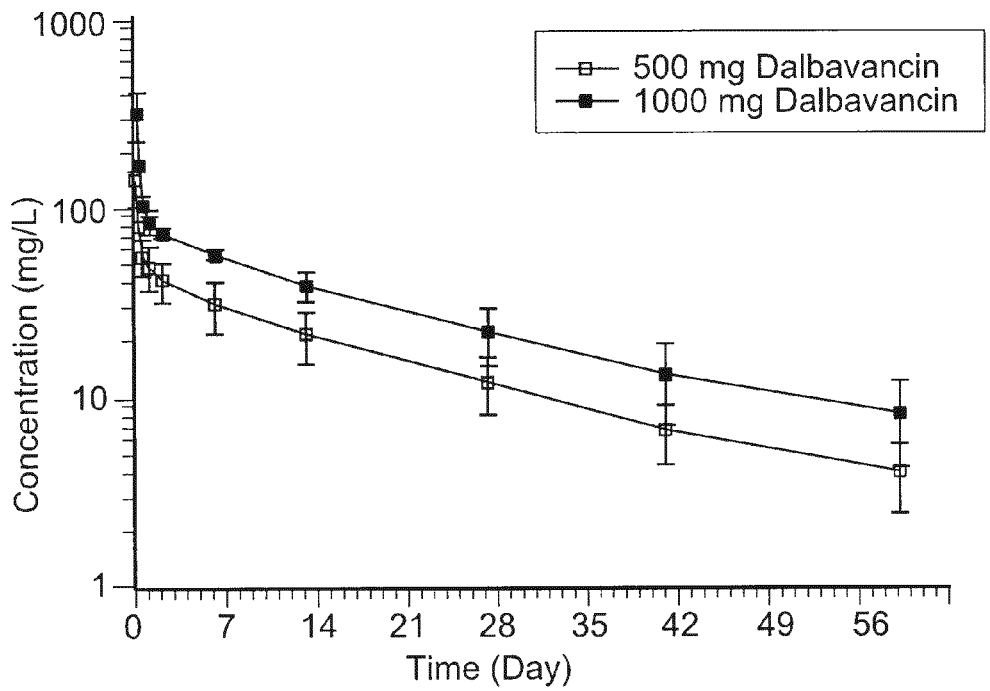
FIG. 20 provides additional mean dalbavancin plasma concentration-time profiles.
Figure 21:
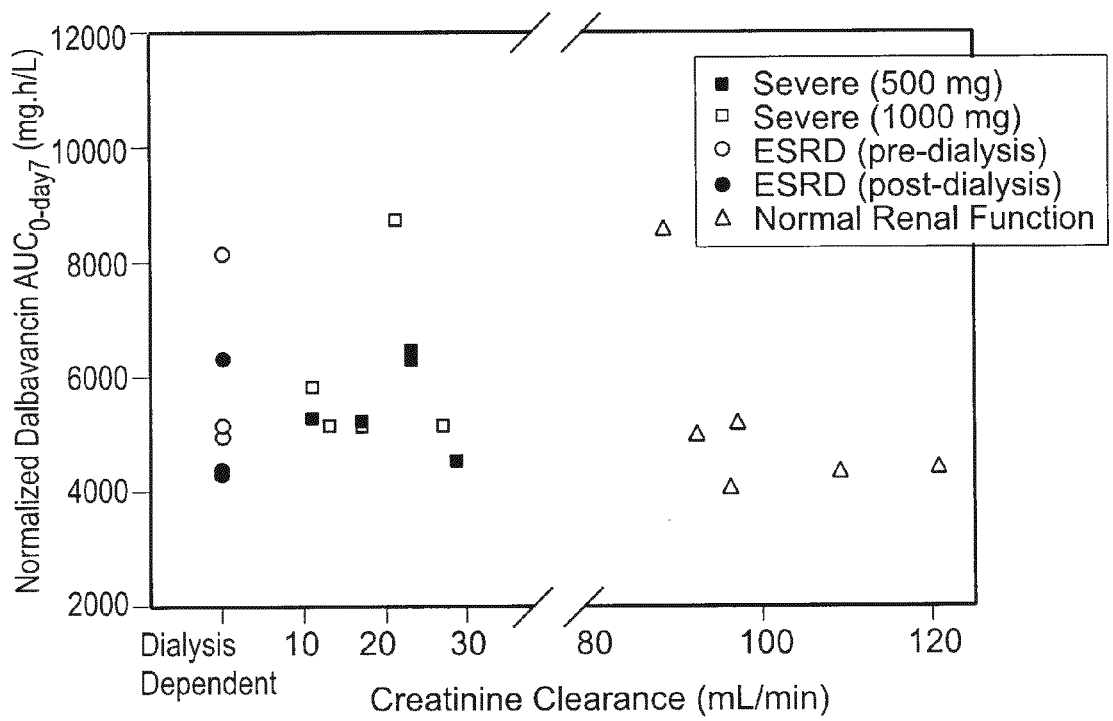
FIG. 21 provides a graph of dalbavancin exposure through the relative treatment period vs. creatinine clearance.

Dalbavancin pharmacokinetic parameters in subjects with severe renal impairment and subjects with ESRD (VER001-11) are compared to subjects with mild or moderate renal impairment (VER001-13) in Table 25. Single doses of 500 and 1000 mg were studied in subjects with severe renal impairment; concentrations and exposures were consistent with dose proportionality (FIG. 20, Table 25). Individual drug exposures within the relative treatment period ($AUC_{0-Day7}$) were generally consistent across individual $CL_{CR}$, with only a small increase in exposure observed for subjects with severe renal impairment (FIG. 21). Differences in exposures were much greater when examined across the entire concentration-time profile. Area under the plasma concentration-time curve extrapolated through infinity ($AUC_{0-inf}$) was increased 97% in subjects with severe renal impairment. Subjects with ESRD had only a 45% increase in $AUC_{0-inf}$, reflecting some compensation in renal insufficiency with regularly scheduled dialysis.

Figure 22:
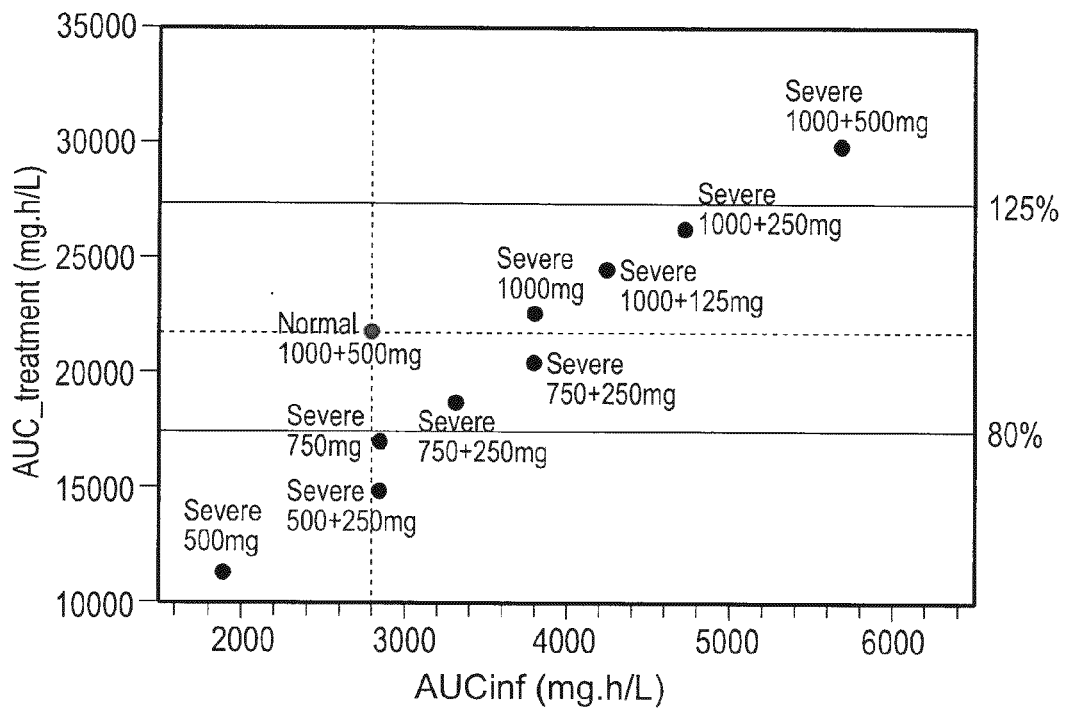
FIG. 22 provides a comparison of exposure during the relative treatment period vs. overall exposure.
Figure 23:
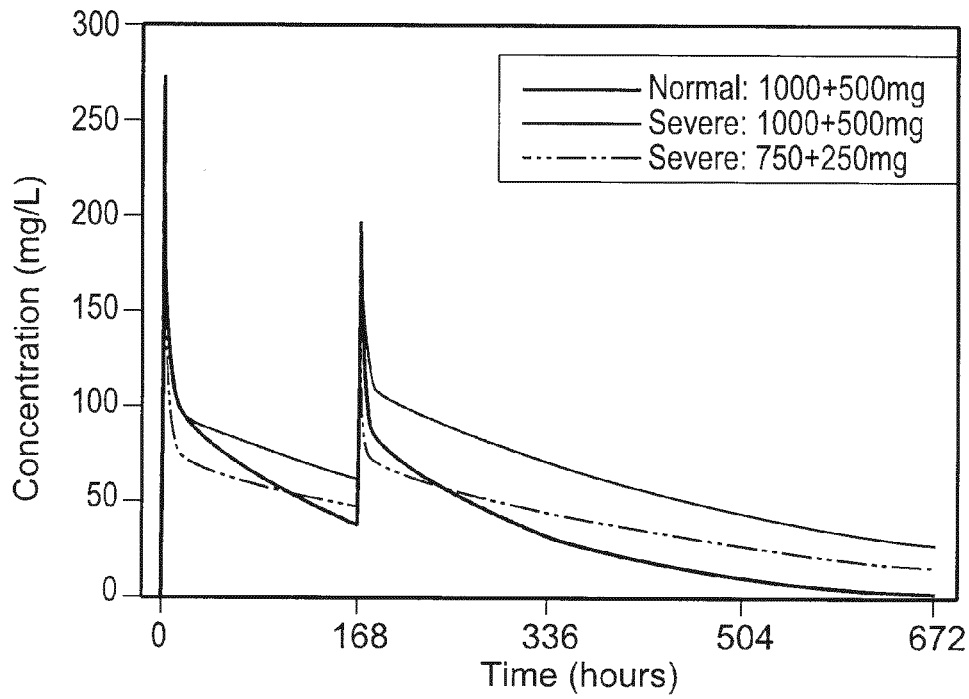
FIG. 23 provides dalbavancin concentration-time profiles for subjects with normal renal function and subjects with severe renal impairment.

Based on the pharmacokinetic parameters and simulations based on the data, a dosage adjustment is recommended for patients with severe renal impairment. The intent of the dosage adjustment is to match concentrations and exposures during the two-dose relative treatment period (14 days), while minimizing the overall exposure of drug. A total of 9 simulated dosage regimens were examined in subjects with severe renal impairment. The results of these simulations are summarized in FIG. 22, showing the exposure during the relative treatment period versus the overall exposure. A dose of 750 mg dalbavancin followed one week later by 250 mg dalbavancin is the recommended dosage adjustment for patients with a $CL_{cr}$<30 mL/min. This dosage regimen maintains concentrations above 20 mg/L, matches the treatment exposures observed for subjects with normal renal function, and minimizes the overall exposure. FIG. 23 shows dalbavancin concentration-time profiles simulated for i) subjects with normal renal function receiving 1000 mg (Day 1)+500 mg (Day 8), ii) subjects with severe renal impairment receiving 1000 mg (Day 1)+500 mg (Day 8), and iii) subjects with severe renal impairment receiving the recommended dosage adjustment of 750 mg (Day 1)+250 mg (Day 8). Patients receiving regular dialysis therapy (2 to 3 times weekly) have some compensated clearance of drug by dialysis and do not require a dosage adjustment.

Figure 24:
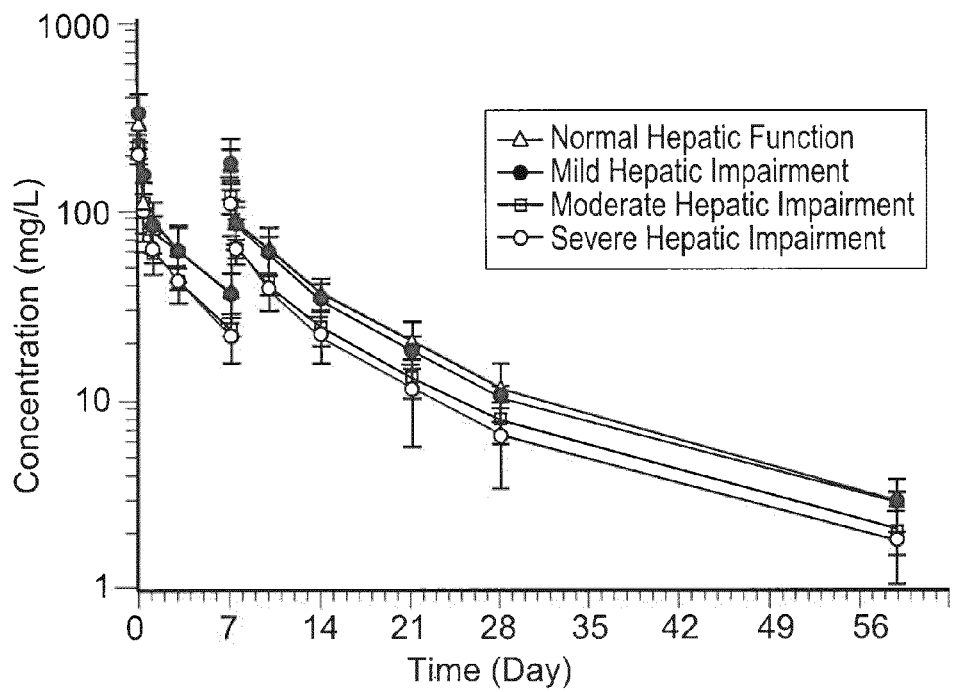
FIG. 24 provides dalbavancin plasma concentration time profiles.

Concentrations and exposures of dalbavancin did not increase with increasing degrees of hepatic impairment (FIG. 24). Dalbavancin administration to subjects with normal hepatic function and subjects with mild hepatic impairment resulted in comparable concentration-time profiles over the 60 day sampling interval. Dalbavancin administration to subjects with moderate hepatic impairment and subjects with severe hepatic impairment resulted in slightly decreased observed concentrations when compared to subjects with normal hepatic function. The drug was well tolerated across all groups.

Figure 25:
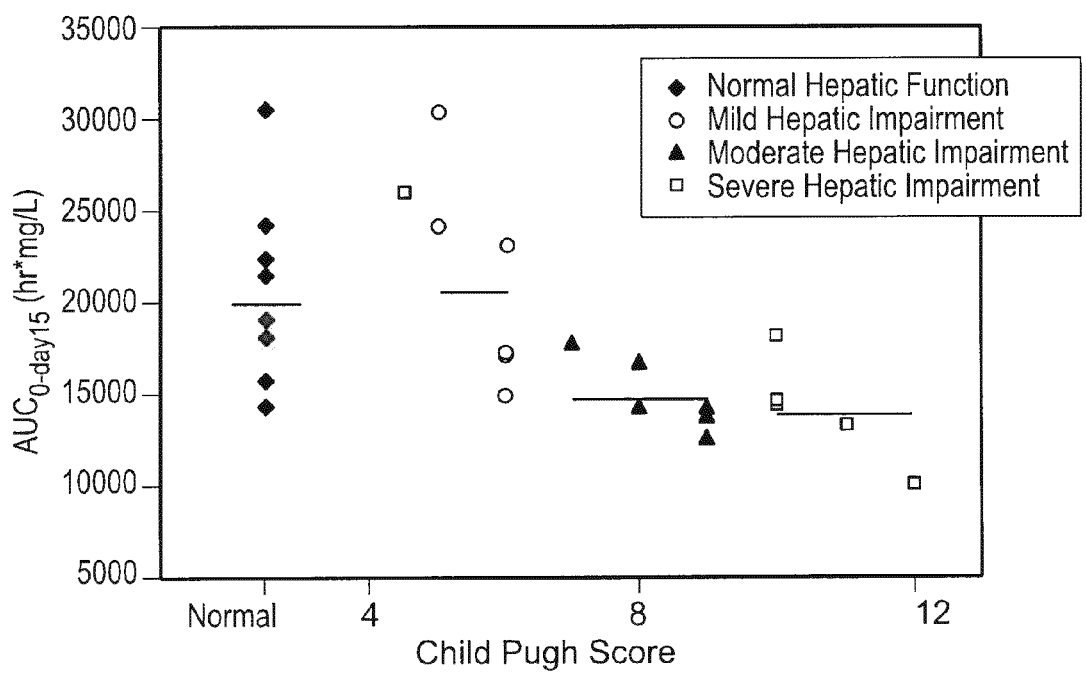
FIG. 25 provides a comparison of dalbavancin exposure through the treatment period.

The exposure to dalbavancin for subjects with normal hepatic function and subjects with mild hepatic impairment was comparable (Table 26). A trend towards a decrease in dalbavancin exposure and an increase in CL was evident for subjects with moderate hepatic impairment and subjects with severe hepatic impairment. Overall, the intersubject variability of the pharmacokinetic parameters was low and generally below 30% and although dalbavancin pharmacokinetic parameters were statistically different between the higher and lower hepatic impairment groups, the ranges of the exposure parameters significantly overlapped (FIG. 25).

Changes in dalbavancin pharmacokinetic parameters appeared to be influenced by the drug's distribution volume. Volumes of distribution increased in the same proportional or

TABLE 25

Dalbavancin Pharmacokinetic Parameters for Healthy and Renally Impaired Subjects
FOLLOWING A single dose of dalbavancin

| Mean (±SD) | Mild Renal Impairment (N = 6) | Moderate Renal Impairment (N = 6) | Normal Renal Function (N = 9) | Severe Renal Impairment (N = 6) | Severe Renal Impairment (N = 4) | ESRD Predialysis (N = 3) | ESRD Postdialysis (N = 3) | Normal Renal Function (N = 6) | Normal Renal Function (N = 3) |
|---|---|---|---|---|---|---|---|---|---|
| Study | VER001-13 | VER001-13 | VER001-13 | VER001-11 | VER001-11 | VER001-11 | VER001-11 | VER001-11 | VER001-2 |
| Dose (mg) | 1000 | 1000 | 1000 | 500 | 1000 | 500 | 500 | 500 | 1120 |
| $C_{max}$ (mg/L) | 266.8 (42.3) | 330.7 (55.7) | 248.8 (33.0) | 136.5 (21.6) | 315.3 (89.7) | 140.7 (26.4) | 145.8 (71.5) | 137.3 (39.5) | 325 (41) |
| $AUC_{0-day7}$ (mg·h/L) | 9714 (1406) | 11050 (2005) | 8992 (1362) | 6077 (1392) | 10653 (1474) | 6069 (1768) | 4969 (1153) | 5245 (1661) | 13644 (1305) |
| $AUC_{0-day14}$ (mg·h/L) | 15333 (1884) | 18060 (3065) | 13765 (1986) | 10412 (2658) | 18698 (1780) | 10620 (2881) | 8500 (2297) | 7971 (2422) | 20207 (2122) |
| $AUC_{0-inf}$ (mg·h/L) | 27047 (4084) | 37665 (7123) | 24561 (5252) | 24074 (6613) | 44497 (11483) | 19772 (5065) | 15587 (6050) | 12219 (3298) | 25790 (2447) |
| CL (L/h) | 0.0376 (0.0048) | 0.0273 (0.0045) | 0.0422 (0.0079) | 0.0222 (0.0064) | 0.0238 (0.0068) | 0.0264 (0.0063) | 0.0350 (0.0113) | 0.0429 (0.0092) | 0.0437 (0.004) |
| Vss (L) | 16.5 (3.3) | 14.7 (2.1) | 18.5 (3.6) | 13.2 (2.9) | 14.2 (0.8) | 12.8 (3.4) | 14.6 (3.2) | 15.0 (4.2) | 8.49 (1.05) |
| $t_{1/2}$ (h) | 389 (59) | 432 (43) | 417 (108) | 454 (102) | 469 (103) | 376 (63) | 347 (78) | 333 (91) | 149 (3.6) |

Example 6

Hepatic Impairment

Dalbavancin is eliminated by both renal and non-renal pathways and dalbavancin will likely be used in patients with various degrees of hepatic impairment. The safety and pharmacokinetics of dalbavancin in subjects with various degrees of hepatic impairment was examined in Clinical Study VER001-12. The study enrolled otherwise healthy subjects with mild, moderate, or severe hepatic impairment (Child-Pugh scores 5 to 6, 7 to 9, and 10 to 15, respectively) and matched control subjects with normal hepatic function. Subjects were given a single 1000 mg IV dose of dalbavancin on Day 1 followed by a 500 mg IV dose of dalbavancin on Day 8.

inversely proportional manner as CL and AUC. The drug terminal elimination half-life was virtually unchanged across the groups. Subjects with moderate and severe hepatic impairment, who have significantly more ascites and edema, have larger volumes of drug distribution and subsequently slightly lower drug exposures.

There was overlap in concentrations through the profiles across groups, with mean concentrations remaining above 20 mg/L in all groups through the intended treatment duration of 14 days. There was also overlap in drug exposure across the groups (FIG. 25). Even with a decrease in mean exposure, subjects with severe hepatic impairment still had a drug exposure through the relative treatment period (14 days) that exceeded parameters required for therapy. No dosage adjustment of dalbavancin is required for patients with any degree of hepatic impairment.

TABLE 26

Dalbavancin Pharmacokinetic Parameters for Healthy and Hepatically Impaired Subjects FOLLOWING 1000 MG dalbavancin ON Day 1 and 500 MG dalbavancin on Day 8

| Mean (±SD) | Mild Hepatic Impairment (N = 6) | Moderate Hepatic Impairment (N = 6) | Severe Hepatic Impairment (N = 5) | Normal Hepatic Function (N = 9) |
|---|---|---|---|---|
| $C_{max1}$ (mg/L) | 331.7 (80.6) | 227.2 (37.5) | 199.0 (30.4) | 278.3 (52.6) |
| $C_{max2}$ (mg/L) | 177.0 (62.4) | 122.7 (27.2) | 118.9 (23.9) | 166.3 (42.9) |
| $AUC_{0\text{-}day\,8}$ (mg · h/L) | 11146 (3478) | 7710 (1099) | 7561 (1540) | 10577 (2493) |
| $AUC_{0\text{-}day\,15}$ (mg · h/L) | 21158 (5808) | 14826 (1925) | 14112 (2911) | 20473 (4883) |
| $AUC_{0\text{-}inf}$ (mg · h/L) | 33117 (6479) | 23628 (3527) | 21639 (5940) | 33851 (8184) |
| CL (L/h) | 0.0466 (0.0084) | 0.0647 (0.0098) | 0.0736 (0.0202) | 0.0466 (0.0110) |
| Vss | 18.1 (5.2) | 24.4 (3.0) | 25.2 (4.0) | 18.3 (3.7) |
| $t_{1/2}$ (h) | 323 (27) | 320 (24) | 322 (68) | 321 (24) |

Example 7

Protein Binding of Dalbavancin Using Isothermal Titration Microcalorimetry

Binding of dalbavancin to proteins was measured by isothermal titration microcalorimetry (ITC) in 20 mM phosphate, 150 mM NaCl, pH 7.4 at 25 and 37° C. using a Microcal VP-ITC instrument. In a typical experiment, 25×10 µl of protein (~150 µM) was injected into a calorimeter cell containing dalbavancin solution (~5 µM). Actual protein and dalbavancin concentrations were determined by measuring absorbence at 280 nm. Control experiments included injections of protein into buffer (in the absence of dalbavancin) to account for the heats of dilution of protein under identical conditions. For comparison, similar experiments with some necessary modifications were performed using teicoplanin.

Experiments with dalbavancin were conducted with each of the following proteins: human albumin; dog albumin; rat albumin; bovine albumin; and human α-glycoprotein. Teicoplanin was studied with human albumin and α-glycoprotein. A comparison of binding affinities at two different temperatures is shown in Table 27.

TABLE 27

Comparison of apparent binding affinities (Ka, ×10⁵ M⁻¹)

| | 25° C. | 37° C. |
|---|---|---|
| Dalbavancin | | |
| Human albumin | 1.35 (±0.2) | 1.33 (±0.15) |
| Rat albumin | 3.1 (±0.5) | 2.8 (±1.8) |
| Dog albumin | 0.62 (±0.09) | 0.50 (±0.13) |
| Bovine albumin | 1.38 (±0.14) | |
| α-glycoprotein | 1.84 (±0.36) | 4.8 (±2.3) |
| Teicoplanin | | |
| Human albumin | 0.96 (±0.08) | |
| α-glycoprotein | 0.07 (±0.01) | |

The ±errors quoted are the standard deviations obtained from the fitting routine.

Integrated heat effects, after correction for heats of dilution, were analyzed by non-linear regression using a simple single-site binding model with the standard Microcal ORIGIN software package. Raw data (µcal/sec) for each injection were integrated to give the total heat effect per addition, then divided by amount of injectant to give kcal/mole of injectant. The same integration was applied for control dilution effects, and this was subtracted from the actual titration data. This provided a differential of the binding curve in which the extent of binding is proportional to the total heat liberated (or absorbed). This was then analyzed by non-linear regression methods in terms of various standard binding models. The simplest model assumes simple non-competitive binding equilibrium, and gives three parameters:

$K_a$(=1/Kdiss) is the binding association (dissociation constant)

$\Delta H$=the enthalpy of binding (the size of signal related to binding)

N=number of binding sites (assuming the binding model is correct)

Figure 6:
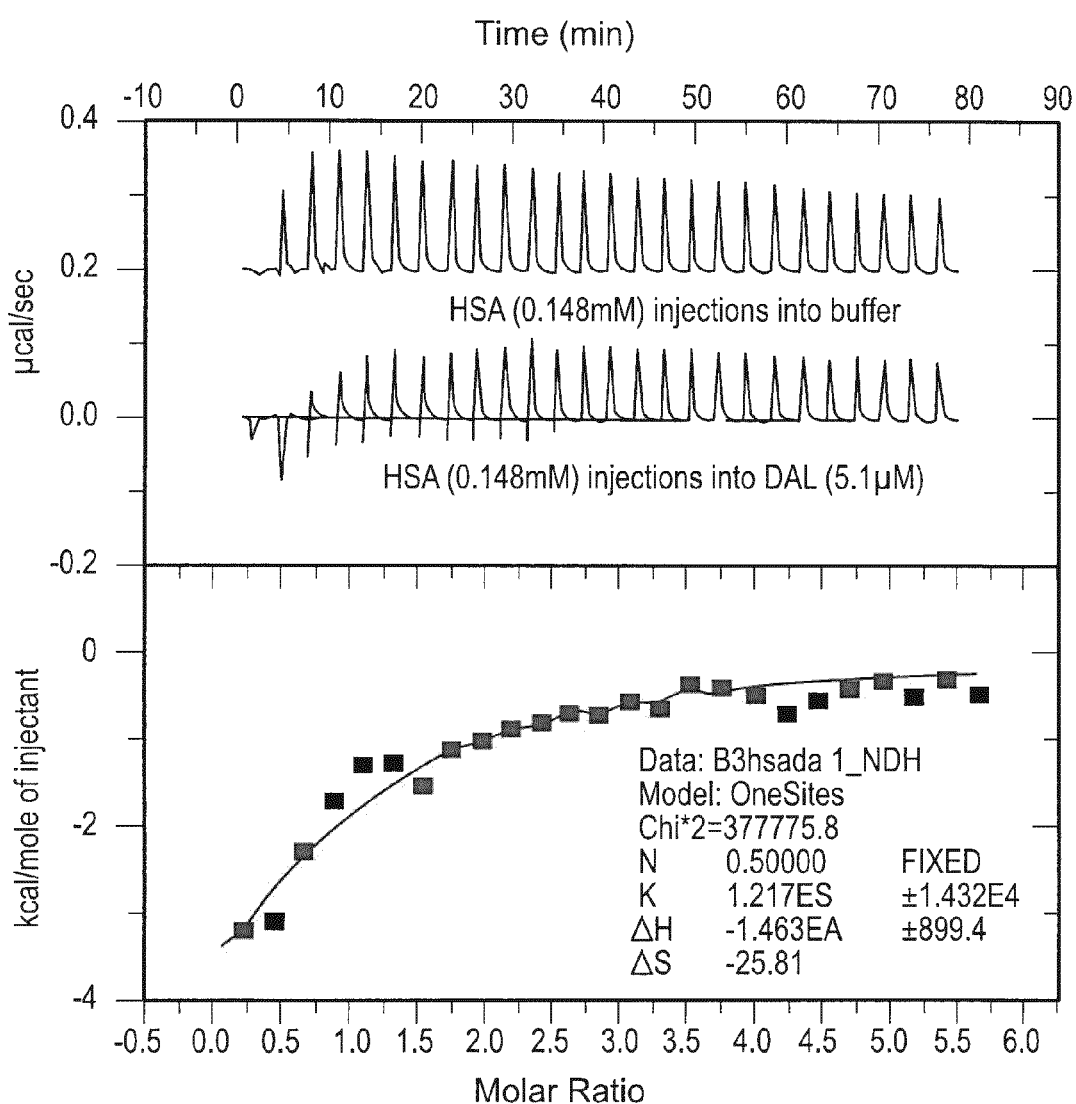
FIG. 6 depicts isothermal titration calorimetry data for dalbavancin binding to human serum albumin (top) and a graphical representation of the data fitted to a curve determined from a 2:1 binding model of dalbavancin:protein (bottom).

Assuming non-competitive binding, N is the (relative) number of moles of injectant required to saturate all the available binding sites in the sample. For the dalbavancin experiments, dalbavancin is the "sample" and the protein (HSA, etc.) is the "injectant." These preliminary results indicate that the binding is relatively weak and, because of the poor solubility of dalbavancin, it is difficult to determine the binding stoichiometry (N) unambiguously. However, as seen in FIG. 6, in all cases, the data fits well with N<1 (i.e., less than one to one protein to dalbavancin). Consequently, a value of N=0.5 means that it only takes half as many moles of protein to bind all the dalbavancin as would be expected. In other words, each protein apparently binds two dalbavancin molecules. It is possible that dalbavancin forms a dimer that binds 1:1 with a protein. Results of binding stoichiometry modeling suggests that two dalbavancin molecules are bound to one molecule of protein, unlike teicoplanin, which exhibits 1:1 binding.

Table 28 presents the calculated percent bound for antibiotic concentrations in the range 1-500 µM, assuming physiological concentrations of human serum albumin (6×10⁻⁴ M) and α-glycopeptide (1.5×10⁻⁵ M). To relate this to the clinical situation, the peak concentration of dalbavancin in man is approximately 300 mg/L, or 165 µM.

TABLE 28

Calculated percent Binding of Teicoplanin and Dalbavancin to Plasma Proteins

| Concentration of antibiotic (µM) | Dalbavancin | Teicoplanin |
|---|---|---|
| Human albumin | | |
| 1 | 98.8 | 98.3 |
| 10 | 98.8 | 98.3 |
| 100 | 98.7 | 98.0 |
| 165 | 98.6 | ND |
| 250 | 98.5 | ND |
| 500 | 98.0 | ND |

TABLE 28-continued

Calculated percent Binding of Teicoplanin and Dalbavancin to Plasma Proteins

| Concentration of antibiotic (μM) | Dalbavancin | Teicoplanin |
|---|---|---|
| Human α-glycoprotein | | |
| 1 | 73.0 | 9.6 |
| 10 | 68.2 | 9.1 |
| 100 | 26.2 | 6.0 |
| 165 | 16.9 | ND |
| 250 | 11.4 | ND |
| 500 | 5.9 | ND |

ND = Not done

In these experiments, the binding of dalbavancin to human serum albumin exceeds 98%. The fraction bound is fairly constant across the selected range of dalbavancin concentrations, i.e. 1-500 μM. This range encompasses the therapeutic concentrations in man. Binding of dalbavancin to α-glycoprotein is much greater than that of teicoplanin. Dalbavancin demonstrates high capacity and low affinity for plasma proteins of different origin, with similar $K_a$ values across proteins from all species tested. These results help to explain some of the unique pharmacokinetic characteristics of dalbavancin. The binding and formation of a 2:1 dalbavancin:protein complex also explains the prolonged half-life, and the apparent volume of distribution, which approximates extracellular water volume. The low affinity helps explain the observed in vivo activity, which greatly exceeds what would be expected for a compound with a free fraction close to 1%. The high capacity for plasma proteins helps to explain the relatively high plasma concentrations achieved in spite of poor solubility of the compound at physiological pH.

Example 8

Pharmacokinetic Attributes and Tissue Distribution of Dalbavancin in Rats

Two studies were performed in rats administered a single IV infusion of 20 mg/kg [$^3$H]-dalbavancin. Excreta and more than 40 different tissues were collected through 70 days post-administration, and the tissue distribution and pharmacokinetics of drug-derived radioactivity were determined.

HPLC-purified [$^3$H]-dalbavancin was used for these studies. Radiolabeled drug was produced via tritium exchange and purified by HPLC.

Rat Mass Balance Study

Mass balance studies were conducted to determine the excretion pattern of dalbavancin following a single intravenous (IV) infusion of dalbavancin in male rats.

Fifteen male Sprague-Dawley rats received a single IV dose of $^3$H-dalbavancin (20 mg/kg, 100 μCi/rat). Following dose administration, urine and feces were collected at 24 hour intervals to 14, 36, and 70 days after the dose (3 rats/final collection time). Water and methanol cage washes were also collected. Carcasses were analyzed at the end of the collection period. All samples were analyzed for total radioactivity content by liquid scintillation counting (LSC).

Following IV administration of $^3$H-dalbavancin in rats, drug-derived radioactivity was eliminated in both urine (~⅔ of excreted radioactivity) and feces (~⅓ of excreted radioactivity). Approximately half of the radioactivity administered was eliminated in the urine and feces within the first week, which is consistent with a plasma $t_{1/2}$ of approximately 1 week. At 70 days post dose, only 4.5% of the dose remained in the carcass. Negligible radioactivity was recovered in the cage washes. Virtually all of the administered radioactivity was accounted for (urine, feces, carcass, cage washes, and tritium exchange) during the study.

Rat Quantitative Tissue Distribution (QTD) Study

Quantitative tissue distribution studies were conducted to assess the tissue distribution of dalbavancin following a single IV infusion of dalbavancin to male rats.

Forty-one male Sprague-Dawley rats received a single IV infusion of $^3$H-dalbavancin (20 mg/kg, 50 μCi/rat). Rats (3 per time-point) were euthanized at 12, 24, 48, 72, 96, 120, 144, 168, 336, 840, 1176 and 1680 hours post dose for collection of blood, plasma, and tissues (including carcass). All samples were analyzed by LSC.

Concentration-time profiles were determined for more than 40 tissues, including kidney, liver, spleen, blood, plasma, lung, and skin. Concentrations and $t_{1/2}$ values of drug-derived radioactivity in tissues, including skin, were comparable to those observed in plasma. Dalbavancin was found to be rapidly and extensively distributed with all tissues having quantifiable concentrations of drug-derived radioactivity within 12 hours after post-infusion. Most tissues reached maximum concentration ($C_{max}$) within 24 h after the dose. Recovered radioactivity after 5 days was <5% of the dose in any single tissue. By 70 days after the dose, only the carcass retained >1% (2.34%) of the administered radioactivity. Thus, dalbavancin did not accumulate in any single tissue, organ, or blood cellular component. Concentrations of radioactivity in the CNS were low but detectable in this healthy animal model. Dalbavancin was found to penetrate the skin with concentrations of drug-derived radioactivity that were as high as or higher than in plasma. Blood to plasma ratio of drug-derived radioactivity remained relatively constant over time and was <1.

As part of the QTD studies, bile samples were collected from bile duct cannulated rats (4 animals) through 384 h (16 days) post-dose. Almost 11% of the dose was recovered in the bile over 384 h after the dose. This represents the majority of the drug-derived radioactivity found in feces.

Example 9

Pharmacodynamic Activity of Dalbavancin

The goal of antimicrobial therapy is to provide active concentrations at the site of infection for an adequate period of time to eradicate invading pathogens. The primary method for assessing antimicrobial activity in vitro is determination of the minimum inhibitory and bactericidal concentrations (MIC and MBC). However, these parameters only measure net effects for a prescribed incubation period and do not characterize the time course of antimicrobial activity. The MBC does not determine if the rate and extent of bactericidal activity can be enhanced by increasing concentrations of drug. Furthermore, MIC determinations do not measure whether there are inhibitory effects on bacteria that persist after drug removal.

An increasing number of studies suggest that the rate of bactericidal activity, its dependence on concentration or the time of exposure, and the presence or absence of a postantibiotic effect more clearly describe the time course of antimicrobial activity and are important pharmacodynamic parameters for determining optimal dosing regimens. For example, bacterial killing by beta-lactam antibiotics shows little concentration dependence and the extent of killing is due primarily to the duration of exposure. In addition, beta-lactams produce short or no postantibiotic effects (PAE) with gram-negative bacilli. Thus, one would predict that dosing regimens that maintain drug levels above the MIC for a sufficient period of time would demonstrate the best efficacy. This has been confirmed in several animal models. On the other hand, fluoroquinolones exhibit concentration-dependent killing and produce prolonged in-vivo postantibiotic effects. One would predict that the amount of drug rather than the frequency of dosing would be the important determinant of efficacy for these drugs. This has also been confirmed in several animal models. More importantly, the magnitude of the pharmacokinetic/pharmacodynamic parameter required for efficacy for both beta-lactams and fluoroquinolones has been similar in animal infection models and human infections.

The following studies were designed to characterize the in-vivo pharmacodynamic characteristics of dalbavancin. The impact of the dosing regimen on the in vivo efficacy of dalbavancin in the experimental thigh infection model in neutropenic mice was determined. Studies were also performed to investigate [1] which pharmacokinetic parameter (peak serum level, area under the concentration-versus-time curve (AUC), the duration of time serum levels exceed the MIC) best predicts efficacy of dalbavancin and [2] whether the magnitude of the PK/PD parameter required for efficacy is similar among common gram-positive bacteria including penicillin-resistant pneumococci and methicillin-resistant S. aureus. Lastly, the effect of infection site on the activity of dalbavancin against both S. pneumoniae and S. aureus in both the thigh and pneumonia infection models was determined.

Study Organisms and MICs to Dalbavancin

The study organisms and their MICs to dalbavancin are listed in Table 29. MICs were determined in MHB by standard NCCLS microdilution techniques. MHB was supplemented with 3% lysed horse blood for MIC determinations with S. pneumoniae. All MICs were performed at least in duplicate.

TABLE 29

In Vitro Activity of Dalbavancin Against S. pneumoniae and S. Aureus Strains.

| Organism | Dalbavancin MIC/MBC (mg/L) | Penicillin MIC (mg/L) | Methicillin MIC (mg/L) |
|---|---|---|---|
| S. pneumoniae strain | | | |
| 1199 | 0.004 | 1.0 | — |
| 1293 | 0.004 | 2.0 | — |
| 1325 | 0.008 | 2.0 | — |
| 1329 | 0.008 | 2.0 | — |
| 10813 | 0.03 | 0.008 | — |
| S. aureus strain | | | |
| 25923 | 0.12/0.50 | — | 0.12 |
| 33591 | 0.12/0.25 | — | >8.0 |
| 31005 | 0.06/0.25 | — | 0.12 |
| MRSA | 0.12/0.25 | — | >8.0 |
| Smith | 0.06/0.50 | — | 0.12 |
| 307109 | 0.06/0.12 | — | >8.0 |

Five pneumococcal and six staphylococcal organisms were utilized. The dalbavancin MICs for the pneumococci ranged from 0.004 to 0.03 mg/L. The range of MICs for the S. aureus isolates were more narrow and higher than those against pneumococci, ranging from 0.06-0.12 mg/L.

Pharmacokinetics

Figure 44:
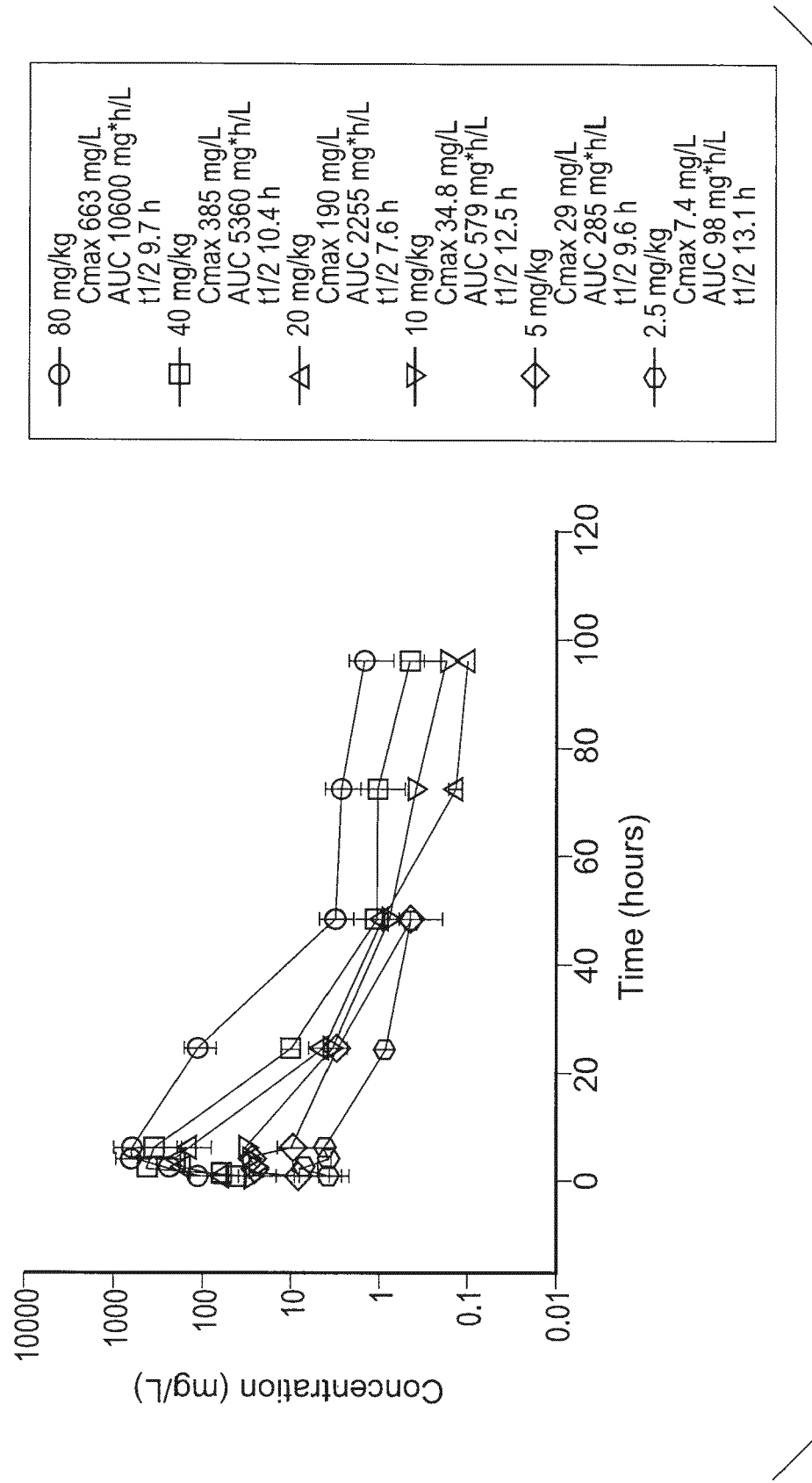
FIG. 44 provides the plasma pharmacokinetics of dalbavancin in thigh-infected mice.

The plasma pharmacokinetics of dalbavancin in thigh-infected neutropenic Swiss ICR mice are shown in FIG. 44. Neutropenia in this and all other studies was produced by injections of cyclophosphamide, 150 mg/kg 4 days prior to study, 100 mg/kg 1 day prior to study and 100 mg/kg every 48 h after start of infection until end of study. Neutrophil counts remained less than 100/mm$^3$ for the duration of study. Doses of 2.5, 5, 10, 20; 40, and 80 mg/kg were studied. Drug was administered by intraperitoneal injection of 0.2 ml volume. Blood was removed from groups of three mice by retroorbital aspiration into heparinized capillary tubes at 0.5, 1, 2, 4, 6, 24, 48, 72, and 96 hours after dosing. Plasma was separated, and dalbavancin plasma concentrations were measured using a microbiologic assay with Bacillus subtilus as the test organism. Peak levels were observed by 4-6 hr. The half-lives of dalbavancin were determined by linear least-squares regression. AUC was calculated by the trapezoidal rule from mean concentrations. The AUC was estimated at 24, 36, 48, 72, 96 hr and extrapolated to infinity. The 24 h AUC was calculated as the 6-day AUC divided by 6. Dalbavancin exhibited linear pharmacokinetics. The half-life was prolonged and varied from 7.6 to 13.1 hours.

Protein Binding

The impact of drug binding to serum and serum proteins was investigated by comparing the MIC of dalbavancin for two strains of S. aureus in broth, infected mouse serum human serum, and albumin (Table 30). MICs for both strains in broth was 0.12 mg/L. The MICs (arithmetic) in 95% mouse serum increased to 32 mg/L. MICs in mouse serum ultrafiltrate rose to only 0.5 mg/L suggesting that the great majority of the difference in the MICs was do to protein binding. Similar study with human serum and albumin resulted in an increase to only 8 mg/L. Based upon the MIC difference between broth and mouse serum, the degree of protein binding was estimated to be 99.6%. This degree of binding was considered in subsequent pharmacodynamic analyses. The degree of binding in human serum would be estimated to be 96%.

TABLE 30

Impact of Serum, Serum Ultrafiltrate, and Human albumin on the In Vitro Activity of Dalbavancin Against Selected S. aureus Strains.

| Organism | MIC Broth | MIC 95% Mouse Serum | MIC 95% Human Serum | MIC 95% Human Albumin | MIC 95% Mouse Serum Ultrafiltrate |
|---|---|---|---|---|---|
| S. aureus strain | | | | | |
| 25923 | 0.12 | 32 | 8.0 | 8.0 | 0.5 |
| MRSA | 0.12 | 32 | 8.0 | 8.0 | 0.5 |

Infection Models

The murine thigh-infection model was used for all organisms throughout the various studies. In this well-established model, approximately $10^6$ Cfu of the study organisms are injected into one or both thighs (in 0.1 ml) two hours before starting therapy. The number of organisms in the thigh at the start of therapy in the following studies varied from $10^{7.15-7.59}$ cfu/thigh. The murine lung-infection model was used only with a single isolate of either S. pneumoniae or S. aureus. In this model, mice are infected by a intranasal inoculation of (approximately $10^{8.5}$ cfu/ml) of 50 ul via the nares of anesthetized mice. Treatment begins 2-hrs after inoculation at which time the mice had $10^{7.4-7.6}$ cfu/lung.

In Vivo Time Kill

Figure 45:
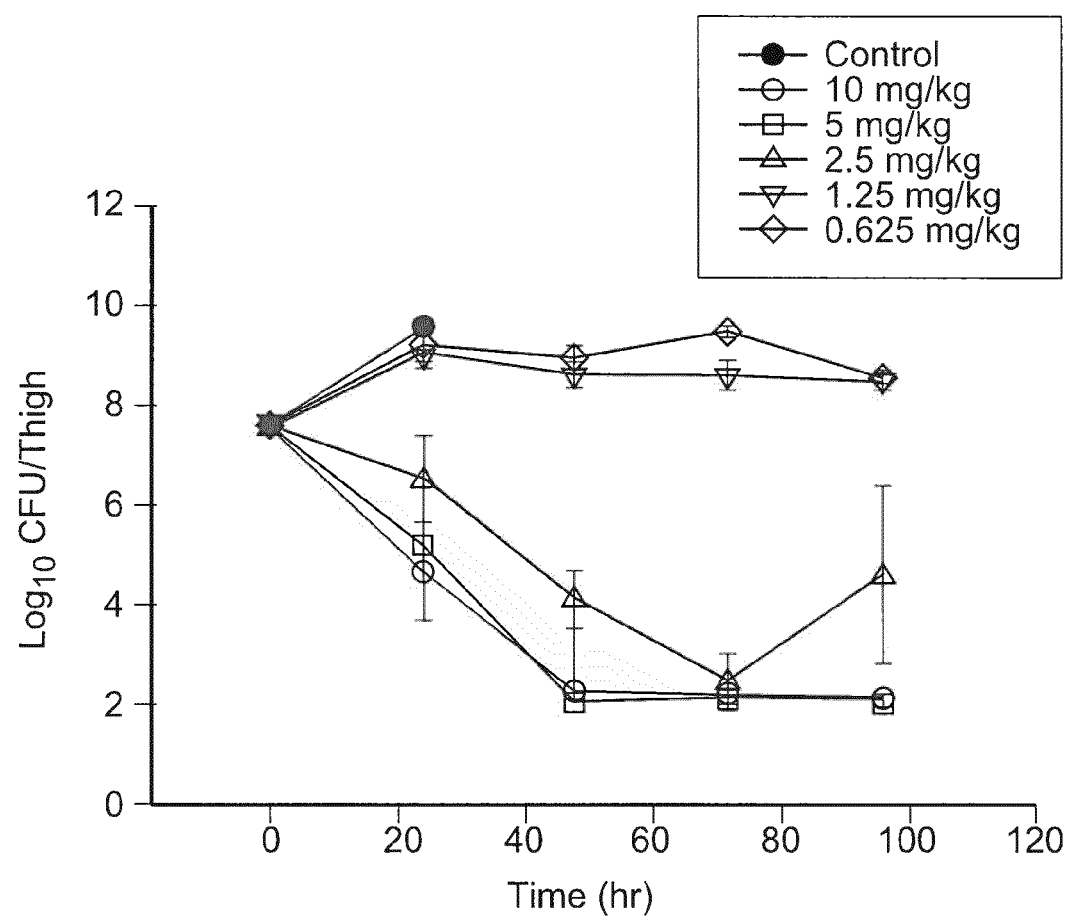
FIG. 45 provides the effect of single doses of dalbavancin on the in vivo killing of S. pneumoniae over time.
Figure 46:
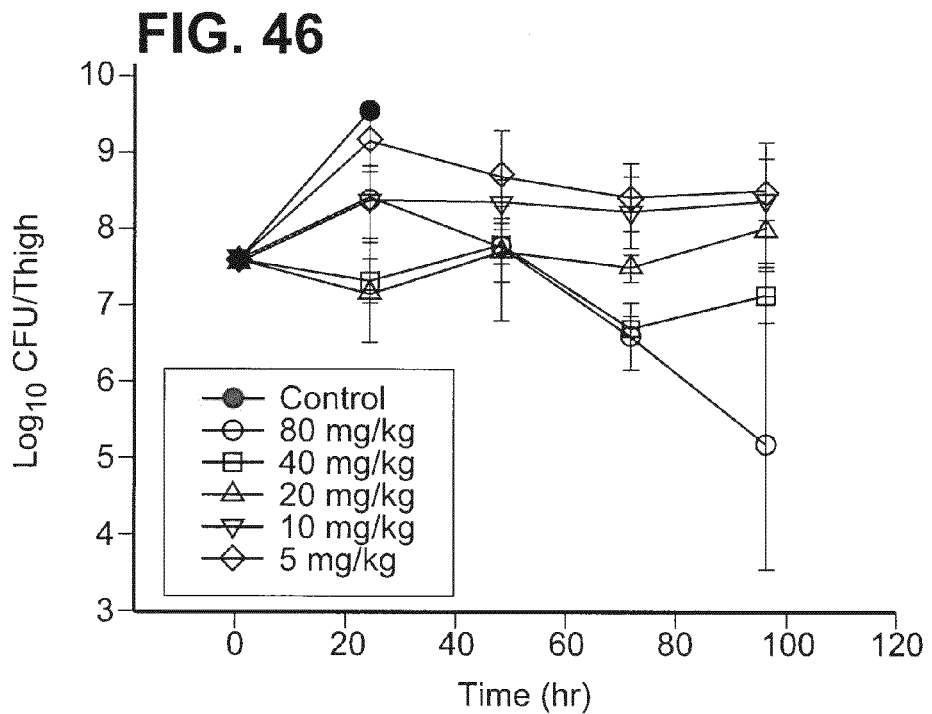
FIG. 46 provides the effect of single doses of dalbavancin on the in vivo killing of S. aureus over time.

The effect of a single doses of dalbavancin on the in-vivo killing of a strain of S. pneumoniae and S. aureus over time are shown in FIGS. 45 and 46. Each point represents the mean of 4 thighs. Five dose levels, ranging 16-fold were used. The dose levels used in the study against S. aureus ranged from 5 to 80 mg/kg. The dose levels used in study against S. pneu-

Figure 47:
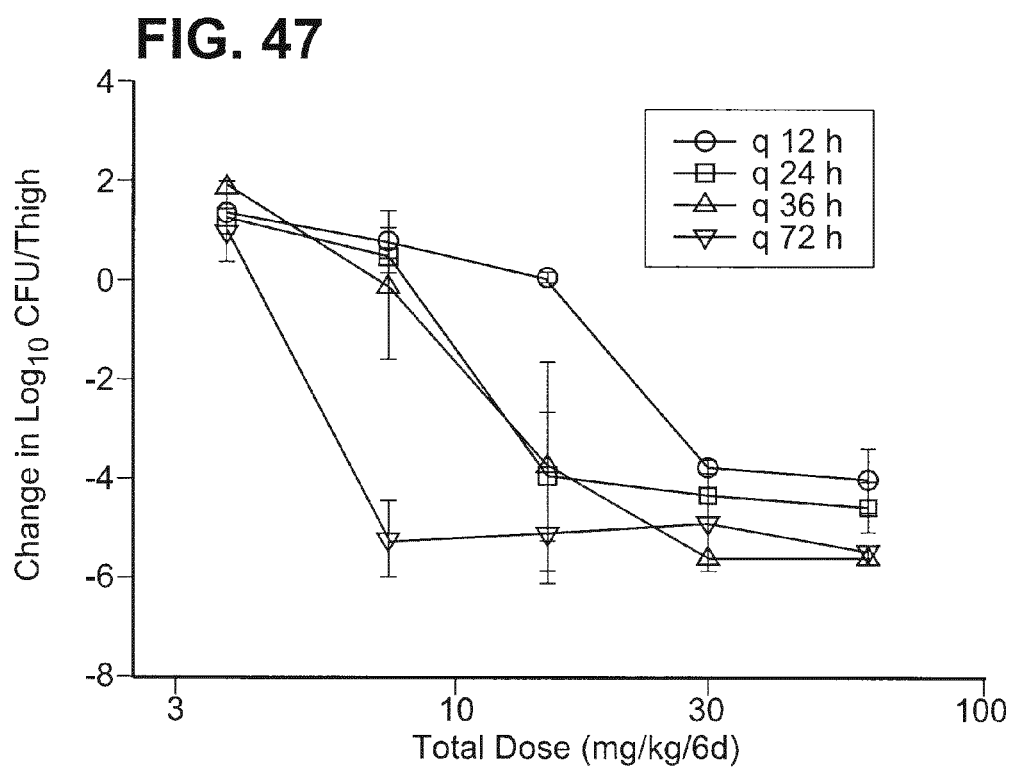
FIG. 47 provides the relationship between dalbavancin dosing interval and efficacy against S. pneumoniae.
Figure 48:
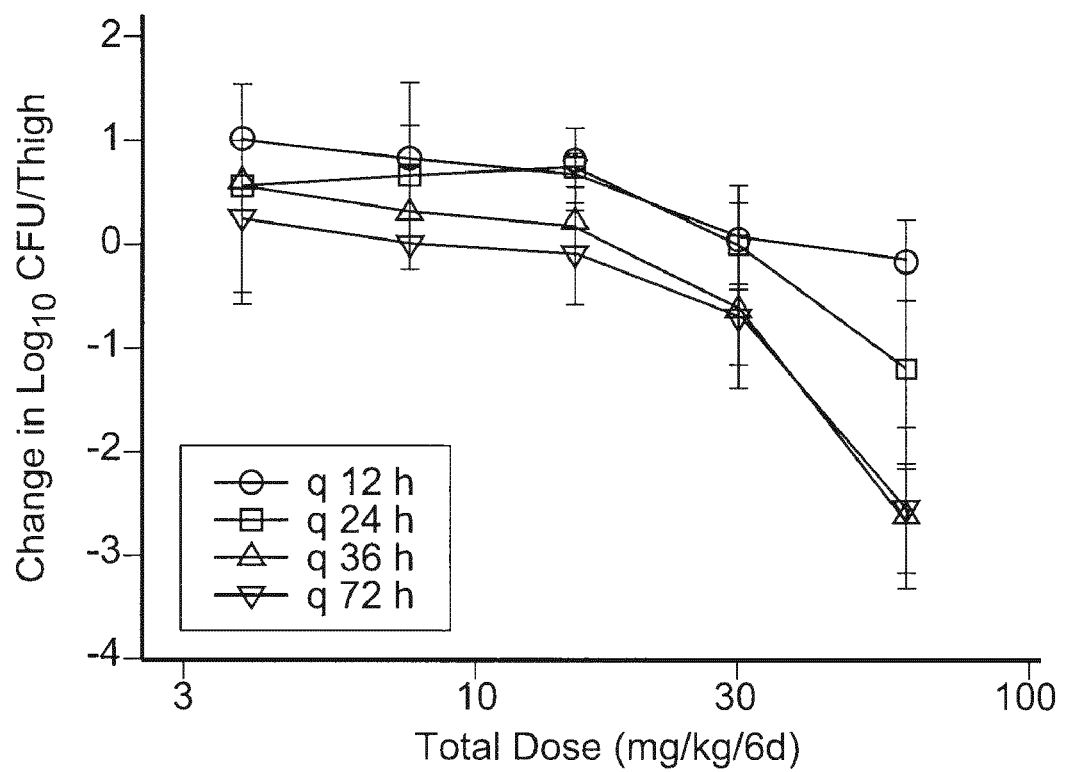
FIG. 48 provides the relationship between dalbavancin dosing interval and efficacy against S. aureus.

*moniae* ranged from 0.625 to 10 mg/kg. The extent of killing both species was extensive (>2 log with the highest doses studied). However, the extent and rate of killing of the pneumococcal isolate was greater than the staphylococcal strain. Study with the two highest doses of dalbavancin resulted in killing of *S. aureus*. Three of the five dose levels used in study against *S. pneumoniae* reduced the burden of organisms nearly four log in the thighs of infected mice Dosing Regimen Studies In these studies, multiple dosing regimens varying the dose and dosage interval were administered intraperitoneally in 0.2 ml volumes to groups of mice for 144 h (6 days). The dosing intervals chosen were 12, 24, 36, and 72 hours. Five different doses (two-fold increases) were used. Study against *S. aureus* utilized total dose (mg/kg/6d) levels ranging from 30 to 480 mg/kg/6d. Study against *S. pneumoniae* utilized total dose levels (mg/kg/6d) ranging from 0.6125 to 10 mg/kg/6d. FIGS. 47 and 48 illustrate the dose-response curves for dalbavancin at the different dosing intervals for the strain of *S. pneumoniae* and *S. aureus* in the thighs of neutropenic mice. Each point represents the mean of 4 thighs. In general, increasing the dosing interval resulted in a slight shift of the dose response curves to the left indicating more efficacy with the regimens for which large doses were administered infrequently.

Each of the dose-response curves was also mathematically characterized using a maximum effect model. This methodology uses the Hill equation to estimate by non-linear regression the maximum effect (Emax), the dose (P50) required to obtain 50% of the Emax, and the slope of the dose-response relationship. From these parameters we could then calculate the dose required to produce a net bacteriostatic effect over the 144 hour treatment period as well as the doses necessary to produce a 1 and 2 log-reduction in organism burden. The static dose and the dose associated with a 1 and 2 log kill for each of the drug organism combinations and the various dosing regimens are shown in Table 31.

study against *S. aureus*. The only dosing regimens that produced a 1 and 2 log kill against *S. aureus* were the 36 and 72 h intervals.

Pharmacodynamic Parameters Correlating with Efficacy

Figure 49:
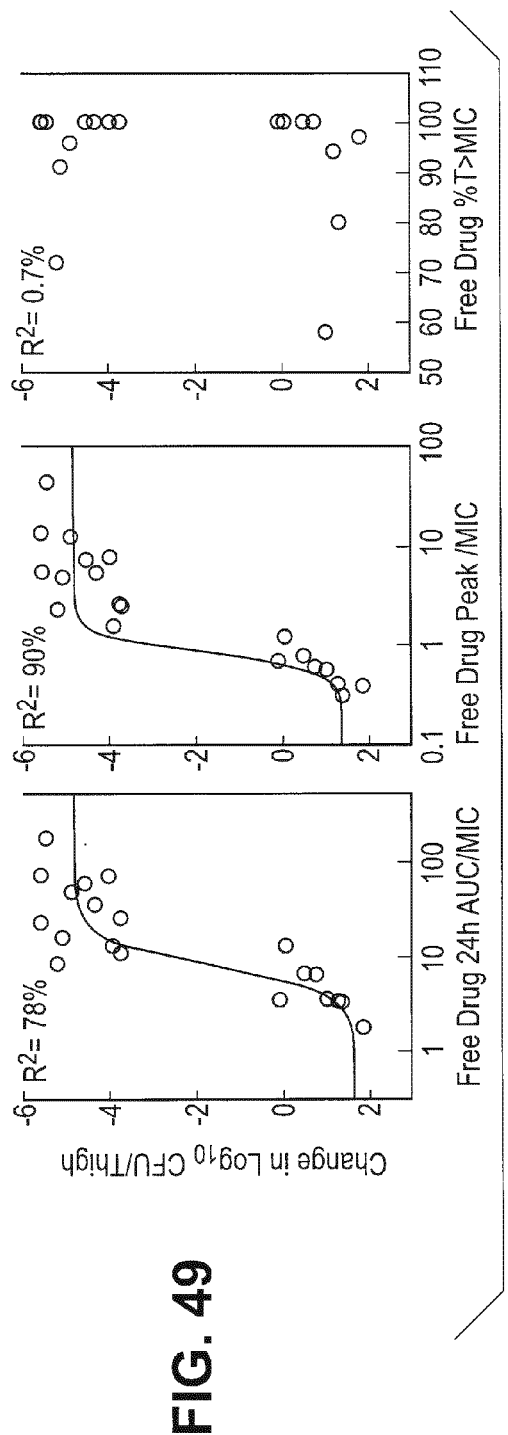
FIG. 49 provides the relationship between dalbavancin PK/PD parameters and efficacy against S. pneumoniae.
Figure 50:
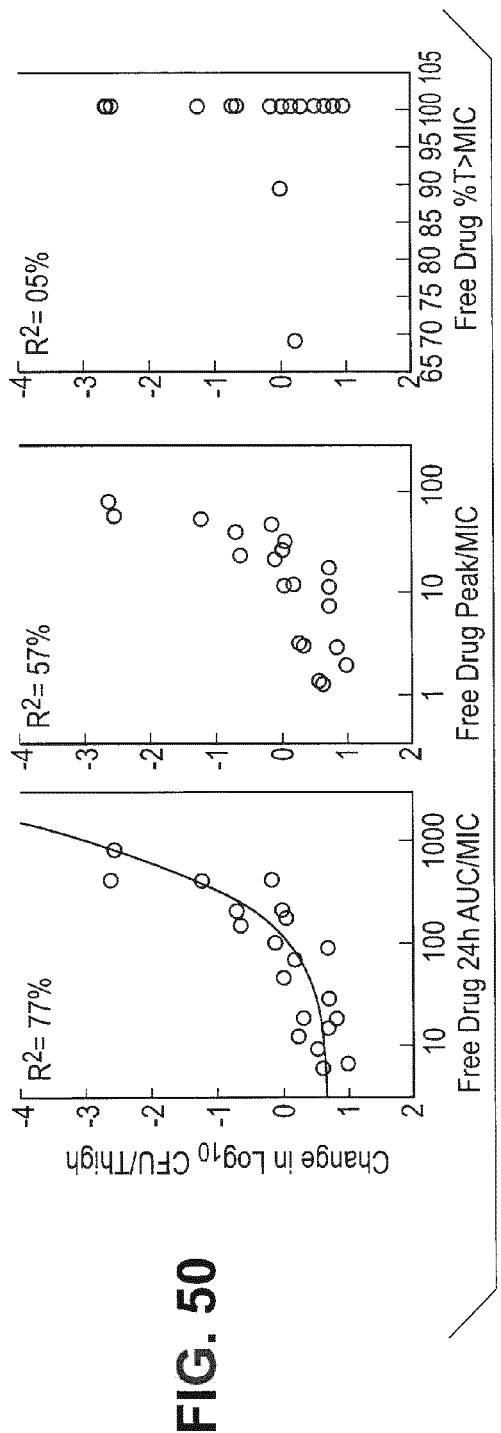
FIG. 50 provides the relationship between dalbavancin PK/PD parameters and efficacy against S. aureus.

We determined which PK/PD parameter correlated best with efficacy by relating the number of bacteria in thigh at the end of 144 hours of therapy with [1] the peak/MIC ratio, [2] the AUC/MIC ratio, and [3] the percentage of the dosing interval that serum levels exceed the MIC for each of the dosage regimens studied. The PK/PD parameter values for those doses not specifically studied were extrapolated from the values of the nearest studied doses. The relationship between log cfu per thigh and the peak/MIC ratio, the 24-hour AUC/MIC ratio and the percentage of time serum levels exceeded the MIC are illustrated in FIG. 49 for *S. pneumoniae* and FIG. 50 for *S. aureus*. Each point represents the mean of four thighs. For both organisms a strong correlation was observed with the 24-hr AUC/MIC and peak/MIC ratios. However, regression of the data with the 24 h AUC/MIC ratio resulted in the strongest correlation. The data illustrated in these figures were also analyzed by the same maximum dose-response model mentioned above, except that the different PK/PD parameters were used in place of the dose. The $R^2$ represents the coefficient of determination observed for the relationship between efficacy and each PK/PD parameter. The coefficient of determination (or $R^2$) represents the percentage of the variance in bacterial numbers that can be attributed to each PK/PD parameter and was high for both AUC/MIC and Cmax/MIC.

PK/PD Parameter Magnitude or Target

Figure 51A:
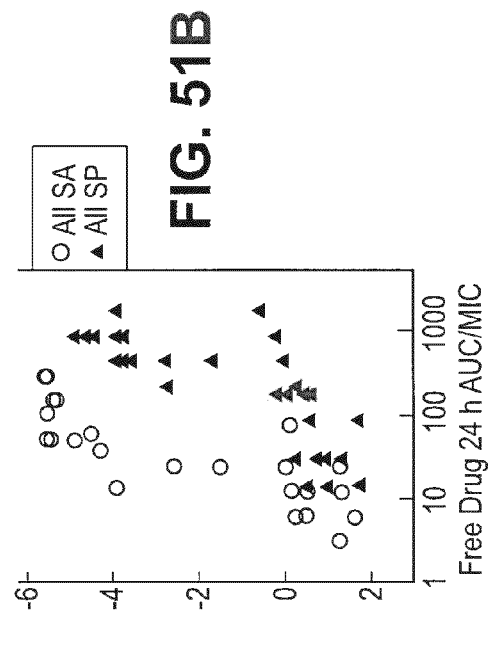
FIG. 51 provides the dose-response curves for dalbavancin against various strains.
Figure 52A:
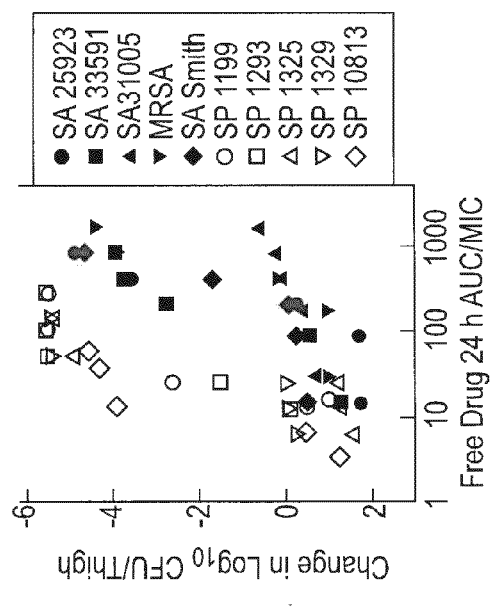
FIG. 52 provides the dose-response curves for dalbavancin against S. pneumoniae and S. aureus.
Figure 51B:
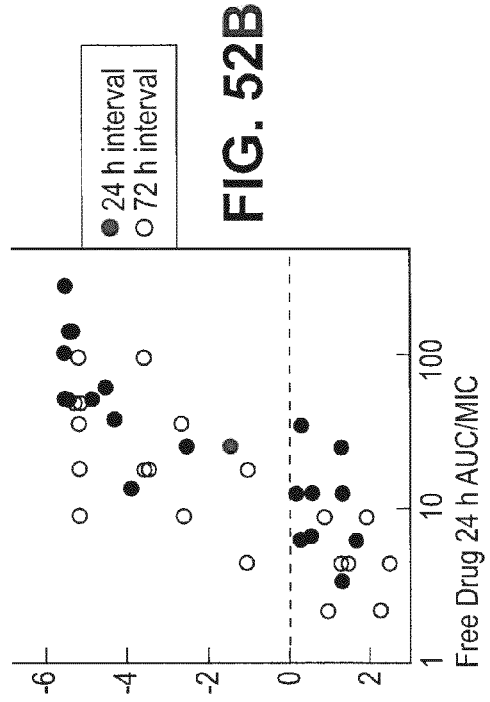
Figure 52B:
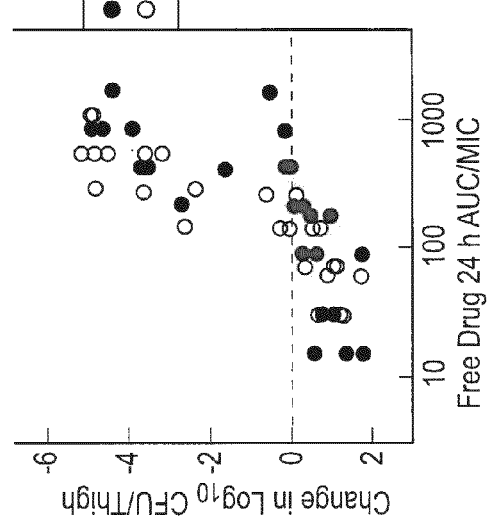

To determine if the AUC/MIC required for a static effect was similar for multiple pathogens, we studied the in vivo activity of 24- and 72-hourly dosing regimens of dalbavancin against 5 strains of *S. pneumoniae* and 6 strains of *S. aureus* after 6 days of therapy. The dose-response curves for dalbavancin against these various strains are shown in FIGS. 51 and 52. In FIGS. 51 and 52 the dose is represented by the free drug

TABLE 31

Dalbavancin Dosages Required to Achieve a Net Static Effect, 1 and 2 Log Kill for Four Different Dosing Intervals in a *S. pneumoniae* and *S. aureus* Infection Model.

| | q 12 h | | | q 24 h | | |
|---|---|---|---|---|---|---|
| Organism | SD mg/kg (95% CI) | 1 log kill mg/kg 95% CI) | 2 log kill mg/kg (95% CI) | SD mg/kg (95% CI) | 1 log kill mg/kg (95% CI) | 2 log kill mg/kg (95% CI) |
| SP10813 | 2.3 (1.9-2.7) | 2.8 (2.3-3.3) | 3.5 (2.8-4.2) | 1.34 (1.14-1.57) | 1.54 (1.34-1.74) | 1.75 (1.47-2.03) |
| SA29213 | 80 (8-152) | — | — | 26 (−39-91) | 267 (−400-934) | — |

| | q 36 h | | | q 72 h | | |
|---|---|---|---|---|---|---|
| Organism | SD mg/kg (95% CI) | 1 log kill mg/kg (95% CI) | 2 log kill mg/kg (95% CI) | SD mg/kg (95% CI) | 1 log kill mg/kg (95% CI) | 2 log kill mg/kg (95% CI) |
| SP10813 | 1.26 (1.16-1.36) | 1.53 (1.41-1.65) | 1.81 (1.67-1.95) | 0.71 (.64-.88) | 0.77 (.59-.95) | 0.82 (.62-1.02) |
| SA29213 | 15 (−14-44) | 36 (−34-106) | 122 (−117-361) | 10 (−18-38) | 31 (−55-117) | 128 (−230-486) | dose presented as total dose over 6 days (mg/kg).

Increasing the dosage regimen from 12 to 36 hours in study against *S. pneumoniae* did not result in an appreciable change in the doses associated with the three microbiologic endpoints. However, efficacy with the 72 h dosing interval required less drug. A similar relationship was observed in mean 24 h AUC/MIC ratio over the 6 day period of study. In general, the shape of the dose-response curves was similar for all strains. The location of the dose-response curve was related to the MIC of the organism. However, the dose response curves for the pneumococcal organisms are shifted slightly to the left. This curve shift suggests less drug was necessary for effect against pneumococci than staphylococci. The static dose, 1 log and 2 log kill and the associated free drug 24-hr AUC/MIC and Cmax/MIC are shown in Table 32. The extent of bacterial killing was relatively similar for most strains. All strains exhibited more than a 4 $\log_{10}$ drop in cfu over the 6 day study.

spaced dosing regimens. When dalbavancin was dosed every 72 h, the 24 h AUC/MIC values associated with the various endpoints were 1.3 to 2.4 fold lower than when drug was dosed every 24 h.

Penicillin-resistance in *S. pneumoniae* and methicillin-resistance in *S. aureus* did not impact the 24 h AUC/MIC required for dalbavancin efficacy.

TABLE 32

Dalbavancin Efficacy Against *S. pneumoniae* and *S. aureus*.

| | | Static Effect | | | 1 Log Kill | | | 2 Log Kill | | |
|---|---|---|---|---|---|---|---|---|---|---|
| Organism | MIC/MBC (mg/L) | f24AUC/ MIC | f24AUC/ MBC | mg/kg/ 24 h | f24AUC/ MIC | f24AUC/ MBC | mg/kg/ 24 h | f24AUC/ MIC | f24AUC/ MBC |
| q 24 h regimen | | mg/kg/ 24 h | | | | | | | | |
| SP1199 | 0.004 | 0.40 | 16.0 | | 0.49 | 19.4 | | 0.57 | 22.7 | |
| SP1293 | 0.004 | 0.44 | 17.4 | | 0.55 | 21.7 | | 0.65 | 25.9 | |
| SP1325 | 0.008 | 1.46 | 29.0 | | 1.6 | 31.8 | | 1.73 | 34.5 | |
| SP1329 | 0.008 | 0.90 | 18.0 | | 1.18 | 23.5 | | 1.45 | 26.7 | |
| SP10813 | 0.03 | 1.34 | 7.5 | | 1.54 | 8.7 | | 1.75 | 9.9 | |
| Mean ± SD | | 0.91 ± 0.44 | 17.6 ± 6.9 | | 1.1 ± 0.47 | 21 ± 7.4 | | 1.23 ± 0.52 | 24.3 ± 8.2 | |
| SA25923 | 0.12/0.25 | 42.7 | 216 | 52 | 51.2 | 250 | 60 | 60 | 289 | 69.3 |
| SA33591 | 0.12/0.25 | 22.3 | 96.2 | 46 | 27.7 | 121 | 58.3 | 33.5 | 157 | 74.3 |
| SA31005 | 0.06/0.12 | 49.3 | 483 | 242 | — | — | — | — | — | — |
| MRSA | 0.06/0.25 | 37.7 | 374 | 90 | 45.3 | 452 | 109 | 53.5 | 519 | 125 |
| SA Smith | 0.12/0.25 | 33.5 | 156 | 75 | 50.7 | 248 | 119 | 73.5 | 361 | 173 |
| Mean ± SD | | 37.1 ± 9.1 | 265 ± 143 | 101 ± 72 | 43.7 ± 9.5 | 268 ± 119 | 86.6 ± 27.6 | 55 ± 14 | 332 ± 131 | 110 ± 42 |
| q 72 h regimen | | mg/kg/ 72 h | | | | | | | | |
| SP1325 | 0.008 | 0.83 | 6.0 | | 0.99 | 8.8 | | 1.16 | 17.6 | |
| SP1293 | 0.004 | 1.01 | 14.1 | | 1.28 | 18 | | 1.68 | 23.8 | |
| SP1199 | 0.004 | 0.72 | 10.3 | | 0.85 | 12.1 | | 0.99 | 35.3 | |
| SP1396 | 0.008 | 0.52 | 4.0 | | 0.61 | 4.3 | | 0.69 | 4.8 | |
| SP10813 | 0.03 | 0.71 | 1.4 | | 0.77 | 1.6 | | 0.82 | 1.6 | |
| Mean ± SD | | 0.77 ± 0.18 | 7.2 ± 4.5 | | 0.93 ± 0.24 | 9.0 ± 5.8 | | 1.13 ± 0.36 | 16.6 ± 12.3 | |
| SA25923 | 0.12/0.50 | 160 | 274 | 66 | 185 | 317 | 76.1 | 214 | 367 | 88.1 |
| SA33591 | 0.12/0.25 | 74 | 123 | 59 | 93 | 160 | 76.6 | 114 | 195 | 94 |
| MRSA | 0.06/0.25 | 43 | 147 | 35.3 | 62 | 202 | 48.8 | 85 | 292 | 70 |
| SA Smith | 0.12/0.25 | 59 | 96 | 46.1 | 95 | 163 | 78.0 | 148 | 254 | 22 |
| SA307109 | 0.06/0.50 | 31 | 94 | 11.3 | 34 | 108 | 12.9 | 37 | 121 | 14.6 |
| SA31005 | 0.06/0.12 | 67.7 | 223 | 112 | 94.6 | 325 | 163 | 127 | 364 | 217 |
| Mean ± SD | | 72 ± 41 | 160 ± 67 | 55 ± 31 | 94 ± 46 | 213 ± 8.14 | 75.9 ± 45.2 | 120 ± 54 | 266 ± 88 | 101 ± 61 |

For the dalbavancin regimens utilizing every 24 h dosing, the free drug 24 h AUC/MIC value associated with a static effect against *S. pneumoniae* and *S. aureus* were 17.6±6.9 and 265±143, respectively. The dose response curves were steep and the 24 h AUC/MIC values associated with a 1 and 2 log kill were not appreciably higher. Therapy against pneumococci, based upon the 24 h AUC/MIC, required 12 to 23 fold less drug, as suggested by the dose response curves. For *S. aureus* the MBC was 2 to 4-fold higher than the MIC. If one considers the AUC/MBC for *S. aureus*, the values would be only 4 to 8-fold higher than for *S. pneumoniae*.

Figure 53:
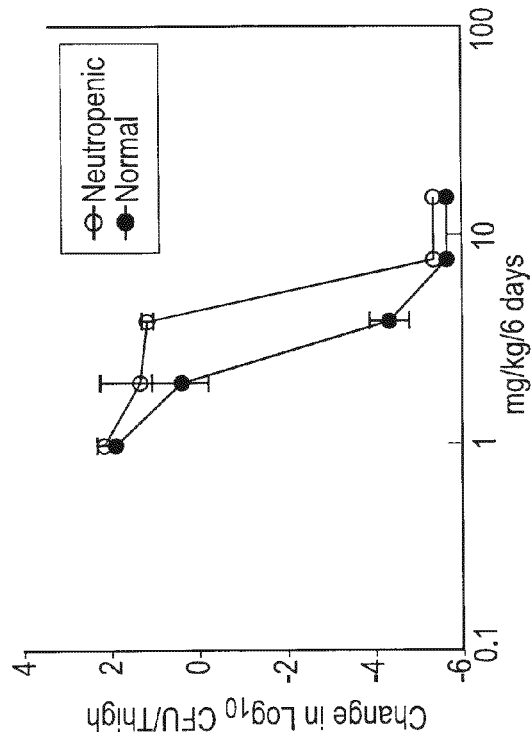
FIG. 53 provides the dose-response curves for dalbavancin in both normal and neutropenic mice infected with S. pneumoniae.

For the regimens that utilized less frequent dosing (every 72 h), the free drug 24 h AUC/MIC values associated with a static effect against *S. pneumoniae* and *S. aureus* were 7.2 i 4.5 and 160±67, respectively. The PK/PD magnitudes necessary to achieve the three in vivo microbiologic endpoints (static dose, 1 and 2 log kill) were lower for the more widely Impact of Neutrophils on Activity of Dalbavancin To determine the effect of neutrophils on the activity of dalbavancin, we compared the dose-response curves with 24-hour dosing of the drug in both normal and neutropenic mice infected with *S. pneumoniae*. The subsequent dose response curves are shown in FIG. 53. Each point represents the mean value from 4 thighs. The static dose, and the doses associated with a 1 and 2 log kill were calculated from the parameters estimated by non-linear regression using the Hill equation. The doses (mg/kg/6 d) required to achieve these endpoints in both normal and neutropenic mice are shown in Table 33. The presence of neutrophils resulted in a 1.7- to 2.1-fold reduction in the doses necessary for efficacy. However, these differences were not statistically significant.

TABLE 33

Impact of Neutrophils on the In Vivo Efficacy of
Dalbavancin Against S. pneumoniae.

|  | SD mg/kg (95% CI) | 1 log kill mg/kg (95% CI) | 2 log kill mg/kg (95% CI) |
|---|---|---|---|
| Normal | 2.03 (1.99-2.07) | 2.35 (2.26-2.44) | 2.66 (2.56-2.76) |
| Neutropenic | 4.13 (0.23-8.0) | 4.38 (0.28-8.50) | 4.62 (0.32-8.90) |

Impact of Infection Site on Activity of Dalbavancin

Figure 54:
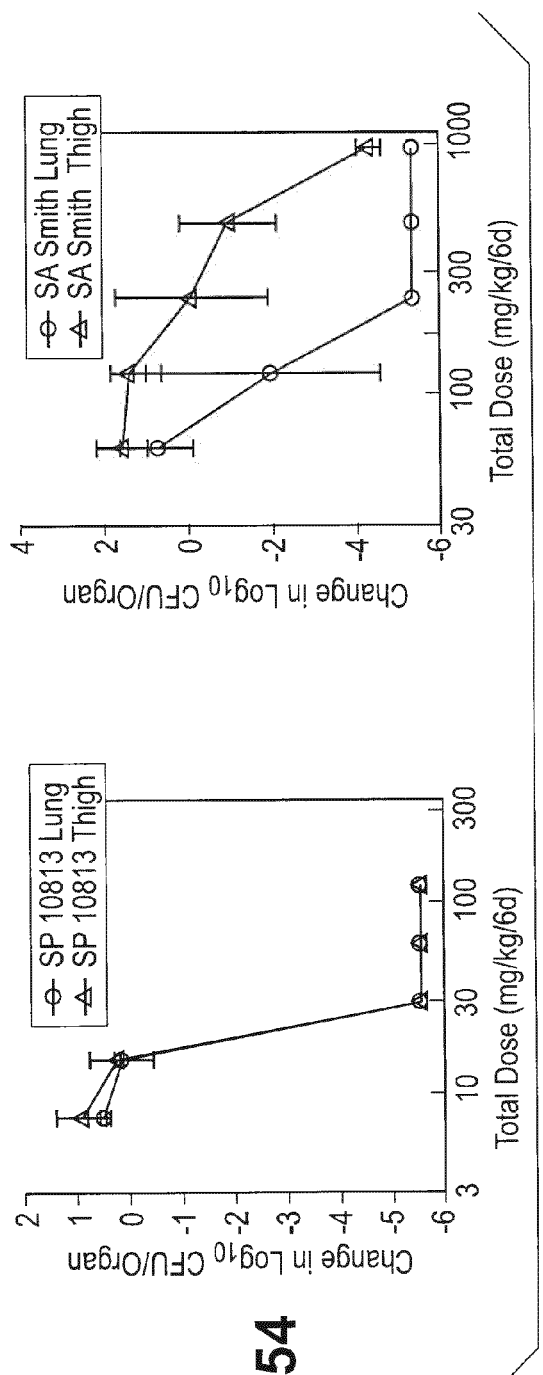
FIG. 54 provides the dose-response curves for dalbavancin in both the lung and thigh infection models.

To determine the impact of infection site on the activity of dalbavancin, we compared the dose-response curves with the 24-hour dosing of the drug in both the thigh and lung infection models (FIG. 54). Both S. pneumoniae and S. aureus were utilized in these models. The dose-response curves in the two models utilizing S. pneumoniae were nearly identical. In similar study against S. aureus the dose response curve in the lung model is shifted to the left suggesting less drug was necessary for efficacy at this site of infection. However, the confidence intervals in the staphylococcal study were large and these differences were not significant.

Conclusions

The above studies have characterized the in-vivo pharmacodynamic activity of dalbavancin against a variety of pathogens. These can be summarized as follows.

- Dalbavancin produced in vivo bactericidal activity against both S. pneumoniae and S. aureus in both the thigh and lung infection modes.
- The efficacy of dalbavancin was dose-dependent.
- The dose-dependent PK/PD parameters, 24 h AUC/MIC and Cmax/MIC, were strongly correlated with the in vivo activity of dalbavancin. Regression of the dose-response data with the 24 h AUC/MIC parameter resulted in the highest coefficients of determination. Therapy with the most widely spaced dosing intervals was more effective in these models.
- The 24 h AUC/MIC values associated with microbiologic effect were similar among the strains within the species studied. Beta-lactam resistance in S. pneumoniae and S. aureus did not impact dalbavancin in vivo activity.
- Efficacy against S. pneumoniae required lower 24 h AUC/MIC values than against S. aureus. This may in part be explained by the species differences in MIC and MBC.
- Efficacy against S. pneumoniae, whether based upon a net static effect, 1 or 2 log kill required a free drug AUC/MIC over the 6 days of therapy near 100 in these infection models. Efficacy against S. aureus, similarly based, required a free drug AUC/MIC over the 6 days of near 1000.
- Neutropenia had minimal impact on in vivo dalbavancin activity.

Example 10

Quantitative Determination of Dalbavancin in Plasma by HPLC-MS/MS

A HPLC-MS/MS method was developed for quantitative measurement of dalbavancin in plasma, as described below.

Preparation of Dalbavancin Calibration and Quality Control Standards

Stock solutions of dalbavancin were prepared by dissolving dalbavancin in deionized water to prepare a 1000 µg/ml solution, followed by serial dilutions in deionized water to prepare 500, 50 and 10 µg/ml solutions.

Calibration standards of 100, 60, and 40 µg/ml dalbavancin concentration were prepared by spiking human plasma with appropriate volumes of a 1000 µg/ml dalbavancin stock solution prepared as described above. Calibration standards of 20 and 10 µg/ml concentration were prepared by spiking human plasma with appropriate volumes of a 500 µg/ml dalbavancin stock solution, and a calibration standard of 0.5 µg/ml was prepared by spiking human plasma with an appropriate volume of a 10 µg/ml stock solution.

Quality control standards of 90 and 30 µg/ml dalbavancin were prepared by spiking human plasma with an appropriate volume of a 1000 µg/ml dalbavancin stock solution prepared as described above. A quality control standard of 1.5 µg/ml was prepared by spiking human plasma with an appropriate volume of a 50 µg/ml solution.

Preparation of Internal Standard Working Solution

A 30 µg/ml working solution of internal standard BI-K0098, which is the diethyl-amino-propyl-amino derivative of A-40926, was prepared as follows. Approximately 10 mg of BI-K0098 was dissolved in approximately 10 ml of mobile phase A (80% of 10 mM Ammonium Formiate/Formic Acid, pH 3 (v/v), 10% of Acetonitrile (v/v), and 10% 2-Propanol (v/v)) to make a 1000 µg/ml internal standard stock solution. The stock solution (300 µl) was then diluted to a volume of 10 ml with mobile phase A to make a 30 µg/ml internal standard solution.

Preparation of Samples for Analysis

Samples were prepared as follows for quantitative determination of dalbavancin concentration in plasma. To 50 µl of calibration or quality control standards prepared as described above, 100 µl of internal standard working standard solution was added and mixed. The mixture was permitted to equilibrate for five minutes at room temperature, followed by addition of 250 µl of acetonitrile. The mixture was then vortexed for 10 seconds, followed by centrifugation for 1 minute at about 10,000 rpm on an ALC micro-centrifugette 4214. Supernatants were transferred to clean tubes and evaporated to dryness in a Savant Speed-Vac System at about 40° C. Samples were then resuspended in 150 µl of mobile phase A.

Analytical Method

50 µl samples prepared for analysis as described above were injected into a Phenomenex Jupiter $C_{18}$ column (50×2 mm, $C_{18}$ 5 µm 300 A), and analyzed under gradient HPLC conditions at a flow rate of 0.3 ml/min. The gradient conditions were: initial, 80% mobile phase A/20% mobile phase B (20% 10 mM Ammonium Formiate/Formic Acid, pH 3 (v/v), 40% Acetonitrile (v/v), 40% 2-propanol (v/v)); 1 minute, 20% mobile phase A/80% mobile phase B; 2 minutes, 20% mobile phase A/80% mobile phase B; 2.5 minutes, back to initial conditions.

The HPLC system was coupled to a PE SCIEX API-2000 triple quadrupole mass spectrometer, with turbo ion spray operating in a positive ionization mode. Air was used to generate a spray in the ion source. Probe temperature was set at 500° C. with nitrogen as curtain gas. Multiple reactions monitoring (MRM) was employed using nitrogen as collision gas. The analytes were detected by monitoring the following ion transitions: 909.3 Da→1429.3 Da for dalbavancin, and 923.3 Da→1457.3 Da for the internal standard (BI-K0098). To avoid mass spectrometer contamination, a post-column flow diversion in the first minute and 2.5 minutes after the beginning of the chromatographic run was performed.

Software Sample Control 1.4 was used for the acquisition of data analysis and software MacQuan 1.6 was used for the integration of chromatographic peaks and statistical data evaluation.

Calibration Curves

Linearity of the assay method was assessed by assaying calibration standards to generate a calibration curve. The concentration of dalbavancin in a plasma sample was determined by calculating the peak area ratio between dalbavancin and the internal standard.

Calibration curves for dalbavancin concentrations over an analytical range of 0.5-100 μg dalbavancin/ml of human plasma were constructed using the equation y=A+Bx (weighted 1/x), where A represents intercept of the curve, B represents the slope of the curve, x represents the dalbavancin concentration of calibration standard (μg/ml), and y represents the peak area ratio of dalbavancin to internal standard. Three separate calibration curves were constructed. The results showed that dalbavancin/internal standard area ratio and dalbavancin concentrations varied linearly over the analytical range. The lower limit of quantitation (LLOQ) was 0.5 μg dalbavancin per ml of human plasma. The slopes for the calibration curves were reproducible and their correlation coefficients were greater than 0.9995.

Stability of Dalbavancin in Plasma

The stability of dalbavancin in plasma samples was tested by analyzing three replicates quality control standards of human plasma samples, prepared as described above, at two different concentrations, 1.5 and 90 μg/ml. Detectable dalbavancin concentration was stable after three cycles of freeze-thaw treatment. Dalbavancin concentration in processed samples was stable after 24 hours at room temperature. No reduction in dalbavancin concentration with respect to time zero samples was observed.

Example 11

Dalbavancin Mass Spectroscopy Analysis

The nature of dalbavancin multimers in solution was investigated and the conditions influencing the population ratio of dalbavancin multimer to dalbavancin monomer were determined by electrospray ion mass spectroscopy (ESI-MS).

Experiments were performed using an Applied Biosystem API III+ mass spectrometer equipped with a TurboIonSpray source, a Triple Quadrupole analyzer, operating in positive ion mode. The optimized conditions are reported in Table 34 below.

TABLE 34

Instrumental Conditions for Dalbavancin Analysis on Applied Biosystem API III+ Mass Spectrometer.

| IonSpray source: | |
| --- | --- |
| IonSpray voltage | 5000 V |
| Orifice plate voltage | 80 V |
| Curtain gas flow | 0.6 L/min |
| Nebulizer gas flow | 1.2 L/min |
| Liquid flow | 5 μL/min |
| Interface heater | 60° C. |
| Scan conditions (Q1 scan): | |
| Step | 0.1 amu |
| Dwell time | 1 msec |
| MS analyzer: | |
| Interface plate voltage | 650 V |
| Q0 road offset voltage | 40 V |
| Q1 park mass | 1000 |
| Q1 resolution | 120.8 |
| Q1 delta mass | 0.2 |
| Q1 road offset voltage | 27 V |
| Lens 7 voltage | −50 V |
| Q2 road offset voltage | −50 V |

TABLE 34-continued

Instrumental Conditions for Dalbavancin Analysis on Applied Biosystem API III+ Mass Spectrometer.

| Q3 park mass | 1000 |
| --- | --- |
| Q3 resolution | 110 |
| Q3 delta mass | 0 |
| Q3 road offset voltage | −70 V |
| Lens 9 voltage | −250 V |
| Faraday plate voltage | −250 V |
| Channel electron multiplier voltage | −3800 V |

Dalbavancin in Solution

Figure 7:
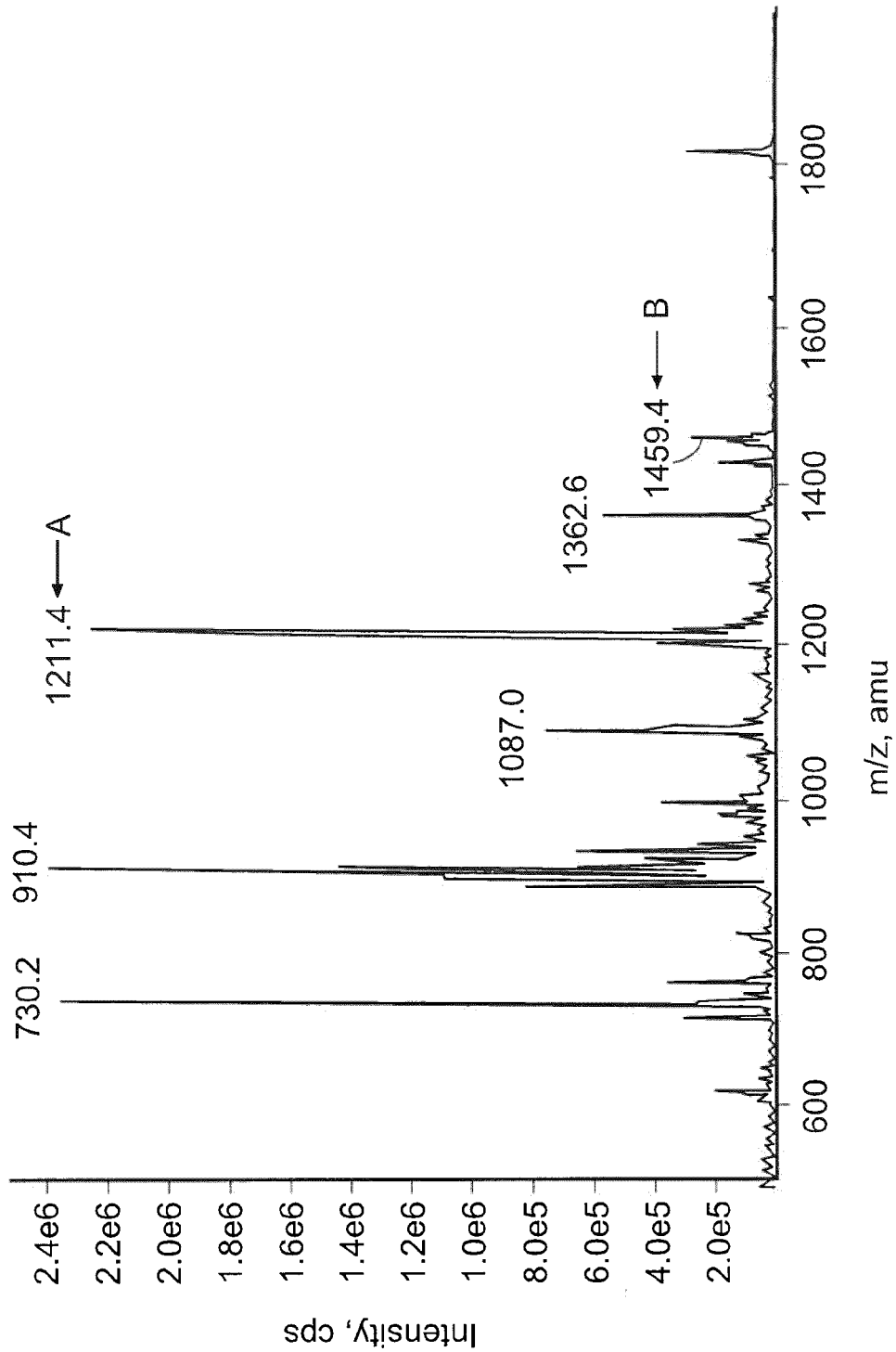
FIG. 7 depicts an electrospray ionization mass spectrum of dalbavancin.

Instrumental parameters were tuned on a dalbavancin solution containing 0.1 mg/ml of dalbavancin dissolved in a 8:2 water:isopropanol solution. A spectrum of dalbavancin in solution was acquired in the range of 500-2000 amu following direct injection of the solution. The resulting spectrum, as seen in FIG. 7, indicates the presence of dalbavancin multimers. As a non-limiting example, one trace of the spectrum is attributable to a homomultimer of $B_0$, which is present as a $(2nM+y(^+3))$ ion species, where n is a positive integer indicating the multiplicity of the homomultimer, e.g., n=1 when the multimer is a homodimer and n=2 when the multimer is a homotetramer, M indicates the mass of the monomer, y=n and $^+3$ indicates a plus three ion charge. For example, the homodimer of $B_0$ is provided when n=1, y=1, and M=mass of $B_0$. This homodimer species is assigned to a (2M+3) ion trace in the mass spectrum.

Figure 8:
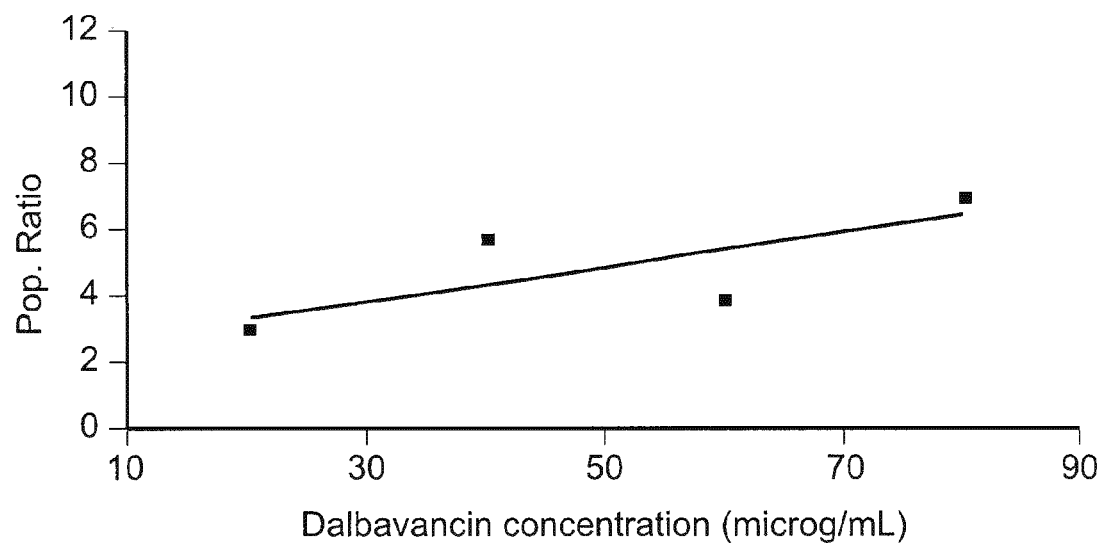
FIG. 8 is a graph of dalbavancin concentration vs. population ratio of dalbavancin multimer to monomer and depicts an increase in population ratio of dalbavancin multimer to monomer with increasing dalbavancin concentration.

Influence of Dalbavancin Concentration on the Population Ratio of Dalbavancin Multimer to Monomer The influence of dalbavancin concentration on the population ratio of multimer to monomer was evaluated by mass spectroscopy using the conditions described above. The spectra were acquired by direct infusion of dalbavancin solutions at concentrations of 20, 40, 60, and 80 μg/mL. The intensities of the main peaks were reported as a function of dalbavancin concentration and the population ratios of dalbavancin multimer to monomer were determined, as shown in FIG. 8.

The data indicate that the population ratio of dalbavancin multimer to dalbavancin monomer increases with increasing concentration. This may help to explain the high drug loading capacities that may be administered to an individual. The role of multimer as a depot of monomer may decrease the tendency of higher concentration samples to form precipitates and enhance the concentrations which may be administered to an individual. The presence of multimers may also allow rapid administration of a dose of dalbavancin to an individual.

A non-limiting example of a method of determining the population ratio of dalbavancin multimer to monomer is provided, for example, by determining the ratio between peak intensities of ions A and B as shown in FIG. 7. Dividing the intensity of peak A by the intensity of peak B provides one measure of the population ratio of dalbavancin multimer to monomer.

Influence of pH on the Population Ratio of Dalbavancin Multimer to Monomer

Figure 9:
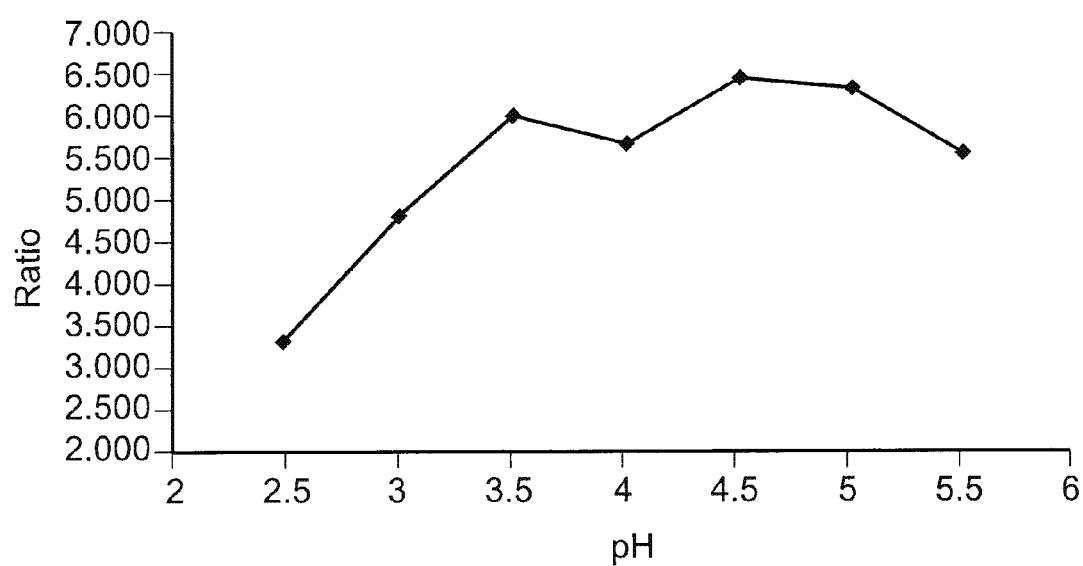
FIG. 9 is a graph of pH vs. population ratio of dalbavancin multimer to monomer and depicts an increase in population ratio of dalbavancin multimer to monomer with increasing pH.

The influence of solution pH on the population ratio of dalbavancin multimer to monomer was evaluated at the instrumental conditions described above and at the following solution pH values: 2.5, 3.0, 3.5, 4.0, 4.5, 5.0, and 5.5. The population ratio of dalbavancin multimer to monomer was determined at each of the pH values and plotted against pH, as seen in FIG. 9. It was determined that the population ratio of dalbavancin multimer to monomer increases with increasing pH.

While not to be limited to theory, it is believed that ionic groups, such as a carboxylate group on a first dalbavancin monomer, aid in the stabilization of dalbavancin multimers by forming ionic interactions with oppositely charged ions, such as tertiary nitrogen groups, on a second dalbavancin monomer. Such ionic interactions can be influenced by pH. It is believed that the increasing tendency of dalbavancin to be present as a multimer at higher pH is indication that ionic interactions are important in multimer stabilization. In particular, it is believed that dalbavancin multimers are destabilized at lower pH, presumably due to interruption of the ionic interactions contributing to multimer stability as certain functional groups, such as carboxylate groups, may be protonated at lower pH values.

Influence of Solution Ionic Strength on the Population Ratio of Dalbavancin Multimer to Monomer The influence of solution ionic strength on the population ratio of dalbavancin multimer to monomer was determined by mass spectrometry. The mass spectra were obtained in electrospray positive mode on a Finnigan LCQ$^{Deca}$ ion trap instrument previously tuned and calibrated in electrospray mode using Ultramark 1621, caffeine and MRFA (L-metionyl-arginyl-phenilalanyl-arginine). All the mass spectra were recorded using the conditions listed in Table 35. The sample parameters that were investigated are listed in Table 36.

TABLE 35

| MS Conditions | |
| --- | --- |
| Sample Inlet Conditions: | |
| Capillary Temperature (° C.): | 200 |
| Sheat Gas (N$_2$, arbitrary units): | 40 |
| Sample Inlet Voltage Settings: | |
| Polarity: | positive |
| Source Voltage (kV): | 4.70 |
| Capillary Voltage (V): | 34 |
| Tube Lens Offset (V): | −60 |
| Full Scan conditions: | |
| Scan range (amu): | 500-2000 |
| Number of microscans: | 3 |
| Maximum ion time (ms): | 200 |
| Zoom Scan conditions: | |
| Scan range (amu): | 1218-1228 |
| Number of microscans: | 5 |
| Maximum ion time (ms): | 50 |

TABLE 36

| Sample Parameters | | | |
| --- | --- | --- | --- |
| Sample | µg/mL | Solvent | pH |
| Dalbavancin | 100 | COO$^-$NH$_4^+$ 5 mM | 5 |
| | 100 | COO$^-$NH$_4^+$ 50 mM | 5 |
| | 100 | COO$^-$NH$_4^+$ 100 mM | 5 |

Figure 10:
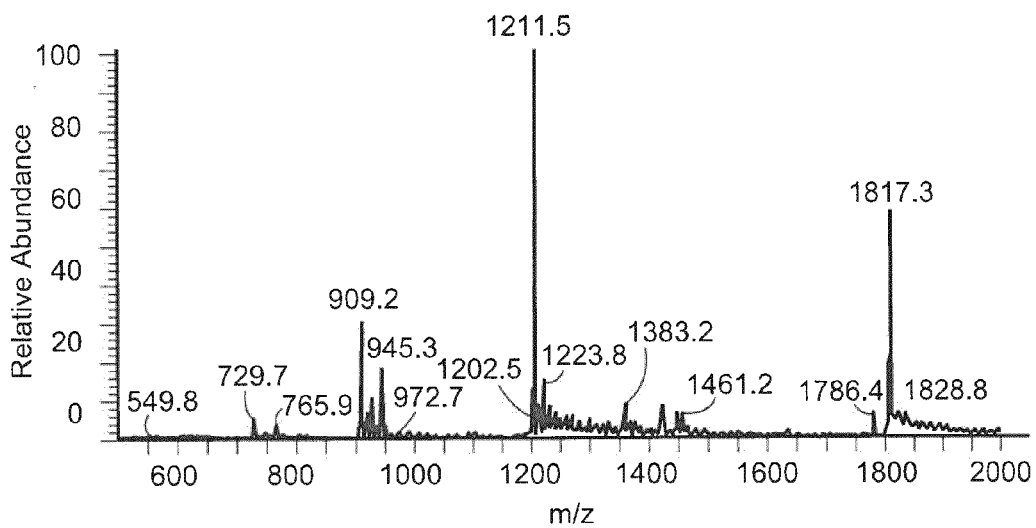
FIG. 10 depicts an electrospray ionization mass spectrum of dalbavancin in an ammonium formate 5 mM pH 5 solution.
Figure 11:
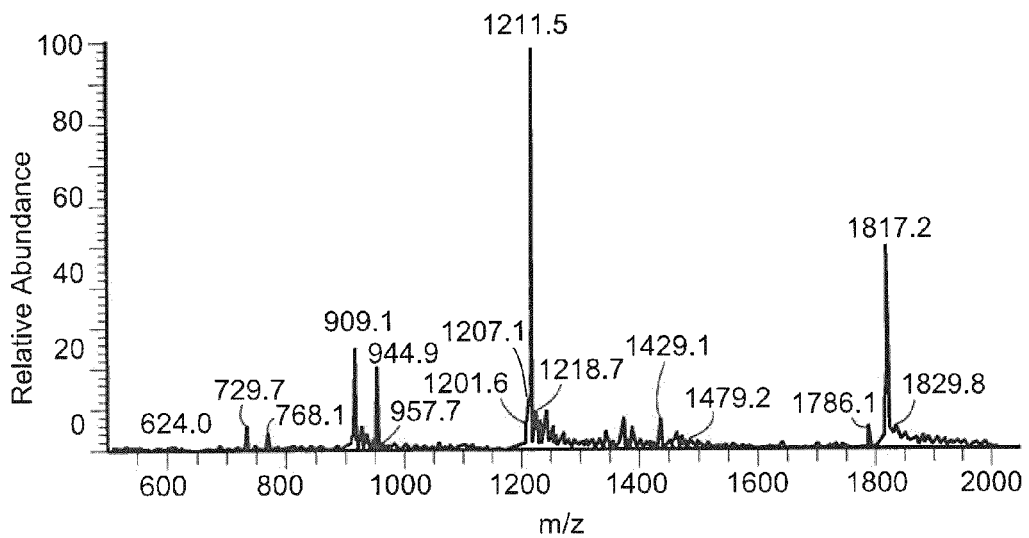
FIG. 11 depicts an electrospray ionization mass spectrum of dalbavancin in an ammonium formate 50 mM pH 5 solution.
Figure 12:
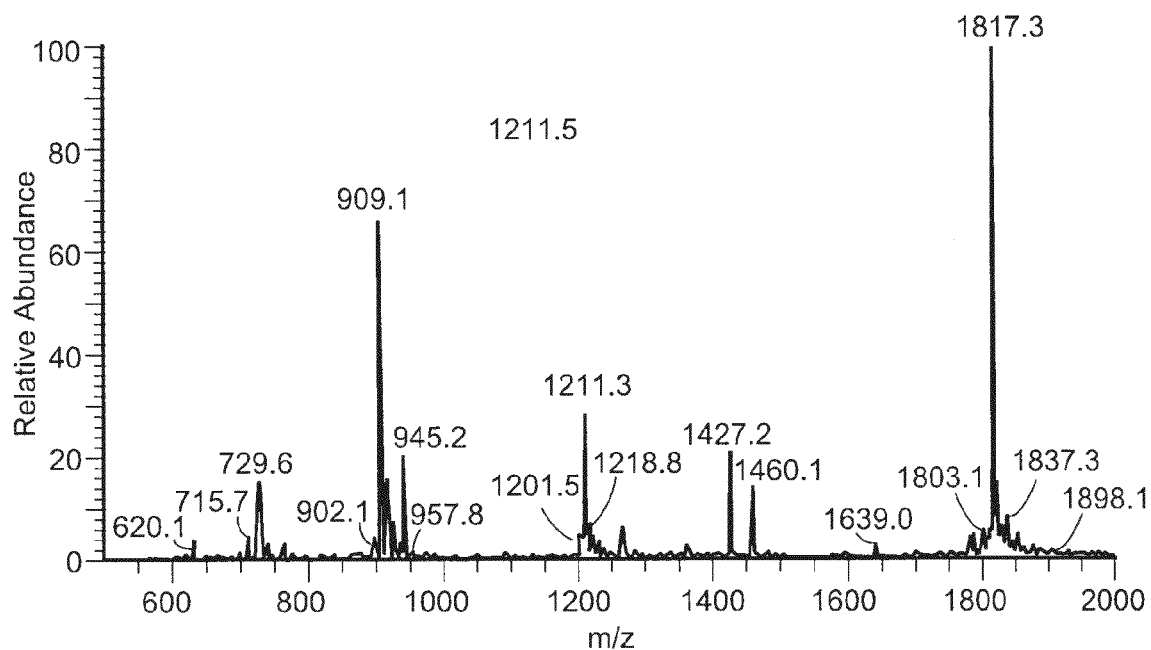
FIG. 12 depicts an electrospray ionization mass spectrum of dalbavancin in an ammonium formate 100 mM pH 5 solution.

Sample water solutions were infused at 10 µL/min via a Harward syringe pump and the mass spectra were obtained as seen in FIGS. 10-12.

The obtained spectra indicate that the population ratio of dalbavancin multimer to monomer is influenced by ionic strength. An increase in buffer concentration was found to correspond to a decrease in multimer mass traces and hence a decrease in dalbavancin multimer to monomer population ratio.

As mentioned, it is believed that ionic interactions are important in dalbavancin multimer stability. The fact that increasing ionic strength was correlated with decreasing intensity of multimer mass traces substantiates the role of ionic interactions in multimer stability. However, as multimer mass traces were present even at higher ionic strengths, another, second, interaction may be involved in multimer stabilization.

While not bound to any theory, it is believed that hydrophobic interactions are important in stabilizing the multimer species of dalbavancin. If the stabilization of these non-covalent dalbavancin multimers was solely due to ionic interactions, it would be expected that an increase in ionic strength would result in total loss of multimer mass species. That is, it would be expected that as the ionic strength of the solution increases, the ionic interactions stabilizing the multimer would be disrupted by the increased population of ions in solution, with which the monomers would more readily associate. Consequently, the solution ionic strength would drive the multimers to disassociate into monomer components and the resulting mass spectra would be free of any multimer mass traces. However, even at high solution ionic strength (such as 100 mM ammonium formate), the presence of dalbavancin multimers is detected in the mass spectrum. Accordingly, the multimers of dalbavancin are deemed to be stabilized, at least in part, by hydrophobic interactions.

Structurally Similar Compound

Figure 13:
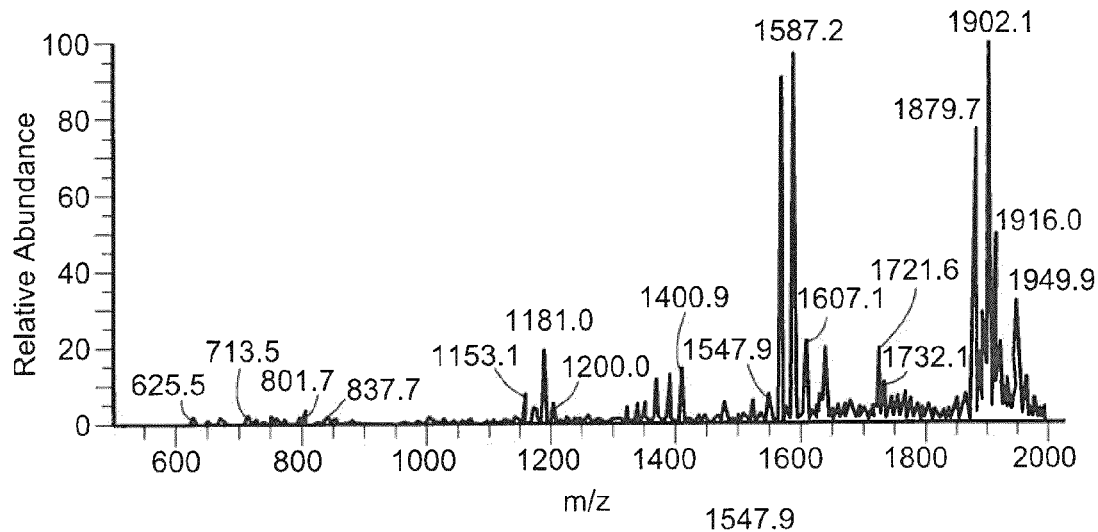
FIG. 13 depicts an electrospray ionization mass spectrum of teicoplanin (50 µg/mL) in water.
Figure 14:
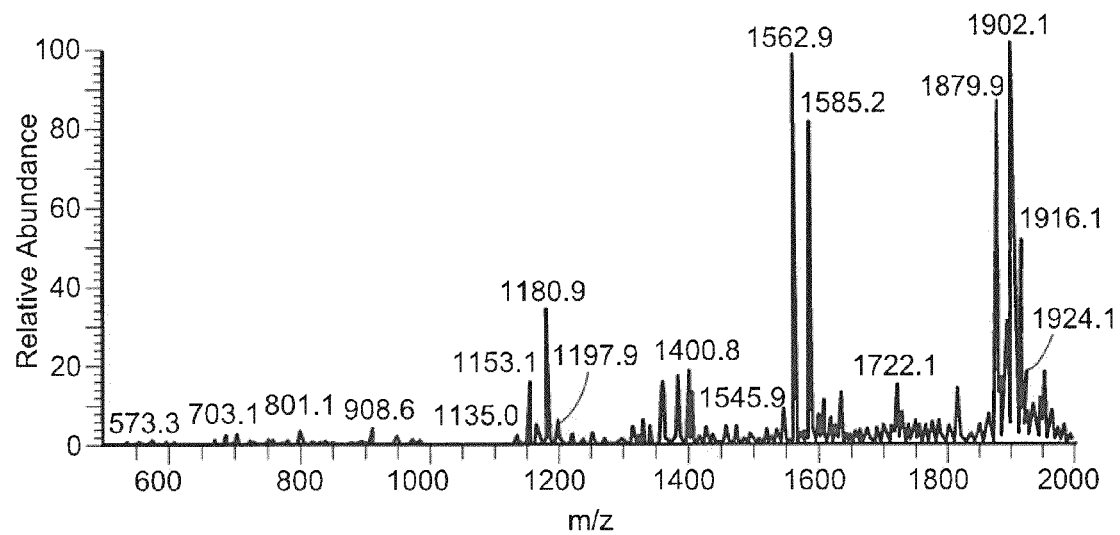
FIG. 14 depicts an electrospray ionization mass spectrum of teicoplanin (100 µg/mL) in water.

It is believed that the improved efficacy of Dalbavancin is due at least in part to its ability to form multimers. It is thought that this unique characteristic is not shared even by very structurally similar compounds. A compound with a chemical structure similar to Dalbavancin was investigated by mass spectroscopy analysis for its ability to form multimers. The mass spectra were obtained in electrospray positive mode on a Finnigan LCQ$^{Deca}$ ion trap instrument previous tuned and calibrated in electrospray mode using Ultramark 1621, caffeine and MRFA (L-metionyl-arginyl-phenilalanyl-arginine). All the mass spectra were recorded using the conditions listed in Table 37. The sample parameters that were investigated are listed in Table 38. Sample water solutions were infused at 10 µL/min via a Harward syringe pump and mass spectra were obtained as seen in FIGS. 13 and 14.

TABLE 37

| Mass Spectra Conditions | |
| --- | --- |
| Sample Inlet Conditions: | |
| Capillary Temperature (° C.): | 200 |
| Sheat Gas (N$_2$, arbitrary units): | 40 |
| Sample Inlet Voltage Settings: | |
| Polarity: | positive |
| Source Voltage (kV): | 4.70 |
| Capillary Voltage (V): | 34 |
| Tube Lens Offset (V): | −60 |
| Full Scan conditions: | |
| Scan range (amu): | 500-2000 |
| Number of microscans: | 3 |
| Maximum ion time (ms): | 200 |
| Zoom Scan conditions: | |
| Scan range (amu): | 1218-1228 |
| Number of microscans: | 5 |
| Maximum ion time (ms): | 50 |

TABLE 38

| Sample Parameters | | | |
| --- | --- | --- | --- |
| Sample | µg/mL | Solvent | pH |
| Teicoplanin | 50 | H$_2$O | n.a. |
| | 100 | H$_2$O | n.a. | n.a. = not adjusted

A similar glycopeptide antibiotic (teicoplanin) does not show multimeric complexes in solution at various concentrations. This supports the indication that structurally similar compounds fail to form multimeric species in solution, and that this phenomenon may play an important role in the activity of the dalbavancin.

Example 12

Matrix-Assisted Laser Desorption/Ionisation Time of Flight (MALDI-TOF) Mass Spectrometry of Protein-Dalbavancin Complexes 10 µl HSA, 0.150 mM was mixed with 10 µl dalbavancin solution (from 0.075 mM, 0.15 mM, 0.3 mM and 1.5 mM) and incubated for 60 min at 37° C. The samples were prepared for analysis using the dried droplet technique. Spectra were obtained on a BRUKER FLEX III, tof mass spectrometer previously tuned and calibrated using standard bovine serum albumin, acquiring and averaging spectra generated by 200 laser shots. Matrix: 9 parts of DHB-9 (2,5-dihydroxy-benzoic acid) saturated in acetonitrile/$H_2O$ (50:50), 1 part of sinapinic acid saturated in acetonitrile/$H_2O$ (50:50). 0.5 ul of sample solution and 0.5 ul of matrix solution were mixed and placed on the laser target.

Dalbavancin binds to the protein as the monomer (1HSA+1 dalbavancin). At very high dalbavancin to protein ratios (1:2, 1:10), the presence of complexes containing 2 molecules of dalbavancin per protein molecule can be observed.

Example 13

Isothermal Titration Calorimetry of Binding of Dalbavancin to N,N'-diacetyl-Lys-D-Ala-D-Ala in the Presence of Human Serum Albumin The binding of dalbavancin to N,N'-diacetyl-Lys-D-Ala-D-Ala, a peptide analog of cell-wall targets of dalbavancin, was investigated by isothermal titration calorimetry (ITC) in the presence of HSA over a range of concentrations (up to 600 µM) at 25° C., with some additional measurements at 37° C. HSA increased the solubility of dalbavancin and reduced its binding affinity for the tri-peptide ligand. Results were compared with those for vancomycin. The observed effects plateaued at relatively low HSA concentrations, consistent with a non-competitive binding model that allows binding of ligand to dalbavancin both free in solution and (more weakly) to the dalbavancin-HSA complex.

Preliminary experiments demonstrated that, in the absence of serum proteins, dalbavancin and vancomycin show similar binding profiles: both give exothermic binding to N,N'-diacetyl-Lys-D-Ala-D-Ala, but no evidence of binding to dipeptide (D-Ala-D-Ala) or to Lys-D-Ala-D-Lactate. For dalbavancin/tri-peptide interaction, the data were consistent with binding with $K_{diss}$=1-10 µM, depending on temperature, similar to vancomycin under the same conditions. In the presence of HSA, the solubility of dalbavancin is significantly increased and the binding affinity for tripeptide is reduced in a manner consistent with competitive or non-competitive binding by HSA for the antibiotic. The experiments described in this Example were designed in order to: (a) compare dalbavancin/tri-peptide measurements at different temperatures (25 and 37° C.) and different HSA concentrations; (b) use these data to construct a binding model to compare with observed numbers.

Dalbavancin was supplied by Biosearch Italia. Other reagents were from Sigma: vancomycin hydrochloride (Sigma V-2002, fw 1485.7), N,N'-diacetyl-Lys-D-Ala-D-Ala (Sigma D-9904, fw 372.4), human albumin (HSA; Sigma A-3782; mw 69,366).

Antibiotics and peptides were dissolved in aqueous buffer (20 mM Na phosphate, 150 mM NaCl, pH 7.4) containing HSA, with gentle stirring immediately before each experiment. Peptide concentrations were determined by weight. Dalbavancin concentrations were determined either by weight or by UV absorbance using the molar extinction coefficients $\epsilon$=12430 (dalbavancin, $A_{280}^{1\%}$=68.42), $\epsilon_{280}$=6690 (vancomycin). HSA concentrations were determined by UV absorbance (HSA, $\epsilon_{280}$=37,700; $A_{280}^{1\%}$=5.44). Spectra were recorded at room temperature in 1 cm pathlength quartz cuvettes using Shimadzu UV-160A or UV-1601 spectrophotometers, with samples diluted quantitatively with buffer if necessary to give absorbance in the 0.1-1 A range.

Isothermal titration calorimetry was performed using a Microcal VP-ITC instrument at 25° C. and 37° C. using standard operating procedures. See, e.g., Wiseman et al., Anal. Biochem. (1989) 179, 131-137; Cooper, et al., Philos. Trans. R. Soc. Lond Ser. A-Math. Phys. Eng. Sci. (1993) 345, 23-35; Cooper, A, Isothermal Titration Microcalorimetry in C. Jones, B. Mulloy and A. H. Thomas (Eds.), Microscopy, Optical Spectroscopy, and Macroscopic Techniques. Humana Press, Totowa, N.J., (1994) p 137-150; Cooper, A., Microcalorimetry of Protein-protein Interactions in J. E. Ladbury and B. Z. Chowdhry (Eds.); Biocalorimetry: The Applications of Calorimetry in the Biological Sciences. Wiley, (1998) p 103-111; and Cooper, A., Curr. Opin. Chem. Biol. (1999) 3, 557-563. Samples were degassed gently prior to loading to prevent bubble formation in the calorimeter cell. Each experiment typically comprised 25×10 µl injections of peptide solution (≈1 mM) into the calorimeter cell (volume≈1.4 ml) containing antibiotic solution (≈20-100 µM). Control experiments involved injection of ligand into buffer under identical conditions to determine heats of peptide dilution, and these values were used for correction of raw binding data prior to analysis. Dalbavancin/tri-peptide binding experiments were repeated several times at each temperature. ITC binding data were analyzed using standard Microcal ORIGIN™ software to determine the apparent number of binding sites (N), the binding affinity ($K_{ass}$=1/$K_{diss}$) and enthalpy of binding (ΔH).

TABLE 39

Thermodynamic data for binding of tri-peptide binding to dalbavancin and vancomycin determined by ITC assuming a simple non-cooperative binding model: effects of temperature and HSA.

|  | T ° C. | N | $K_{ass}$ $M^{-1}$ | Kdiss µM | ΔH kcal/mol | ΔS eu | [HSA] µM |
|---|---|---|---|---|---|---|---|
| Dalbavancin | 10 | 0.59 | 6.70E+05 | 1.49 | −10.26 | −9.60 | 0 |
|  | 10 | 0.59 | 9.20E+05 | 1.09 | −8.95 | −4.30 | 0 |
|  | 10 | 0.59 | 6.85E+05 | 1.46 | −10.30 | −9.60 | 0 |

TABLE 39-continued

Thermodynamic data for binding of tri-peptide binding to dalbavancin and vancomycin determined by ITC assuming a simple non-cooperative binding model: effects of temperature and HSA.

|  | T °C | N | $K_{ass}$ $M^{-1}$ | Kdiss μM | ΔH kcal/mol | ΔS eu | [HSA] μM |
|---|---|---|---|---|---|---|---|
|  | 10 | 0.56 | 6.24E+05 | 1.60 | −10.30 | −9.90 | 0 |
|  | 25 | 0.6 | 3.13E+05 | 3.19 | −10.10 | −8.90 | 0 |
|  | 25 | x | 3.30E+05 | 3.03 | −11.30 | −12.60 | 0 |
|  | 25 | x | 3.20E+05 | 3.13 | −11.70 | −14.00 | 0 |
|  | 25 | x | 2.80E+05 | 3.57 | −14.30 | −23.00 | 0 |
|  | 25 | 0.57 | 3.03E+05 | 3.30 | −12.60 | −17.00 | 0 |
|  | 25 | 0.74 | 3.19E+05 | 3.13 | −11.20 | −12.50 | 0 |
|  | 25 | 0.54 | 3.93E+05 | 2.54 | −12.90 | −17.60 | 0 |
| with HSA | 25 | 0.37 | 1.18E+05 | 8.47 | −26.40 | −65.50 | 13.6 |
| with HSA | 25 | 0.35 | 1.18E+05 | 8.47 | −27.80 | −70.10 | 13.6 |
| with HSA | 25 | 0.68 | 3.50E+04 | 28.57 | −20.00 | −46.20 | 34.2 |
| with HSA | 25 | 0.83 | 2.76E+04 | 36.23 | −16.90 | −36.50 | 80.7 |
| with HSA | 25 | 1.38 | 3.49E+04 | 28.65 | −18.60 | −41.70 | 104 |
| with HSA | 25 | 0.9 | 3.10E+04 | 32.26 | −21.05 | −50.00 | 288 |
| with HSA | 25 | 1.242 | 2.84E+04 | 35.21 | −19.50 | −44.90 | 430 |
| with HSA | 25 | 0.86 | 2.18E+04 | 45.87 | −15.00 | −30.40 | 601 |
|  | 37 | 0.82 | 1.30E+05 | 7.69 | −12.50 | −16.80 | 0 |
|  | 37 | 0.6 | 1.10E+05 | 9.09 | −17.40 | −33.20 | 0 |
| with HSA | 37 | 0.179 | 1.25E+04 | 80.00 | −98.60 | −299.00 | 482 |
| with HSA | 37 | 0.5 | 9568 | 104.52 | −26.60 | −67.60 | 516 |
| Vancomycin | 10 | 1.1 | 6.90E+05 | 1.45 | −9.49 | −6.80 | 0 |
|  | 25 | 0.91 | 3.40E+05 | 2.94 | −10.70 | −10.60 | 0 |
|  | 25 | 0.97 | 3.60E+05 | 2.78 | −12.90 | −17.80 | 0 |
| with HSA | 25 | 1.05 | 2.90E+05 | 3.45 | −10.09 | −8.80 | 513 |

ITC experiments on the binding of tri-peptide to dalbavancin in the absence of HSA give consistent data for binding affinities, with average $K_{diss}$ in the region of 1.4, 3.1, and 8.4 μM at 10, 25, and 37° C. respectively (Table 39). Binding is exothermic. Concentration calculations here indicate that N is closer to 0.5 under these conditions. This is consistent with the binding of one tri-peptide molecule per dalbavancin dimer under these conditions. These binding affinities and enthalpies of binding are comparable to those observed with vancomycin under the same conditions (Table 39, and D. McPhail, A. Cooper, *J. Chem. Soc.-Faraday Trans.* (1997) 93, 2283-2289.). Note also that vancomycin undergoes ligand-induced dimerization at higher concentrations.

Figure 15:
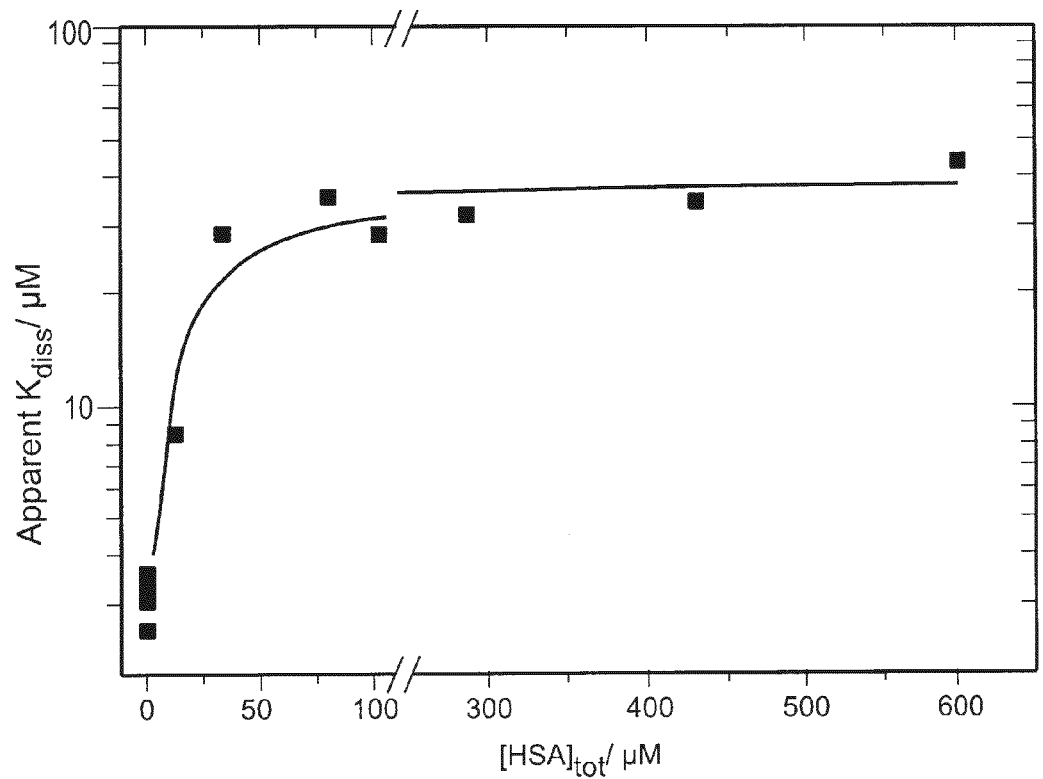
FIG. 15 depicts the effect of HSA on the apparent dissociation constant for dalbavancin/tri-peptide binding at 26° C. (pH 7.4).

Addition of HSA to the dalbavancin mixtures reduces the apparent binding affinity between tri-peptide and dalbavancin, though the binding is apparently more exothermic (Table 39). The HSA concentration dependence for this at 25° C. is shown in FIG. 15. After an initial rise (weakening) in apparent $K_{diss}$ up to 35 μM HSA, it remains relatively constant for higher HSA concentrations approaching physiological levels (600 μM). The plateau level at high concentrations of HSA ($K_{diss}$≈35 μM) corresponds to around 10-12× weaker binding affinity than in the absence of HSA. A similar reduction is seen at 37° C.

The HSA effect was not due to interaction with the tri-peptide. Control ITC experiments for binding of vancomycin to tri-peptide in the presence of HSA gave results comparable to those seen in the absence of HSA (see Table 39). This indicates that neither the peptide nor the closely related antibiotic, vancomycin, interact with HSA in solution. It follows that any effect of HSA on dalbavancin/tri-peptide interaction must be due to interaction between HSA and dalbavancin.

Although not wishing to be bound by theory, the above data are consistent with a non-competitive binding model. This model assumes that the tri-peptide ligand (L) can bind to dalbavancin (D) both in the free state and (possibly with different affinity) in the dalbavancin-HSA complex.

$$D+L \rightleftharpoons DL; K_L=[D][L]/[DL]$$

$$D+HSA \rightleftharpoons D.HSA; K_{HSA}=[D][HSA]/[D.HSA]$$

$$D.HSA+L \rightleftharpoons LD.HSA; K_{LDHSA}=[D.HSA][L]/[LD.HSA]$$

Apparent (Observed) Ligand Binding Dissociation Constant (Non-Competitive):

$$K_{app,L} = [\text{total } D][L]/[\text{total } DL \text{ complex}]$$
$$= ([D]+[D \cdot HSA])[L]/([DL]+[LD \cdot HSA])$$
$$= K_L\{1+[HSA]/K_{HSA}\}/\{1+[HSA] \cdot K_L/K_{HSA} \cdot K_{LDHSA}\}$$

This shows a hyperbolic dependence of $K_{app,L}$ on free HSA concentration that agrees well with the observed data (FIG. 15). At high [HSA] this reaches an asymptotic (plateau) value $$K_{app,L}=K_{LDHSA} \text{ (for large } [HSA])$$

This suggests that the binding affinity for tri-peptide is around 35 μM when dalbavancin is bound to HSA, compared to 3 μM for free dalbavancin (25° C. figures).

Figure 16:
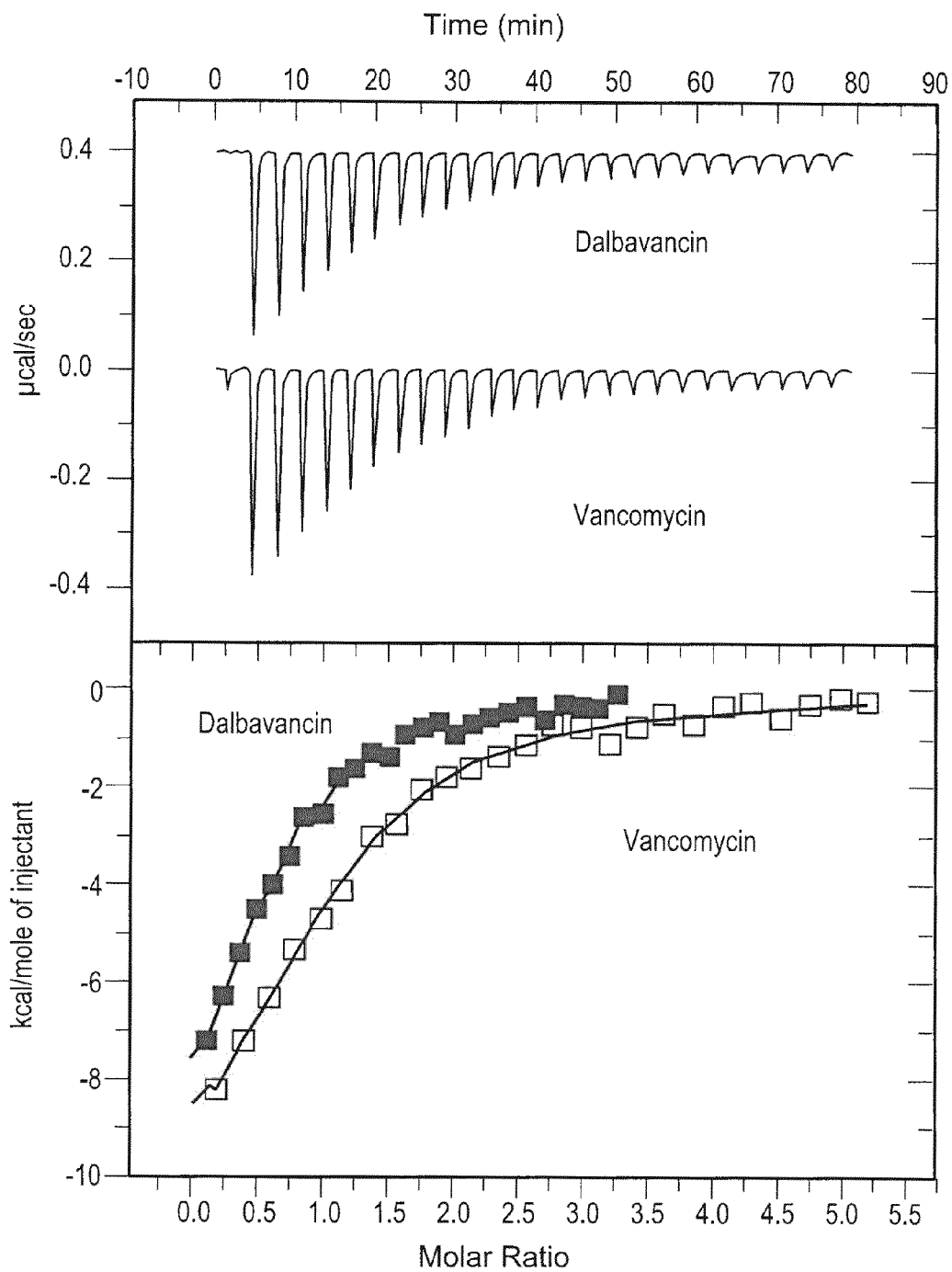
FIG. 16 depicts a comparison of isothermal calorimetry (ITC) data for binding of tri-peptide to vancomycin and dalbavancin under identical conditions, using the same tri-peptide solution.

Further mechanisms may be suggested in terms of whether dalbavancin is acting as a monomer or a dimer in its interactions with peptides or proteins. Direct comparison of dalbavancin with vancomycin (which shows unambiguous 1:1 binding at these low concentrations) shows that binding is complete at lower molar ratios (lower N) for dalbavancin (FIG. 16). This is consistent with a 2:1 dalbavancin:peptide complex.

Figure 17A:
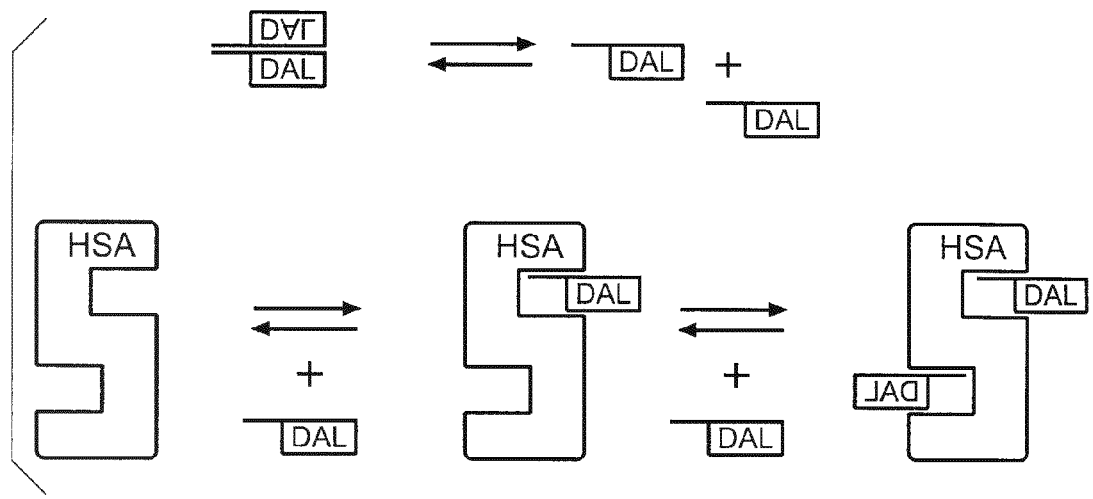
FIGS. 17A and 17B depict the possible interaction of dalbavancin monomers and multimers (including dimers) with tri-peptide ligand and HSA.
Figure 17B:
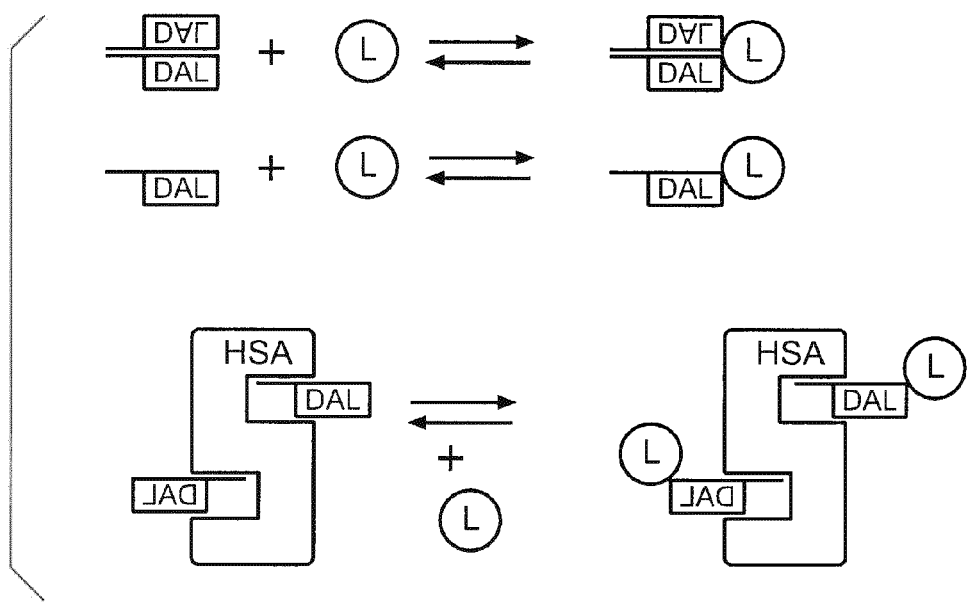

However, in the presence of HSA, the apparent N values increase (Table 39), and may be more consistent with 1:1 complexation. Although not wishing to be bound by theory, the model shown in FIG. 17, showing the possible interaction of dalbavancin monomers and dimers with tri-peptide ligands and HSA, is consistent with these observations. FIG. 17A depicts dalbavancin as in monomer-dimer equilibrium in solution (predominantly as dimer), but binding as monomer to two separate sites on HSA. This is consistent with the N=0.5 values observed by ITC for binding of serum proteins to dalbavancin (Example 3). FIG. 17B depicts ligand binding to the dalbavancin dimer in solution, and (more weakly) to the dalbavancin monomers attached to HSA. This is consistent with the non-competitive binding of dalbavancin to both tri-peptide and to HSA, with variable apparent stoichiometries.

In sum, this Example shows that HSA reduces the binding affinity of dalbavancin for tri-peptide ligand in a manner consistent with a non-competitive mechanism and that dalbavancin bound to HSA retains its ability to bind tri-peptide ligands, albeit with reduced affinity. These results are also consistent with a model in which dalbavancin is in monomer-multimer equilibrium, predominantly multimeric in solution, with strong affinity of multimers for peptide ligand. Dalbavancin monomers, both free and bound to serum albumin, may also bind peptides with a reduced affinity.

Example 13

A-40926 and Dalbavancin Preparations

Preparation of A-40926

A-40926, the natural glycopeptide produced by fermentation, was the starting material for producing Dalbavancin. It was produced by a *Nonomuria* sp ATCC 39727 as a mixture of A-40926 and its acetyl derivative (see U.S. Pat. No. 4,935, 238 and B. Golstain et al. *Antimicrobial Agent and Chemotherapy*, December 1987, p. 1961-1966). The acetyl derivative was first deacetylated to A-40926. After deacetylation, A-40926 was purified by column chromatography on polyamide as described below. The following description is representative of the current production method. The amounts reported here are about ¼ of the amounts usually worked in an industrial preparation.

Deacylation of A-40926

10 m$^3$ of fermentation broth (23° C.) containing a total of about 1 g/L of A-40926 and its acetyl derivative were adjusted, under stirring, at pH 11.4 with NaOH 30%. Stirring was continued for 6 hours, then the temperature was reduced to 15° C. and the broth was microfiltered (Koch Protosep IV Microfilter with a 0.12 m$^2$ ceramic membrane 0.1μ). During microfiltration, water was continuously added to the retentate in order to obtain, at the end of the process, a permeate of 20-25 m$^3$ and a retentate of 4.5-5 m$^3$ (one half of the starting value).

The permeate, which contained A-40926, was analyzed by HPLC. When the deacetylation was completed, the pH of the permeate solution was adjusted at pH 7 with 30% sulfuric acid (stored at 20° C.). In this example, 25 m$^3$ of filtered broth containing 6.62 Kg of A-40926 (268 mg/L) was obtained. The deacetylation yield was 66.2%. If the microfiltration process was carried out for longer time and higher extraction volume than those employed in this process, the yield can be increased up to 90%.

Purification of A-40926 on Polyamide Column

After extraction, A-40926 contained in filtered broth was purified on a polyamide column, as described below. The amount reported in this description is about ¹⁄₁₀ of the amount usually worked in an industrial preparation and is representative of the current production method.

500 L of polyamide resin SC6 (from Macherey Nagel) were suspended in demineralized water and loaded into a column. The resin was then conditioned at pH 6-6.5 by eluting the column with at least 2 BV (bed volume) of a buffer solution prepared by dissolving 4 Kg of sodium carbonate in 800 L of water and adjusting the pH of the resulted solution with acetic acid.

The A-40926 filtered broth (9000 L; assay 0.275 mg/L; A-40926 2475 g; pH 6±0.2; temperature 10±3° C.) was loaded into the column at about 5 g of activity per liter of resin (activity/resin ratio of 5-8 g/L was usually used). The column was washed with the following solutions: 3 BV (1500 L) of a solution at pH 6 prepared by dissolving 7.5 Kg of sodium carbonate in 1500 L of demineralized water and adjusting the pH with acetic acid; 4 BV (2000 L) of a solution at pH 8 prepared by dissolving 10 Kg of sodium carbonate in 2000 L of demineralized water and adjusting the pH with acetic acid; 1.5 BV (750 L) of a solution at pH 9 prepared by dissolving 4 Kg of sodium carbonate in 750 L of demineralized water and adjusting the pH with acetic acid.

A-40926 was recovered from the column by eluting with 4 BV (2000 L) of a buffer solution at pH 10 prepared by dissolving 10 Kg of sodium carbonate in 2000 L of demineralized water and adjusting the pH with acetic acid. The fractions containing purified A-40926 (concentration of A-40926 greater than 0.5 g/L and HPLC area % of the main component (Bo+B$_1$) greater than 80%) were collected, neutralized with 1N HCl, and analyzed by HPLC. About 2000 L of final clear solution were obtained.

The resin used for the purification was regenerated with 1.5 BV of 1:1 mixture of isopropanol/5% NaOH followed by a washing with 5 BV of demineralized water.

A-40926 Concentration

The solution coming from the column was subject to several rounds of dilution/concentration steps to eliminate most of the inorganic salts in the solution. The solution was concentrated to 80 L by nanofiltration using a membrane with a cut-off of 250 D, diluted with 80 L of demineralized water, and re-concentrated at the starting volume (80 L) by nanofiltration. This operation was repeated at least 5 times. The pH of the final solution (80 L, pH 7.5) was adjusted at pH 6.3 with 23% HCl. The solution was then diluted with 80 L of acetone, and its pH was adjusted again at pH 2.6 with 23% HCl.

Decoloring 680 g of charcoal PA 200 C (~0.3 g/g A-40926) was added under stirring to the solution obtained in the above step (160 L). Stirring was continued for at least 30 minutes at room temperature, then about 0.5-0.6 Kg of filter aid (DIF-BO) was added. The mixture was filtered through a filter cartridge. The clear solution obtained was concentrated under vacuo (45° C.) in order to reduce the acetone below 10%. The final volume was about 100 L. The pH was then adjusted at 6.7 with aq. NaOH, and the concentration step was continued using the usual nanofilter until the A-40926 concentration was around 100 g/L. 20 L concentrated solution was obtained (A-40926 1884 g, 94.2 g/L).

Precipitation and Drying

The previous solution was diluted under stirring with 20 L of acetone, and its pH was adjusted at 5.1 with 10% HCl. To this solution additional 5 volumes of acetone (100 L) were added to complete the A-40926 precipitation. If water content was not <15% at this point, additional acetone was added. After 2 hours the suspension was centrifuged, and the solid was washed with 3×10 L of fresh acetone. The mother liquors were analyzed and discharged after having ascertained the absence of product.

Solid A-40926 was dried under reduced pressure at 30-35° C. in a static drier until the residual acetone was below 2% and the water was less than 10%. The product was then sieved through a 50 mesh sieve obtaining 2.08 Kg of purified A-40926 (HPLC assay 81.4%; water 6.2%; sulphated ashes 4.8%). The yield, starting from the activity loaded on the column, was 68.4%.

Synthesis of Dalbavancin

Dalbavncin (BI-397) was prepared from the natural glycopeptide A-40926 through a three-step synthesis as described in Malabarba and Donadio (1999), Drugs of the Future, 24(8):839-846. Specifically, A-40926 was first subject to an esterification step to make MA, which was then subject to an amidation step to make MA-A-1. A final hydrolysis step then converted MA-A-1 into dalbavancin.

Esterification Step (Step 1)

The following description is representative of the current method in use.

Preparation of $H_2SO_4$ 96%/MeOH (Solution A)

In a 15 L round bottomed flask equipped with a mechanical stirrer and a thermometer, 2.28 L of $H_2SO_4$ 96% (~300 mL of $H_2SO_4$ 96% per Kg of A-40926 powder) was added drop wise to 7.9 L of MeOH. An external ice bath was used to maintain the temperature between 0 and 5° C.

Reaction Procedure

Starting material A-40926 (7.6 kg; batch 019, assay 85.09%; activity 6.46 kg; 3.73 mol) was suspended in a 140 L glass-lined reactor in MeOH (46 L), and the resulting suspension was cooled at 0° C.±2° C. At this temperature the suspension was treated with the previously prepared Solution A ($H_2SO_4$/MeOH). The resulting solution was stirred at 0° C. for 22-26 hours while the reaction (a reaction aliquot diluted 100 times with 1:1 acetonitrile/water mixture) was monitored by HPLC analysis every two hours. The esterification was considered complete when the residual A-40926 was less than 5% and diester was not more than 10% as HPLC area %.

Ester (MA) Isolation

When the reaction was complete, the mixture was cooled at −5° C. (+/−2° C.) and diluted with a same volume of cold water (54 L) maintaining the temperature below 5° C. The product (MA) was precipitated by adjusting the pH of the solution at 5.5 (+/−0.2) by slowly adding 10.2 L of triethylamine (TEA). Stirring was continued for an additional hour at 0-2° C., then the solid obtained was centrifuged, washed with water (10 L per Kg of A-40926) and finally with MeOH (3 L of MeOH per Kg of starting A-40926) previously cooled at 10-15° C. Washing with water was done primarily to remove sulphates from MA.

Mother liquors and washings were separately analyzed and discharged if contained less than 1-2% of activity. The product was dried in vacuo (50 mmHg) at 35-40° C. (external temperature) until the residual water was less than 10%. 7.6 Kg of MA (5.63 kg activity, 3.23 mol) was obtained as a brownish powder.

The analysis showed the following values of HPLC area %: MA 89.8,

A-40926 3.2, Diester derivative 5.9. The HPLC assay was 74.2%, activity 5.637 Kg; 3.23 mol; yield=86.5%. This material was used in the following step without any further purification.

Amidation Step (Step 2)

The following description is representative of the current production method.

Preparation of the DMSO/HCl Mixture (Solution B)

DMSO (1.6 L) was placed into a 10 L round bottomed flask, equipped with a mechanical stirrer and a thermometer, and cooled with an ice bath below 10° C. HCl 37% (1 L) was then slowly added under stirring maintaining the temperature of the mixture below 25° C.

Amidation Procedure (Production of MA-A-1)

Starting material MA 5.95 kg (assay 76.3%, KF 8.9%; 2.68 mol) was slowly dissolved under stirring in 19.2 L of 1:1 DMSO/MeOH mixture (~1.6 L DMSO and 1.6 L MeOH per Kg of MA powder) at room temperature. After 1 hour of stirring 709 mL of 3-(dimethylamino)-propylamine (DMEPA, MW 102.1; density=0.812 g/mL; 5.63 mol; 1.96 mols per mol of starting MA) and 325 g of 1-hydroxybenzotriazole hydrate (HOBT.$H_2O$; MW 153.1; 2.04 mol; 0.71 mol per mol of starting MA) were added to the reaction mixture. Stirring was continued until a complete solution was obtained, then the mixture was adjusted at pH 3-3.1 (measured after diluting an aliquot of the reaction 10 times with water) by slowly adding about 2.0 L of Solution B (DMSO/HCl).

A dicyclohexylcarbodiammide (DCC) solution, prepared by dissolving 1.03 Kg of DCC (4.99 mol; MW 206.3; 1.74 mol per mol of MA) in 4.1 L of 1: I DMSO/MeOH mixture, was added to the stirred reaction mixture in 10 minutes. Stirring was continued for 5 hours, then additional 51.5 g of solid DCC (0.25 mol) was added to the reaction mixture in order to lower the residual MA under 5%, maintaining the level of isoureas lower than 4-5%. Isoureas are a group of by-products produced by further reaction of Dalbavancin with the excess of DCC.

Typically after 2 additional hours (7 hours total) the reaction was completed. At the end the mixture was diluted with water (60 L) to lower the DMSO concentration to 15% (v/v) and adjusted at pH 2.3 with HCl 1N (0.85 L) to destroy any residual DCC.

Hydrolysis of MA-A-1 to Dalbavancin (Step 3)

After 30 minutes the mixture was adjusted at pH 12.0-12.1 with 15% NaOH (8 L). Stirring was continued for 4 hours maintaining the mixture at this pH with small additions of NaOH 15%. After this time the residual MA-A-1 was less than 0.2% as HPLC area %.

The mixture was then acidified at pH 3.0 with 1N HCl (19 L), and the suspension was filtered to remove the dicyclohexylurea formed. The solid cake was washed on the filter with demineralized water (2×20 L). Washings and filtrate were gathered together, obtaining a clear solution which was analyzed by HPLC. 152.8 L of solution containing 21.74 g/L of Dalbavancin (total activity 3322 g; 1.828 mol, yield=68.2%) was obtained.

Purification of Dalbavancin

The following description is representative of the current production method.

The 152.8 L of solution obtained from the hydrolysis step and containing 3322 g of Dalbavancin activity was split into two parts and each one was purified separately on the same chromatographic column containing 400 L of polyamide. In these two purification runs the activity/resin ratio were 4.3 and 4.0 g/L respectively.

Polyamide Column Preparation

The glass-lined column (internal diameter=40 cm, h=320 cm) containing 400 L of polyamide resin was cleaned according to the resin regeneration procedures (see below) and conditioned with 2 BV (800 L) of demineralized water acidified with 4 L of AcOH (pH=3.2).

Purification of the First Portion

The first portion of 76.4 L of starting solution was diluted with $H_2O$ (56 L) in order to lower the DMSO content under 5% (v/v), and acidified to pH 2.78 with 1 N HCl (3.4 L). This solution was then loaded onto the column at a flow rate of 150 L/h. After loading, the resin was washed with the following solutions: 4 BV (1600 L) of $H_2O$ acidified with AcOH (8 L), pH=3.2; 5 BV (2000 L) of AcONa 0.1 M, pH=8.2; 1 BV (400

L) of H$_2$O acidified with AcOH (1 L), pH=3.2. Dalbavancin was eluted with 4 BV (2400 L) of H$_2$O/MeOH (8:2) acidified with AcOH (6 L), pH=3.4.

During the elution step, 22 fractions of 50-60 L each were collected and analyzed by HPLC. Fractions from 9 to 25 (concentration of Dalbavancin higher than 0.5 g/L and HPLC area % of (B$_0$+B$_1$)≧80%) were pooled together, obtaining 969 L of solution with 1.56 Kg of Dalbavancin (yield=93.9%). This solution was then concentrated by nanofiltration, obtaining 125.7 L of solution with 1.38 Kg of Dalbavancin. 850 L of permeate, containing 145 g of impure Dalbavancin (8.7%), were neutralized and discharged.

Resin Regeneration

Before re-using the resin was washed with the following solutions: 2.5 BV (1000 L) of 1:1 MeOH/water acidified with acetic acid (2.5 mL/L); 2.5 BV (1000 L) of 1:1 0.5% NaOH/isopropanol; 10 BV (4000 L) of demineralized water. The resin was then re-equilibrated with BV (800 L) of water acidified with acetic acid (2.5 mL/L).

Purification of the Second Portion

The second portion of the starting solution coming from the hydrolysis step (76.5 L) was diluted with H$_2$O (56 L) to lower the DMSO content under 5% (v/v) and acidified to pH 2.87 with 3.0 L of 1 N HCl. The portion was then purified as previously described in the purification of the first portion. The pooled fractions (vol.=972 L, Dalbavancin 1.54 Kg, yield=92.7%) were concentrated by nanofiltration, obtaining 133 L of solution with 1.46 Kg of activity. 850 L of permeate, containing 73 g of Dalbavancin (4.3%), was discharged.

The concentrated solutions coming from the two purification steps were re-analyzed and pooled together giving 258 L of solution containing 2840 g of purified Dalbavancin. The purification yield was 86%. The total yield, starting from MA, was 58.3%.

Final Polyamide Regeneration

After the second purification run polyamide was regenerated with: 2.5 BV of 1:1 MeOH-water, acidified with AcOH (2.5 L) at pH=3.4; 2.5 BV of 1:1 0.5% NaOH-isopropanol; 10 BV of demineralized water.

Decoloration and Precipitation of Dalbavancin 1.5 mol of 1N HCl per mol of Dalbavancin and 0.3 g of charcoal CG1 (0.85 Kg, from NORIT) per gram of Dalbavancin were added to the 258 L solution obtained above. The mixture was stirred at room temperature for at least 45 min. The pH was 3.1. The suspension was then filtered on a SUPRA DISC cartridge mod. SDP-EK1 from SEITZ-SCHENK, and the cake was washed with 50 L of H$_2$O/MeOH 8:2. The filtrate was analyzed and concentrated again by nanofiltration, using a MPS 44 membrane with a cut off of 250 D. 21.3 L of concentrated solution containing 119 g/L of Dalbavancin (pH 4.1; MeOH 1.9%, GC) was obtained. 909 mL of 1 N HCl was finally added to adjust the pH at 2.63, which corresponds to the salification ratio of 1.65 mol$_{HCl}$/mol$_{Dalbavancin}$.

The solution (22.2 L) was poured out, under stirring, in 200 L of acetone. The solid obtained after decanting was centrifuged and washed with 14 L of fresh acetone. The product was then dried under reduced pressure (50 mmHg) at 35° C., maintaining the internal temperature under 30° C. for 17 hours. During the drying process, 1 L of low endotoxin water (<250 EU/mL), divided in two portions of 0.5 L each, was sprayed on the solid after three and five hours in order to remove the residual acetone that otherwise is difficult to eliminate. The product was then sieved (50 mesh), obtaining 2592 g of Dalbavancin (HPLC Assay 82.4%; water (KF) 14%; Cl$^-$ 3.0%).

Example 14

Alternative Methods for A-40926 and Dalbavancin Preparation

The methods described below are alternative methods that can used in the A-40926 and Dalbavancin preparation process.

A-40926 Preparation on XAD-7HP

Deacetylation and Mycelium Microfiltration

150 L of fermentation broth containing A-40926 (pH 7) were stirred in a suitable reactor at room temperature (24° C.), and adjusted at pH 11.5 with a 2.5 N NaOH solution (2.5 L). After 4 hours of stirring, the broth was adjusted at pH 10.6 with 15% HCl, and microfiltered through a 0.2 micron membrane. 439 L of clear permeate was collected and then concentrated by nanofiltration using a MPS 44 membrane with a 250 D cut off. The A-40926 concentrated solution obtained (58.6 L; 3.89 g/L) was adjusted at pH 6.4 and stored at 4° C. until used.

Column Preparation and Purification.

XAD-7 HP resin (8 L) was suspended in a 1:1 water/methanol solution, filtered, and loaded into a proper glass-column (internal diameter 12 cm) with a peristaltic pump.

The resin was then washed with water and equilibrated with 6 BV of a sodium carbonate aqueous solution buffered at pH 6 prepared by dissolving 5 g of sodium carbonate per liter of water and adjusting the pH with acetic acid.

A portion of concentrated broth containing 194 g of A-40926 was loaded into the XAD-7 HP column. The resin was then washed with the following two buffered solutions, at a flow rate of BV/hour, in order to eliminate part of the hydrophilic and the colored substances present: 3 BV (24 L) of aq. 0.5% Acetic Acid solution adjusted at pH 5 with 30% sodium hydroxide; 5 BV (40 L) of a 8:2 mixture water/acetone with 5 mL of acetic acid/L of water.

A-40926 was finally eluted with 8 BV (64 L) of a 1:1 water/acetone mixture acidified with 5 mL of acetic acid/L of water. 16 fractions of 4 L each were collected. The rich fractions (from 5 to 15) in which A-40926 concentration was greater than 0.5 g/L were gathered together obtaining a solution containing 163.4 g of A-40926 (43 L, 3.8 g/L). The column yield was 81.3%. The other fractions (200 L) containing 0.23 g/L (45.3 g; 22.2%) of less pure A-40926 were discharged.

After the elution the resin was regenerated with 6 BV (55 L) of NaOH 0.5%/isopropanol (1:1) mixture, and finally washed to neutral with 10 BV of water.

Charcoal Treatment.

The collected fractions were adjusted at pH 2.5 with HCl 37% (70 mL) and then decolorized with 50 g charcoal type PA 200 (0.3 g/g of A-40926). The suspension obtained was stirred for 2 hours at room temperature and then filtered through a KS 50 filter (d=25 cm, time=2.5 hours), obtaining 45.6 L of a slightly yellow A-40926 solution (3.5 g/L; yield=96.4%).

Concentration.

The decolorized solution was adjusted at pH 7 with NaOH 30% (230 mL) and concentrated by nanofiltration and ultrafiltration. The use of these techniques was important for the elimination of the hydrophilic substances that were detected on the HPLC chromatograms at Rt=2-4 minutes. When the retentate was concentrated to 1/10 of the starting volume (4 L), the same volume of water was added and the solution obtained was concentrated again. This concentration/dilution step was repeated three times in order to reduce the residual acetone to 0.25%. The final solution (2.2 L, 146.3 g of A-40926, 66.5 g/L, yield=91.5%) was analyzed by HPLC. The purification yield was 75.4%.

A-40926 Crystallization.

A 300 mL portion of the A-40926 solution (19.9 g of A-40926) was further concentrated to 100 mL by using a laboratory scale ultrafilter and then heated at 60-65° C. The pH of this solution was adjusted at 7 (30% NaOH), and 1.2 mL of 5:1 acetone/isopropanol mixture per mL of concentrated solution was added drop wise at this temperature. The resulted mixture was left to cool at 20° C. After 1.5 hours, the solid obtained was filtered, washed on the filter with acetone, and dried at 40° C. for 15 hours. 20.6 g of product (HPLC assay 82.0%; A-40926 16.9 g) was obtained. The precipitation yield was 84.9%. The overall yield, starting from the filtered broth, was about 64%.

A-40926 Preparation on CG-71

Column Preparation

CG-71 resin (350 mL) was poured into a glass-column (internal diameter=4 cm) and washed with water. The resin was equilibrated with 3 BV of a sodium carbonate solution, prepared by dissolving 5 g of sodium carbonate in water at pH 6 with acetic acid. 250 mL fermentation broth (pH 7) containing 14.7 g of A-40926 was loaded into the column (42 g/L resin). The resin was washed with the following three solutions: 1050 mL (3 BV) of aqueous solution of sodium carbonate (5 g/L) adjusted at pH 6 with acetic acid; 1750 mL (5 BV) of aqueous solution of sodium carbonate (5 g/L) adjusted at pH 8 with acetic acid; 3150 mL (9 BV) of aqueous solution of sodium carbonate (5 g/L) adjusted at pH 9 with acetic acid.

The activity was then eluted with 10 BV of demineralized water. 20 fractions of 500 mL each were collected. Fractions 12 to 15 were pooled together, obtaining 2.2 L purified solution containing 11.7 g of A-40926 (yield=79.6%). This solution was then concentrated by ultrafiltration and the concentrate solution was further diluted with demineralized water and ultrafiltered again. The solution obtained was further concentrated under reduced pressure to 50 mL.

A-40926 Crystallization.

The concentrated solution was heated at 60° C. and treated under stirring with a 5:1 acetone/IPA mixture (60 mL). The mixture was then slowly cooled at room temperature. The solid obtained was filtered, washed with acetone on the filter, and dried under vacuum at 35° C. for 80 hours. 8.9 g of purified A-40926 (HPLC assay 84.2%) was obtained. The overall yield was 51%.

Alternative Amidation Step in Dalbavancin Synthesis Using N-Methyl-2-pyrrolidine (NMP) as a Solvent MA mixture was added portion wise under stirring to a 1:1 NMP/MeOH mixture (64 mL). Stirring at 20-25° C. was continued until complete solution, then DMEPA (2.42 mL; 1.96 mol/eq$_{MA}$) and HOBT (1.06 g; 0.71 mol/eq$_{MA}$) were added. The pH of the reaction mixture (checked on a sample diluted 1:10 with water) was adjusted to 3.0 with 9.37 mL of 15% HCl in NMP (previously prepared from 34.0 mL HCl 37% dissolved in 57.7 mL NMP). Then a solution of DCC (3.17 g; 1.57 mol/eq$_{MA}$) in NMP/MeOH 1:1 (12.7 mL) was added under stirring. The reaction was monitored by HPLC. The reaction was complete after about 6 hours (MA-A-1 88.9%, MA 7.3%, ISO 3.7%). This experiment suggests that NMP can be a convenient alternative to DMSO for the amidation reaction. The whole process was not influenced by this solvent change and the final Dalbavancin obtained was chemically equivalent to other batches.

Alternative Method of Dalbavancin Preparation: One-Pot Procedure 10 g of A-40926 complex (HPLC titer 80.66%, 4.6 mmole) was suspended in 24 mL of MeOH under stirring at room temperature in a 100 mL glass reactor. The mixture was cooled at 0° C., and a solution of 4 g of HCl (g) in 16.4 mL of MeOH was added to complete the product solubilization. The temperature was then left to rise to 20° C. while stirring was continued for additional 24 hours.

After this time, 40 mL of DMSO and 0.4 g of HOBT were added to the reaction mixture.

1,1-dimethylamine propylamine was then added, adjusting the pH of the resulting reaction mixture between 3-3.1 (measured after diluting a sample 9:1 with water). 1.8 g of solid DCC was then added and stirring was continued for additional 15 hours. After this time the reaction mixture was transferred in a 1 L glass reactor and diluted with 80 mL of water. The pH was then brought to 12 by adding 240 mL of 15% NaOH. Stirring was continued for additional 60 minutes, and the mixture was acidified at pH 2.8 with 260 mL of 15% aq. HCl. About 800 mL of final clear solution containing 6.4 g of Dalbavancin was obtained (yield=76%).

HPLC analyses showed that the profile of the product obtained is comparable with that obtained with the other manufacturing processes.

$N^{15},N^{15}$-Dialkyl Antibiotic Compounds

Figure 26:
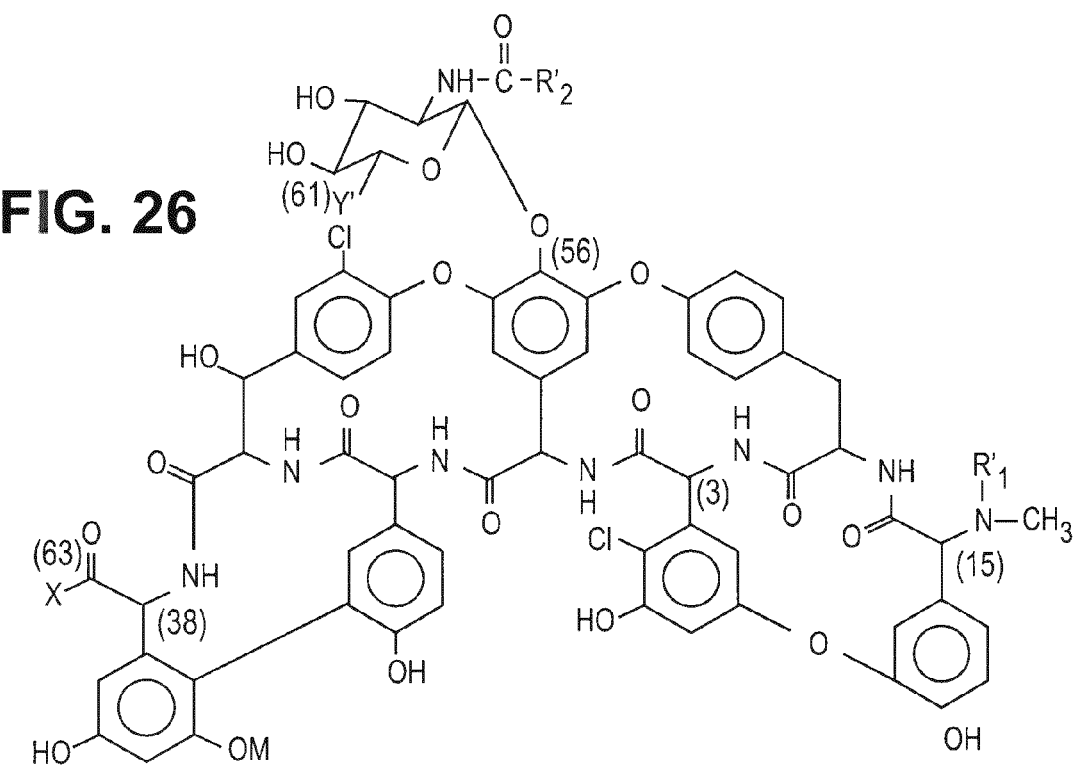
FIG. 26 provides the structure of antibiotic A 40926 compounds and dalbavancin compounds including the numbering of selected atoms.
Figure 27:
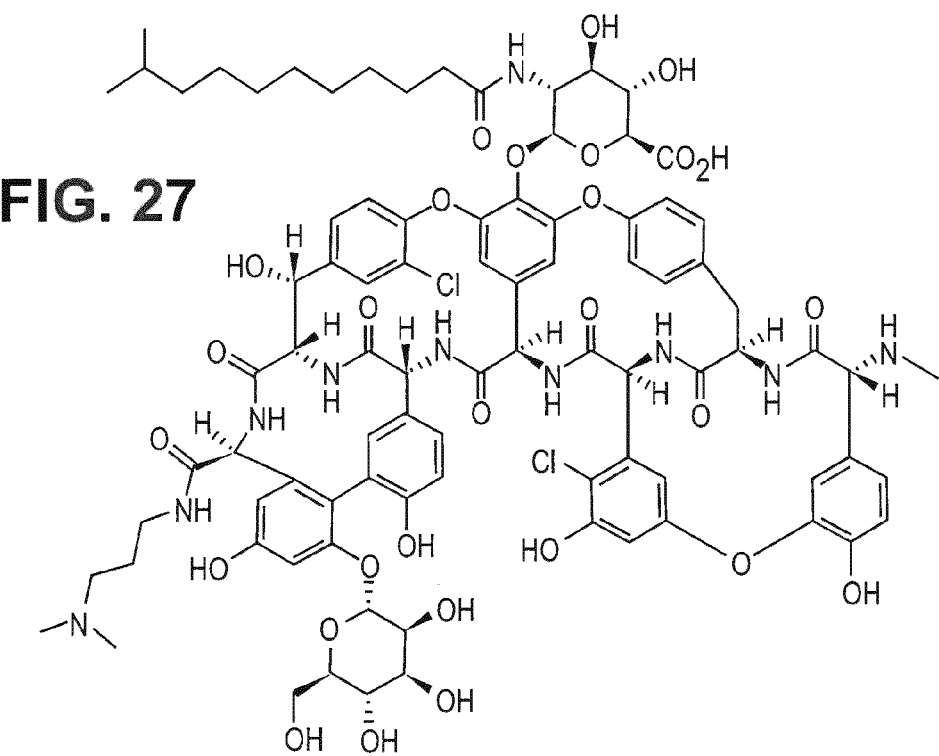
FIG. 27 provides the structure of dalbavancin $B_0$.

The present invention provides $N^{15},N^{15}$-dialkyl antibiotic compounds useful, for example, for preventing and/or treating microbial infections in mammals. For convenience, in the description herein, dalbavancin compounds are numbered according to U.S. Pat. No. 5,750,509 and as depicted in FIG. 26.

In certain embodiments, the present invention provides $N^{15},N^{15}$-dialkyl antibiotic compounds according to formula (III), or a pharmaceutically acceptable salt or solvate thereof:

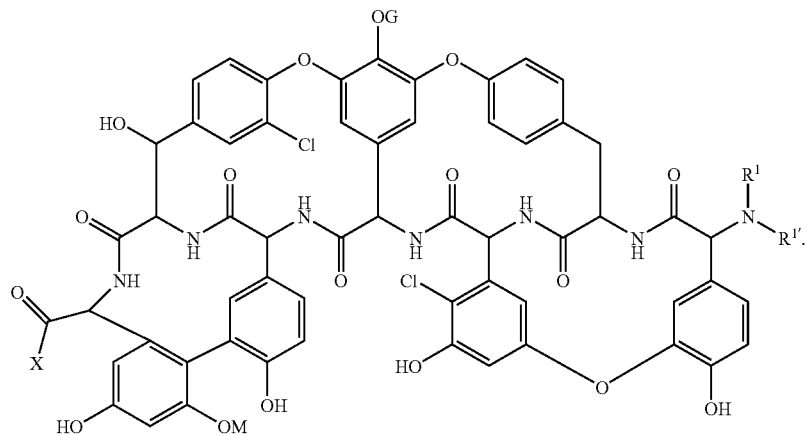

(III)

In certain embodiments, the present invention provides $N^{15},N^{15}$-dialkyl antibiotic compounds according to formula (IV), or a pharmaceutically acceptable salt or solvate thereof:

The $N^{15},N^{15}$-dialkyl antibiotic compounds of the invention can be glycosylated in one or more positions, as is known to those of skill in the art. In preferred embodiments, the $N^{15}$, (IV)

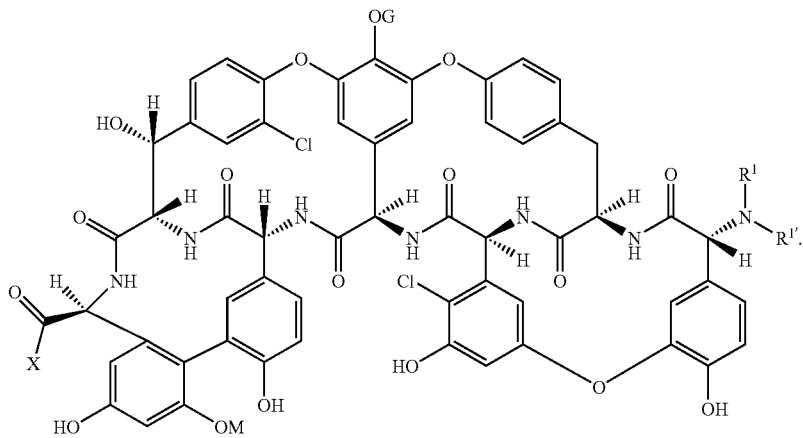

Formulas (III) and (IV) provide the peptide core of the $N^{15},N^{15}$-dialkyl antibiotic compounds of the invention. The peptide comprises seven amino acids with the amino terminus at the right side, as depicted in formulas (III) and (IV), and the carboxy terminus at the left. According to this aspect of the invention, the $N^{15},N^{15}$-dialkyl antibiotic compounds comprise two alkyl substituents on the amino terminal nitrogen, or $N^{15}$. In other words, in formulas (III) and (IV) $R^1$ and $R^{1'}$ are alkyl.

In preferred embodiments, $R^1$ and $R^{1'}$ are $C_{1-4}$ alkyl. In certain embodiments, $R^1$ and $R^{1'}$ are each independently selected from propyl, ethyl and methyl. In further embodiments, $R^1$ and $R^{1'}$ are each independently selected from ethyl and methyl. In more preferred embodiments, at least one of $R^1$ and $R^{1'}$ is methyl. In most preferred embodiments, $R^1$ and $R^{1'}$ are methyl.

The remainder of the molecule can be modified in the same manner as dalbavancin compounds known to those of skill in the art. Accordingly, X is an aminoalkylamino group, as defined in the sections above. Exemplary aminoalkylamino groups are described in U.S. Pat. No. 5,750,509. In certain embodiments, X is N,N-dimethylaminopropylamino.

Thus, in particular embodiments, the invention provides compounds according to formula (V), or a pharmaceutically acceptable salt or solvate thereof:

$N^{15}$-dialkyl antibiotic compounds are glycosylated at positions G and M of formula (III) or (IV). In particular embodiments, M is hydrogen or a sugar moiety. For example, M can be hydrogen, α-D-mannopyrannosyl or 6-O-acetyl-α-D-mannopyrannosyl. In particular embodiments, G is hydrogen or a sugar moiety. For example, G can be hydrogen or glucuronamine.

In certain embodiments, one or both of the sugar moieties can be acylated or acetylated, or both. For example, when G is glucuronamine, the glucuronamine moiety can be acylated with a fatty acid. The fatty acid can be any fatty acid known to those of skill in the art. In particular embodiments, the fatty acid is selected from the group consisting of 8-methyl nonanoic acid, n-decanoic acid, 9-methyl-decanoic acid, n-undecanoic acid, 10-methyl-undecanoic acid, n-dodecanoic acid, 11-methyl-dodecanoic acid, n-tridecanoic acid, 12-methyl-tridecanoic acid and n-tetradecanoic acid. In preferred embodiments, the fatty acid is a $C_{12}$ fatty acid. In particular embodiments, the fatty acid is 10-methyl-undecanoic acid.

In certain embodiments, the present invention provides a compound according to formula (VI), or a pharmaceutically acceptable salt or solvate thereof:

(V)

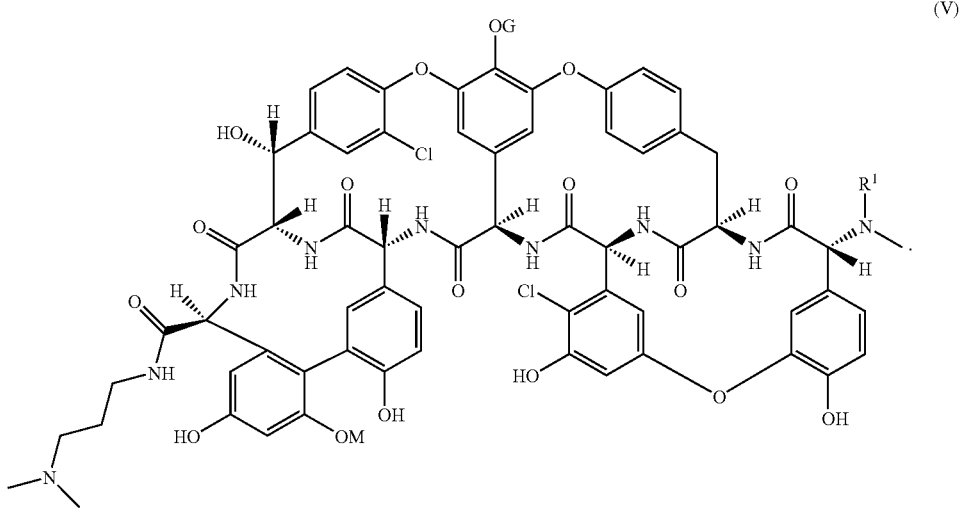

(VI)

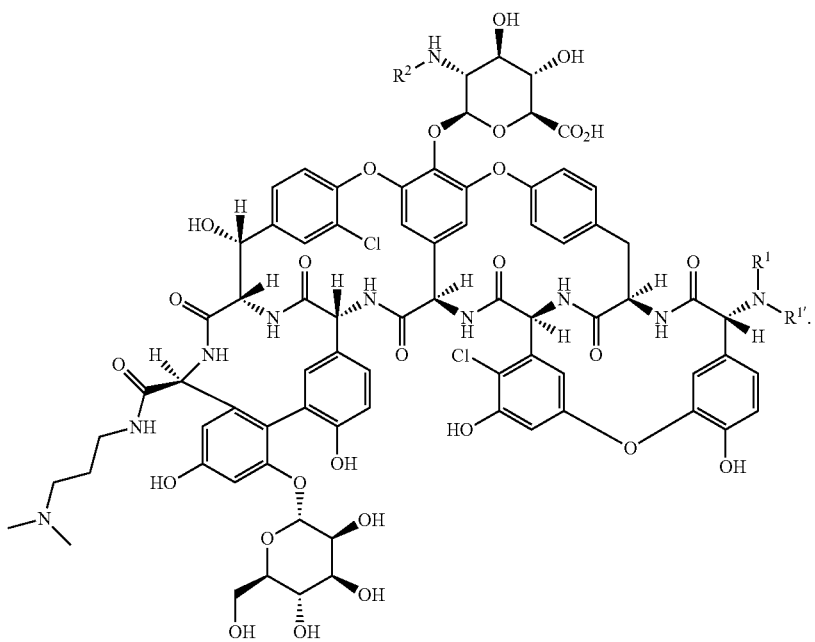

In formula (VI), $R^2$ is $C_{10-14}$ acyl. In particular embodiments, $R^2$ is selected from the group consisting of 8-methyl nonanoic acid, n-decanoic acid, 9-methyl-decanoic acid, n-undecanoic acid, 10-methyl-undecanoic acid, n-dodecanoic acid, 11-methyl-dodecanoic acid, n-tridecanoic acid, 12-methyl-tridecanoic acid and n-tetradecanoic acid. In preferred embodiments, $R^2$ is a $C_{12}$ fatty acid. In particular embodiments, $R^2$ is 10-methyl-undecanoic acid.

As described in the synthetic sections below, $N^{15},N^{15}$-dimethyl antibiotic compounds can be synthesized from dalbavancin compounds. Accordingly, certain $N^{15},N^{15}$-dimethyl antibiotic compounds of the invention possess the sugar moieties and fatty acids of dalbavancin $A_0$, $A_1$, $B_0$, $B_1$, $C_0$ and $C_1$.

In particular embodiments, the present invention provides $N^{15},N^{15}$-dimethyl antibiotic compounds. An $N^{15},N^{15}$-dimethyl antibiotic compound comprises formula (I) or (II) with two methyl groups at $N^{15}$. $N^{15},N^{15}$-dimethyl antibiotic compound can be glycosylated with one or more sugar moieties as described above. In certain embodiments, a $N^{15},N^{15}$-dimethyl antibiotic compound is acylated on one or more of these sugar moieties. In preferred embodiments, the acyl group is 10-methyl-undecanoic acid.

In preferred embodiments, the present invention provides the $N^{15},N^{15}$-dimethyl antibiotic compound according to the following structure (VII), or a pharmaceutically acceptable salt or solvate thereof:

(VII)

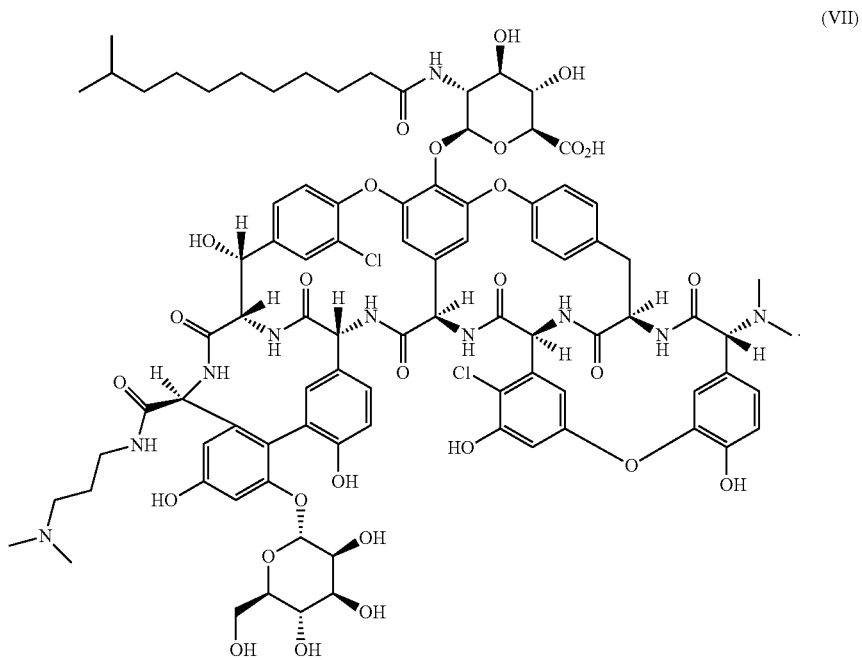

In certain embodiments, the $N^{15},N^{15}$-dialkyl antibiotic compound of the invention is purified. As used herein, the term purified indicates that the $N^{15},N^{15}$-dialkyl antibiotic compound is enriched relative to other dalbavancin compounds in a composition. For example, the $N^{15},N^{15}$-dialkyl antibiotic compound can be enriched relative to a mixture in which the $N^{15},N^{15}$-dialkyl antibiotic compound is produced, for instance a mixture derived from a fermentation broth as described in the examples below. In certain embodiments, the $N^{15},N^{15}$-dialkyl antibiotic compound is enriched two, three, five, ten, one hundred, one thousand or ten thousand fold.

In further embodiments, the $N^{15},N^{15}$-dialkyl antibiotic compound is isolated. As used herein, the term isolated indicates that the $N^{15},N^{15}$-dialkyl antibiotic compound is enriched relative to non-dalbavancin compounds in a composition. For example, the $N^{15},N^{15}$-dialkyl antibiotic compound can be enriched relative to a mixture in which the $N^{15},N^{15}$-dialkyl antibiotic compound is produced, for instance a mixture derived from a fermentation broth as described in the examples below. In certain embodiments, the $N^{15},N^{15}$-dialkyl antibiotic compound is enriched two, three, five, ten, one hundred, one thousand or ten thousand fold.

In still further embodiments, the $N^{15},N^{15}$-dialkyl antibiotic compound is purified and isolated. As used herein, the term purified and isolated indicates that the $N^{15},N^{15}$-dialkyl antibiotic compound is enriched relative to non-dalbavancin compounds and relative to other dalbavancin compounds in a composition. For example, the $N^{15},N^{15}$-dialkyl antibiotic compound can be enriched relative to a mixture in which the $N^{15},N^{15}$-dialkyl antibiotic compound is produced, for instance a mixture derived from a fermentation broth as described in the examples below. In certain embodiments, the $N^{15},N^{15}$-dialkyl antibiotic compound is enriched two, three, five, ten, one hundred, one thousand or ten thousand fold.

$N^{15},N^{15}$-Dialkyl Antibiotic Compounds

The present invention also provides $N^{15},N^{15}$-dialkyl antibiotic compounds having a carboxylic acid group at carbonyl 63. These compounds are useful, for example, for preparing $N^{15},N^{15}$-dialkyl antibiotic compounds of the invention. In certain embodiments, these $N^{15},N^{15}$-dialkyl antibiotic compounds are also useful for preventing and/or treating microbial infections in mammals.

In certain embodiments, the present invention provides $N^{15},N^{15}$-dialkyl antibiotic compounds according to formula (VIII), or a pharmaceutically acceptable salt or solvate thereof:

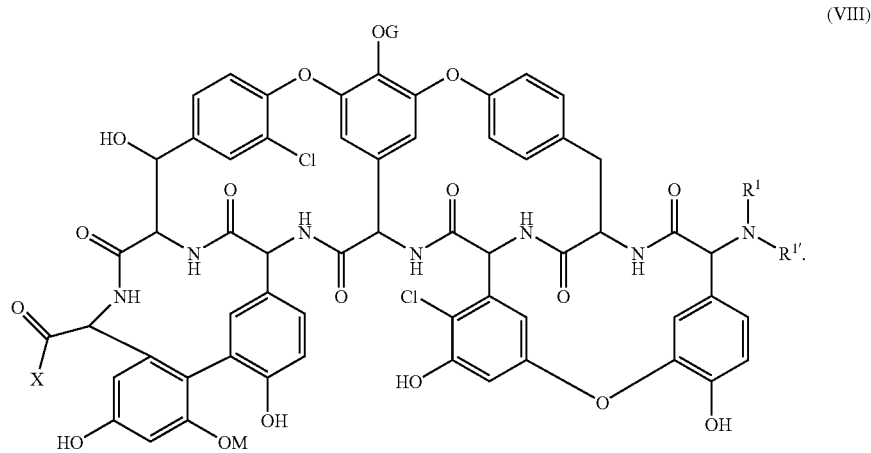

(VIII)

In certain embodiments, the present invention provides $N^{15},N^{15}$-dialkyl antibiotic compounds according to formula (IX), or a pharmaceutically acceptable salt or solvate thereof:

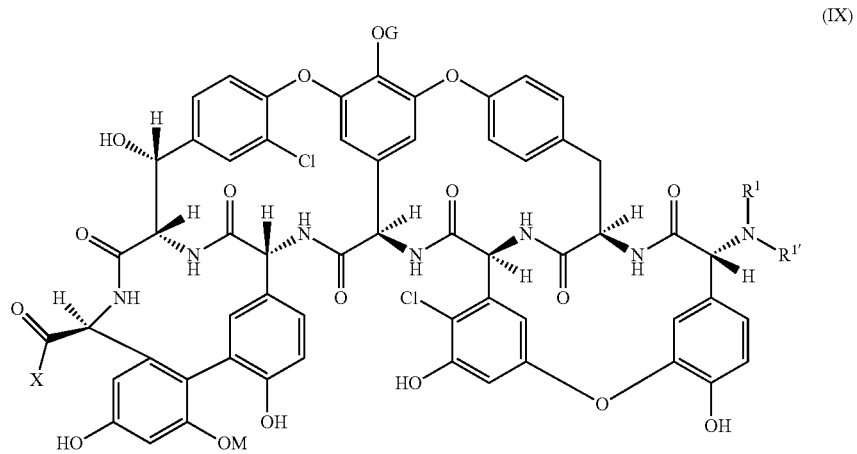

(IX)

Formulas (VIII) and (IX) provide the peptide core of the $N^{15},N^{15}$-dialkyl antibiotic compounds of this aspect of the invention. The peptide comprises seven amino acids with the amino terminus at the right side, as depicted in formulas (III) and (IV), and the carboxy terminus at the left. According to this aspect of the invention, the $N^{15},N^{15}$-dialkyl antibiotic compounds comprise two alkyl substituents on the amino terminal nitrogen, or $N^{15}$. In other words, in formulas (I) and (II) $R^1$ and $R^{1'}$ are alkyl. Further, in Formulas (VIII) and (IX), X is OH as in antibiotic A 40926 compounds known to those of skill in the art.

In preferred embodiments, $R^1$ and $R^{1'}$ are $C_{1-4}$ alkyl. In certain embodiments, $R^1$ and $R^{1'}$ are each independently selected from propyl, ethyl and methyl. In further embodiments, $R^1$ and $R^{1'}$ are each independently selected from ethyl and methyl. In more preferred embodiments, at least one of $R^1$ and $R^{1'}$ is methyl. In most preferred embodiments, $R^1$ and $R^{1'}$ are methyl.

The $N^{15},N^{15}$-dialkyl antibiotic compounds of the invention can be glycosylated in one or more positions, as is known to those of skill in the art. In preferred embodiments, the $N^{15},N^{15}$-dialkyl antibiotic compounds are glycosylated at positions G and M of formulas (VIII) and (IX). In particular embodiments, M is hydrogen or a sugar moiety. For example, M can be hydrogen, α-D-mannopyrannosyl or 6-O-acetyl-α-D-mannopyrannosyl. In particular embodiments, G is hydrogen or a sugar moiety. For example, G can be hydrogen or glucuronamine.

In certain embodiments, one or both of the sugar moieties can be acylated or acetylated, or both. For example, when G is glucuronamine, the glucuronamine moiety can be acylated with a fatty acid. The fatty acid can be any fatty acid known to those of skill in the art. In particular embodiments, the fatty acid is selected from the group consisting of 8-methyl nonanoic acid, n-decanoic acid, 9-methyl-decanoic acid, n-undecanoic acid, 10-methyl-undecanoic acid, n-dodecanoic acid, 11-methyl-dodecanoic acid, n-tridecanoic acid, 12-methyl-tridecanoic acid and n-tetradecanoic acid. In preferred embodiments, the fatty acid is a $C_{12}$ fatty acid. In particular embodiments, the fatty acid is 10-methyl-undecanoic acid.

In certain embodiments, the present invention provides a compound according to formula (X), or a pharmaceutically acceptable salt or solvate thereof:

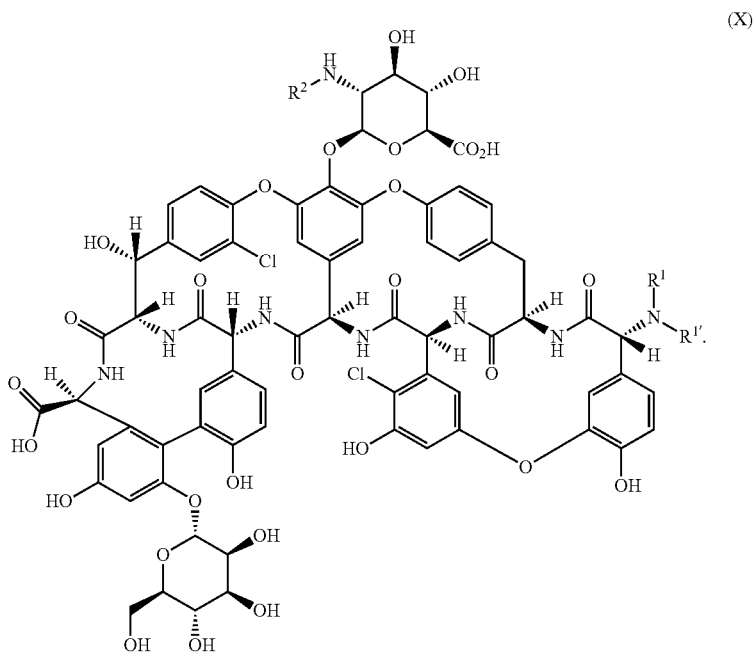

(X)

In formula (X), $R^2$ is $C_{10-14}$ acyl. In particular embodiments, $R^2$ is selected from the group consisting of 8-methyl nonanoic acid, n-decanoic acid, 9-methyl-decanoic acid, n-undecanoic acid, 10-methyl-undecanoic acid, n-dodecanoic acid, 11-methyl-dodecanoic acid, n-tridecanoic acid, 12-methyl-tridecanoic acid, and n-tetradecanoic acid. In preferred embodiments, $R^2$ is a $C_{12}$ fatty acid. In particular embodiments, $R^2$ is 10-methyl-undecanoic acid.

As described in the synthetic sections below, the $N^{15},N^{15}$-dimethyl antibiotic compounds can be synthesized from antibiotic A 40926 compounds. Accordingly, certain $N^{15},N^{15}$-dimethyl antibiotic compounds of the invention possess the sugar moieties and fatty acids of antibiotic A 40926 factor $A_0$, $A_1$, $B_0$, $B_1$, $C_0$ and $C_1$.

In particular embodiments, the present invention provides $N^{15},N^{15}$-dimethyl antibiotic compounds. An $N^{15},N^{15}$-dimethyl antibiotic compound comprises formula (VIII) or (IX) with two methyl groups at $N^{15}$. An $N^{15},N^{15}$-dimethyl antibiotic compound can be glycosylated with one or more sugar moieties as described above. In certain embodiments, a $N^{15},N^{15}$-dimethyl antibiotic compound is acylated on one or more of these sugar moieties. In preferred embodiments, the acyl group is 10-methyl-undecanoic acid.

In preferred embodiments, the present invention provides the $N^{15},N^{15}$-dimethyl antibiotic compound according to the following structure (XI), or a pharmaceutically acceptable salt or solvate thereof:

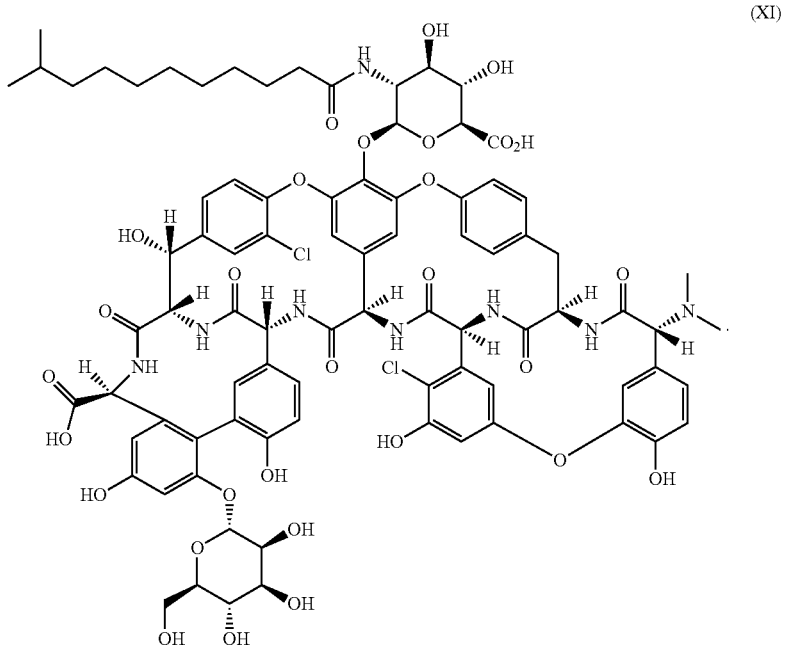

(XI)

In certain embodiments, the $N^{15},N^{15}$-dialkyl antibiotic compound of the invention is purified. As used herein, the term purified indicates that the $N^{15},N^{15}$-dialkyl antibiotic compound is enriched relative to other antibiotic compounds in a composition. For example, the $N^{15},N^{15}$-dialkyl antibiotic compound can be enriched relative to a mixture in which the $N^{15},N^{15}$-dialkyl antibiotic compound is produced, for instance a mixture derived from a fermentation broth as described in the examples below. In certain embodiments, the $N^{15},N^{15}$-dialkyl antibiotic compound is enriched two, three, five, ten, one hundred, one thousand or ten thousand fold.

In further embodiments, the $N^{15},N^{15}$-dialkyl antibiotic compound is isolated. As used herein, the term isolated indicates that the $N^{15},N^{15}$-dialkyl antibiotic compound is enriched relative to non-antibiotic compounds in a composition. For example, the $N^{15},N^{15}$-dialkyl antibiotic compound can be enriched relative to a mixture in which the $N^{15},N^{15}$-dialkyl antibiotic compound is produced, for instance a mixture derived from a fermentation broth as described in the examples below. In certain embodiments, the $N^{15},N^{15}$-dialkyl antibiotic compound is enriched two, three, five, ten, one hundred, one thousand or ten thousand fold.

In still further embodiments, the $N^{15},N^{15}$-dialkyl antibiotic compound is purified and isolated. As used herein, the term purified and isolated indicates that the $N^{15},N^{15}$-dialkyl antibiotic compound is enriched relative to non-antibiotic compounds and relative to other dalbavancin compounds in a composition. For example, the $N^{15},N^{15}$-dialkyl antibiotic compound can be enriched relative to a mixture in which the $N^{15},N^{15}$-dialkyl antibiotic compound is produced, for instance a mixture derived from a fermentation broth as described in the examples below. In certain embodiments, the $N^{15},N^{15}$-dialkyl antibiotic compound is enriched two, three, five, ten, one hundred, one thousand or ten thousand fold.

Methods of Making the Compounds of the Invention

The compounds of the invention can be made according to any method apparent to those of skill in the art for preparing such $N^{15},N^{15}$-dialkyl antibiotic compounds.

For instance, in certain embodiments, an $N^{15},N^{15}$-dialkyl antibiotic compound or composition of the invention can be prepared by alkylating the corresponding $N^{15}$-monomethyl compound or composition by any technique apparent to one of skill in the art. For example, an $N^{15}$-monomethyl compound or composition can be methylated by contacting the compound or composition with a mixture of HCHO, $NaBH_3CN$, DMF, $H_2O$ and $NaHCO_3$ at room temperature as illustrated in Scheme 1. In a particular embodiment, an $N^{15}$-monomethyl dalbavancin compound or composition is dissolved in water and DMF, to which formaldehyde and sodium bicarbonate are added followed by $NaBH_3CN$ to yield the $N^{15},N^{15}$-dimethyl antibiotic compound or composition.

Scheme 1

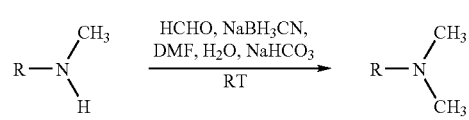

The corresponding $N^{15}$-monomethyl compound or composition can be prepared according to published techniques, such as those described extensively in U.S. Pat. No. 5,750,509 and U.S. Patent Application Publication No. US 2004/0142883, the contents of which are incorporated by reference in their entireties. To the extent that the compounds or compositions have protecting groups on their $N^{15}$ nitrogen, they can be removed by any technique known to the person of skill in the art.

Suitable starting materials include dalbavancin $A_0$, $A_1$, $B_0$, $B_1$, $C_0$ and $C_1$ and antibiotic A 40926 factors $A_0$, $A_1$, $B_0$, $B_1$, $C_0$ and $C_1$. As shown in the examples below, $N^{15},N^{15}$-dimethyl dalbavancin $B_0$ was prepared from dalbavancin $B_0$ according to this method. The preparation of these dalbavancin compounds is described extensively in U.S. Patent Application Publication No. US 2004/0142883. These dalbavancin compounds have the following structures:

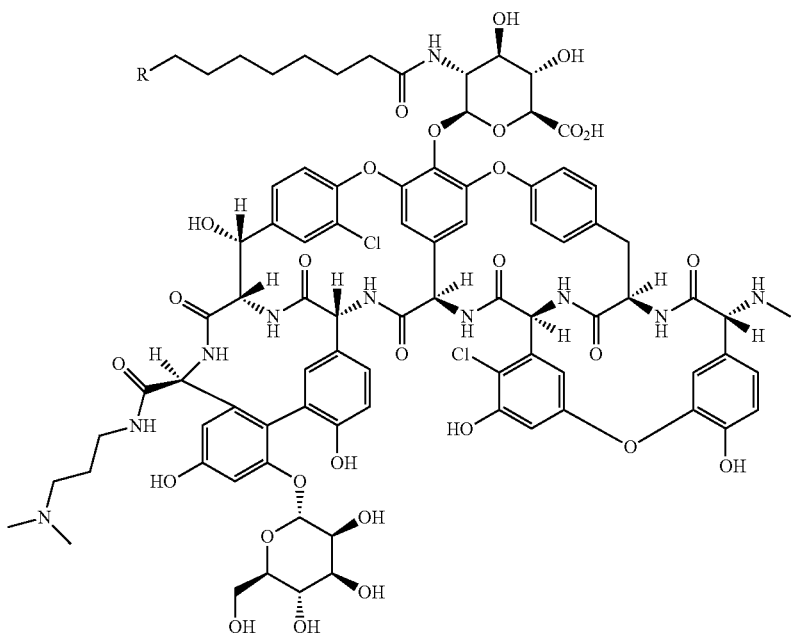

wherein R is as follows:

| Dalbavancin Compound | R |
|---|---|
| $A_0$ | —CH(CH$_3$)$_2$ |
| $A_1$ | —CH$_2$CH$_2$CH$_3$ |
| $B_0$ | —CH$_2$CH(CH$_3$)$_2$ |
| $B_1$ | —CH$_2$CH$_2$CH$_2$CH$_3$ |
| $C_0$ | —CH$_2$CH$_2$CH(CH$_3$)$_2$ |
| $C_1$ | —CH$_2$CH$_2$CH$_2$CH$_2$CH$_3$ |

In further embodiments, an $N^{15},N^{15}$-dialkyl antibiotic compound of the invention can be prepared from antibiotic A 40926 fermentation broth. The fermentation broth comprising antibiotic A 40926 and related compounds can be prepared according to techniques described, for example, in U.S. Pat. No. 5,750,509 and U.S. Patent Application Publication No. US 2004/0142883. The broth can be purified to yield the desired antibiotic A 40926 compounds, which can be esterified, amidated and hydrolyzed according to U.S. Pat. No. 5,750,509 and U.S. Patent Application Publication No. US 2004/0142883 to yield a mixture of dalbavancin compounds. $N^{15},N^{15}$-dialkyl antibiotic compounds can be purified and/or isolated from the mixture according to any technique apparent to those of skill in the art. In the examples below, HPLC techniques are used to purify $N^{15},N^{15}$-dialkyl antibiotic compounds of the invention.

Compositions

In another aspect, the present invention provides compositions comprising one or more compounds of the invention. Generally, the compositions of the invention comprise a compound of the invention and one or more other compounds. The other compounds can be compounds of the invention, compounds known to those of skill in the art, compounds yet to be discovered or published or other compounds.

In certain embodiments, the compositions are pharmaceutical compositions, described in more detail in the sections below.

In particular embodiments, the compositions comprise a $N^{15},N^{15}$-dialkyl antibiotic compound of the invention and a dalbavancin or antibiotic A 40926 compound. The dalbavancin or antibiotic A 40926 compound can be any dalbavancin or antibiotic A 40926 compound known to those of skill in the art. Exemplary dalbavancin compounds include those described in U.S. Pat. No. 5,750,509 and U.S. Patent Application Publication No. US 2004/0142883, the contents of which are hereby incorporated by reference in their entireties. Exemplary antibiotic A 40926 compounds are described in U.S. Pat. Nos. 4,935,238, 4,868,171 and 4,782,042, the contents of which are hereby incorporated by reference in their entireties.

Exemplary dalbavancin compounds include dalbavancin $A_0$, $A_1$, $B_0$, $B_1$, $C_0$ and $C_1$. The preparation of these dalbavancin compounds is described extensively in U.S. Patent Application Publication No. US 2004/0142883. These dalbavancin compounds are further described in the sections above. Of course, the compositions of the invention can comprise additional dalbavancin compounds not listed among the exemplary dalbavancin compounds above.

In certain embodiments the compositions comprise multimers of compounds of the invention. The multimers can be dimers, trimers or larger. The multimers can be homomultimers, heteromultimers or a mixture of homomultimers and heteromultimers. For instance, the multimer can comprise a combination of any of the factors present in the dalbavancin composition, including any of dalbavancin factors $A_0$, $A_1$, $B_0$, $B_1$, $B_2$, $C_0$, $C_1$, $D_0$, $D_1$, MAG, or iso$B_0$. For example, the multimer may comprise a $N^{15}$-alkyl dalbavancin compound and a $N^{15},N^{15}$-dialkyl dalbavancin compound. In certain embodiments, the present invention also provides homodimers of the compounds of the invention. In further embodiments, the present invention provides heterodimers of the compounds of the invention with dalbavancin compounds. The dalbavancin compounds can be dalbavancins of the invention or dalbavancins known to those of skill in the art.

In certain embodiments, the compositions of the invention comprise a significant amount of an $N^{15},N^{15}$-dialkyl antibiotic compound of the invention relative to dalbavancin or antibiotic A 40926 compounds. In certain embodiments, relative to the dalbavancin or antibiotic A 40926 compounds, the $N^{15},N^{15}$-dialkyl antibiotic compound of the invention is at least 0.05, 0.1, 0.15, 0.2, 0.25, 0.5, 0.75, 1.0, 1.25, 1.5, 1.6, 1.7, 1.75, 1.8, 1.9, 2.0, 2.5, 5, 10, 15, 20, 25, 30, 40, 50, 60, 70, 80, 90, 95, 96, 97, 98 or 99% of the composition. In preferred embodiments, the compound is according to formula (V).

In certain embodiments, the compositions of the invention comprise a significant amount of an $N^{15},N^{15}$-dialkyl antibiotic compound of the invention relative to dalbavancin compounds. In certain embodiments, relative to the dalbavancin compounds, the $N^{15},N^{15}$-dialkyl antibiotic compound of the invention is at least 0.05, 0.1, 0.15, 0.2, 0.25, 0.5, 0.75, 1.0, 1.25, 1.5, 1.6, 1.7, 1.75, 1.8, 1.9, 2.0, 2.5, 5, 10, 15, 20, 25, 30, 40, 50, 60, 70, 80, 90, 95, 96, 97, 98 or 99% of the composition. In preferred embodiments, the compound is according to formula (V).

In certain embodiments, the compositions of the invention comprise a significant amount of an $N^{15},N^{15}$-dialkyl antibiotic compound of the invention relative to antibiotic A 40926 compounds. In certain embodiments, relative to the antibiotic A 40926 compounds, the $N^{15},N^{15}$-dialkyl antibiotic compound of the invention is at least 0.05, 0.1, 0.15, 0.2, 0.25, 0.5, 0.75, 1.0, 1.25, 1.5, 1.6, 1.7, 1.75, 1.8, 1.9, 2.0, 2.5, 5, 10, 15, 20, 25, 30, 40, 50, 60, 70, 80, 90, 95, 96, 97, 98 or 99% of the composition. In preferred embodiments, the compound is according to formula (V).

In certain embodiments, the compositions of the invention comprise a significant amount of an $N^{15},N^{15}$-dialkyl antibiotic compound of the invention relative to other compounds. In certain embodiments, the $N^{15},N^{15}$-dialkyl antibiotic compound of the invention is at least 0.05, 0.1, 0.15, 0.2, 0.25, 0.5, 0.75, 1.0, 1.25, 1.5, 1.6, 1.7, 1.75, 1.8, 1.9, 2.0, 2.5, 5, 10, 15, 20, 25, 30, 40, 50, 60, 70, 80, 90, 95, 96, 97, 98 or 99% of the composition relative to other compounds. In preferred embodiments, the compound is according to formula (V).

In further embodiments, the present invention provides compositions comprising dalbavancin $A_0$, $A_1$, $B_0$, $B_1$, $C_0$ and $C_1$ together with an $N^{15},N^{15}$-dialkyl antibiotic compound of the invention wherein the amount of the compound of the invention is enriched relative to one or more or all of dalbavancin $A_0$, $A_1$, $B_0$, $B_1$, $C_0$ and $C_1$. The composition can be enriched, for example, so that the $N^{15},N^{15}$-dialkyl antibiotic compound is at least 0.05, 0.1, 0.15, 0.2, 0.25, 0.5, 0.75, 1.0, 1.25, 1.5, 1.6, 1.7, 1.75, 1.8, 1.9, 2.0, 2.5, 5, 10, 15, 20, 25, 30, 40, 50, 60, 70, 80, 90, 95, 96, 97, 98 or 99% of the composition relative to one or more or all of dalbavancin $A_0$, $A_1$, $B_0$, $B_1$, $C_0$ and $C_1$. In preferred embodiments, the compound is according to formula (V).

In certain embodiments, the present invention provides compositions comprising dalbavancin $B_0$ and an $N^{15},N^{15}$-dialkyl antibiotic compound of the invention. In further embodiments, the present invention provides compositions comprising dalbavancin $B_1$ and an $N^{15},N^{15}$-dialkyl antibiotic compound of the invention. In further embodiments, the present invention provides compositions comprising dalbavancin $B_0$, dalbavancin $B_1$ and an $N^{15},N^{15}$-dialkyl antibiotic compound of the invention. In preferred embodiments, the $N^{15},N^{15}$-dialkyl antibiotic compound of the invention is according to formula (V). In particularly preferred embodiments, the present invention provides compositions comprising the compound of formula (V), dalbavancin $B_0$ and dalbavancin $B_1$. These compositions can be purified, isolated or purified and isolated. In certain embodiments, the compositions are 90, 91, 92, 93, 94, 95, 96, 97, 98, 98.5, 99 or 99.5% pure. By "pure" is meant that the compositions comprise that amount of the compounds of the composition. For instance, the composition comprising the compound of formula (V), dalbavancin $B_0$ and dalbavancin B, would comprise at least 90, 91, 92, 93, 94, 95, 96, 97, 98, 98.5, 99 or 99.5% of the three compounds relative to other compounds in the composition. Purity can be assessed by any means known to those of skill in the art such as HPLC, for instance by % area under the curve.

In the compositions of the invention, the amount of each component can be calculated by weight, by molar amount or by any other technique known to those of skill in the art.

Methods of Use

Methods are provided for administration of a $N^{15},N^{15}$-dialkyl antibiotic compound or composition of the invention to an individual in need of treatment for a bacterial infection. In one embodiment, the $N^{15},N^{15}$-dialkyl antibiotic compound is according to formula (V). Treatment can include prophylaxis, therapy, or cure. Methods include administration of a $N^{15},N^{15}$-dialkyl antibiotic compound or composition in a therapeutically or prophylactically effective amount.

As used herein, "therapeutically effective amount" refers to the amount of a compound or composition that, when administered to a subject for treating a disease, will render a desired therapeutic outcome (e.g., reduction or elimination of a bacterial infection). A "therapeutically effective amount" can vary depending on, inter alia, the compound, the disease and its severity, and the age, weight, etc., of the subject to be treated, and may be administered in one or more doses. A "prophylactically effective amount" refers to an amount of a $N^{15},N^{15}$-dialkyl antibiotic compound or composition sufficient to prevent or reduce severity of a future bacterial infection when administered to an individual who is susceptible to and/or who may contract a bacterial infection, e.g., by virtue of a medical procedure or stay in the hospital, or exposure to an individual with a bacterial infection. A $N^{15},N^{15}$-dialkyl antibiotic compound or composition can be administered in a pharmaceutically acceptable carrier.

A $N^{15},N^{15}$-dialkyl antibiotic compound or composition can be administered as a "unit dose" in a $N^{15},N^{15}$-dialkyl antibiotic formulation which includes an amount of the compound sufficient to provide a therapeutically or prophylactically effective plasma level of the compound for several days, at least about 5 days, one week, or 10 days, when administered to an individual. In some embodiments, the compound is according to formula (V). In some embodiments, the compound is a component of a formulation, which includes an amount of the compound sufficient to provide therapeutically or prophylactically effective level of the compound for several days, often at least about 5 days, one week, or 10 days. The dosing interval, or time between doses, can be, for example, any of about 2, 3, 4, 5, 6, 7, 8, 9, 10, 11, 12, 13, 14, 15, 16, 17, 18, 19, 20, 21, 22, 23, 24, 25, or more days.

As used herein, the terms "individual" or "subject" or "patient" are used interchangeably and refer to a vertebrate, typically a mammal, often a human.

In addition, a compound or composition of the invention can be formulated with a stabilizer that inhibits degradation of the compound, the composition, and/or one or more other $N^{15},N^{15}$-dialkyl antibiotic or other antibiotic components present in the composition. In some embodiments, the stabilizer is selected from the group consisting of mannitol, lactose, sucrose, sorbitol, glycerol, cellulose, trehalose, maltose, raffinose, and mixtures thereof. In one embodiment, a formulation comprises mannitol. In another embodiment, a formulation further comprises lactose. In one embodiment, the composition can be formulated with a 1:2 weight ratio of mannitol:$N^{15},N^{15}$-dialkyl antibiotic compound. In another embodiment, the composition can be formulated with a 1:1:4 weight ratio of mannitol:lactose: $N^{15},N^{15}$-dialkyl antibiotic compound.

In some embodiments, a composition or other formulation comprises a $N^{15},N^{15}$-dimethyl antibiotic compound, a dalbavancin compound, or a combination thereof. A composition or other formulation can be administered at a dosage that results in therapeutically effective (i.e., bactericidal) plasma levels of the drug for several days, often at least about 5 to about 10 days, often at least about one week. For example, $N^{15},N^{15}$-dialkyl antibiotic compounds or compositions can be maintained in plasma at or above the minimum bactericidal concentration of about 4 mg/l for at least 5 days. $N^{15},N^{15}$-dialkyl antibiotic compounds or compositions can be maintained at a plasma level of at least about 5 mg/l, at least about 10 mg/l, at least about 20 mg/l, at least about 30 mg/l, at least about 40 mg/l, for at least 5 days, at least about one week or longer. Plasma levels of $N^{15},N^{15}$-dialkyl antibiotic compounds or compositions can be measured by methods that are well known in the art, such as liquid chromatography, mass spectrometry, or microbiological bioassay.

Upper limits for $N^{15},N^{15}$-dialkyl antibiotic compound or composition plasma concentration levels can be dictated by dosages that inhibit unacceptable adverse effects in the patient population treated.

A $N^{15},N^{15}$-dialkyl antibiotic compound or composition can be administered in a single dose or in multiple doses. When administered as a single dose, a $N^{15},N^{15}$-dialkyl antibiotic compound or composition can be formulated to contain a sufficient amount of the $N^{15},N^{15}$-dialkyl antibiotic compound(s) to effect antibacterial properties in vivo for at least 5 days, alternatively for at least 6 days, alternatively for at least 7 days, alternatively for at least 8 days, alternatively for at least 9 days, alternatively for at least 10 days, alternatively for at least 11 days, alternatively for at least 12 days, alternatively for at least 13 days, alternatively for at least 14 days, alternatively for at least 15 days.

When multiple doses are employed, a $N^{15},N^{15}$-dialkyl antibiotic compound or composition can be administered weekly for two or more weeks. In one embodiment, a $N^{15},N^{15}$-dialkyl antibiotic compound or composition can be administered in at least two doses, often in two doses about 5 to about 10 days apart, more often once a week for two weeks. In certain embodiments, such a regimen provides significant advantages over conventional antibiotic treatment protocols.

A $N^{15},N^{15}$-dialkyl antibiotic compound or composition can also be administered in multiple doses two or more days or at least one week apart, or in one or more biweekly doses. In some embodiments, a $N^{15},N^{15}$-dialkyl antibiotic compound or composition can be administered weekly, followed by biweekly, or monthly administration. In some embodiments, a $N^{15},N^{15}$-dialkyl antibiotic compound or composition can be administered at weekly intervals for 2, 3, 4, 5, 6, or more weeks.

Most advantageously, daily dosing of a $N^{15},N^{15}$-dialkyl antibiotic compound or composition is not required because higher, less frequent doses can be used. Single or multiple doses can range, for example, from about 0.1 to about 5 grams. A single dose of about 0.1 to about 4 grams, e.g., about 3 grams, can be administered for various infection treatments. Where multiple doses are administered, for example, weekly, each dose can range, for example, from about 0.25 to about 5 grams.

For embodiments in which a single dose can be administered to treat an infection, the amount of the dose can be, for example, about 0.1 to about 5 grams, or about 0.5 to about 4 grams, or about 1 to about 3.5 grams, or about 2 to about 3 grams, e.g., about 3 grams. In some embodiments, a single dose of about 1, 1.5, 2, 2.5, or 3 grams can be administered for treatment of a bacterial infection. For embodiments in which a single dose can be administered for prophylaxis, the amount of the dose may be, for example, about 0.1 to about 3 grams, or about 0.1 to about 1 gram, e.g., about 0.5 or about 0.25 gram.

In dosing schemes that include multiple dosages, the individual dosages may be the same or different. In some embodiments, a first, higher dose can be administered, that can be, for example, about 1.5 to 3 times higher, than one or more subsequent doses. For example, the first dose may be about 0.5 grams to about 5 grams and the second dose about 0.25 grams to about 2.5 grams, the first dose may be about 0.8 to about 2 gram and the second dose about 0.4 to about 1 gram, or the first dose may be about 0.4 to about 3 gram and the second dose about 0.2 to 1.5 gram.

In some embodiments, at least two dosages are administered wherein the first dosage includes about twice as much of a $N^{15},N^{15}$-dialkyl antibiotic compound or composition as subsequent dosages. In an embodiment, a first dosage includes about 1 gram of the $N^{15},N^{15}$-dialkyl antibiotic compound or composition and a subsequent dosage of about 0.5 gram. In another embodiment, a first dosage includes about 0.5 gram and a subsequent dosage of about 0.25 gram.

In some embodiments, a $N^{15},N^{15}$-dialkyl antibiotic compound or composition can be administered in two doses of equal or different amounts two or more days or at least about one week apart. For example, two doses of about 0.2 to about 1.5 grams of a $N^{15},N^{15}$-dialkyl antibiotic compound or composition can be administered about 5 to about 10 days apart, or about 1 week apart. In one embodiment, a first dosage of about 1 gram and a second dosage of about 0.5 gram of a $N^{15}$-dialkyl antibiotic compound or composition can be administered about 1 week apart.

In a multiple dosing regimen, the time between doses may range, for example, from about 5 to about 10 days, often about one week. Dose frequency can be, for example, two weekly doses, or multiple weekly doses. The dosing interval, or time between doses, can be, for example, any of about 2, 3, 4, 5, 6, 7, 8, 9, 10, 11, 12, 13, 14, 15, 16, 17, 18, 19, 20, 21, 22, 23, 24, 25, or more days. The number of doses given, can be, for example, one, two, three, four, five, six or more doses, each dose after the initial dose being given after the selected dosage interval.

In the multiple dosing schemes of certain embodiments, the "trough level," or the level of a $N^{15},N^{15}$-dialkyl antibiotic compound or composition in plasma after a first dose, and just prior to administration of a second dose, can be at least about 4 mg/l. The trough level of $N^{15},N^{15}$-dialkyl antibiotic compound or composition at the end of a dosing interval such as about one week can be at least about 20 mg/l, at least about 30 mg/l, or at least about 40 mg/l.

A $N^{15},N^{15}$-dialkyl antibiotic compound or composition can be administered parenterally, e.g., intramuscularly (i.m.), intravenously (i.v.), subcutaneously (s.c.), intraperitoneally (i.p.), or intrathecally (i.t.). The dosing schedule and actual dosage administered may vary depending on such factors as the nature and severity of the infection, the age, weight, and general health of the patient and the tolerance of a particular patient to the $N^{15},N^{15}$-dialkyl antibiotic compound or composition, but will be ascertainable to health professionals. In one embodiment, a one gram intravenous dose of a $N^{15},N^{15}$-dialkyl antibiotic compound or composition can be followed by a 0.5 gram intravenous dose one week later.

Administration and delivery of the drug to the patient, e.g., intravenously, can be done at a controlled rate, so that the concentration in the blood does not increase too quickly or cause precipitation to occur. In some embodiments, a $N^{15},N^{15}$-dialkyl antibiotic compound or composition can be administered at an appropriate rate such that the drug forms a complex with endogenous protein(s) in the bloodstream. Without intending to be bound to a particular theory, it can be believed that endogenous protein, such as human serum albumin, can form a complex in vivo with one or two molecules of a $N^{15},N^{15}$-dialkyl antibiotic compound. When a sufficient amount of $N^{15},N^{15}$-dialkyl antibiotic composition is present, up to two molecules of $N^{15},N^{15}$-dialkyl antibiotic compound can bind to the endogenous protein, and this complex can be formed by binding of separate $N^{15},N^{15}$-dialkyl antibiotic compounds at two different binding sites. Alternatively, it is possible that dimeric $N^{15},N^{15}$-dialkyl antibiotic can bind to a single binding site on the endogenous protein.

The infusion duration of the $N^{15},N^{15}$-dialkyl antibiotic compound or composition can be, for example, about 1 minute to about 2 hours. For example, an infusion duration of about 30 minutes can be used with a $N^{15},N^{15}$-dialkyl antibiotic compound or composition, and the dose can be about 0.5 to about 1 gram. Intravenous administration under controlled rate conditions can generate concentrations of $N^{15},N^{15}$-dialkyl antibiotic compound or composition in the body that are in great excess of what can be achieved in the solution phase at physiological pH in vitro. Although not wishing to be limited by theory, this may be due to the formation of a complex of $N^{15},N^{15}$-dialkyl antibiotic with endogenous protein(s) such as serum albumin, which may increase the capacity of plasma to absorb the $N^{15},N^{15}$-dialkyl antibiotic compound or composition.

In certain embodiments, formation of a $N^{15},N^{15}$-dialkyl antibiotic complex in vitro or ex vivo can permit faster administration, such as at least about 1 minute, at least about 10 minutes or at least about 20 minutes. Such a complex can be achieved by mixing human serum albumin and/or another endogenous protein with a $N^{15},N^{15}$-dialkyl antibiotic compound or composition, thereby forming the complex in vitro or ex vivo, and then administering this complex to the treated patient. Alternatively, the human serum albumin or other endogenous protein may be obtained from autologous sources or by expression from a microorganism modified to contain the gene for the protein.

The amount of the $N^{15},N^{15}$-dialkyl antibiotic compound or composition administered can be any of the dosages disclosed herein. The dose can be chosen such that one or more $N^{15},N^{15}$-dialkyl antibiotic compounds will remain at a therapeutically or prophylactically effective (i.e., bactericidal) plasma level for an extended period of time, such as at least 5 days, or about one week or longer. Administration of a dose of a $N^{15},N^{15}$-dialkyl antibiotic compound or composition which produces and maintains bactericidal concentrations for at least about one week (or about 5 to about 10 days) are preferred. A bactericidal concentration can be defined as the concentration of a $N^{15},N^{15}$-dialkyl antibiotic compound or composition required to kill at least about 80%, at least about 85%, at least about 90%, or at least about any one of 95%, 96%, 97%, 98% or 99% of the bacteria present at the initiation of an in vitro experiment over a 24 hour period. A minimum bactericidal concentration of a $N^{15},N^{15}$-dialkyl antibiotic compound or composition in plasma can be about 4 mg/l.

Examples of indications that can be prevented or treated using the $N^{15},N^{15}$-dialkyl antibiotic compounds, compositions, and methods of the invention include both complicated and uncomplicated SSTIs, blood stream infections (BSI), catheter-related blood stream infections (CRBSI), osteomyelitis, prosthetic joint infections, surgical prophylaxis, endocarditis, hospital or community acquired pneumonia, pneumococcal pneumonia, empiric treatment of febrile neutropenia, joint space infections, and device infections (e.g., pace makers and internal cardiac defibrillators). Gram-positive or antibiotic-resistant bacterial infections can be prevented or treated, such as a *Bacillus, Corynebacteria, Listeria, Enterococcus, Staphylococcus, Streptococcus, Neisseria,* or *Clostridium* genus infection, in particular *Staphylococcus aureus, Staphylococcus epidermidis, Staphylococcus hemolyticus, Streptococcus pyogenes, Streptococcus pneumoniae,* Groups A and C *Streptococcus, Enterococcus faecalis, Bacillus subtilis, Neisseria gonorrhoeae,* or *Clostridium difficile*. Other infections that can be prevented or treated using the $N^{15},N^{15}$-dialkyl antibiotic compounds, compositions, and methods of the invention include gram negative bacterial, such as a *Bartonella, Brucella, Campylobacter, Enterobacter, Escherichia* (as well as other *Proteobacteria*), *Francisella, Helicobacter, Hemophilus, Klebsiella, Legionella, Leptospira, Morganella, Moraxella, Proteus, Providencia, Pseudomonas, Salmonella, Serratia, Shigella, Stenotrophomonas, Vibrio,* and *Yersinia* genus infection, in particular *Escherichia coli, Proteus vulgaris, Pseudomonas aeruginosas,* and yeast, such as *Candida albicans,* infections.

The invention also encompasses the prevention or treatment of other infectious bacteria using the compounds, compositions, and methods of the invention, such as *Helicobacter pyloris, Borelia burgdorferi, Legionella pneumophilia, Mycobacteria sporozoites* (sp.) (e.g. *M. tuberculosis, M. avium, M. intracellulare, M. kansaii, M. gordonae), Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus bovis, Streptococcus* (anaerobic sps.), pathogenic *Campylobacter* sp., *Enterococcus* sp., *Haemophilus influenzae, Bacillus antracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira,* and *Actinomyces israelli* infection.

The prevention and treatment of infections and disorders described herein may be accomplished using the compounds, compositions and methods of the invention. In one embodiment, the $N^{15},N^{15}$-dialkyl antibiotic compound is according to formula (V). In some embodiments, the subject has not previously been treated with one or more antibiotics, such as vancomycin, or teicoplanin. In other embodiments, the subject has not been previously treated with a $N^{15},N^{15}$-dialkyl antibiotic compound or composition. In some embodiments, the patient has previously been tested for bacterial resistance to an antibiotic. In other embodiments, the patient has not been previously tested for bacterial resistance to an antibiotic.

The invention also encompasses methods for the prevention or treatment of SSTIs. Patients who may benefit from this prevention or treatment may have either deep Pr superficial infections. SSTI may involve deeper soft tissue and/or require significant surgical intervention, such as for example a major abscess, infected ulcer, major burn, or deep and extensive cellulitis. Infected surgical wounds may also be prevented or treated.

The clinical presentation of skin and skin structure infection may vary from mild folliculitis to severe necrotizing fasciitis. The mode of acquisition may also vary with community-acquired skin and skin structure infections, which are often preceded by injuries resulting from occupational exposure or recreational activities, and are usually associated with a greater diversity of pathogens. Hospital-acquired skin and skin structure infections are generally associated with surgical procedures, the development of pressure sores, and catheterization. Post-surgical infections are the third most frequent nosocomial infection and account for 17% of all nosocomial infections reported to the National Nosocomial Infection Surveillance System (NNIS). The most frequent source of infection can be the patient's endogenous flora. *Staphylococcus aureus*, coagulase-negative staphylococci, and *Enterococcus* spp. are the pathogens most frequently isolated from SSTIs.

Symptoms of SSTI infections can include erythema, tenderness or pain, heat or localized warmth, drainage or discharge, swelling or induration, redness, or fluctuance. Patients that may benefit from treatment with the methods of the invention include those with deep or complicated infections or infections that require surgical intervention, or patients with underlying diabetes mellitus or peripheral vascular disease. These infections are often caused by Gram-positive bacteria such as *Staphylococcus* or *Streptococcus* species, such as *Staphylococcus aureus* or *Streptococcus pyogenes*. Methods for treatment of a skin or soft tissue bacterial infection include administering a therapeutically effective amount of a $N^{15},N^{15}$-dialkyl antibiotic compound or composition to an individual in need of treatment, in an amount and according to a dosing regime as discussed above. In one embodiment, the $N^{15},N^{15}$-dialkyl antibiotic compound is according to formula (V). In one embodiment, a $N^{15},N^{15}$-dialkyl antibiotic compound or composition is administered intravenously in two doses, about 5 to about 10 days apart, or about 1 week apart. In some embodiments, the first dosage includes at least twice as much of the a $N^{15},N^{15}$-dialkyl antibiotic compound or composition as the second dosage. In one embodiment, the first dosage is about 1000 mg and the second dosage is about 500 mg.

As is understood by those skilled in the art, the dosing methods described herein can vary depending on, inter alia, the compound, the disease and its severity, and the age, weight, etc., of the subject to be treated, but are ascertainable by a physician without undue experimentation.

The invention also encompasses methods for prophylactic prevention of the onset of a bacterial infection, for example an infection caused by *Staphylococcus aureus*, or by a *Neisseria* or *Clostridium* genus bacterium. In a prophylactic method of the invention, a prophylactically effective amount of a $N^{15}$, $N^{15}$-dialkyl antibiotic compound or composition is administered to an individual who may be susceptible to contracting a bacterial infection, for example, through a medical procedure. The $N^{15},N^{15}$-dialkyl antibiotic compound or composition can be administered in an amount sufficient to provide a prophylactically effective plasma level for at least about 1 day, at least about 3 days, at least about 5 days, or at least about one week or longer. The $N^{15},N^{15}$-dialkyl antibiotic compound or composition can be administered, for example, parenterally, e.g., via i.m., i.v., i.p., s.c., or i.t. injection, prior to, subsequent to, or at the same time as surgery as a preventative step against infection. The $N^{15},N^{15}$-dialkyl antibiotic compound or composition can be administered immediately prior or subsequently to, one or more days or about one week prior or subsequently to, or during an invasive medical procedure such as surgery or a stay in a medical care facility such as a hospital to prevent infection. A prophylactic method can be used in any situation in which it can be possible or likely that an individual may contract a bacterial infection, including situations in which an individual has been exposed to or can be likely to be exposed to a bacterially infected individual. For prophylactic methods, $N^{15},N^{15}$-dialkyl antibiotic compound or composition can be administered as either a single dose or as two or more doses of equal or different amount that are administered several days to about one week apart. In one embodiment, a $N^{15},N^{15}$-dialkyl antibiotic compound or composition can be administered prior to or simultaneously with insertion of an intravenous catheter in order to prevent a bloodstream related infection. In one embodiment, the $N^{15},N^{15}$-dialkyl antibiotic compound is according to formula (V).

For prophylactic methods, a $N^{15},N^{15}$-dialkyl antibiotic compound or composition can be administered in a single dose or in multiple doses, according to any of the dosing schemes described above. A $N^{15},N^{15}$-dialkyl antibiotic compound or composition can be administered as a single dose comprising about 0.1 to about 3 grams, or about 0.1 to about 1 gram, e.g., about 0.25 gram or about 0.5 gram. In one embodiment, a single dose of about 0.25 gram can be administered intravenously over a time frame of about 2 minutes to about 1 hour, e.g., about 30 minutes. In another embodiment, the $N^{15},N^{15}$-dialkyl antibiotic compound or composition can be administered intravenously simultaneously with administration of another pharmaceutical (e.g., antibiotic) treatment.

In any of the therapeutic or prophylactic methods described above, the $N^{15},N^{15}$-dialkyl antibiotic compound or composition can be administered either simultaneously or sequentially with at least one other antibiotic. In some embodiments, at least one other antibiotic that can be effective (e.g., bactericidal) against one or more Gram-negative bacterial species and/or a Gram-positive bacterial strain against which the $N^{15},N^{15}$-dialkyl antibiotic compound is not effective can be administered in addition to the $N^{15},N^{15}$-dialkyl antibiotic. In some embodiments, $N^{15},N^{15}$-dialkyl antibiotic compound and at least one antibiotic that can be effective (e.g., bactericidal) against at least one Gram-negative bacterial species can be administered as a mixture in the dalbavancin composition.

Pharmaceutical Compositions

The invention provides pharmaceutical compositions formulated for administration of a $N^{15},N^{15}$-dialkyl antibiotic compound or composition according to the methods described above. Pharmaceutical compositions of the invention can be in the form of a unit dose of a $N^{15},N^{15}$-dialkyl antibiotic compound or composition that includes an amount of a $N^{15},N^{15}$-dialkyl antibiotic compound or composition sufficient to provide a therapeutically or prophylactically effective plasma level of the $N^{15},N^{15}$-dialkyl antibiotic compound or composition for several days, at least about 3 days, at least about 5 days, or at least about one week or longer when the compound or composition is administered to an individual, and a pharmaceutically acceptable carrier. A therapeutically or prophylactically effective plasma level of $N^{15},N^{15}$-dialkyl antibiotic compound or composition can be at least about 4 mg per liter of plasma. Plasma levels of $N^{15},N^{15}$-dialkyl antibiotic compound or composition can be measured by methods that are well known in the art, such as liquid chromatography, mass spectrometry, or microbiological bioassay. As is known by those skilled in the art, levels of other $N^{15},N^{15}$-dialkyl antibiotic compounds or compositions in the serum can be quantitated in the serum using similar methodologies.

$N^{15},N^{15}$-dialkyl antibiotic compounds and compositions, can optionally be in a pharmaceutically acceptable form for administration to an individual, for example, as a pharmaceutically acceptable, non-toxic salt.

Examples of suitable salts of a $N^{15},N^{15}$-dialkyl antibiotic compound include salts formed by standard reaction with both organic and inorganic acids such as, for example, hydrochloric, hydrobromic, sulfuric, phosphoric, acetic, trifluoroacetic, trichloroacetic, succinic, citric, ascorbic, lactic, maleic, glutamic, camphoric, glutaric, glycolic, phthalic, tartaric, lauric, stearic, salicylic, methanesulfonic, benzenesulfonic, sorbic, picric, benzoic, cinnamic, and the like acids. Representative examples of bases that can form salts with dalbavancin include alkali metal or alkaline earth metal hydroxides such as sodium, potassium, calcium, magnesium, and barium hydroxide, ammonia and aliphatic, alicyclic, or aromatic organic amines such as methylamine, dimethylamine, diethylamine, ethanolamine, and picoline. (See, for example, U.S. Pat. No. 5,606,036.)

In some embodiments, a pharmaceutically acceptable aqueous formulation of a $N^{15},N^{15}$-dialkyl antibiotic compound or composition can be provided that is suitable for parenteral administration, such as, for example, intravenous injection. In one embodiment, the $N^{15},N^{15}$-dialkyl antibiotic compound is according to formula (V). For preparing such an aqueous formulation of a $N^{15},N^{15}$-dialkyl antibiotic compound or composition, methods well known in the art may be used, and any pharmaceutically acceptable carriers, diluents, excipients, or other additives normally used in the art may be used. In one embodiment, a pharmaceutically acceptable aqueous formulation for intravenous injection includes 5% dextrose.

A pharmaceutical composition for parenteral administration comprises a $N^{15},N^{15}$-dialkyl antibiotic compound or composition and a physiologically acceptable diluent such as deionized water, physiological saline, 5% dextrose, water miscible solvent (e.g., ethyl alcohol, polyethylene glycol, propylene glycol, etc.), non-aqueous vehicle (e.g., oil such as corn oil, cottonseed oil, peanut oil, and sesame oil), or other commonly used diluent. The formulation may further comprise a solubilizing agent such as polyethylene glycol, polypropylene glycol, or other known solubilizing agent, buffers for stabilizing the solution (e.g., citrates, acetates, and phosphates) and/or antioxidants (e.g., ascorbic acid or sodium bisulfite) (See, e.g., U.S. Pat. No. 6,143,739). Other suitable pharmaceutical carriers and their formulations are described in "Remington's Pharmaceutical Sciences" by E. W. Martin. As is known in the art, pharmaceutical preparations of the invention can also be prepared to contain acceptable levels of particulates (e.g., particle-free) and to be non-pyrogenic (e.g., meeting the requirements of an injectable in the U.S. Pharmacopeia).

In one embodiment, a pharmaceutical composition is provided by dissolving a dried (e.g., lyophilized) dose of a $N^{15}$, $N^{15}$-dialkyl antibiotic compound or composition, often comprising a stabilizer or mixture of stabilizers, in an amount of water and preferably deionized water in a volume sufficient for solubilization. For example, the amount of water sufficient for solubilization can be approximately 10 mL and the resulting pH can be above 3.0, and about 3.5 to 4.5. Diluting this solution by adding it to a second amount of an aqueous diluent, containing 5% dextrose, such as an amount contained in a drip bag for intravenous administration, can raise the pH of the solution to about 5 to 5.5. In another embodiment, the pH of the solution in a drip bag can be about 4.5. The second amount of aqueous solution can be deionized or sterile, or both deionized and sterile. In one embodiment, the aqueous diluent is 5% dextrose. Other solubilization methods, and the $N^{15},N^{15}$-dialkyl antibiotic formulations thereof, will be readily apparent to those skilled in the art.

Pharmaceutical compositions for parenteral administration can be made up in sterile vials containing one or more unit doses of the $N^{15},N^{15}$-dialkyl antibiotic compound or composition in a therapeutically or prophylactically effective amount as described above, optionally including an excipient, under conditions in which bactericidal effectiveness of $N^{15}$, $N^{15}$-dialkyl antibiotic compound or composition can be retained. The compound or composition may or may not be in the form of a dry (e.g., lyophilized) powder. Prior to use, a physiologically acceptable diluent can be added and the solution withdrawn via syringe for administration to a patient. A pharmaceutical formulation as described above can be sterilized by any acceptable means including, for example, e-beam or gamma sterilization methods, or by sterile filtration.

A formulation for parenteral administration can include the $N^{15},N^{15}$-dialkyl antibiotic compound or composition at a concentration such as about 0.1 to about 100 mg, about 0.5 to about 50 mg, about 1 to about 10 mg, about 1 to about 5 mg, or about 2 to about 4 mg of the $N^{15},N^{15}$-dialkyl antibiotic compound or composition per ml of final preparation. In one embodiment, the $N^{15},N^{15}$-dialkyl antibiotic compound is according to formula (V).

In some embodiments, a pharmaceutical composition in accordance with the invention comprises a mixture of a $N^{15}$, $N^{15}$-dialkyl antibiotic compound or composition and one or more additional antibiotics. Preferably, at least one non-dalbavancin antibiotic in the mixture can be effective (e.g., bactericidal) against one or more species of Gram-negative bacteria, such as, for example, azthreonam, and/or against one or more Gram-positive bacterial strains against which the $N^{15}$, $N^{15}$-dialkyl antibiotic compound or composition can be not effective, such as, for example, linezolide or daptomycin. The mixture can also include a pharmaceutically acceptable carrier as described above. In some embodiments, the pharmaceutical composition comprises a $N^{15},N^{15}$-dialkyl antibiotic compound or composition and one or more additional antibiotics. In some embodiments, the $N^{15},N^{15}$-dialkyl antibiotic composition comprises a $N^{15},N^{15}$-dimethyl antibiotic compound according to formula (V).

In some embodiments, pharmaceutical compositions of the invention comprise one or more stabilizing substances that inhibit degradation of one or more $N^{15},N^{15}$-dialkyl antibiotic compounds to less active or inactive materials. As used herein, "stabilizing substance" or "stabilizer" refers to a substance that stabilizes the level of one or more $N^{15},N^{15}$-dialkyl antibiotic compounds present in the composition. A "stabilizing effective amount" refers to an amount of a stabilizer sufficient to enhance long-term stability of one or more $N^{15}$, $N^{15}$-dialkyl antibiotic compounds that can be present in the composition that can be present in the composition. In some embodiments, a stabilizing effective amount may be provided by a mixture of two or more stabilizing substances, each of which alone can be not present in an amount sufficient to provide a stabilizing effect.

Examples of stabilizers include, for example, nonionic substances such as sugars, e.g., mono-, di-, or polysaccharides, or derivatives thereof, sugar alcohols, or polyols. Such stabilizing substances include, for example, mannitol, lactose, sucrose, sorbitol, glycerol, cellulose, trehalose, maltose, raffinose, or mixtures thereof.

In one embodiment, a $N^{15},N^{15}$-dialkyl antibiotic formulation comprises mannitol. In another embodiment, a $N^{15},N^{15}$-dialkyl antibiotic formulation further comprises lactose. In one embodiment, the $N^{15},N^{15}$-dialkyl antibiotic composition is formulated with a 1:2 weight ratio of mannitol:$N^{15},N^{15}$-dialkyl antibiotic compound. In another embodiment, the $N^{15},N^{15}$-dialkyl antibiotic composition is formulated with a 1:1:4 weight ratio of mannitol:lactose: $N^{15},N^{15}$-dialkyl antibiotic compound. A combination of mannitol and lactose can provide a greater stabilizing effect than either substance alone. The pH of a pharmaceutical composition of the invention can be, for example, about 2 to about 9, alternatively from about 3 to about 8, alternatively from about 4 to about 7, alternatively from about 5 to about 6, alternatively from about 3.5 to about 4.5. The pH of a pharmaceutical composition of the invention can also be, for example, less than about 9, alternatively less than about 8, alternatively less than about 7, alternatively less than about 6, alternatively less than about 5, or alternatively less than about 4. The pH of a pharmaceutical composition of the invention can also be, for example, greater than about 2, greater than about 3, alternatively greater than about 3.5, alternatively greater than about 4, alternatively greater than about 4.5, alternatively greater than about 5.0, alternatively greater than about 5.5, alternatively greater than about 6.0, alternatively greater than about 6.5, or alternatively greater than about 7.0.

In some embodiments, one or more procedures can be employed to reduce formation of MAG (a derivative of a $N^{15},N^{15}$-dialkyl antibiotic compound of the invention or a dalbavancin compound lacking an acylglucoronamine moiety) and/or other degradants. For example, freeze drying of a $N^{15},N^{15}$-dialkyl antibiotic compound or composition in the presence of a stabilizing substance, such as mannitol, can be employed to reduce the amount of MAG formed.

Storage of $N^{15},N^{15}$-dialkyl antibiotic compounds and compositions can be at lower than ambient temperature, such as at about 5° C., to enhance stability.

Weekly dosing of a $N^{15},N^{15}$-dialkyl antibiotic compound or composition at high dosage levels (i.e., resulting in surprisingly high and long-lasting serum levels) can show a surprisingly good safety profile, similar to, or better than, that observed with the standard therapy of lower doses of conventional antibiotics administered daily or even 2-4 times daily, as demonstrated by the Examples herein. A high dosage (i.e., resulting in high and long-lasting serum levels, e.g. 200-5000 mg) of a $N^{15},N^{15}$-dialkyl antibiotic compound or composition can be administered, with less frequency than other antibiotics, and without adverse side effects, enabling improved efficacy and patient compliance.

In certain embodiments, treatment with a $N^{15},N^{15}$-dialkyl antibiotic composition results in a low incidence of adverse events. Serious adverse events include any adverse drug experience occurring at any dose that results in death, can be life-threatening, results in hospitalization or prolongation of existing hospitalization, or persistent or significant disability or incapacity.

Kits

The invention also encompasses kits for use in methods of treatment or prophylaxis of bacterial infections. The kits can include a pharmaceutical compound or composition of the invention, for example comprising at least one unit dose of a $N^{15},N^{15}$-dialkyl antibiotic compound or composition, and instructions providing information to a health care provider regarding usage for treating or preventing a bacterial infection. Instructions may be provided in printed form or in the form of an electronic medium such as a floppy disc, CD, or DVD, or in the form of a website address where such instructions may be obtained. A unit dose of a $N^{15},N^{15}$-dialkyl antibiotic compound or composition can include a dosage such that when administered to an individual, a therapeutically or prophylactically effective plasma level of a $N^{15},N^{15}$-dialkyl antibiotic compound or composition can be maintained in the individual for at least 5 days. In some embodiments, a kit includes two unit dosages to be administered at least 5 days apart, about one week apart, or including a first dosage of a $N^{15},N^{15}$-dialkyl antibiotic compound or composition that can be about 1.5 to about 3 times higher than the second dosage. In some embodiments, a $N^{15},N^{15}$-dialkyl antibiotic compound or composition can be included as a sterile aqueous pharmaceutical composition or dry powder (e.g., lyophilized) composition. In one embodiment, the $N^{15},N^{15}$-dialkyl antibiotic compound is according to formula (V).

In some embodiments, suitable packaging is provided. As used herein, "packaging" refers to a solid matrix or material customarily used in a system and capable of holding within fixed limits a $N^{15},N^{15}$-dialkyl antibiotic compound or composition suitable for administration to an individual. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Kits can also optionally comprise equipment for administration of the a $N^{15},N^{15}$-dialkyl antibiotic compound or composition, such as, for example, syringes or equipment for intravenous administration, and/or a sterile solution, e.g., a diluent such as 5% dextrose, for preparing a dry powder (e.g., lyophilized) composition for administration.

Kits of the invention may also comprise in addition to the a $N^{15},N^{15}$-dialkyl antibiotic compound or composition, a non-dalbavancin antibiotic or mixture of non-dalbavancin antibiotics, for use with the a $N^{15},N^{15}$-dialkyl antibiotic compound or composition as described in the methods above.

The following synthetic and biological examples are offered to illustrate this invention and are not to be construed in any way as limiting the scope of this invention.

Examples

Example 15

Purification of $N^{15},N^{15}$-Dimethyl Dalbavancin $B_0$

The preparation of A-40926 and subsequent synthesis of dalbavancin is described above. The instant example describes the purification of the $N^{15},N^{15}$-dimethyl antibiotic compound according to formula (V), i.e. $N^{15},N^{15}$-dimethyl dalbavancin $B_0$, from a mixture of dalbavancin compounds prepared according to the invention. As will be apparent to those of skill in the art, $N^{15},N^{15}$-dimethyl dalbavancin $B_0$ is a modified dalbavancin $B_0$ with two methyl groups on $N^{15}$. For the purposes of this example and following examples, $N^{15},N^{15}$-dimethyl antibiotic $B_0$ is referred to as "Compound A" in the sections where the compound has yet to be fully characterized. Also, for convenience in later sections, $N^{15},N^{15}$-dimethyl dalbavancin $B_0$ is referred to as dalbavancin $B_2$. $N^{15},N^{15}$-dimethyl antibiotic $B_0$, dalbavancin $B_2$ and Compound A are the same molecule.

Sample Preparation

About 2 L of organic-aqueous solution from a purification of dalbavancin prepared according to the methods herein were concentrated by acetonitrile and water evaporation under vacuum. Adding diethyl ether to the residual afforded 6 g of crude solid. After dissolution in a mixture water/acetonitrile 90/10 v/v the solid was purified on silanized silica gel (bed volume 1 L; column id=5 cm) using a water (pH 3 acetic acid)/acetonitrile step-gradient elution. The compound A containing fractions were pooled, concentrated to small volume (few ml) and submitted to preparative HPLC purification.

The enriched fractions were collected. After acetonitrile evaporation under vacuum and lyophilization a few μg of compound A were recovered.

Example 16

Identification of the $N^{15}$ Amine Substituents of Compound A

Compound A has a molecular weight of 1828 Da, 14 units more than dalbavancin components $B_0$ and $B_1$ (M.W. 1814). HPLC-ESI-MS analysis demonstrated that unlike the other components of the complex, the variation is on the terminal amino group at $N^{15}$.

Other dalbavancin compounds, possessing a methylamine group (R—$NHCH_3$) show in their fragmentation mass spectra (ESI-MS/MS) a neutral loss of 31 units (—$NH_2CH_3$). The fragmentation spectrum of Compound A shows a loss of 45 units instead of 31 units. This type of neutral loss can be explained by two structural hypotheses: $N^{15}$ could be a N,N-dimethylamine group (R—$N(CH_3)_2$, tertiary amine) or a N-ethylamine group (R—$NHCH_2CH_3$, secondary amine).

Figure 29:
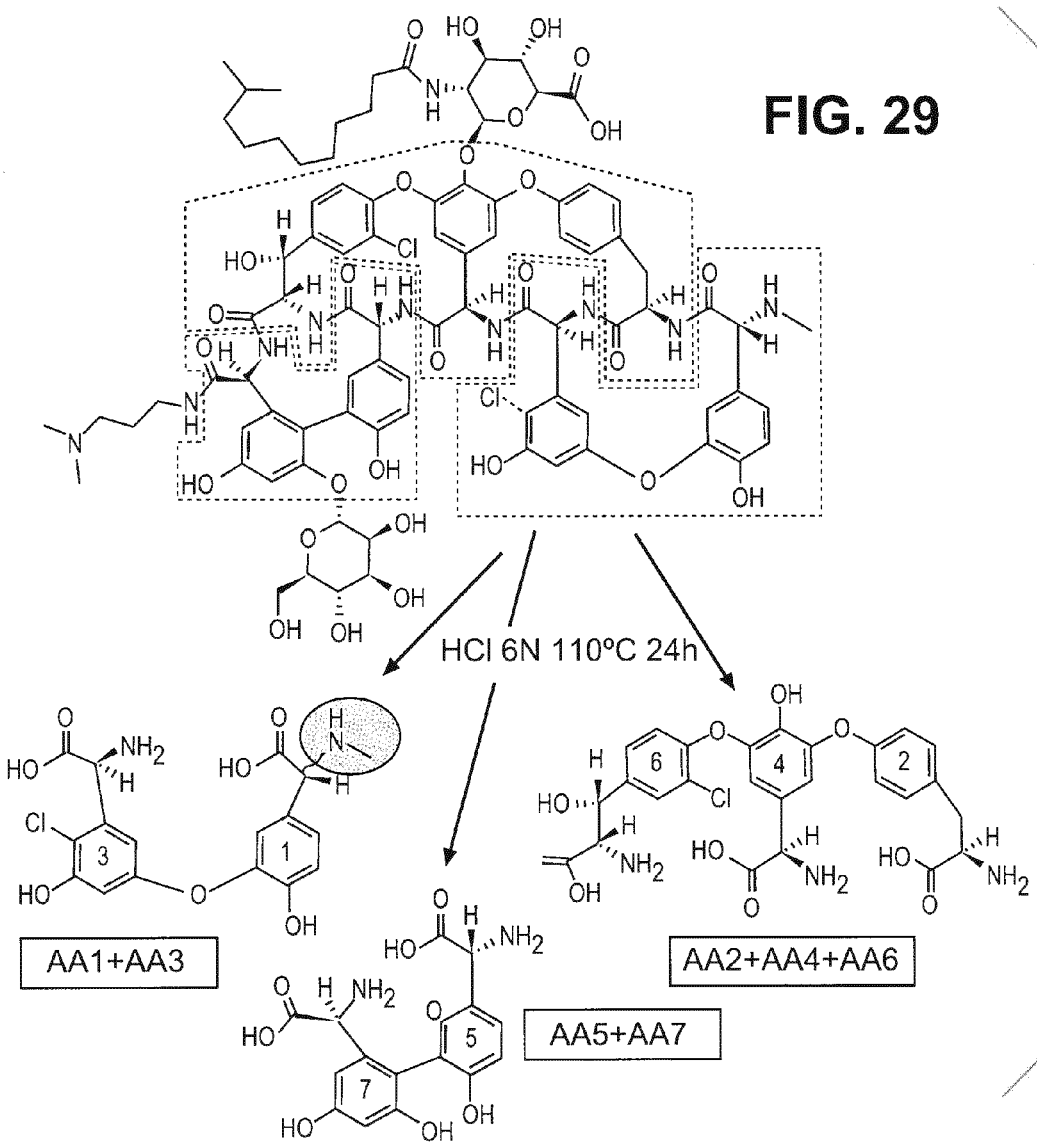
FIGS. 29-31 provide schemes illustrating examples of the invention that verify the structure of an $N^{15},N^{15}$-dimethyl antibiotic compound of the invention.

HPLC-ESI-MS analysis of the hydrolyzed and derivatized Compound A can discriminate between those two hypotheses. FIG. 29 shows the three peptidic fragments originated from $B_0$ after acid hydrolysis. Two di-peptides, "AA1+AA3", with amino group $N^{15}$ and a chlorine atom, "AA5+AA7", and a tri-peptide "AA2+AA4+AA6", with a chlorine atom, are formed. Other hydrolysis products are the fatty acid and the DMEPA4 (dimethylamino-propylamino) chains.

Figure 30:
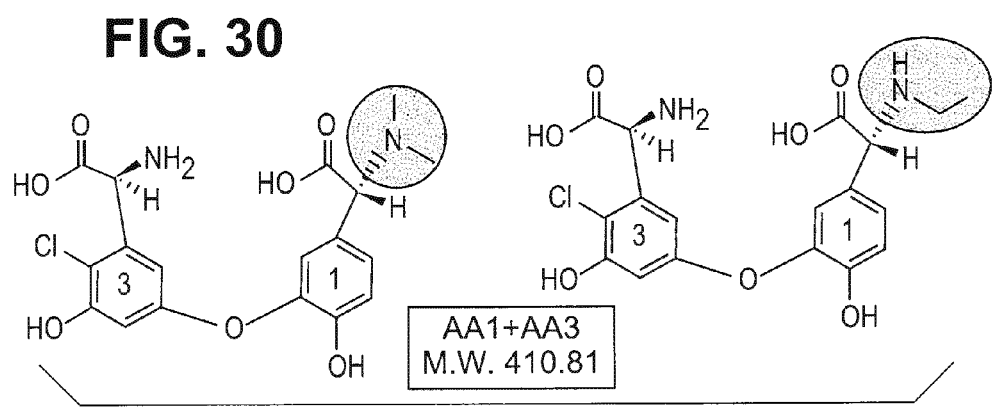

In the case of Compound A the dipeptide "AA1+AA3" must be different as reported in FIG. 30. The correct hypothesis can be verified by reacting the hydrolysate with a derivatizing agent that reacts with primary and secondary amines only (see FIG. 31).

Figure 31A:
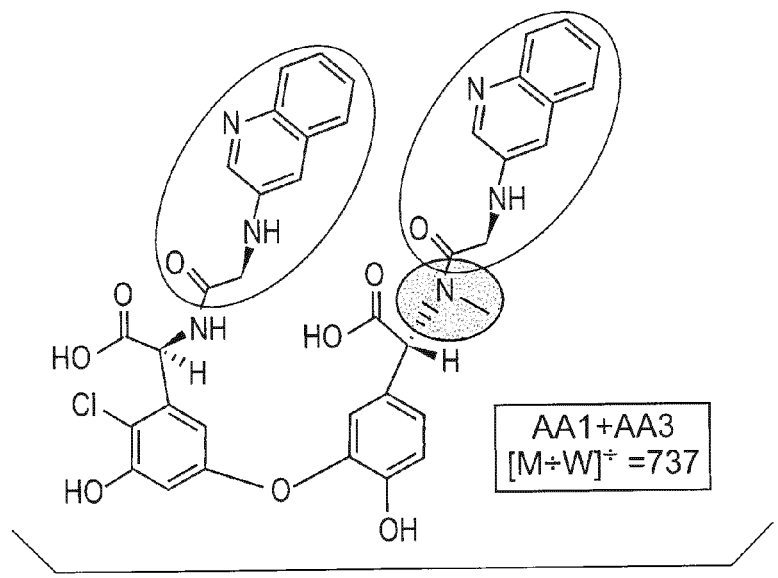
Figure 31B:
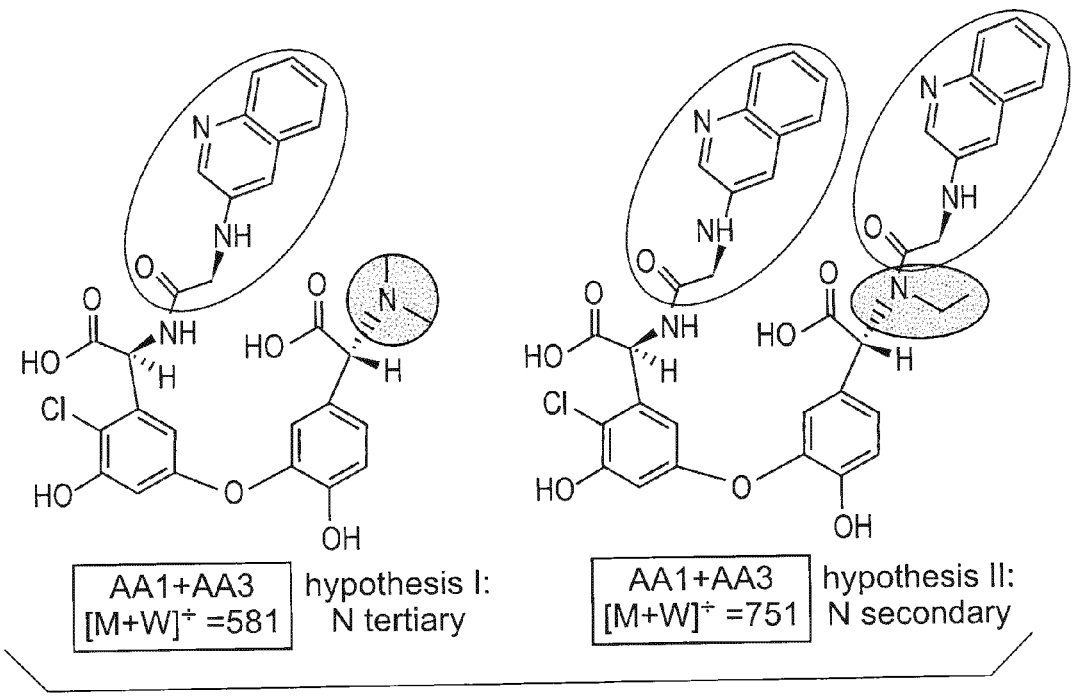
Figure 32:
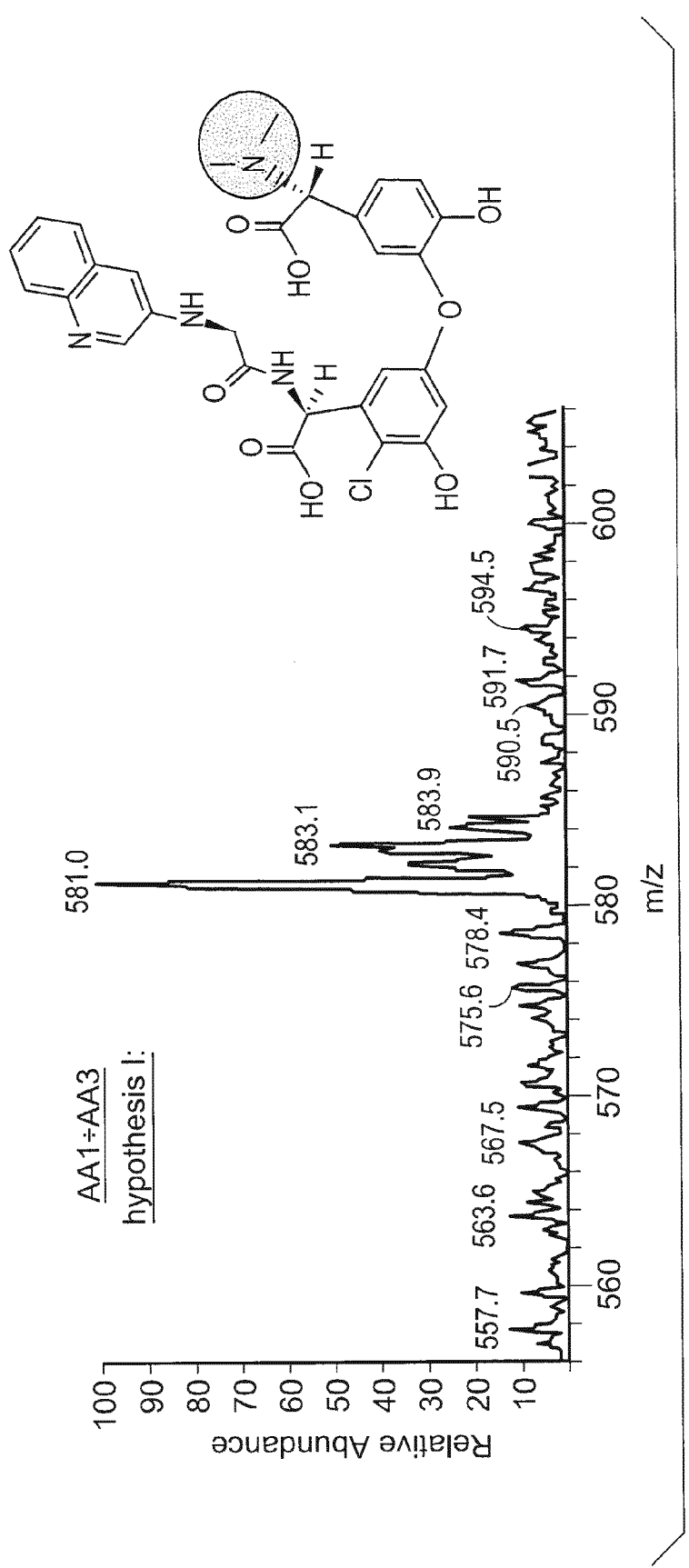
FIGS. 32-33 provide ESI and HPLC chromatograms verifying the structure of the $N^{15},N^{15}$-dimethyl antibiotic compound.

The di-peptide "AA1+AA3" of component $B_0$ should react with two groups of derivatizing agent (see FIG. 31a). In the case of Compound A two different derivatized peptides "AA1+AA3" can be obtained depending on the amino group $N^{15}$ (FIG. 31b). The two molecules, theoretically expected according to the hypotheses proposed, will have molecular weights easily distinguishable by mass spectrometric analysis.

Materials
Compound A
Dalbavancin
Hydrochloric acid 37%, reagent grade, Rudi Pont cod. 750-11
Methanol HPLC grade, J. T. Backer cod. 8402
AccQ Tag™ Chemistry Package, Waters cod. WAT052880
Hydrolysis The hydrolysis of both the sample and the standard was carried out in a PICO-TAG Work Station (Waters, Mildoford, Mass., USA).

All of the 360 μg of Compound A and about 1 mg of the dalbavancin standard were hydrolyzed at 105° C. in the presence of 6N HCl containing 1% (w/v) phenol for 24 hours. The reaction mixtures were cooled, evaporated to dryness and brought to a final volume of 500 L with methanol.

Derivatization

Waters AccQ-Fluor™ reagent Kit was chosen for peptide derivatization. AccQ-Fluor reagent is one of the N-hydroxysuccinimide-activated heterocyclic carbamate amine derivatizing compounds. The structure of the derivatization agent and the scheme of reaction is reported in Scheme 2.

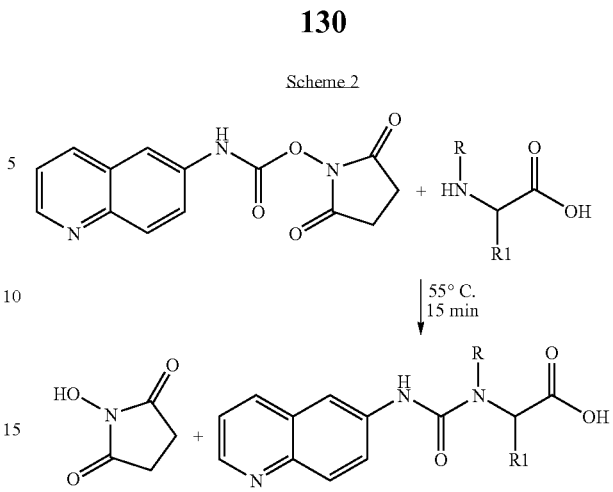

Scheme 2

1 mL of "Reagent Diluent" was added to the vial containing "Reagent Powder". The vial was vortexed for 10 seconds and warmed up at 55° C. until complete dissolution. Reconstituted AccQ-Fluor reagent was approximately 10 mM in acetonitrile. 20 μl of hydrolyzed sample or standard were put into a vial with conical insert and 20 μl of "AccQ-Fluor Borate Buffer" were added and vortexed briefly. At this point 40 μl of reconstituted AccQ-Fluor reagent were added and the sample vortexed for 30 sec. Vials were heated at 55° C. for 10 min. In these conditions the amino groups should react and eventual by-products should be minimized. After this reaction the samples were ready for HPLC analysis.

HPLC-UV-MS Analysis

Thermo Finnigan Surveyor MS pump, diode array detector and autosampler,

ThermoQuest Finnigan LCQ Deca mass detector equipped with ESI interface.

Chromatography: Column: AccQ-Tag™ (Waters C18 NovoPak 4_m 3.9×150 mm); Column temperature: 37° C.; Flow: 1 mL/min; Phase A: ammonium acetate 140 mM pH 5 (acetic acid); Phase B: water/acetonitrile 60/40 v/v; UV detection: 254 nm; Injection volume: 20 μL. The eluate from the column was split to allow simultaneous UV and mass detection.

Mass Spectrometry
Sample inlet condition: capillary temperature: 200° C.
sheath gas: $N_2$, 40 (arbitrary units)
auxiliary gas $N_2$, 20 (arbitrary units)
Sample inlet voltage setting: polarity: positive
source voltage: 4.7 kV
capillary voltage: 10 V
tube lens offset: 40 V
Scan conditions: scan mode: full ms
scan range: 100-700 amu
number of microscans 3
maximum ion time 50 ms
Results Derivatized and hydrolyzed fragments of dalbavancin were separated by HPLC and evaluated by ESI-MS (data not shown). Fragment AA1+AA3 had a size of 737 (m/z), fragment AA5+AA7 had a size of 689 (m/z), and fragment AA2+AA4+AA6 had a size of 1086 (m/z).

Derivatized and hydrolyzed fragments of Compound A were separated by HPLC and evaluated by ESI-MS. Fragment AA1+AA3 had a size of 737 (m/z), fragment AA5+AA7 had a size of 581 (m/z), and fragment AA2+AA4+AA6 had a size of 1086 (m/z).

The size of the AA5+AA7 confirmed that Compound A is an N15,N15-dimethyl compound.

Example 17

Methylation of Dalbavancin B₀

Dalbavancin B₀ was prepared following the methods outlined generally above and purified by HPLC following methods described in U.S. Patent Application Publication No. 2004/0142883. A sample of dalbavancin B₀ was submitted to selective secondary amine N-methylation to yield $N^{15},N^{15}$-dimethyl antibiotic B₀. The reaction mixture was then analyzed by HPLC-UV and HPLC-UV-MS in the Example below.

Materials
Dalbavancin B₀
Water, MmilliQ grade
NaBH₃CN, sodium cyanoborohydride, Fluka cod. 71435
DMF, N,N-dimethylformamide, Carlo Erba cod. 444926
HCHO, formaldehyde solution, 36.5% water solution, Reidel de Haën cod. 33220.
NaHCO₃, sodium bicarbonate, reagent grade Method 49.5 mg of dalbavancin were dissolved in 12.5 ml of water and 1.5 mL of DMF into a round-bottom flask (pH 3.5). Three aliquots of 200 µL of were withdrawn and diluted with 800 µL of water (t0). 76 µL of a 36% (v/V) water solution of formaldehyde and 2.5 mg of sodium bicarbonate (pH 5.8) were added. 8 mg of NaCNBH₃ were added under stirring after sodium bicarbonate complete dissolution. Three aliquots of 200 µL of this reaction mixture were immediately withdrawn and diluted with 800 µL of water and 300 µL of CH₃CN in order to get a clear solution (t0'). The reaction mixture was left at room temperature for 30 minutes. Samples were taken from the reaction medium after 10 and 30 minute by extracting 3 aliquots of 200 µl and diluting each with 800 µl of water and 300 µl of CH₃CN (t10 and t30).

After 30 minutes the reaction was stopped by cooling down to −20° C. the flask. The reaction was monitored by HPLC-UV and HPLC/UV/MS analysis.

Example 18

Structural Confirmation of $N^{15},N^{15}$-Dimethyl Antibiotic B₀

This example demonstrates that Compound A and $N^{15},N^{15}$-dimethyl antibiotic B₀ from the previous example are identical.

The reaction samples t0, t0', t10 and t30 were analyzed by HPLC-UV and compared with the reference standard. Chromatograms of t0', t10 and t30 were very similar, demonstrating that methylation occurs immediately.

Figure 33:
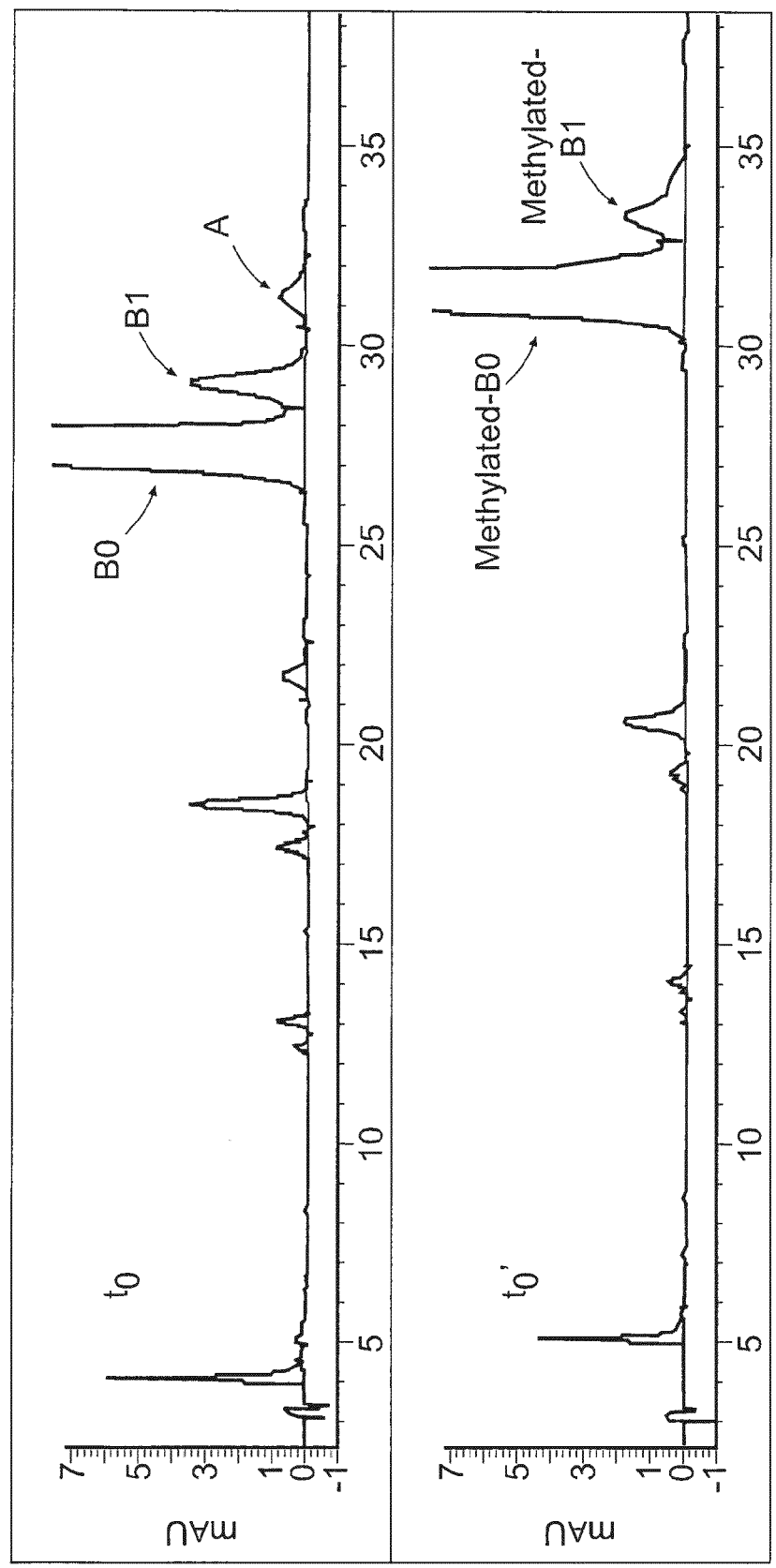

In FIG. 33, t0' vs t0 chromatograms are shown. Methylated B₀ showed the same retention time as Compound A, from Example 15, above. The hypothesis that Compound A is the methylated derivative of B₀ and consequently that the fatty acid chain of Compound A is a 10-methyl undecanoic acid was thus demonstrated.

The HPLC-UV-MS results confirmed the HPLC-UV structural conclusion reported in the last paragraph. N,N'-dimethyl B₀ peak was perfectly overlapped to that of Compound A.

Figure 28:
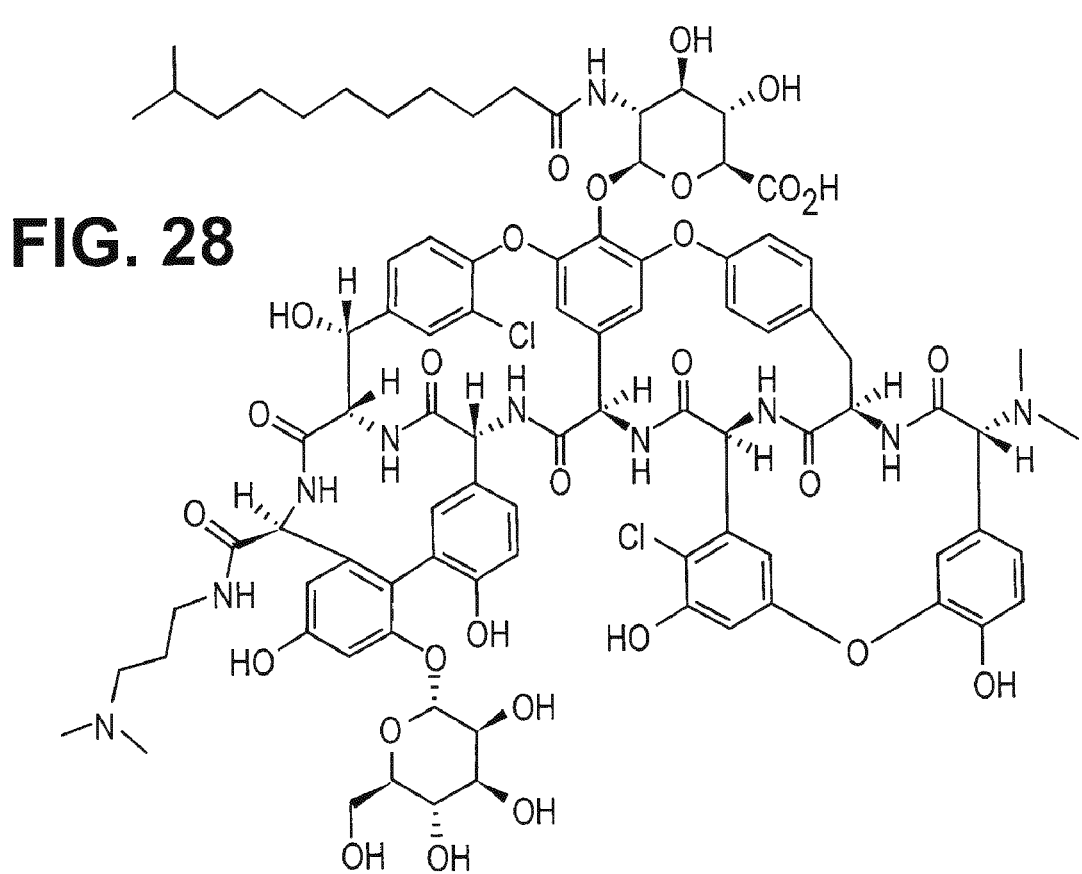
FIG. 28 provides the structure of an exemplary $N^{15},N^{15}$-dimethyl antibiotic compound of the invention.

It was thus demonstrated that the group at $N^{15}$ of Compound A is a dimethylamine group and not an ethylamine. The elucidated structure of component Compound A is reported in FIG. 28.

The structure of compound A was further confirmed by NMR, ESI-MS and IR. NMR spectra were recorded on a Bruker AMX 600 at 313K. The sample was dissolved in DMSO-d6 and proton and carbon NMR assignments were determined by COSY-DFTP, ROESY, and HMQC spectra. A mixing time of 350 msec was selected for the ROESY experiment. Mass spectra were determined by electrospray ionization in positive mode on a Thermoquest Finnigan LCQ$^{deca}$ at 250° C. The infrared spectrum was recorded in KBr on a Bruker IFS 48 instrument.

Figure 34:
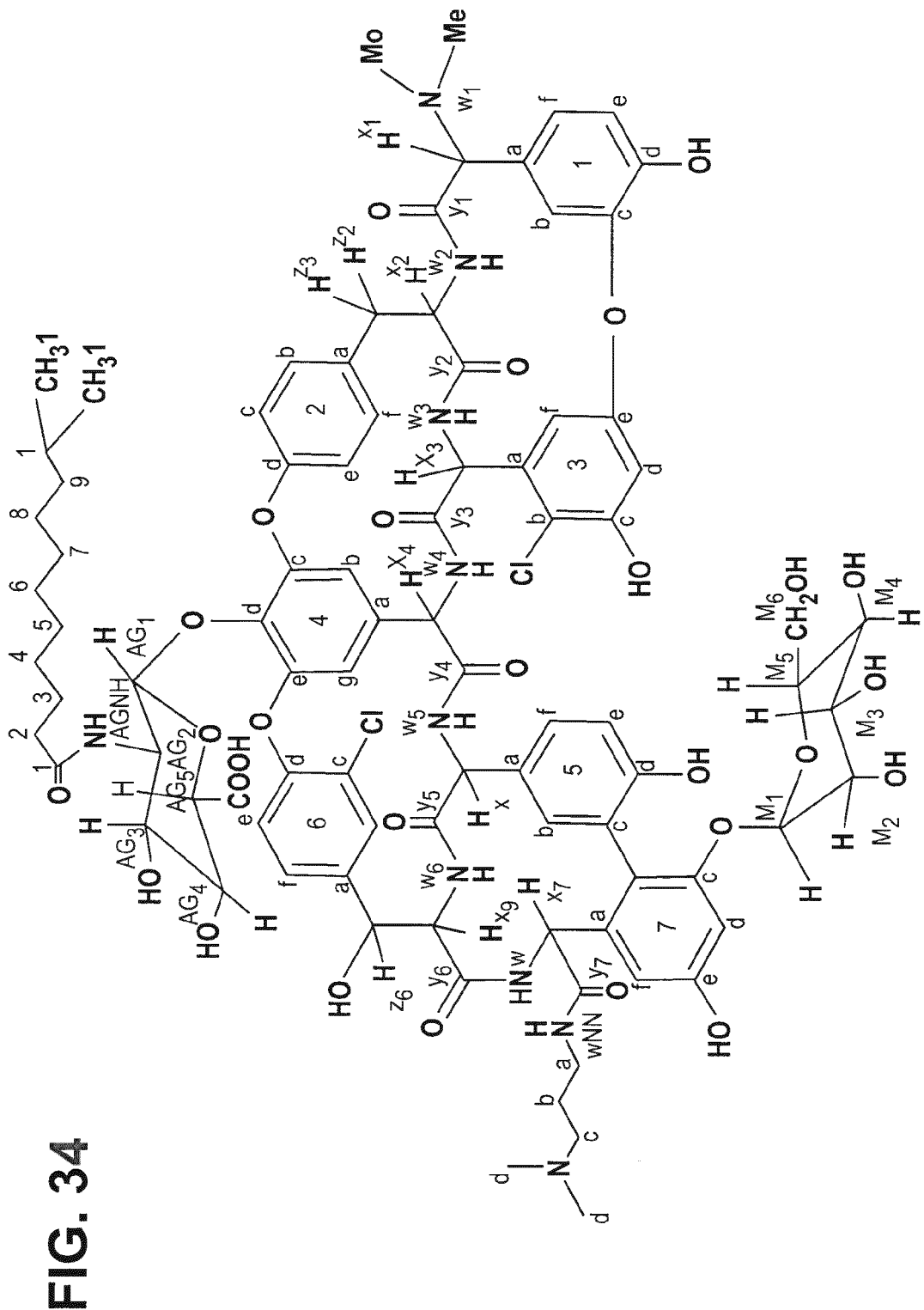
FIG. 34 provides the structure of dalbavancin $B_2$.

NMR peak assignments are provided in FIG. 34. Table 40 reports 1H assignments of B₂ in comparison with B₀. The NMR spectra of B₂ reveal many similarities with dalbavancin B₀. The fatty acid chain contains an isopropylic terminal group. Most of the proton and carbon chemical shifts are about the same as found for the B₀ component. The major chemical shift deviations are observable for signals belonging to the amino acid 1. In particular, the singlet at 2.31 ppm ($^{13}$Cδ 40.06 ppm) gives integral corresponding to six protons and NOE correlations with the protons x1, 1f and 1e. Its chemical shift and the dipolar correlations suggest that this signal is due to dimethylamino group belonging to the first amino acid spin system.

TABLE 40

|     | B₂ | B₀ | |
| --- | --- | --- | --- |
|     | δ¹H | δ¹H | δ¹³C |
| w1  | — | n.a. | — |
| CH₃ | 2.31 | 2.45 | 30.99 |
| x1  | 4.43 | 4.33 | 66.07 |
| 1b  | 6.70 | 6.71 | 118.5 |
| 1e  | 6.93 | 7.05 | 117.6 |
| 1f  | 7.00 | 7.23 | 126.65 |
| w2  | 7.36 | 8.2 | — |
| x2  | 4.83 | 4.79 | 55.9 |
| z2  | 2.81; 3.32 | 2.95; 3.37 | n.a. |
| 2b  | 7.09 | 7.1 | 130.6 |
| 2c  | 7.17 | 7.07 | 123.4 |
| 2e  | 6.97 | 6.97 | 122.33 |
| 2f  | 7.63 | 7.87 | 131.29 |
| w3  | 7.58 | 7.54 | — |
| x3  | 6.10 | 6.09 | 54.31 |
| 3d  | 6.72 | 6.55 | 107.5 |
| 3f  | 6.49 | 6.78 | 107.1 |
| w4  | 7.64 | 7.44 | — |
| x4  | 5.60 | 5.59 | 54.63 |
| 4b  | 5.80 | 5.78 | 108.8 |
| 4f  | 5.11 | 5.08 | 103.8 |
| w5  | 8.36 | 8.48 | — |
| x5  | 4.41 | 4.35 | 57.72 |
| 5b  | 7.10 | 7.13 | 135.01 |
| 5e  | 6.71 | 6.71 | 116.0 |
| 5f  | 6.71 | 6.71 | 125.8 |
| w6  | 6.62 | 6.62 | — |
| x6  | 4.14 | 4.19 | 61.97 |
| z6  | 5.20 | 5.38 | 70.8 |
| 6b  | 7.69 | 7.75 | 126.6 |
| 6e  | 7.26 | 7.28 | 123.2 |
| 6f  | 7.42 | 7.44 | 126.9 |
| w7  | 8.41 | 8.47 | — |
| x7  | 4.42 | 4.45 | 53.3 |
| 7d  | 6.73 | 6.75 | 101.1 |
| 7f  | 6.43 | 6.40 | 107.9 |
| AG1 | 5.48 | 5.40 | 101.9 |

TABLE 40-continued

| | B$_2$ | B$_0$ | |
|---|---|---|---|
| | δ$^1$H | δ$^1$H | δ$^{13}$C |
| AG2 | 3.72 | 3.71 | 55.98 |
| AG3 | 3.62 | 3.62 | 76.11 |
| AG4 | 3.41 | 3.51 | n.a |
| AG5 | n.a. | 4.27 | 66.28 |
| AG-NH | 7.71 | 7.77 | — |
| FA2 | 2.02 | 2.01 | 35.8 |
| FA3 | 1.43 | 1.42 | 24.84 |
| FA4-FA9 | 1.11-1.22 | 1.0-1.2 | 28.8-29.3 |
| FA10 | 1.50 | 1.49 | 27.2 |
| FA11 | 0.84 | 0.84 | 22.34 |
| FA12 | 0.84 | 0.84 | 22.34 |
| wNN | 7.96 | 8.19 | — |
| NNa | 3.31; 3.20 | 3.17; 3.40 | 35.38 |
| NNb | 1.65 | 1.87 | 23.37 |
| NNc | 2.39 | 2.96 | 53.94 |
| NNd | 2.24 | 2.71 | 42.05 |
| M1 | 5.27 | 5.32 | 96.7 |
| M2 | 3.25 | 3.3 | 70.24 |
| M3 | n.a. | 3.49 | 73.6 |
| M4 | n.a. | 3.69 | 72.91 |
| M5 | n.a. | 3.50 | n.a. |
| M6 | n.a. | 3.50 | 60.68 |

Figure 35:
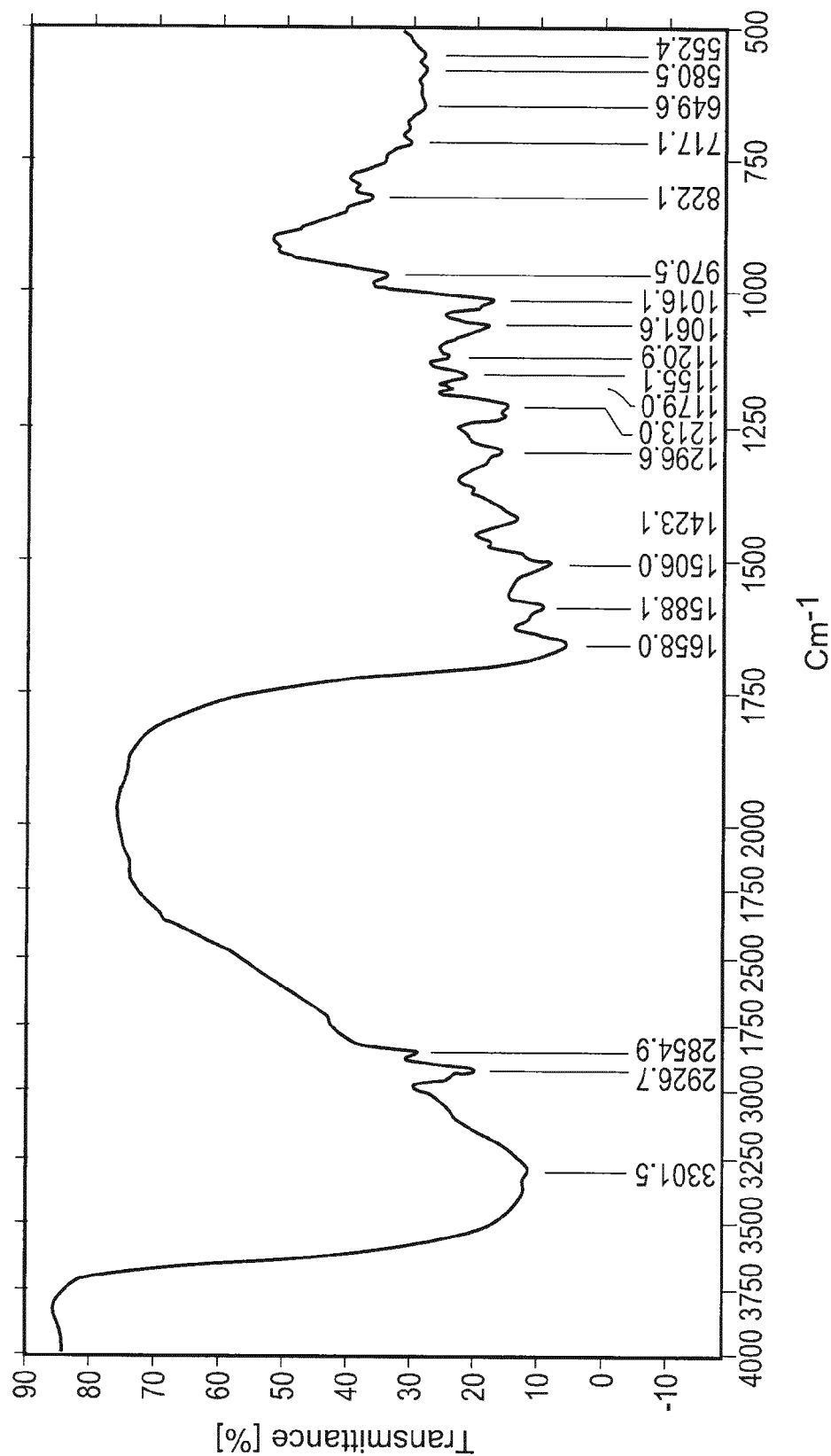
FIG. 35 provides an infrared spectrum of dalbavancin $B_2$ ($N^{15},N^{15}$-dimethyl dalbavancin $B_0$)
Figure 36:
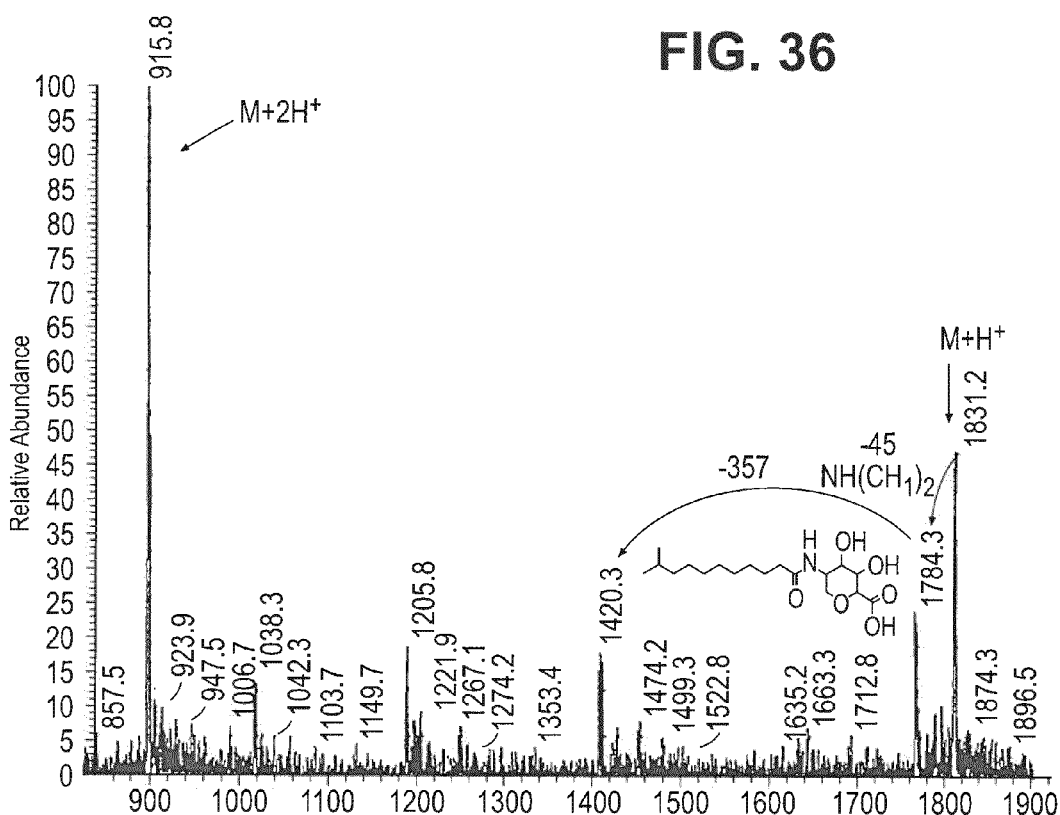
FIG. 36 provides an ESI-MS spectrum of dalbavancin $B_2$ ($N^{15}$,$N^{15}$-dimethyl dalbavancin $B_0$)

An infrared spectrum is provided at FIG. 35. ESI-MS is provided at FIG. 36. The data confirmed the structure of compound A as dalbavancin B$_2$ (N$^{15}$,N$^{15}$-dimethyl dalbavancin B$_0$).

Example 19

Activity of Dalbavancin B$_2$ (N$^{15}$,N$^{15}$-Dimethyl Dalbavancin B$_0$)

N$^{15}$,N$^{15}$-dimethyl dalbavancin B$_0$, several N$^{15}$-monomethyl dalbavancin compounds and several known antibiotics were isolated and tested in vitro for their antibacterial activity. The compounds were prepared according to the examples above and the methods described in U.S. Patent Application Publication No. 2004/0142883. Individual dalbavancin compounds were purified by HPLC.

Sample Preparation

Isolated N$^{15}$-monomethyl dalbavancin compounds and N$^{15}$,N$^{15}$-dimethyl antibiotic compounds were dissolved in 0.01N HCl:DMSO:95:5 v/v. Before dissolution, each sample was analyzed by HPLC and quantified. The solutions were prepared at 256 μg/ml for the N$^{15}$-monomethyl dalbavancin compounds (A$_0$, A$_1$, B$_0$, and B$_1$ dalbavancin) and at 128 μg/ml for the isolated N$^{15}$,N$^{15}$-dimethyl antibiotic B$_0$ (referred to as "B$_2$ dalbavancin" in the tables below).

The chromatogramic purity of the principal peak was evaluated in area % vs. total chromatogram area as reported in Table 41:

TABLE 41

CHROMATOGRAPHIC PURITY OF PRINCIPAL PEAK OF VARIOUS N$^{15}$-MONOMETHYL AND N$^{15}$,N$^{15}$-DIMETHYL ANTIBIOTIC COMPOUNDS

| ID | Status | Concentration (μg/ml) | % Main Peak |
|---|---|---|---|
| A$_0$ dalbavancin | Solution | 256 | 82 |
| A$_1$ dalbavancin | Solution | 256 | 80 |
| B$_0$ dalbavancin | Solution | 256 | 96 |
| B$_1$ dalbavancin | Solution | 256 | 79 |
| B$_2$ dalbavancin | Solution | 128 | 72 |

Microbiological Characterization

The compounds tested included the isolated N$^{15}$-monomethyl dalbavancin compounds and N$^{15}$,N$^{15}$-dimethyl antibiotic compounds described above as well as a dalbavancin composition ("DA 025/A") comprising a N$^{15}$,N$^{15}$-dimethyl antibiotic compound, vancomycin (VA) (Sigma Chemical Co., St. Louis, Mo.), Gentamycin (GE) (Sigma Chemical Co., St. Louis, Mo.), Penicillin G (Pen.G) (Sigma Chemical Co., St. Louis, Mo.), and Amphotericin B (Amph.B) (Sigma Chemical Co., St. Louis, Mo.).

Microorganisms

The microorganisms used were reference strains obtained from the American Type Culture Collection (ATCC) (Rockville, Md.), SmithKline and French Laboratories (SKF), and the Upjohn Company (UC) (Kalamazoo, Mich.).

Minimum Inhibitory Concentration (MIC) Determinations

MICs were determined by the broth microdilution methodology following the standard NCCLS procedure (NCCLS Document M7-A6, Vol. 23, No. 2, "Methods for dilution antimicrobial susceptibility tests for bacteria that grow aerobically." Approved Guideline. January 2003, which can be herein incorporated by reference in its entirety), with or without 30% adult bovine serum (BS) (PAA Laboratories GMBH, Haidmannweg Pasching Austria), using bacterial innocula at approximately 5×10$^5$ CFU/ml. The media employed included cation-adjusted Müller Hinton broth (Difco Laboratories, Detroit, Mich.) that was used that was adjusted with CaCl$_2$ and MgCl$_2$ to a final concentration of 20 mg/L and 10 mg/L, respectively. Tests were read following 20-24 hours of incubation at 35° C.

Results

The MIC results are summarized in Table 42 below. Against a panel of gram positive bacteria, the activity of the various isolated N$^{15}$-monomethyl dalbavancin compounds and the N$^{15}$,N$^{15}$-dimethyl antibiotic compound ("B$_2$") was comparable or slightly higher than the DA composition, which comprises a mixture of the N$^{15}$,N$^{15}$-dialkyl antibiotic compounds. Blank solution (HCL 0.01N/DMSO 95:5) used to dissolve test compounds was inactive.

Significantly, the N$^{15}$,N$^{15}$-dimethyl antibiotic compound ("B$_2$") showed activity against the gram-positive bacteria that was comparable to or greater than the N$^{15}$-monomethyl dalbavancin compounds. For instance, the activity of the N$^{15}$,N$^{15}$-dimethyl antibiotic compound ("B$_2$") is comparable to or greater than the activity of B$_0$ across the range of gram-positive bacteria.

Quite significantly, the N$^{15}$,N$^{15}$-dimethyl antibiotic compound ("B$_2$") also showed activity against the range of gram-negative bacteria tested. In fact, the only compound that was active against the representative panel of gram-negative bacteria in this assay was the isolated N$^{15}$,N$^{15}$-dimethyl antibiotic compound ("B$_2$"), which showed activity with a MIC range of 16-32 mg/L.

The MIC values of the VA and GE reference compounds against the ATCC reference strains were in the range of NCCLS values.

TABLE 42

IN VITRO ACTIVITY OF VARIOUS $N^{15},N^{15}$-DIALKYL
ANTIBIOTIC COMPOUNDS AND REFERENCE STRAINS

| | MIC (mg/L) | | | | | | | | | | |
|---|---|---|---|---|---|---|---|---|---|---|---|
| Microorganism | $A_0$ | $A_1$ | $B_0$ | $B_1$ | $B_2$ | DA 025/A | VA | GE | Pen.G | Amph.B | Blank* |
| Staphylococcus aureus Smith ATCC 19636 | 0.125 | 0.125 | 0.25 | 0.125 | 0.125 | 0.25 | 1 | 0.5 | 0.06 | >64 | >1:2 |
| S. aureus Smith + 30% BS | 1 | 2 | 2 | 2 | 2 | 2 | 2 | ≦0.125 | 0.06 | >64 | >1:2 |
| S. aureus ATCC 29213 ref. strain[1] | 0.125 | 0.125 | 0.125 | 0.125 | 0.125 | 0.25 | 2 | 8 | 8 | >64 | >1:2 |
| S. epidermidis ATCC 12228 | 0.125 | 0.125 | ≦0.06 | ≦0.06 | ≦0.03 | 0.125 | 2 | ≦0.125 | >32 | >64 | >1:2 |
| Streptococcus pyrogenes SKF 13400 | 0.015 | ≦0.06 | ≦0.06 | ≦0.06 | ≦0.03 | 0.06 | 1 | 4 | ≦0.03 | 32 | >1:2 |
| S. pneumoniae Felton UC41 | 0.125 | ≦0.06 | ≦0.06 | ≦0.06 | ≦0.03 | 0.015 | 0.5 | 8 | ≦0.03 | >64 | >1:2 |
| Enterococcus faecalis ATCC 7080 | 0.125 | 0.125 | 0.125 | 0.125 | 0.06 | 0.25 | 1 | 8 | 32 | >64 | >1:2 |
| E. faecalis ATCC29212 ref. strain[2] | ≦0.06 | 0.125 | 0.125 | 0.125 | 0.125 | 0.25 | 2 | 32 | 4 | >64 | >1:2 |
| Bacillus subtilis ATCC 6633 | ≦0.06 | ≦0.06 | ≦0.06 | ≦0.06 | ≦0.03 | ≦0.007 | ≦0.125 | 0.25 | ≦0.03 | >64 | >1:2 |
| Escherichia coli SKF 12140 | >64 | >64 | >64 | >64 | 32 | >64 | >128 | 2 | >32 | >64 | >1:2 |
| E. coli ATCC25922 ref. strain[3] | >64 | >64 | >64 | >64 | 32 | >64 | >128 | 1 | >32 | >64 | >1:2 |
| Proteus vulgaris ATCC 881 | >64 | >64 | >64 | >64 | 32 | >64 | >128 | 2 | >32 | >64 | >1:2 |
| Pseudomonas aeruginosas ATCC 10145 | >64 | >64 | >64 | >64 | 16 | >64 | >128 | 1 | >32 | >64 | >1:2 |
| Candida albicans SKF 2270 | >64 | >64 | >64 | >64 | 32 | >64 | >128 | >128 | >32 | 0.125 | >1:2 |

*Lowest dilution factor not showing activity.
Quality control range of MICs for reference strains (NCCLS M100 S-12, Vol. 22, No. 1, Jan. 2002):
[1]VA 0.5-2 mg/L
[2]VA 1-4 mg/L
[3]GE 0.25-1 mg/L Example 20

Preparation of a Dalbavancin Composition Comprising Dalbavancin $B_2$

A composition comprising purified dalbavancin $B_0$, dalbavancin $B_1$ and dalbavancin $B_2$ was produced by preparative HPLC.

Figure 37:
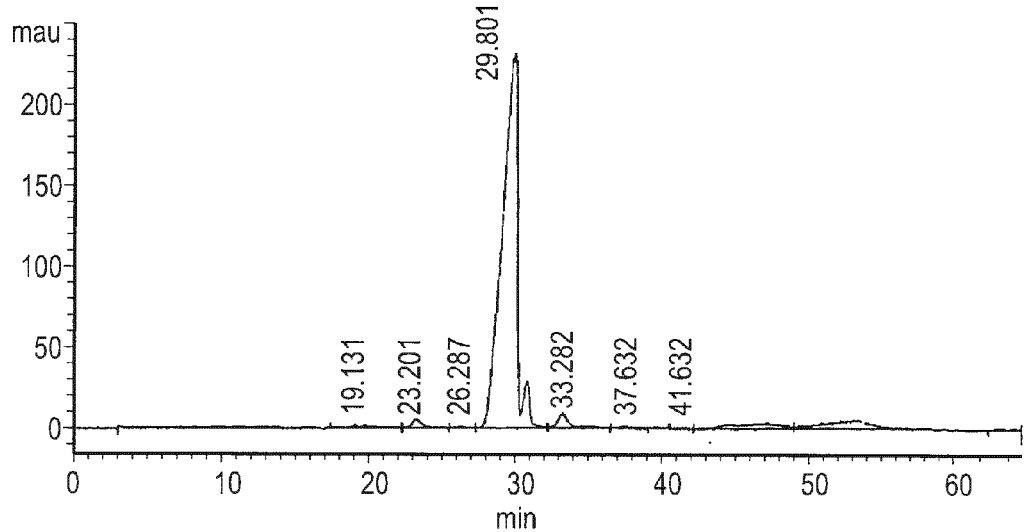
FIG. 37 illustrates an HPLC trace of a composition of the invention.

A dalbavancin mixture prepared according to the methods above was purified by HPLC. The purification was carried out on Kromasil C18, 16 µm, 100 Å pore size. The buffer system was a 50 mmolar $NH_4H_2PO_4$ aqueous solution with the pH adjusted to 5.5. The mobile phase for the elution was mixture 66/34 buffer/acetonitrile. The process yielded a dalbavancin composition comprising 97% dalbavancin $B_0$, dalbavancin B, and dalbavancin $B_2$ by HPLC analysis. A typical analytical HPLC chromatogram is at FIG. 37, with dalbavancin $B_0$ at about 29.901, dalbavancin $B_1$ at about 30.79 (unlabeled) and dalbavancin $B_2$ at about 33.282.

Characterization of $IsoB_0$

Figure 38:
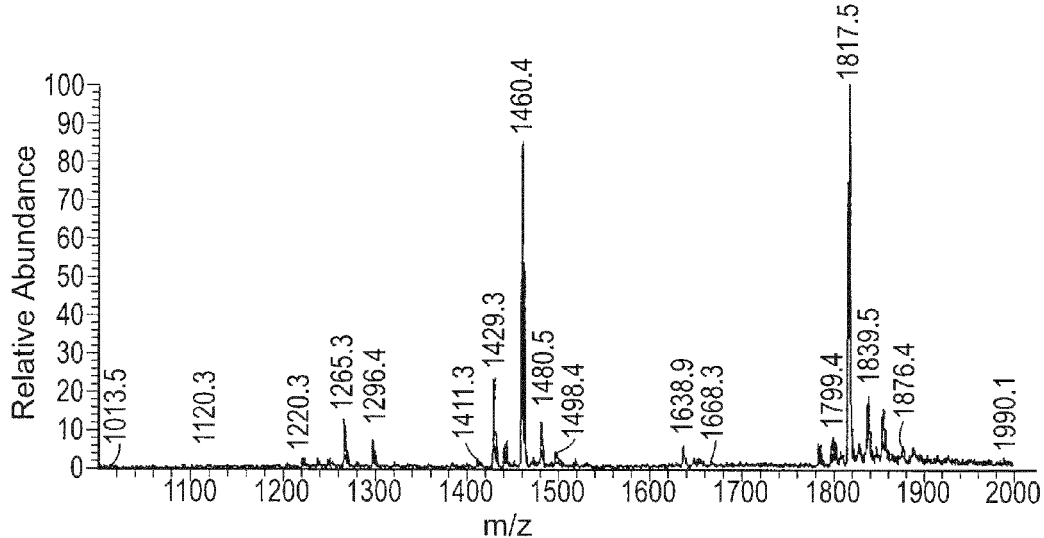
FIG. 38 provides a mass spectrum of iso$B_0$.

The mass spectrum of $IsoB_0$ (FIG. 38) shows an ion at m/z 1817 corresponding to the mono-protonated molecule and other ions due to cation adducts or partial source fragmentations. The molecular weight of 1816 Da and the fragmentation pattern is the same as that observed for B components, which supports the identification of $IsoB_0$ as a diastereomer of $B_0$ (the same molecule with one or more stereocenters having inverted chirality).

The level of $IsoB_0$ was found to increase whenever the pH increased too much in the various preparation steps. Therefore, $IsoB_0$ was prepared by basic treatment of dalbavancin.

Sample Preparation (BI-K0096)

About 300 mg of $IsoB_0$ were obtained from 10 g of dalbavancin batch 027 by long (approximately 165 hours) treatment with NaOH in water (pH 12.7) at room temperature. After neutralization, the reaction product was recovered as a brown crude solid that was subjected to a double chromatographic purification on a silanized silica gel column performed eluting with water (pH 3.5; acetic acid)/acetonitrile in step-gradient mode.

Figure 39:
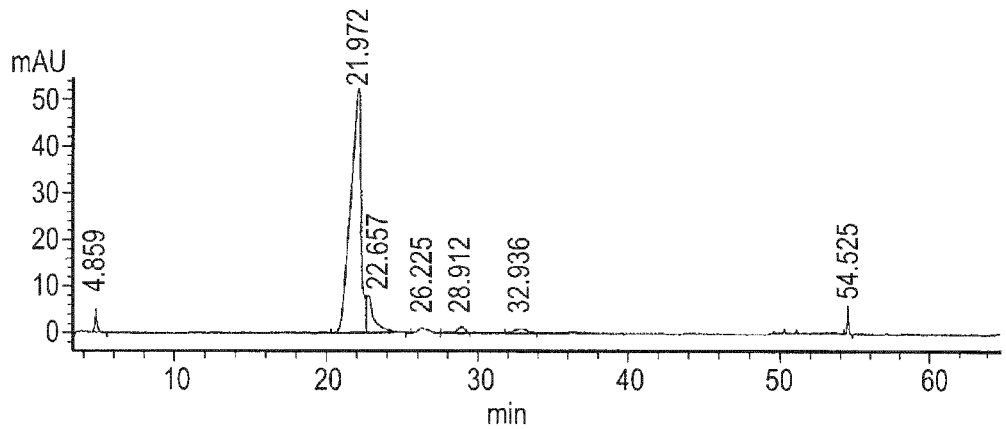
FIG. 39 illustrates an HPLC trace of iso$B_0$.

From the rich fractions, a solid 79.98% area of BI-K0096 was isolated. The HPLC profile is reproduced in FIG. 39.

To verify the correspondence of BI-K0096 with the dalbavancin impurity $IsoB_0$, the prepared compound BI-K0096 was analyzed by HPLC using three different methods. In all of the conditions tested, BI-K0096 was chromatographically identical to the $IsoB_0$ impurity.

Structural Analysis

Figure 40A:
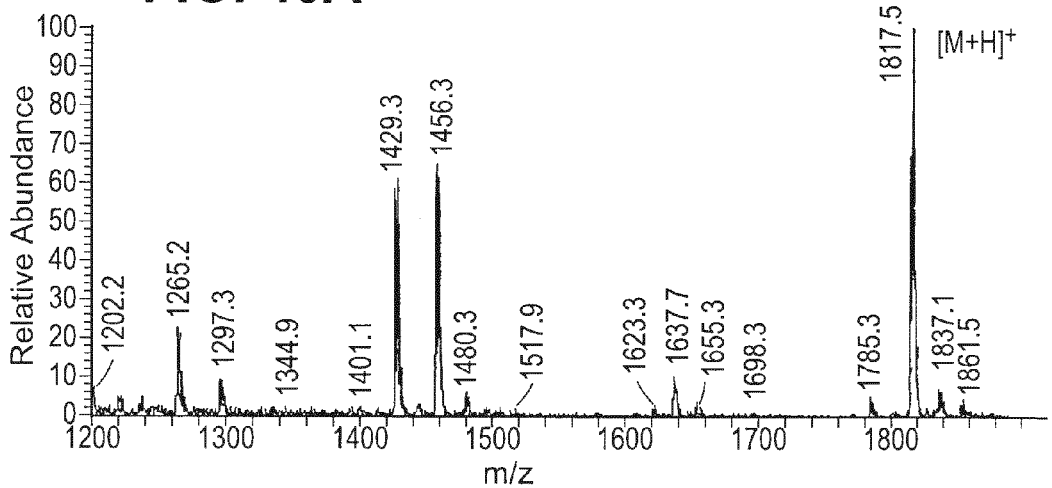
FIGS. 40A-C provides mass spectra of iso$B_0$.
Figure 40B:
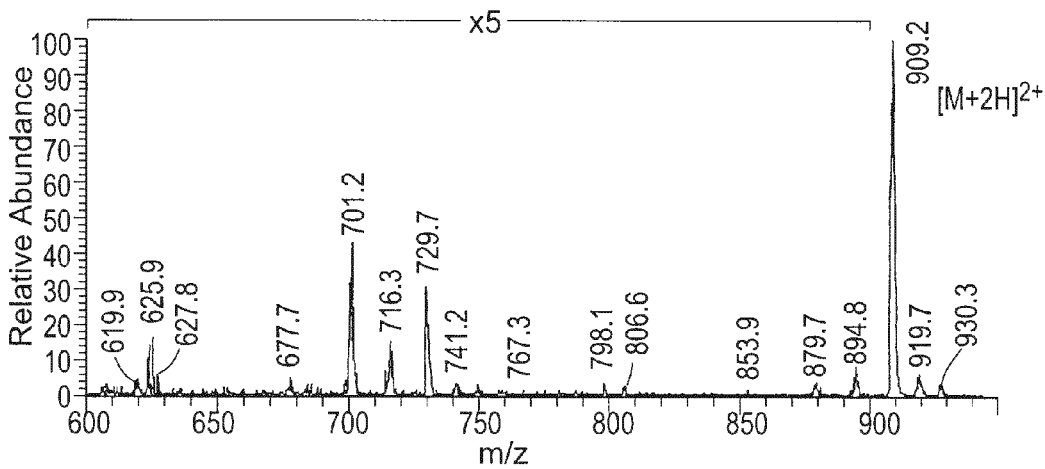
Figure 40C:
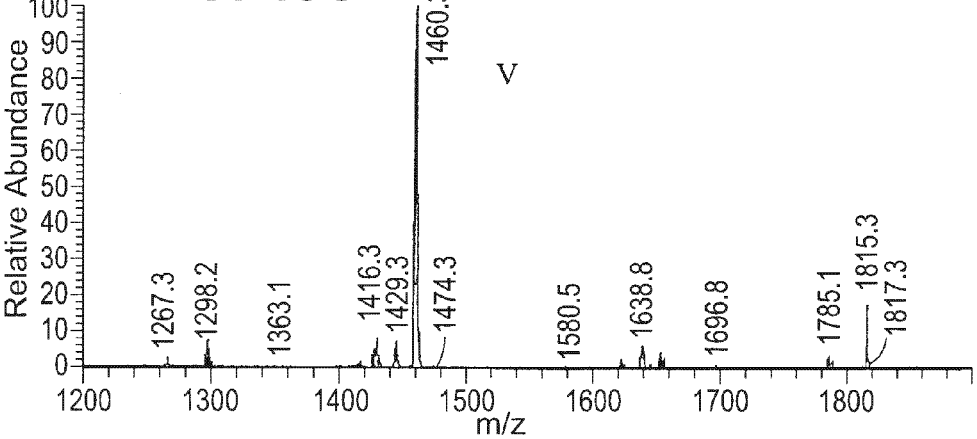

MS and MS/MS spectra are reported in FIGS. 40 A-C. These mass spectra are identical to that of component $B_0$. From this mass analysis, it is not possible to confirm the stereochemical variation.

Figure 41:
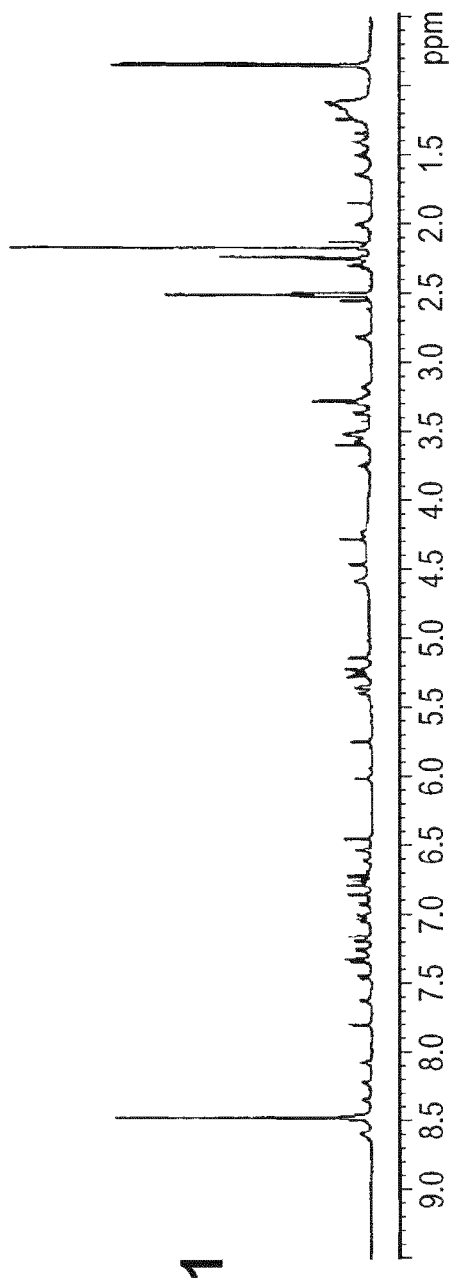
FIG. 41 provides a $^1$H-NMR spectrum of iso$B_0$.
Figure 42:
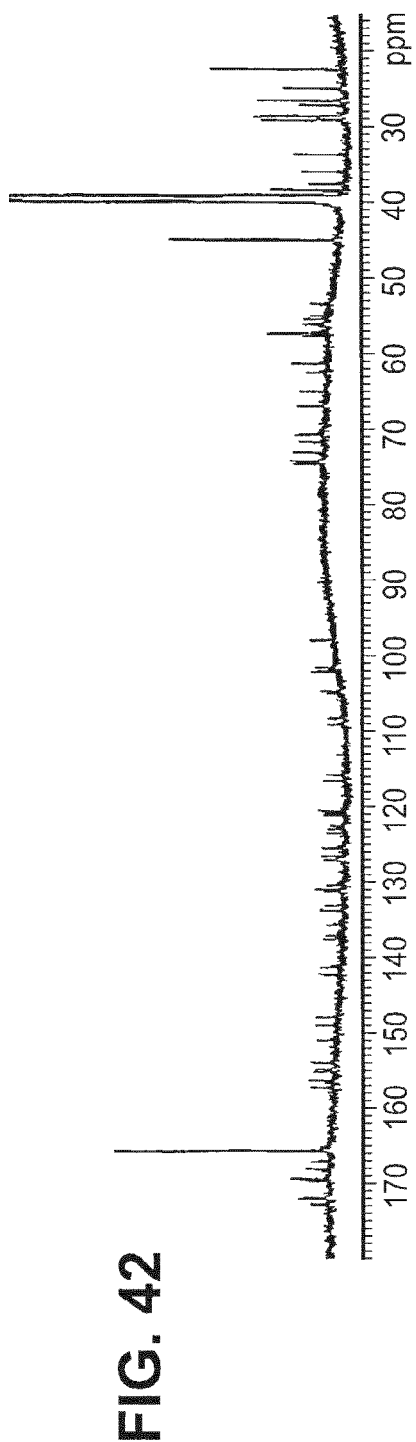
FIG. 42 provides a $^{13}$C-NMR spectrum of iso$B_0$.
Figure 43:
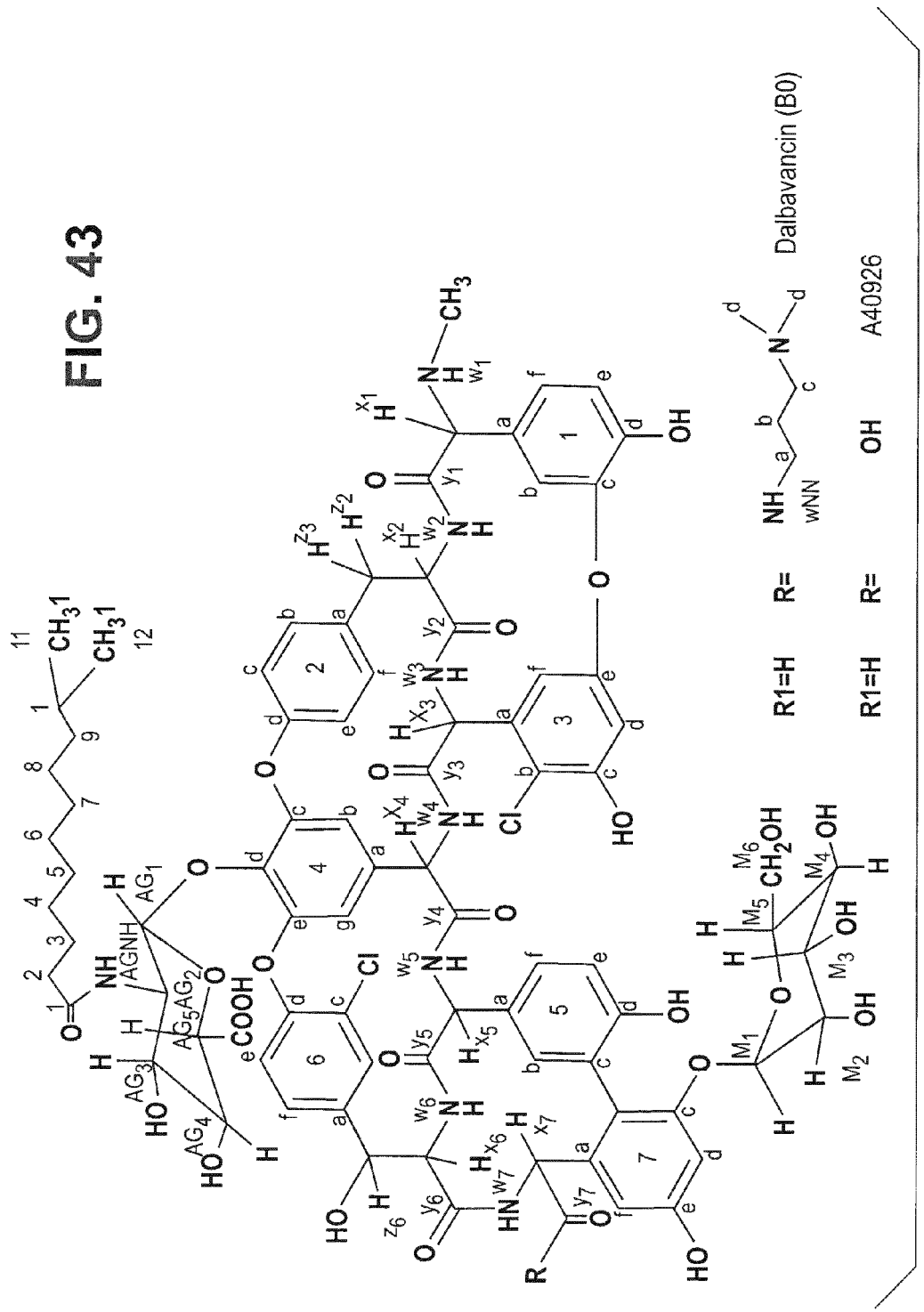
FIG. 43 provides the identification of the location of the protons for dalbavancin.

$^1H$ and $^{13}C$ NMR spectra of $IsoB_0$, recorded in DMSO-$d^6$ on a 600 MHz spectrometer, revealed many similarities with dalbavancin's spectra but also important differences (see FIGS. 41 and 42, respectively). The assignments for $IsoB_0$ and $B_0$ are reported in TABLE 43 and the corresponding location of the protons are identified in FIG. 43.

TABLE 43

NMR Assignments of Dalbavancin Iso $B_0$

| Assignment | iso $B_0$ $\delta^1H$ | iso $B_0$ $\delta^{13}C$ |
|---|---|---|
| w1 | n.a. | — |
| $CH_3$ | 2.24 | 33.70 |
| x1 | 4.26 | 64.65 |
| 1b | 7.13 | 120.5 |
| 1e | 6.82 | 116.6 |
| 1f | 6.97 | 120.87 |
| w2 | 8.19 | — |
| x2 | 4.53 | 55.67 |
| z2 | 2.80 | 38.59 |
| 2b | 7.01 | n.a. |
| 2c | 6.90 | n.a. |
| 2e | 7.29 | n.a. |
| 2f | 7.22 | n.a. |
| w3 | 8.44 | — |
| x3 | 5.34 | 54.65 |
| 3d | 6.51 | 104.7 |
| 3f | 6.0 | 101.36 |
| w4 | 8.59 | — |
| x4 | 5.38 | 55.07 |
| 4b | 5.74 | 109.07 |
| 4f | 5.12 | 104.5 |
| w5 | 8.32 | — |
| x5 | 4.56 | 53.20 |
| 5b | 7.16 | 135.3 |
| 5e | 6.70 | 115.88 |
| 5f | 6.70 | n.a. |
| w6 | 6.59 | — |
| x6 | 4.21 | 62.04 |
| z6 | 5.26 | 71.27 |
| 6b | 7.77 | 126.8 |
| 6e | n.a. | n.a. |
| 6f | 7.42 | 126.9 |
| w7 | 8.56 | — |
| x7 | 4.45 | n.a. |
| 7d | 6.75 | 101.5 |
| 7f | 6.43 | 108.18 |
| AG1 | 5.23 | 102.0 |
| AG2 | 3.72 | 55.91 |
| AG3 | 3.55 | n.a. |
| AG4 | 3.48 | n.a. |
| AG5 | 3.26 | n.a. |
| AG-NH | 7.60 | — |
| FA2 | 2.0 | n.a. |
| FA3 | 1.41 | n.a. |
| FA4-FA9 | 1.11-1.30 | n.a. |
| FA10 | 1.49 | n.a. |
| FA11 | 0.85 | n.a. |
| FA12 | 0.85 | n.a. |
| wNN | 8.05 | — |
| NNa | 3.15; 3.23 | n.a |
| NNb | 1.63 | n.a. |
| NNc | 2.30 | n.a. |
| NNd | 2.16 | n.a. |
| M1 | 5.21 | 97.7 |
| M2 | n.a. | n.a. |
| M3 | n.a. | n.a. |
| M4 | n.a. | n.a. |
| M5 | n.a. | n.a. |
| M6 | n.a. | n.a. |

For some parts of the molecule, proton and carbon chemical shifts are about the same as for the $B_0$ component. The major chemical shift deviations are observable for signals belonging to the amino acids sequence 1-4. The protons of these spin systems show a negligible positive or negative $\Delta\delta$ (chemical shift difference). The amino acid 3 in particular exhibits the greater number of relevant changes (x3, w3, 3f, 3d); x3 is also the only resonance displaying an important modification of its $^3J_{HH}$, the coupling constant CH(x3)-NH (w3) is now 6.54 Hz compared to about 10.4 in $B_0$. Furthermore, ROESY experiments indicate differences in dipolar correlations for x3 as well as for most protons close to x3. The NMR findings reported and literature data published on teicoplanin epimers make clear that x3 is the epimerization center and the epimerization induces a change in the conformation in at least in a part of the molecule.

Microbiological Characterization

The compounds used were:

$IsoB_0$ as previously described above

Dalbavancin (DA) (BI-K397 batch 025/A/AS1) Ref std.

Vancomycin (VA) (batch 121K1140 Sigma Chemical Co. St Louis, Mo., USA).

Gentamicin (GE) (batch 57H1099 Sigma Chemical Co. St Louis, Mo., USA)

Penicillin G (Pen.G) (batch 43H1134 Sigma Chemical Co. St Louis, Mo., USA)

Amphotericin B (Amph.B) (batch 61H4039 Sigma Chemical Co. St Louis, Mo., USA).

Vancomycin, Dalbavancin and Amphotericin B were dissolved at 10 mg/mL in dimethyl sulfoxide (DMSO) and diluted in distilled water; gentamycin and Penicillin G were dissolved in distilled water.

Media

Müller Hinton broth (Difco Laboratories, Detroit, Mich., USA) adjusted with $CaCl_2$ and $MgCl_2$ to a final concentrations of 20 mg/L and 10 mg/L respectively.

Sera

Adult bovine serum (BS) (batch A05123-159 PAA Laboratories GmBH Haidmannweg Pasching Austria).

Microorganisms

The microorganisms used are reference standard strains from the American Type Culture Collection (ATCC, Rockville, USA), Smith Kline and French Laboratories (SKF) and the Upjohn Company (UC, Kalamazoo, Mich., USA).

Minimum Inhibitory Concentration (MIC)

MICs were determined by the broth microdilution methodology following the standard NCCLS procedure [13], with or without 30% bovine serum, using bacterial inocula of approximately $5\times10^5$ CFU/mL. Tests were read after 20-24 h incubation at 35° C.

Results

Against a panel of gram-positive bacteria, the activity of $isoB_0$ is very similar to dalbavancin. (See TABLE 44)

TABLE 44

In Vitro Activity of IsoB₀ and Reference Compounds

| | MIC (mg/L) | | | | | | |
|---|---|---|---|---|---|---|---|
| Microorganism | IsoB$_0$ | DA 025/A | VA | GE | Pen. G | Amph. B | Blank activity* |
| *Staphylococcus aureus* Smith ATCC19636 | 0.5 | 0.25 | 1 | 0.5 | 0.06 | >64 | >1:2 |
| *S. aureus* Smith + 30% BS | 16 | 2 | 2 | ≦0.125 | 0.06 | >64 | >1:2 |
| *S. aureus* ATCC29213 ref. strain[1] | 0.25 | 0.25 | 2 | 8 | 8 | >64 | >1:2 |
| *S. epidermidis* ATCC12228 | 0.125 | 0.125 | 2 | ≦0.125 | >32 | >64 | >1:2 |
| *Streptococcus pyogenes* SKF13400 | 0.06 | 0.06 | 1 | 4 | ≦0.03 | 32 | >1:2 |
| *S. pneumoniae Felton* UC41 | 0.125 | 0.015 | 0.5 | 8 | ≦0.03 | >64 | >1:2 |
| *Enterococcus faecalis* ATCC7080 | 0.25 | 0.25 | 1 | 8 | 32 | >64 | >1:2 |
| *E. faecalis* ATCC29212 ref. strain[2] | 0.25 | 0.25 | 2 | 32 | 4 | >64 | >1:2 |
| *Bacillus subtilis* ATCC6633 | ≦0.06 | ≦0.007 | ≦0.125 | 0.25 | ≦0.03 | >64 | >1:2 |
| *Escherichia coli* SKF12140 | 64 | >64 | >128 | 2 | >32 | >64 | >1:2 |
| *E. coli* ATCC25922 ref. strain[3] | 64 | >64 | >128 | 1 | >32 | >64 | >1:2 |
| *Proteus vulgaris* ATCC881 | >64 | >64 | >128 | 2 | >32 | >64 | >1:2 |
| *Pseudomonas aeruginosas* ATCC10145 | >64 | >64 | >128 | 1 | >32 | >64 | >1:2 |
| *Candida albicans* SKF2270 | >64 | >64 | >128 | >128 | >32 | 0.125 | >1:2 |

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention, which is delineated by the appended claims.

All publications, patents, and patent applications cited herein are hereby incorporated by reference in their entirety for all purposes and to the same extent as if each individual publication, patent, or patent application were specifically and individually indicated to be so incorporated by reference.

What is claimed is:

1. A method for treating a bacterial infection in a human in need thereof, the method comprising:
   administering initial and subsequent therapeutically effective doses of dalbavancin in a pharmaceutically acceptable carrier to the patient,
   wherein each dose is separated by five to ten days and
   wherein the amount of the initial dose is about 100 mg to about 5000 mg, and
wherein the amount of the initial dose is at least about two times the amount of dalbavancin contained in the subsequent dose.

2. The method of claim 1, the method comprising administering a single subsequent dose.

3. The method of claim 2, wherein the subsequent dose is administered about one week after the initial dose without any intervening dose of dalbavancin.

4. The method of claim 1, the method comprising administering multiple subsequent doses.

5. The method of claim 4, wherein said subsequent doses are administered at about one week intervals without any intervening doses of dalbavancin.

6. The method of claim 1, wherein the bacterial infection is a skin and soft tissue infection.

7. The method of claim 1, wherein the amount of the initial dose is about 200 mg to about 1500 mg.

8. The method of claim 1, wherein the amount of the initial dose is about 1000 mg.

9. The method of claim 1, wherein the amount of the initial dose is about 800 mg.

10. The method of claim 1, wherein the amount of the initial dose is about 500 mg.

11. The method of claim 1, wherein the amount of each subsequent dose is about 400 mg to about 1200 mg.

12. The method of claim 1, wherein the amount of each subsequent dose is about 500 mg.

13. The method of claim 1, wherein the amount of each subsequent dose is about 400 mg.

14. The method of claim 1, wherein the amount of each subsequent dose is about 250 mg.

15. The method of claim 1, wherein the amount of each subsequent dose is about 200 mg.

16. The method of claim 1, wherein the amount of the initial dose is about 1000 mg and the amount of each subsequent dose is about 250 mg.

* * * * *